United States Patent
Pitari et al.

(10) Patent No.: US 12,059,400 B2
(45) Date of Patent: Aug. 13, 2024

(54) MEDICAL COMPOUND

(71) Applicant: VERA SALUS RICERCA S.R.L., Augusta (IT)

(72) Inventors: Giovanni Mario Pitari, Augusta (IT); Claudia Giovanna Leotta, Sant'Agata li Battiati (IT); Carmelo Drago, Scordia (IT); Giovanni Nicolosi, Catania (IT)

(73) Assignee: VERA SALUS RICERCA S.R.L., Augusta (IT)

( * ) Notice: Subject to any disclaimer, the term of this patent is extended or adjusted under 35 U.S.C. 154(b) by 137 days.

(21) Appl. No.: 16/628,564

(22) PCT Filed: Jul. 5, 2018

(86) PCT No.: PCT/IB2018/054981
§ 371 (c)(1),
(2) Date: Jan. 3, 2020

(87) PCT Pub. No.: WO2019/008537
PCT Pub. Date: Jan. 10, 2019

(65) Prior Publication Data
US 2020/0323814 A1    Oct. 15, 2020

(30) Foreign Application Priority Data
Jul. 5, 2017    (IT) .......... 102017000075637

(51) Int. Cl.
A61K 31/35    (2006.01)
A61K 31/352    (2006.01)
A61K 47/54    (2017.01)
A61K 47/55    (2017.01)
A61P 35/00    (2006.01)

(52) U.S. Cl.
CPC .......... *A61K 31/352* (2013.01); *A61K 47/542* (2017.08); *A61K 47/543* (2017.08); *A61K 47/55* (2017.08); *A61P 35/00* (2018.01)

(58) Field of Classification Search
CPC .................................................. A61K 31/352
See application file for complete search history.

(56) References Cited

U.S. PATENT DOCUMENTS

| | | | |
|---|---|---|---|
| 8,747,915 B1 | 6/2014 | Giampapa | |
| 2015/0296755 A1 | 10/2015 | Kirkland et al. | |
| 2019/0330199 A1 | 10/2019 | Beausoleil et al. | |
| 2020/0323814 A1 | 10/2020 | Pitari et al. | |

FOREIGN PATENT DOCUMENTS

| | | |
|---|---|---|
| CA | 3043103 A1 | 6/2019 |
| CN | 1837226 A | 9/2006 |
| CN | 101574338 A | 11/2009 |
| CN | 101879156 A | 11/2010 |
| CN | 102659735 A | 9/2012 |
| CN | 102993148 A | 3/2013 |
| CN | 103275051 A | 9/2013 |
| CN | 106137959 A | 11/2016 |
| CN | 109646317 A | 4/2019 |
| EP | 1752131 A1 | 2/2007 |
| JP | 2003002820 A | 1/2003 |
| WO | 9966062 A | 12/1999 |
| WO | 2005112960 A1 | 12/2005 |
| WO | 2007109802 A2 | 9/2007 |
| WO | 2009064485 A1 | 5/2009 |
| WO | 2015110977 A1 | 7/2015 |
| WO | 2015116735 A1 | 8/2015 |
| WO | 2017156147 A1 | 9/2017 |
| WO | 2019008537 A1 | 1/2019 |
| WO | 2019150292 A1 | 8/2019 |
| WO | 2019183282 A1 | 9/2019 |

(Continued)

OTHER PUBLICATIONS

Huang, et al. European Journal of Medicinal Chemistry (2009), 44(5), 1982-1988(abstract) STN[databaseonline]. CAPLUS[retrievedon-Nov. 18, 2021].Accession No. 2009:379293.*
Li, et al. Bioorganic & Medicinal Chemistry (2014), 22(12), 3146-3158(abstract) STN[databaseonline].CAPLUS[retrievedonNov. 18, 2021].Accession No. 2014:725381.*
Lim, et al. Journal of Biological Chemistry (2013), 288(29), 21126-21235(abstract) STN[databaseonline].CAPLUS[retrievedonNov. 18, 2021].Accession No. 2013:1137158.*
Ryu, et al. Journal of Functional Foods (2016), 27, 674-684(abstract) STN[databaseonline].CAPLUS[retrievedonNov. 18, 2021]. Accession No. 2016:1764573.*
Sassi, et al. Pharmacological Research 124 (2017) 9-19.*

(Continued)

*Primary Examiner* — Shawquia Jackson
(74) *Attorney, Agent, or Firm* — Vorys, Sater, Seymour and Pease LLP

(57) ABSTRACT

Provided is a medical compound including a synthetic flavone derivative, according to the formula (I) with allotment in position C-3 of a group as shown below:

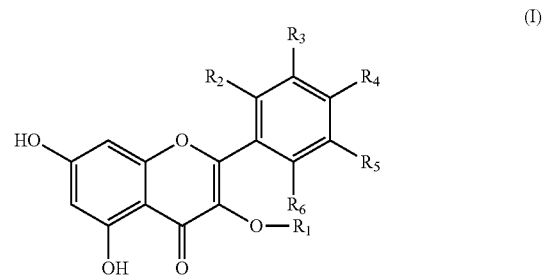

Figure 1A:
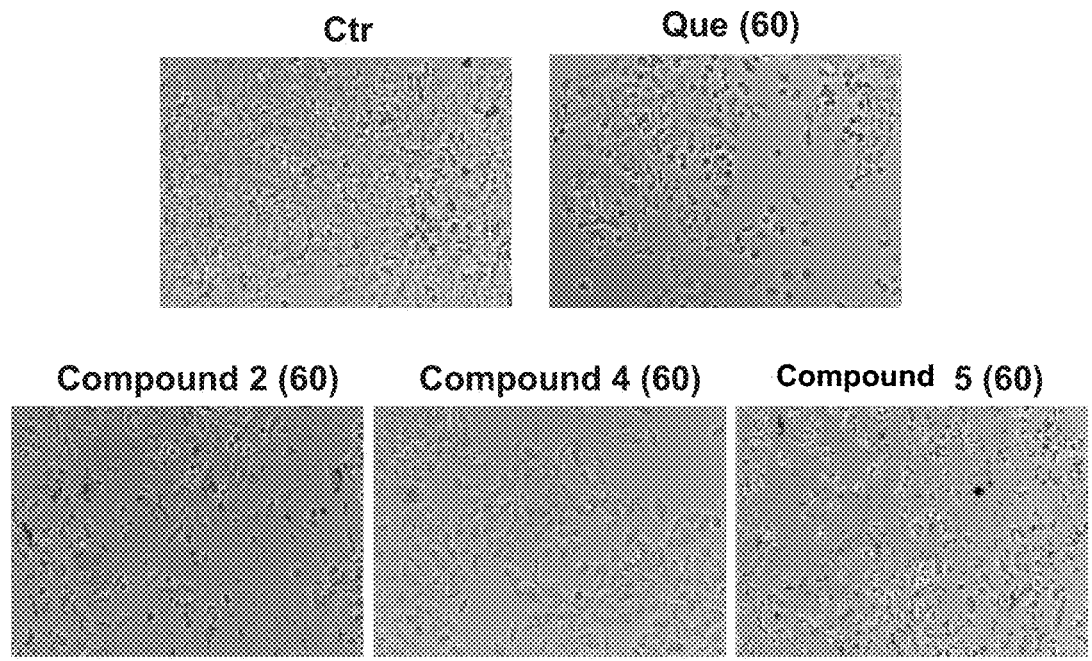

wherein at least two of $R_2$-$R_6$ are H, and the remaining are independently selected from: H, OH, $R_1$, $OR_1$, $NO_2$, $NH_2$, $NHR_1$, F, Cl, Br, I, where $R_1$ is a radical.

21 Claims, 22 Drawing Sheets

(56) References Cited

FOREIGN PATENT DOCUMENTS

| WO | 2019241567 A1 | 12/2019 |
| WO | 2022118183 A1 | 6/2022 |

OTHER PUBLICATIONS

Lala, et al. Cancer and Metastasis Reviews 17 (1998), 91-106.*
Golub, et al. Science 286, (1999) 531-537.*
Cancer [online] retrieved from the internet on Jul. 6, 2007. URL http://www.nlm.nih.gov/medlineplus/cancer.html).*
Dell'Albani et al., "Quercetin derivatives as potent inducers of selective cytotoxicity in glioma cells", European Journal of Pharmaceutical Sciences, 2017, vol. 101, pp. 56-65.
Lee et al., "Design and Synthesis of Novel Antidiabetic Agents", Arch Pharm Res, 2005, vol. 28, No. 2, pp. 142-150.
Li et al., "Quercetin-3-Methyl Ether Inhibits Lapatinib-Sensitive and -Resistant Breast Cancer Cell Growth by Inducing G2/M Arrest and Apoptosis", Molecular Carcinogenesis, 2013, vol. 52, pp. 134-143.
Lu et al., "Synthesis and Bioactivity of Quercetin Aspirinates", Bull. Korean Chem. Soc., 2014, vol. 35, No. 2, pp. 518-520.
Shi et al., "Synthesis, biological evaluation and SAR analysis of O-alkylated analogs of quercetin for anticancer", Bioorganic & Medicinal Chemistry Letters, 2014, vol. 24, pp. 4424-4427.
The Italian Search Report for corresponding Italian Application No. 201700075637, completed Apr. 19, 2018, ten pages.
Tchkonia et al., "Cellular senescence and the senescent secretory phenotype: therapeutic opportunities", The Journal of Clinical Investigation, Mar. 1, 2013, B M J Group, GB, DOI: https://dx.doi.org/10.1172/JCI64098, vol. 123, No. 3, pp. 966-972, NPL Ref. No. XP055347148.
Inoue et al., "SMARCD1 regulates senescence-associated lipid accumulation in hepatocytes", npj Aging and Mechanisms of Disease, Dec. 1, 2017, vol. 3, No. 1, URL: http://www.nature.com/articles/s41514-017-0011-1.pdf, NPL Ref. No. XP055822156.
The International Search Report and Written Opinion for PCT/IB2021/061106, mailed Mar. 1, 2022.
The Italian Search Report for IT 102020000029225, completed Jul. 22, 2021.

* cited by examiner

A375 Cell

A431 Cells

*Fig. 3a* Colorectal cancer
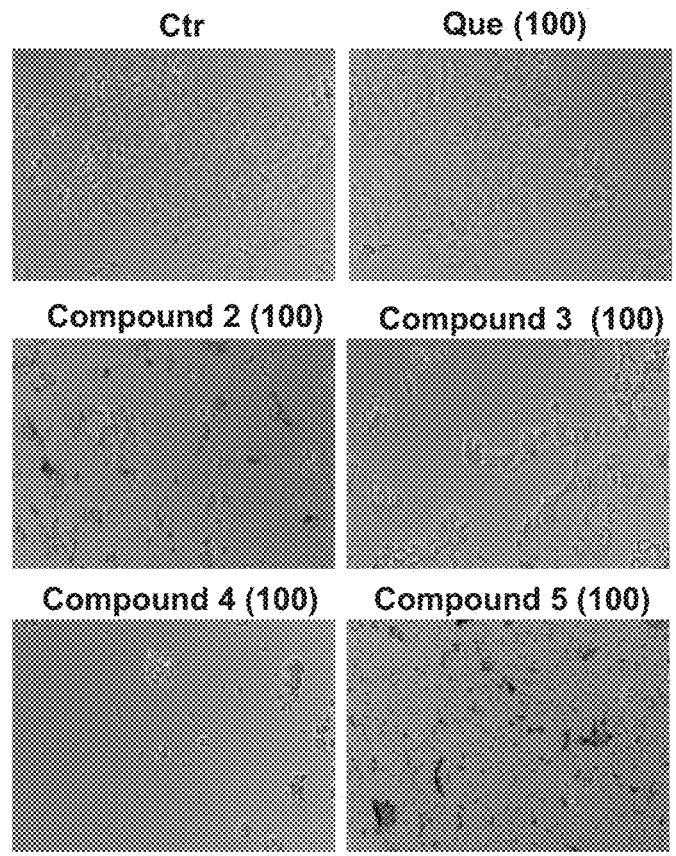
*Fig. 3b*
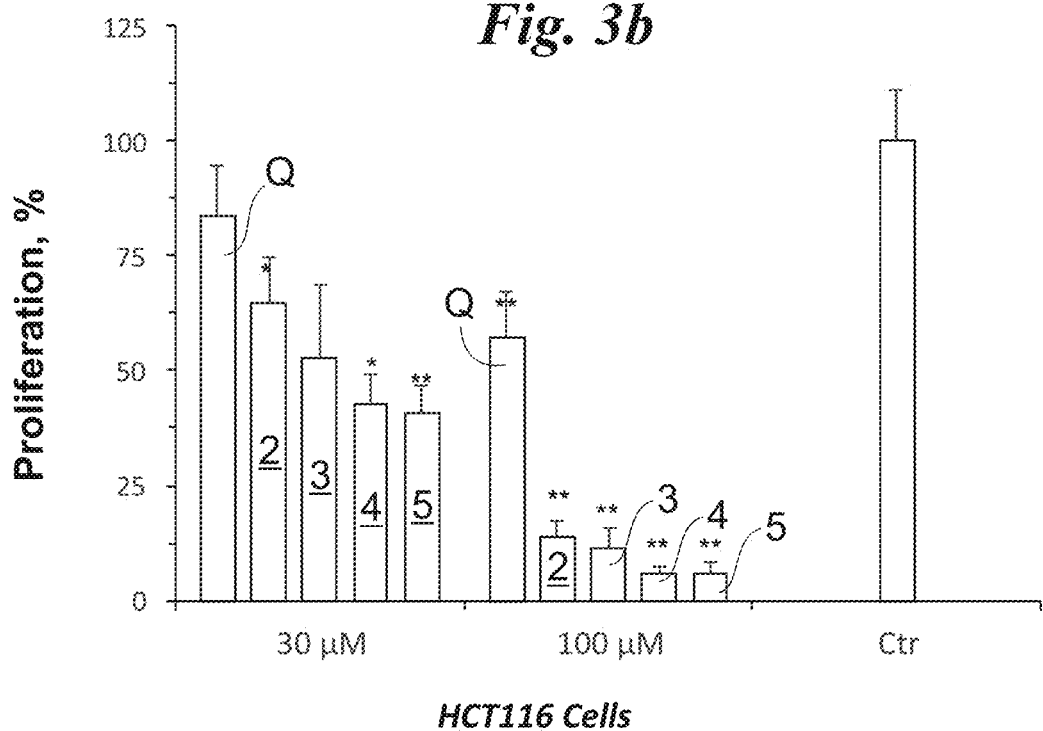
HCT116 Cells

*Fig. 4a* Renal cell carcinoma

786-O Cells

*Fig. 7a* Tongue cancer

CAL27 Cells

HepG2 Cells

PANC-1 Cells

Colorectal cancer

HCT116 Cells

MEDICAL COMPOUND

The present invention relates to a medical compound, particularly for the treatment of malignant tumours, more particularly malignant epithelial tumours and lung carcinoma, colon carcinoma, melanoma and skin squamous carcinoma, or for anti-inflammatory and analgesic activities of the type specified in the preamble of the first claim.

In recent decades, neoplastic disease is emerging as one of the biggest challenges for medicine as well as one of the major causes of mortality, in both developing and industrialized countries. Every year, about 1.6 million new cases of neoplasia are diagnosed and to date more than 100 different types of neoplasia are known, including a huge variety of epithelial tumours, especially breast, lung, colorectal, prostate, liver and skin carcinomas.

Despite the progress made in the treatment of neoplastic disease, further advances are undoubtedly required, mainly due to the severe side effects associated with the most common anti-cancer therapies, such as chemo- and radiotherapy.

In the effort to find new drugs, several studies have attempted to investigate the anti-tumour potential of substances derived from fruit and vegetables, called plant protection products. Among the plant protection products known to date, flavones and flavonoids, particularly quercetin, in many studies have shown anti-neoplastic properties against different tumour cell lines, such as leukaemia HL-60, colon carcinoma SW-480, murine mammary carcinoma 4T1 and epidermoid carcinoma A431.

Quercetin (3,3',4',5,7-pentahydroxyl flavone) is a natural flavonoid characterized by the presence of 5 hydroxyl groups responsible for its biological activity. It occurs in a wide variety of plants, in particular broccoli, tea leaves, onion, carrots. In nature, its activity allows the bilateral growth of embryos in plants to be inhibited. The most representative quercetin derivatives are glycosides and esters. Numerous studies have shown the antioxidant power of quercetin, which is attributable to the presence of the hydroxyl group in ring A and the catechol group in ring B. These characteristics allow quercetin to remove the oxygen free radicals, by transferring hydrogen or electrons or chelating metal ions, thus inhibiting the pro-inflammatory enzymatic activities.

Flavonoid compounds inhibit lipid peroxidase activity, by preventing LDL (low density lipoprotein) oxidation and cell membrane damage. In addition, flavonoids raise glutathione levels and prevent the formation of free radicals.

The therapeutic efficacy of quercetin is closely related to its bioavailability after oral administration. After ingestion, quercetin is hydrolyzed by intestinal glycosidase enzymes and absorbed as an aglycone through the stomach or the gut. Subsequent enzymatic modifications of the molecule transform it into pharmacologically active forms, such as quercetin-3-glycoside, quercetin-3-sulphate, quercetin-3-glucuronide, quercetin-3-methyl ether.

Quercetin metabolic process in the human body is very fast, therefore its availability in the active form is limited. Moreover, quercetin is poorly water-soluble, further affecting its therapeutic potential. It is therefore necessary to increase the water-solubility and delay the metabolism of quercetin in order to obtain extended blood and tissue levels of the molecule.

The anti-neoplastic effects of quercetin involve multiple aspects:

1) Cell growth inhibition: quercetin has shown anti-proliferative effects in different types of neoplasia, both in vitro and in vivo. In vitro, it inhibited cell growth in L1210 and P388 leukemia cell lines, mammary tumour, COLO 20DM colon carcinoma, OVCA 43 ovarian carcinoma, and A431 epidermoid carcinoma. The molecular mechanisms involved appear to be the modulation of pro-proliferative intracellular cascades such as PI3K/akt, Her-2/neu, Wnt/beta-catenin, and EGFR. Quercetin appears to inhibit the activity of mammalian Target Of Rapamycin (mTOR), which is hyperactive in neoplastic cells and essential in controlling intracellular growth signals, in apoptosis mechanisms, protein synthesis and PI3K/Akt activation. In addition to suppressing the activation of PI3K/Akt, quercetin down-regulates Her-2/neu (human epidermal growth factor receptor 2) over-expressed in some mammary neoplasms and allows for inhibition of the Wn/beta-catenin signalling pathway, resulting in reduced cell growth. In addition to modulating the pro-proliferative intracellular signalling pathways described above, quercetin interferes with normal cell cycle progression, leading to reduced cell growth.

2) Inhibition of the metastatic process: the metastatic process is closely linked to the production of metalloproteinases (MMPs), which are enzymes responsible for extracellular matrix degradation and invasion of surrounding tissues by tumour cells. Several studies have analysed the potential of quercetin in the inhibition of MMPs.

3) Induction of apoptosis: apoptosis, or programmed cell death, is essential in the homeostasis of the human body. Dysregulation and defects in apoptotic processes lead to the development of neoplasms. Quercetin has been shown to increase the synthesis of pro-apoptotic factors in mammary and colorectal carcinoma cell lines. Despite these promising aspects of flavones and flavonoids, their current use as potential candidates for the treatment of malignant tumours suffers from some limitations. In fact, as previously mentioned, these molecules exhibit low solubility in $H_2O$ (1 mcg/mL), low intrinsic activity, low absorption (<10%), a fast metabolism (<1 hr), a fast clearance from the body (>40%), multiple inactive metabolic products. These features indicate that it is strictly necessary to identify quercetin derivatives having greater bioavailability and greater biological activity in order to use these plant protection products in the treatment of malignant neoplasms.

In this context, the technical task underlying the present invention is to devise a medical compound, particularly for the treatment of malignant, particularly epithelial tumours, or for anti-inflammatory activity, or the like, which is capable of substantially obviating at least some of the above-mentioned drawbacks.

Within the scope of said technical task, a major object of the invention is to obtain a medical compound for the treatment of malignant tumours in general, and in particular lung carcinoma, colon carcinoma, melanoma, skin squamous carcinoma, and basal cell carcinoma (basalioma).

The technical task and the specified objects are achieved by means of a medical compound as claimed in the appended claim 1.

The features and advantages of the invention will be apparent from the detailed description of preferred embodiments of the invention, with reference to the accompanying drawings, in which:

FIGS. 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12, 13a, 13b, 14, 15, 16, 17, 18, 19, 20, 21, 22a, 22b show the results of tests carried out following treatments performed with standard compounds and with the medical compound according to the invention.

PREFERRED EMBODIMENTS ARE DESCRIBED IN THE DEPENDENT CLAIMS

In the present document, the measures, values, shapes and geometric references (such as perpendicularity and parallelism), when associated with terms like "about" or other similar terms such as "almost" or "substantially", are to be understood as unless measurement errors or inaccuracies due to production and/or manufacturing defects and, especially, unless a slight difference from the value, measure, shape, or geometric reference with which it is associated. For example, these terms, if associated with a value, preferably indicate a difference not exceeding 10% of the value itself.

Furthermore, when used, terms such as "first", "second", "higher", "lower", "main" and "secondary" do not necessarily identify an order, a priority relationship or a relative position, but can simply be used to distinguish more clearly the different components from each other.

The measurements and the data reported in this text are to be considered, unless otherwise indicated, as carried out in the International Standard Atmosphere ICAO (ISO 2533).

The medical compound according to the invention is particularly used for the treatment of malignant tumours, in particular malignant epithelial tumours. The term "epithelial tumours" is intended to mean malignant neoplasms derived from epithelial tissue (skin, mucosa, glandular system). Neoplastic transformation changes the numerical homeostasis of cells in the tissue, causing uncontrolled growth and genomic instability.

In particular, the compound according to the invention is used for one or more of the following malignant tumours, in particular malignant epithelial tumours: colon carcinoma, melanoma and/or skin squamous carcinoma, lung carcinoma, mammary carcinoma, basal cell carcinoma (basalioma).

In addition, the compound according to the invention is preferably used to stem the proliferation of the aforementioned tumours, since it affects the tumours' proliferative ability and apoptosis. It can also be used both to induce cell death and apoptosis, for example by increasing ROS (reactive oxygen species), disrupting the mitochondrial activity, damaging the DNA or activating caspases 3, 8 and 9, and to cause cell cycle arrest.

Furthermore, the compound according to the invention is used for one or more of the following malignant tumours: head and neck cancer, stomach cancer, liver cancer, pancreatic cancer, breast cancer, prostate cancer, bladder cancer, kidney cancer, mesothelioma, and ovarian cancer.

The compound according to the invention does not apply to the treatment of hepatitis C and the consequent malignant liver tumours or hepatocellular carcinoma induced by hepatitis C virus infection.

Still further, the compound according to the invention is used for one or more of the following malignant tumours: salivary gland tumours, esophageal cancer, small intestine tumours, gall bladder and extrahepatic biliary tract cancer, soft tissue sarcoma, cervical cancer, uterine cancer, testicular cancer, urinary tract tumours, choroidal melanoma, thyroid cancer, endometrial cancer, retinal tumour, uveal melanoma, anal canal cancer and anal cancer, bone and joint cancer.

Finally, the compound according to the invention is used for non-tumour therapeutic uses of our compounds, namely for:
- anti-inflammatory activity,
- analgesic activity,
- antimicrobial activity (bacteria, viruses, fungi),
- immunomodulatory activities,
- antioxidant activity,
- cytoprotective and nourishing activity,
- anti-degenerative and anti-ageing activities,
- in idiopathic chronic inflammatory diseases (Crohn's disease, ulcerative rectocolitis, irritable colon syndrome, fibromyalgia, arthritis, myopathy),
- in neurodegenerative diseases (Alzheimer's disease, Huntington's disease, ALS, Parkinson's disease, senile dementia, glaucoma),
- in syndromes from long-term toxicity of chemotherapy and radiotherapy (central and peripheral neurotoxicity, inflammation, oxidative stress, fatigue, vomiting, nausea, diarrhea, constipation, impotence, hearing loss, heart disease).

The compound according to the invention is preferably a synthetic flavone derivative, according to the formula (I) with allotment in position C-3 of a group as shown below.

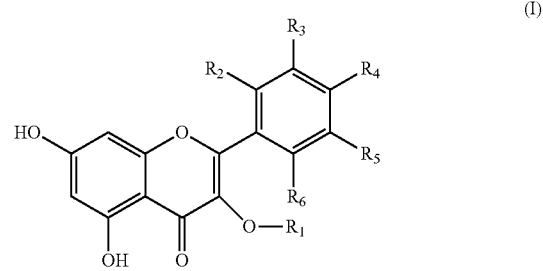

(I)

wherein at least two of $R_2$-$R_6$ are H, and the remaining are independently selected from: H, OH, $R_1$, $OR_1$, $NO_2$, $NH_2$, $NHR_1$, F, Cl, Br, I, and more particularly $R_2$, $R_3$, $R_6$ are H, and $R_4$ and $R_5$ are OH, where $R_1$ is a radical preferably selected from:

H;

$C_{1-24}$ alkyl or heteroalkyl, $C_{1-24}$ alkenyl or heteroalkenyl; $C_{1-24}$ alkynyl or heteroalkynyl an acyl residue of a fatty acid. Said fatty acid can be saturated, unsaturated, polyunsaturated, of either synthetic or natural origin.

Preferably, $R_1$ is:

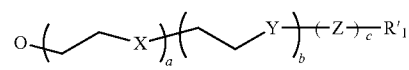

where $R'_1$ is selected from the same compounds as $R_1$, where a, b, and c each range from 0 to 12, where X, Y, and Z are each independently selected from: $CH_2$, O, $N(R_1)$, S, NH, SO, $SO_2$, OC(O), CO, NHC(O), C(O)NH, NH—C(O)—NH, NH—C(S)—NH.

As regards the synthesis of quercetin ethers 1, 2 and 3, the synthetic strategy provides an orthogonal protection of quercetin as reported by Rolando et al. (Tetrahedron Letters, 2011, 52, 4738). The synthesis of quercetin ethers 1, 2 and 3, starting from commercial rutin 6, provides extensive benzylation of the free hydroxyl groups, followed by selective hydrolysis of the disaccharide in position 3 and consequent alkylation with the appropriate alkyl bromide, and finally, removal of the benzyl groups through Pd/C-catalysed hydrogenation. The strategy is simplified below:

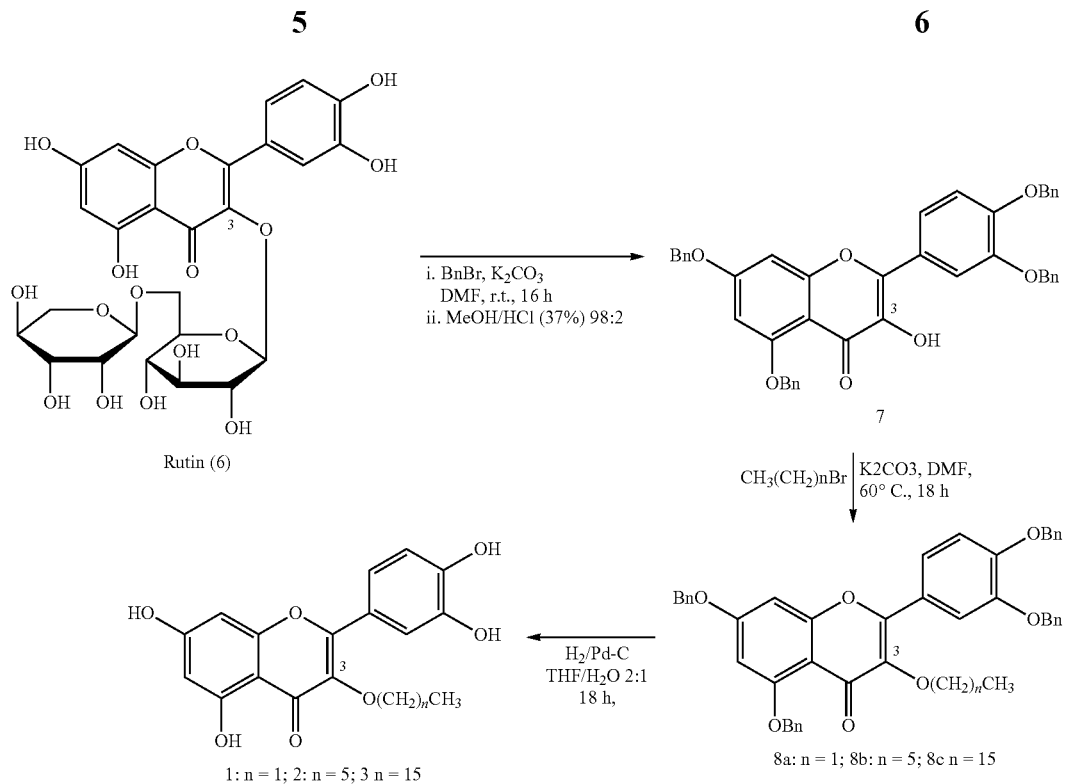

The synthesis of quercetin esters 4 and 5 is carried out by means of the enzymatic strategy reported by D. Lambusta et al. (J. Mol. Catal. B-Enzymatic, 2003, 22, 271). The strategy comprises the esterification of quercetin 9 on all five hydroxyl groups, followed by selective alcoholysis mediated by the appropriate selection of lipases from *Candida antarctica* (CAL) and *Mucor miehei* (MML), as shown in the following scheme.

Similarly as described for the synthesis of products 8, shown below is the synthesis of products of the series 11, as set forth in the following scheme.

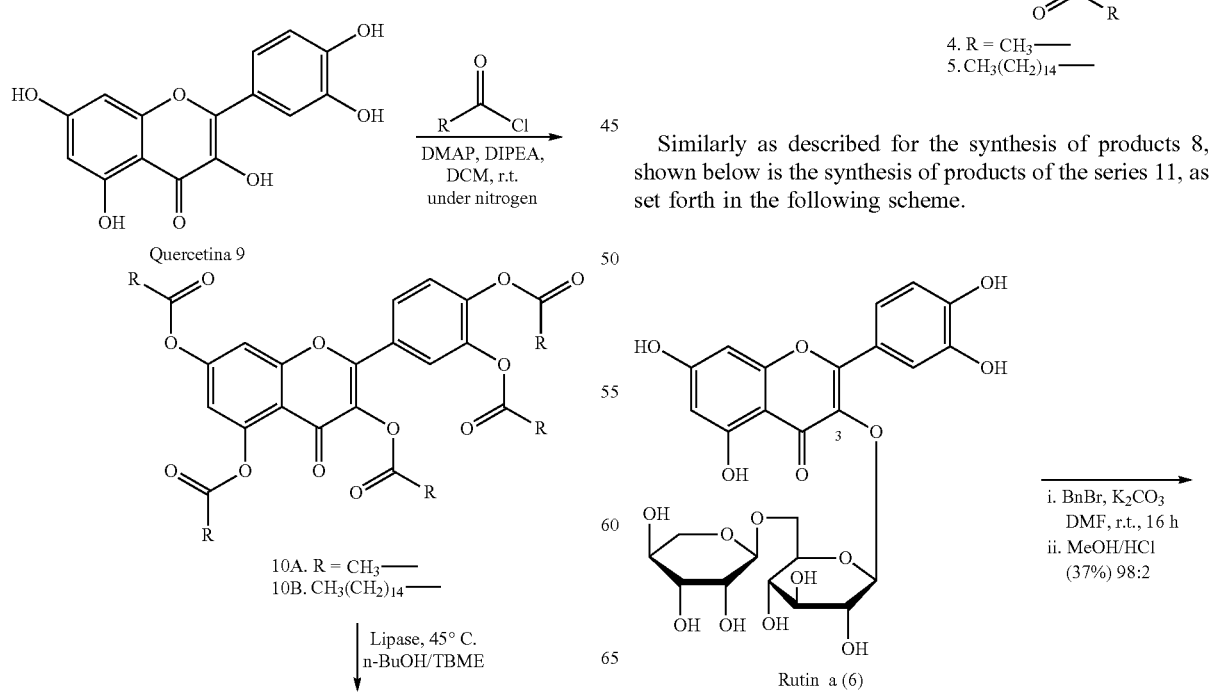

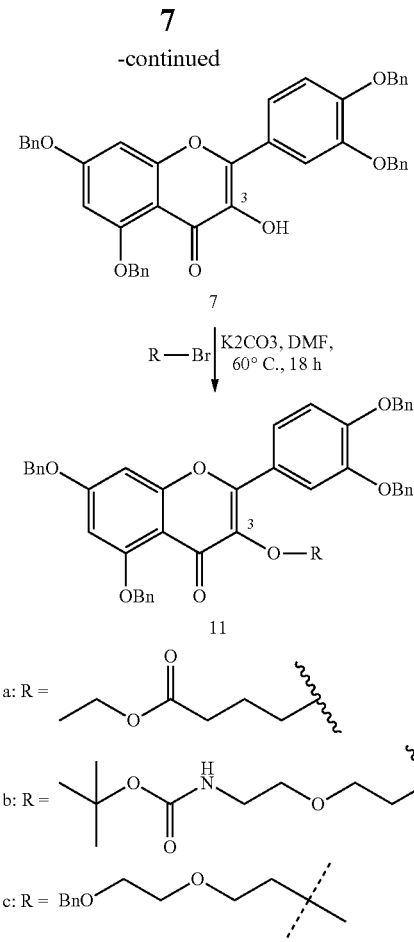

The compounds according to the invention also include di-, tri- and tetra-meric molecules, where two or more quercetin units are linked, through position 3 and a spacer, to a suitable central linker (scaffold), as reported below.

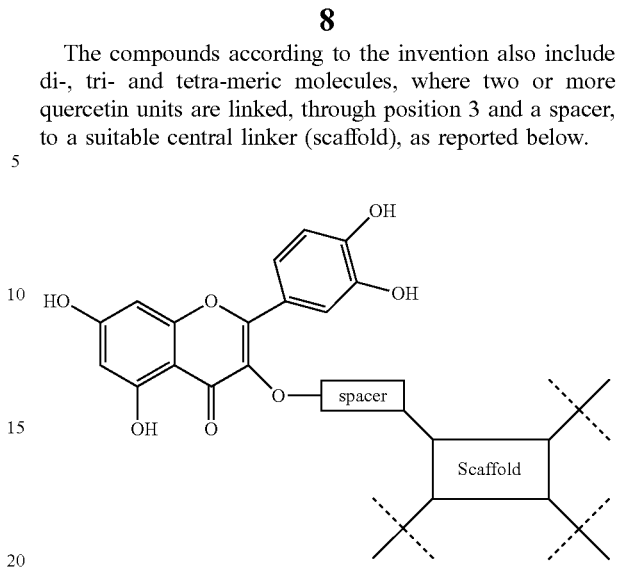

The selection of both the spacer and the central scaffold was made attempting to investigate the effect due to the flexibility and the distance between the quercetin units. A first group of dimeric molecules was synthesized by the strategy shown in the following scheme, where the ethyl-ester of the intermediate 11a is hydrolyzed by treatment with sodium hydroxide in THF/H$_2$O and the corresponding carboxylic acid 12, activated with EDC/HOBt, is condensed with the suitable diamine (H2N-linker-NH2) 13. Lastly, the final products 15 were obtained by extensive debenzylation of the intermediates 14 carried out by a classical catalytic hydrogenation.

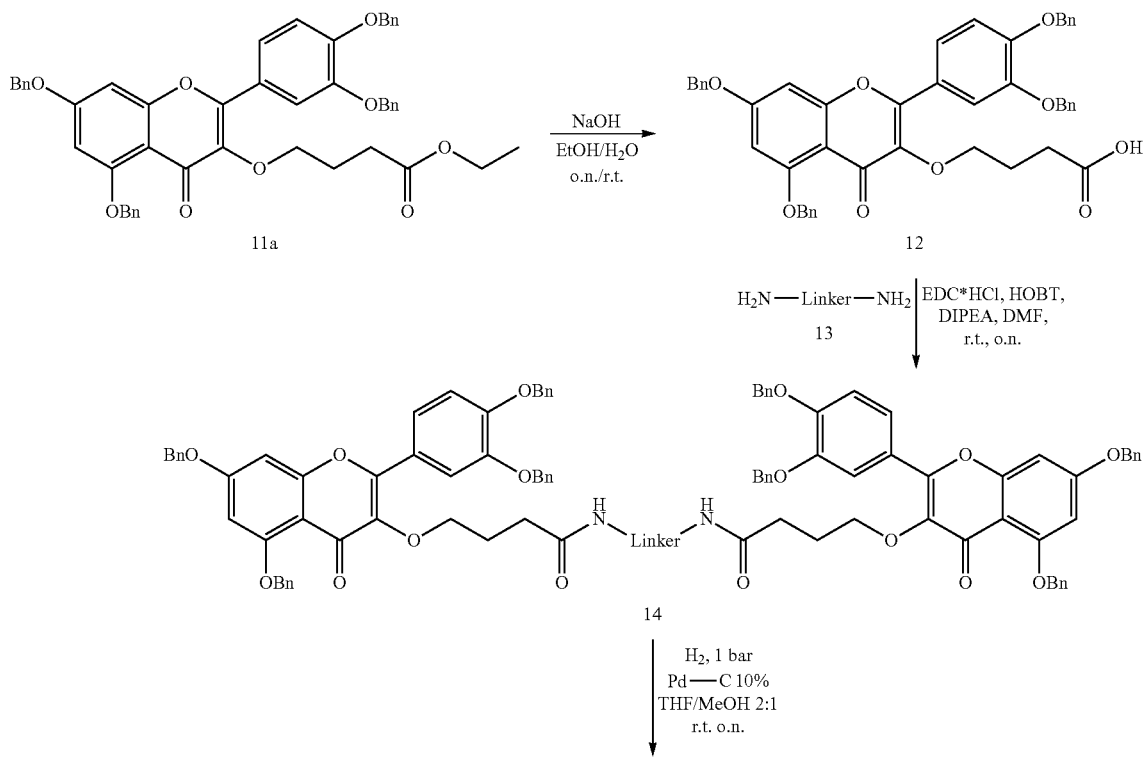

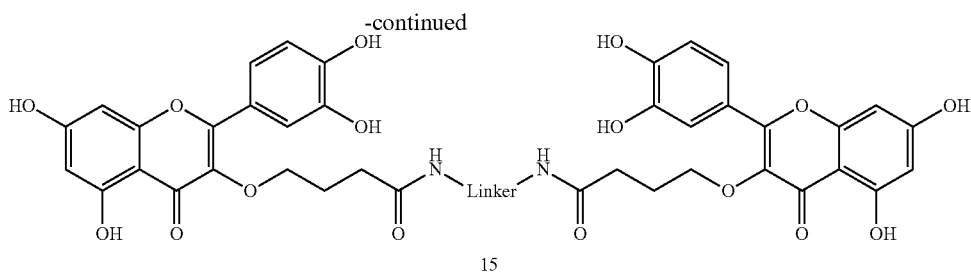

15

A second group of dimeric molecules was synthesized by the strategy shown in the following scheme, which comprises the removal of the protective group (BOC) from the amine 11b by treatment with 4N HCl in THF/H2O. The corresponding amine 16 is then condensed with the suitable dicarboxylic molecule 17, upon activation with EDC/HOBt. Lastly, the final products 19 were obtained by extensive debenzylation of the intermediates 18 carried out by catalytic hydrogenation.

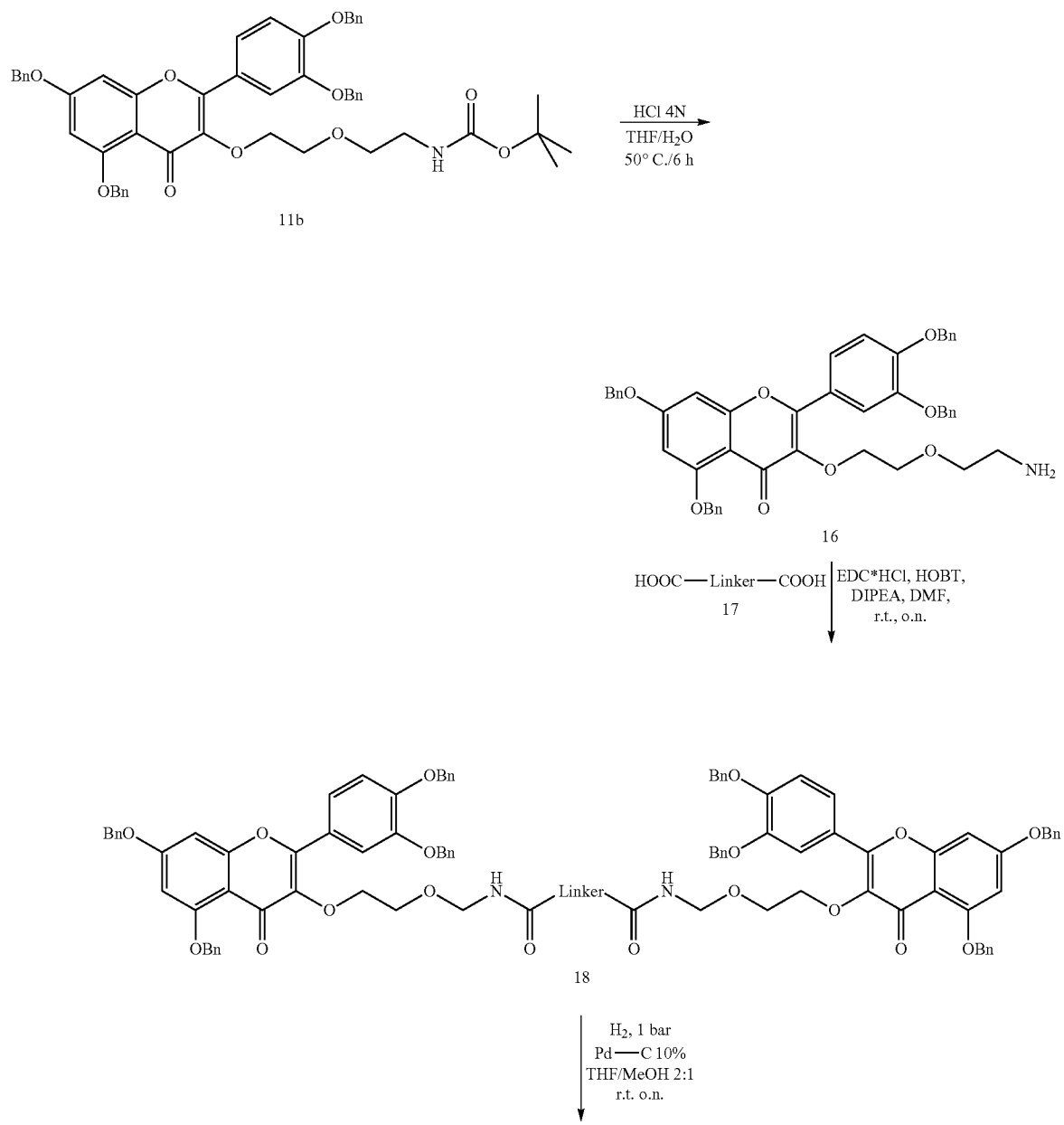

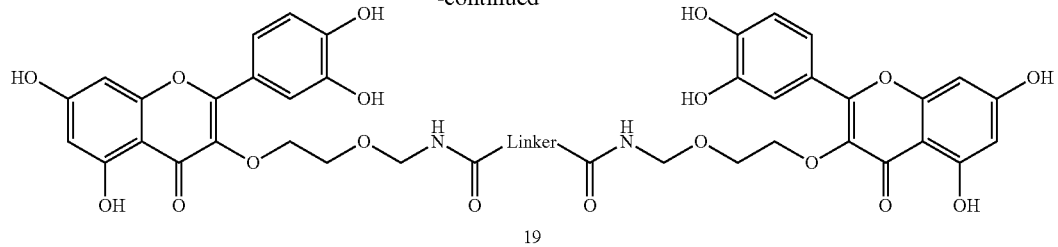
Similarly, the trimeric molecules were synthesized starting from intermediate 16 by condensation with the appropriately selected tricarboxylic molecule 20, upon activation with EDC/HOBt (scheme below). The final products 22 were obtained by extensive debenzylation of the intermediates 21 carried out by a classical catalytic hydrogenation.
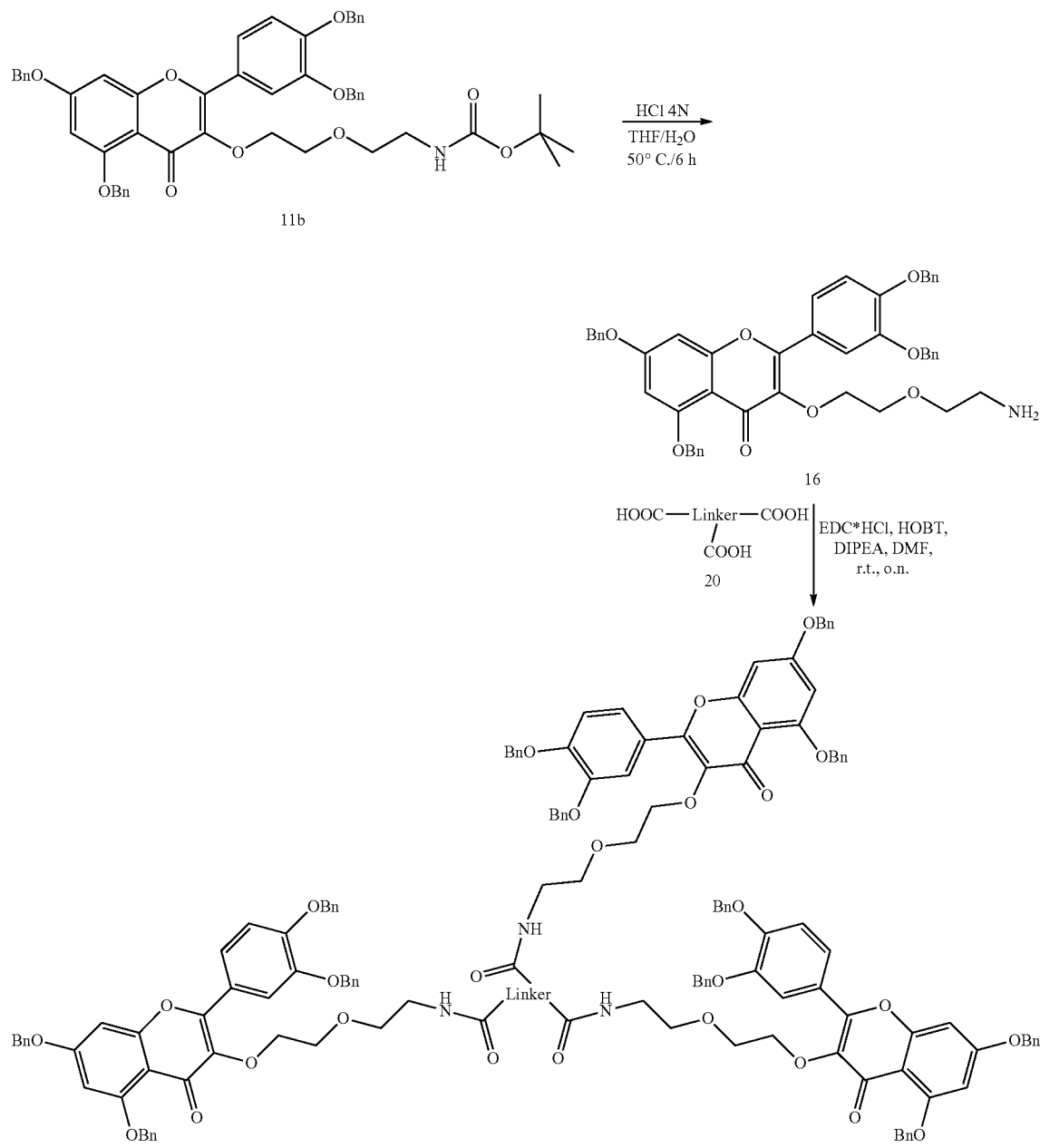

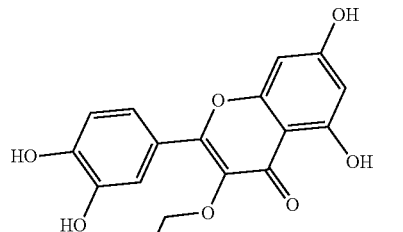
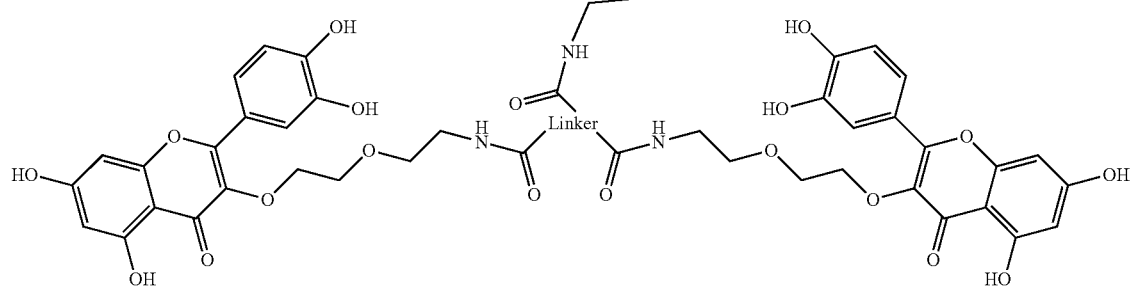
22
The tetrameric molecules are synthesized starting from intermediate 16 by condensation with the appropriately selected tetracarboxylic molecule 23, upon activation with EDC/HOBt (scheme below).
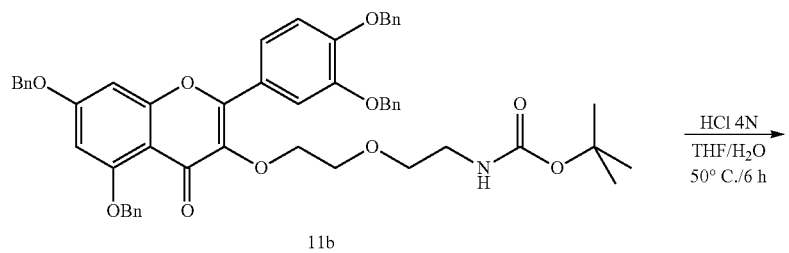
11b
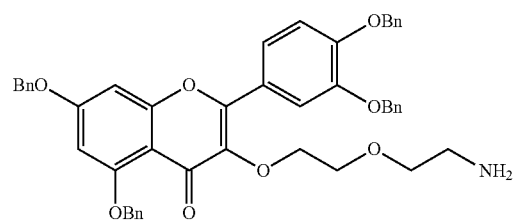
16
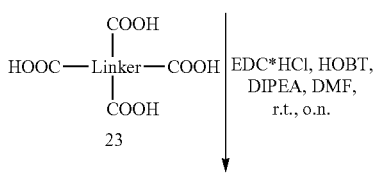
23

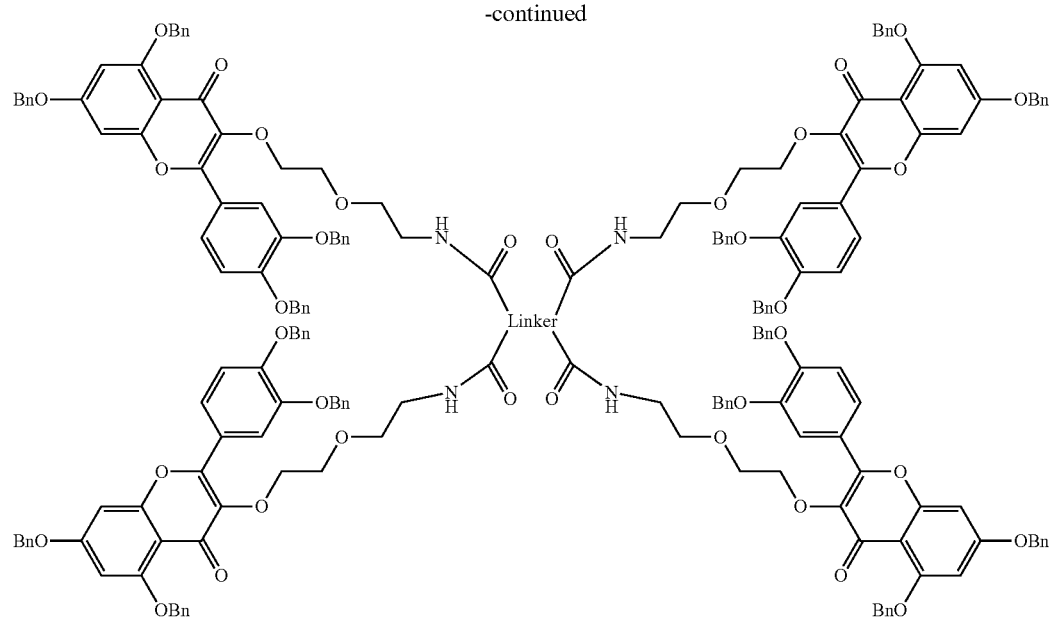
24
Lastly, the final products 25 were obtained by extensive debenzylation of the intermediates 24 carried out by a classical catalytic hydrogenation (scheme below).
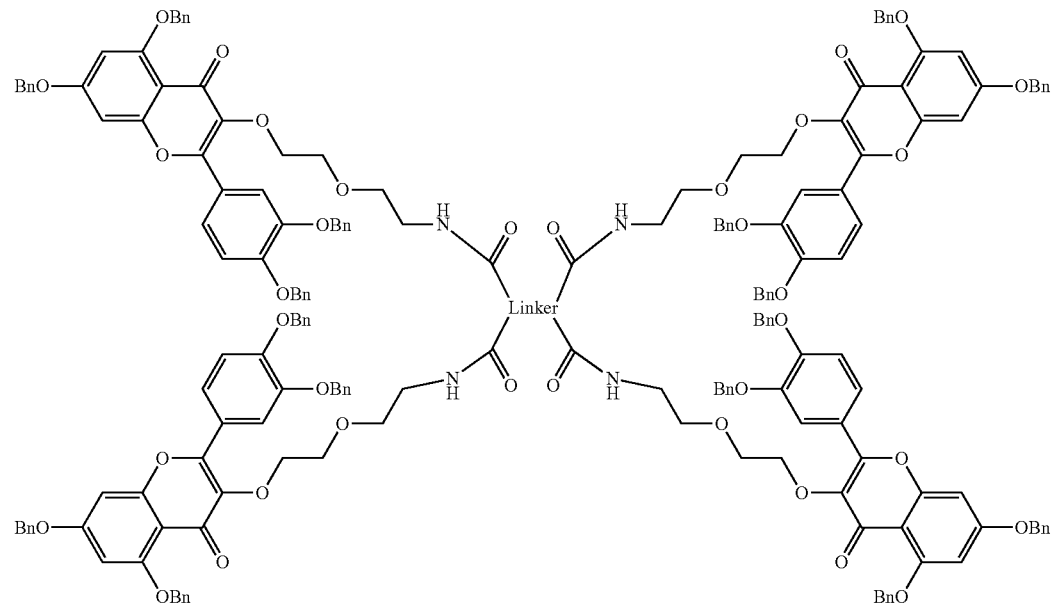
24
H₂, 1 bar
Pd—C 10%
THF/MeOH 2:1
r.t. o.n.

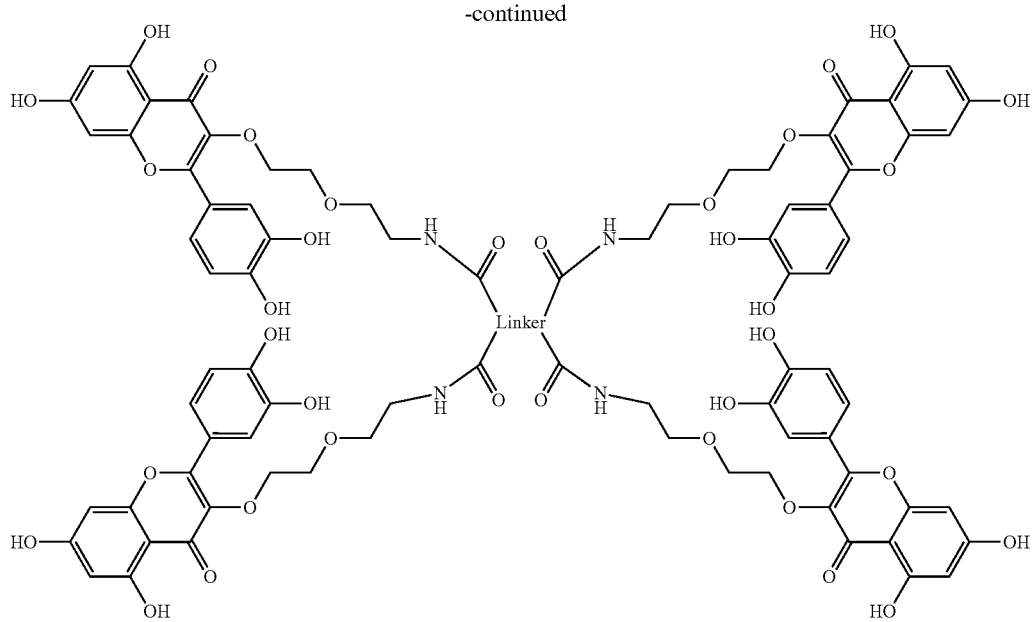

25

Other compounds according to the invention include molecules in which a pharmacophore appendage is linked, through an appropriate spacer bridge, to the oxygen in position 3 of quercetin (Figure below).

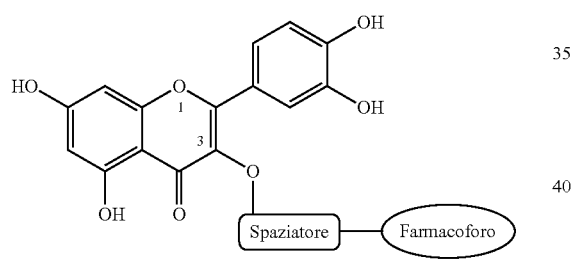

["Spaziatore"=Spacer;
"Farmacoforo"=Pharmacophore]

These molecules were synthesized starting from compounds 11(b-c), thereby obtaining quercetin derivatives 26 (obtained by complete debenzylation of 11c) and 16 (obtained by removing the protecting group Boc from 11b in an acidic environment), according to the following scheme.

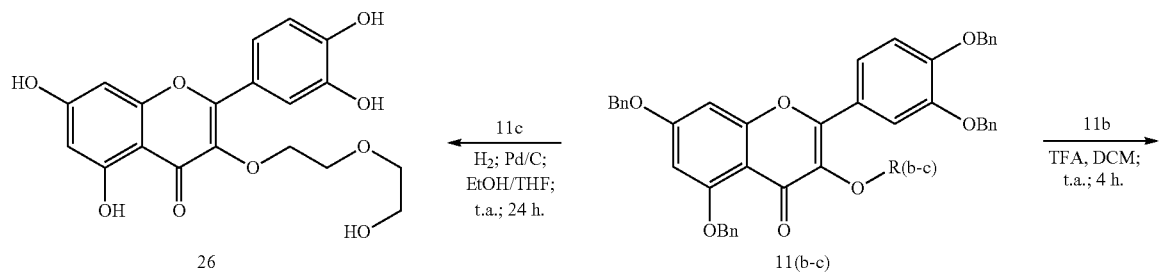

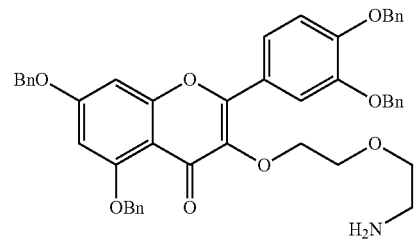

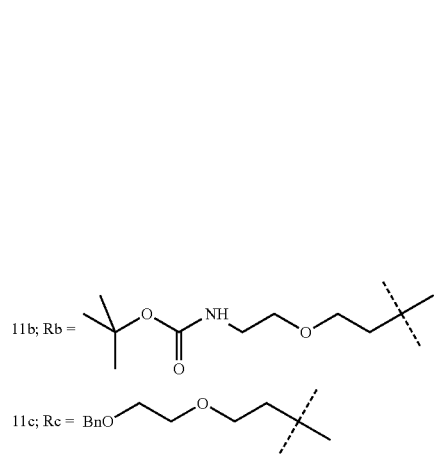

Some of the compounds according to the invention exhibit, as the pharmacophore group, a chemical structure relatable to endocannabinoids and N-acylethanolamines (NAEs; the structures of biological compounds relevant to humans are shown in the following figure).

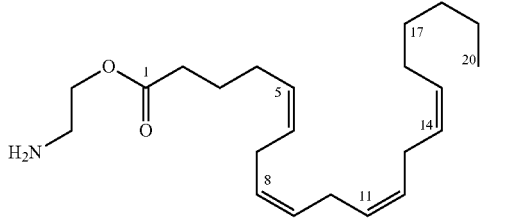

Virodamina

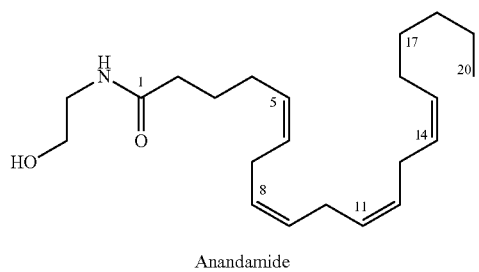

Anandamide

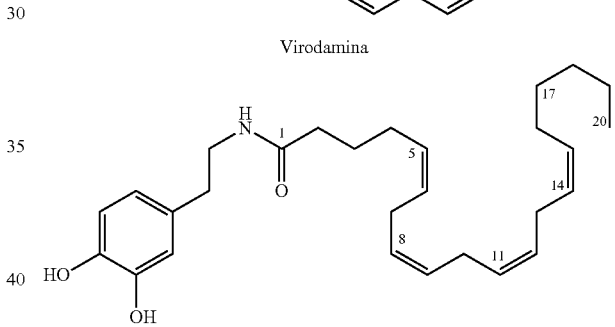

N-arachidonoildopamina

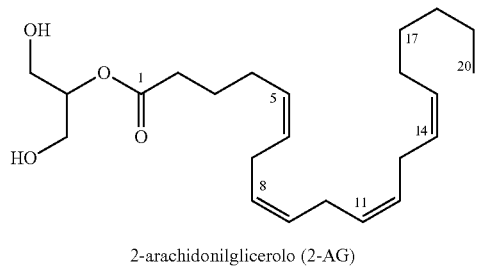

2-arachidonilglicerolo (2-AG)

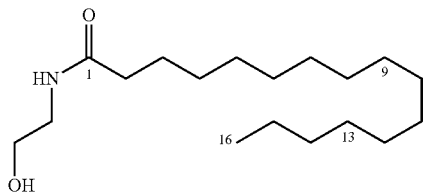

Palmitoiletanolammide (PEA)

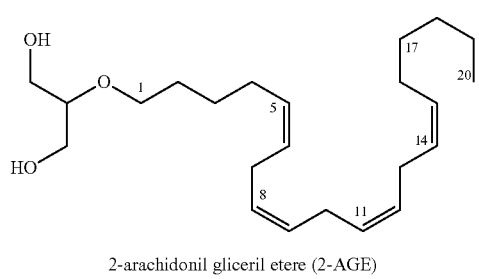

2-arachidonil gliceril etere (2-AGE)

["2-arachidonilglicerolo"=2-arachidonylglycerol;
"2-arachidonil gliceril etere"=2-arachidonyl glyceryl ether;
"Virodamina"=Virodamine;
"N-arachidonoildopamina"=N-arachidonoyl dopamine;
"Palmitoiletanolammide"=Palmitoylethanolamide]

As an example, palmitic acid ethanolamide (PEA), arachidonic acid (anandamide) ethanolamide, and dopamine amide with arachidonic acid (N-arachidonoyl dopamine) can be mentioned among the main structures listed in the figure above. By comparing these structures with that of quercetin derivative 27 (scheme below), it appears that in the latter the chain linked to the oxygen in position 3 can mimic, in its final aminoethanol portion, the ethanolamine portion of endocannabinoids and NAEs, while the innermost ethylene portion acts as a spacer between quercetin and the pharmacophore (e.g. in the following figure, which shows PEA at the top, the formation of the compound according to the invention containing the PEA structure, by joining the quercetin derivative 27 with a suitable acyl group, the ethylene bridge between the two oxygens separating the two structures, at the bottom).

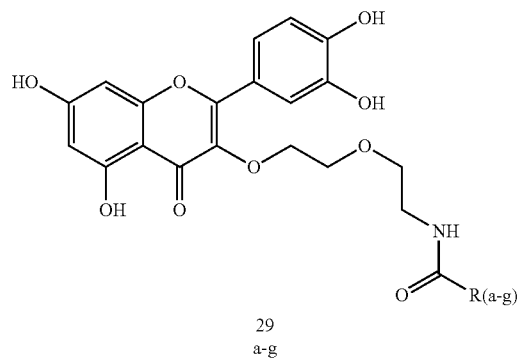

29
a-g

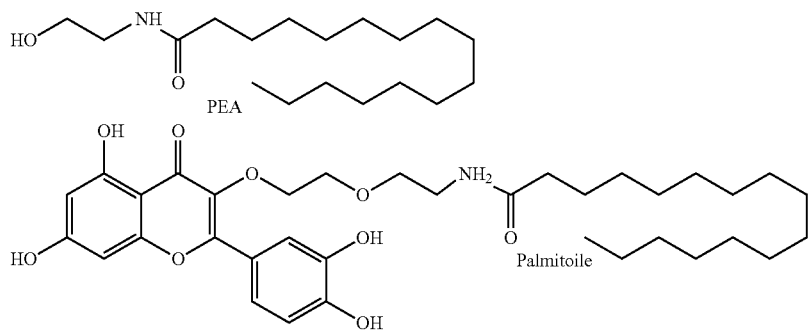

PEA

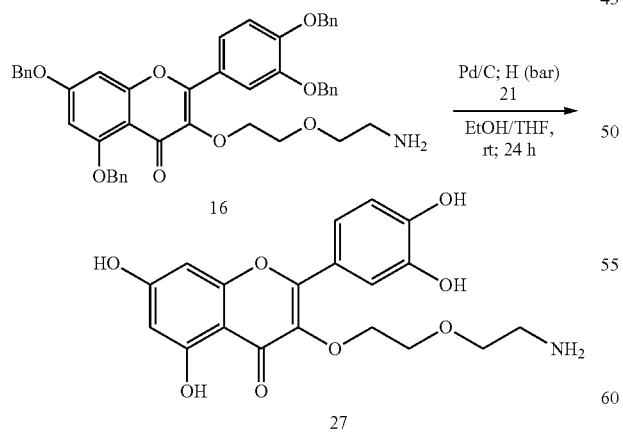

Palmitoile

27

["Palmitoile"=Palmitoyl]

Therefore, by binding the appropriate acyl portion to the quercetin derivative 27, quercetin molecules are obtained, whose oxygen in position 3 is joined, through an ethylene spacer, to an endocannabinoid or a NAE. Quercetin derivative 27, obtained by debenzylation of compound 16, through its amine function, has thus been channeled into a parallel synthesis process for obtaining amides, wherein each time it was reacted with a different acid (28(a-g)) previously activated with EDC and HOBt to obtain amides 29(a-g) (scheme below).

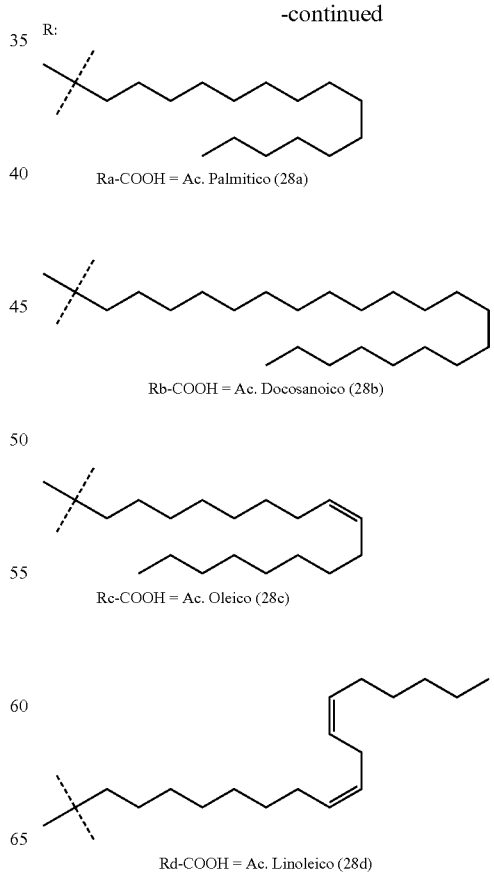

-continued

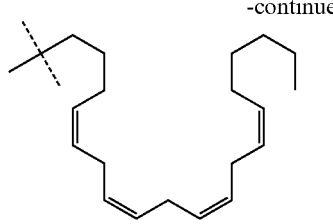

Re-COOH = Ac. Arachidonico (28e)

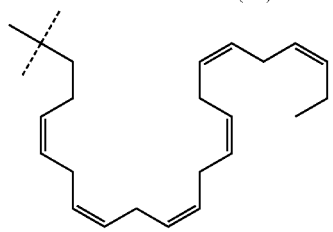

Rf-COOH = Ac. Docosaesaenoico (28f)

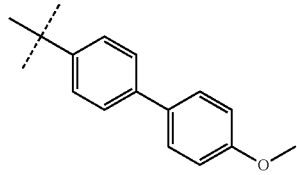

Rg-COOH = Ac. -4″-Metossibifenil-4-Carbossilico (28g)

["Ac. Palmitico"=Palmitic acid;
"Ac. Docosanoico"=Docosanoic acid;
"DMF anidra"=Anhydrous DMF;
"t.a."=r.t.;
"Ac. Oleico"=Oleic acid;
"Ac. Linoleico"=Linoleic acid;
"Ac. Arachidonico"=Arachidonic acid;
"Ac. Docosaesaenoico"=Docosahexaenoic acid;
"Ac. 4″-Metossibifenil-4-Carbossilico"=4″-Methoxybiphenyl-4-carboxylic acid]

Compounds according to the invention with different, unique and new acyl residues (compounds 29b, 29c, 29d, 29f) were therefore synthesized in addition to those containing PEA (29a) and anandamide (29e), so as to also obtain information about the importance of the type of fatty acid present in the molecule. A molecule (29g) was also made in which the acyl substituent was no longer a long chain fatty acid but a diphenyl derivative, in order to obtain information and assessment about the effects and the biological activity associated with the transition from a linear polyunsaturated system to an aromatic one.

Furthermore, the compounds according to the invention include quercetin-NAE hybrid structures, such as heterotrimeric molecules of the Q2E type, i.e. containing two quercetin units (Q) and one endocannabinoid or NAE unit (E). For this purpose, the endocannabinoid arachidonoyl dopamine (FIG. 3), in which the two dopamine phenolic groups allow attachment of two quercetin units, was taken as a model. The molecule 36, in which arachidonic acid (present in the reference template, i.e. the endocannabinoid arachidonoyl dopamine) is replaced by palmitic acid and each Q2E quercetin is bridged to a different dopamine hydroxyl group (scheme below), was prepared as the first representative of this class of compounds.

In short, the dopamine 30 was reacted with EDC/HOBt-activated palmitic acid to yield the amide 31, which in turn was converted into the diester 33 by reaction with

["DMF anidra"=Anhydrous DMF;
"t.a."=r.t.]

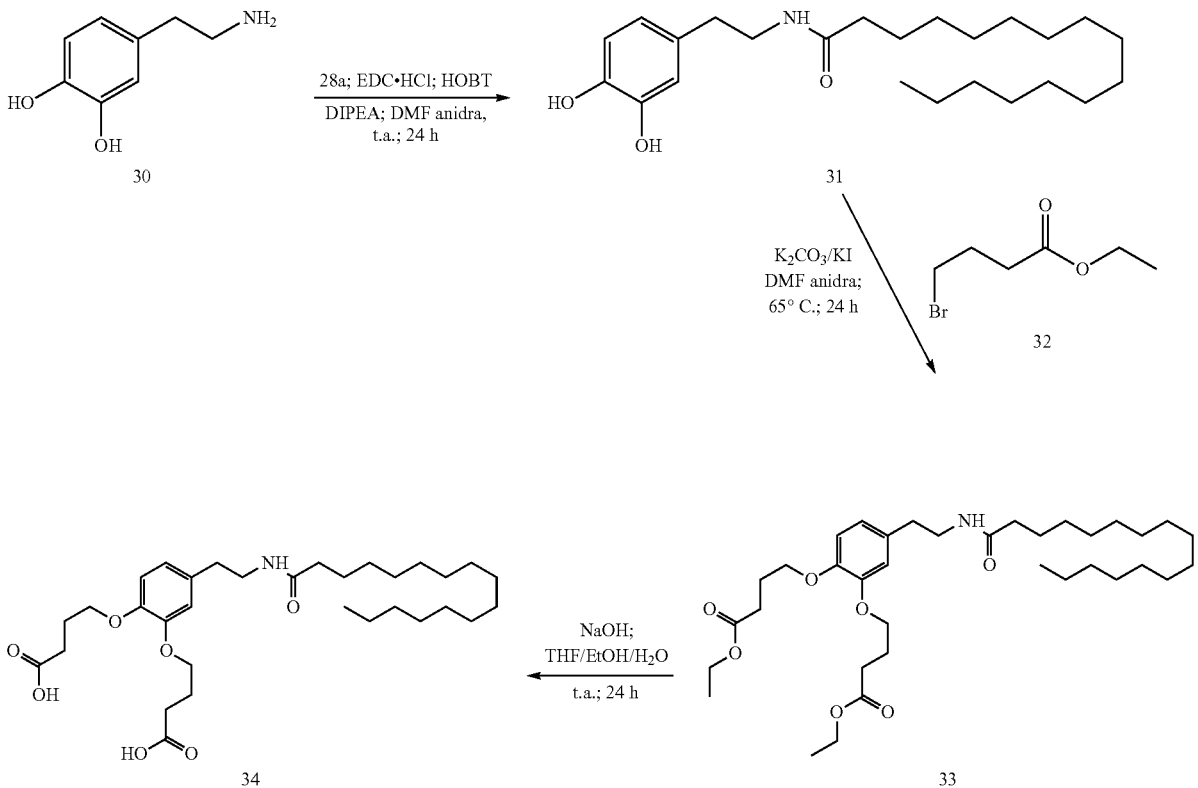

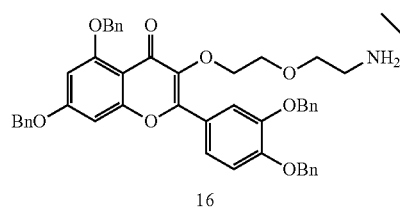

-continued

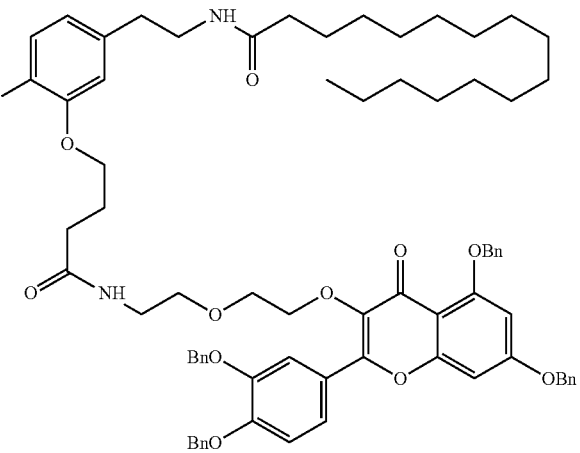

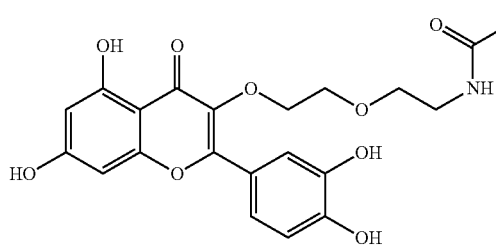

the bromide 32. The basic hydrolysis of the diester afforded the diacid 34, which, upon activation with EDC and HOBt, was reacted with an excess of quercetin tetrabenzylate 16 to obtain the compound 35, which by hydrogenation in the presence of Pd/C was completely debenzylated to yield the target molecule 36. A molecule was thus obtained, in which an artificial analogue of the endocannabinoid arachidonoyl dopamine, i.e. palmitoyl dopamine, is linked to two quercetin units, thereby forming a heterotrimer of the Q2E type.

Examples of synthesis of the various components are set out below. All chemical reagents used were of analytical grade and were used as received. $^1$H and $^{13}$C-NMR experiments were recorded in deuterated solvents indicated in a Bruker Avance 400™ spectrometer at 400.13 and 100.62 MHz, respectively. Coupling constants are reported in Hertz and rounded off to the nearest 0.1 Hz. Where required, chromatographic purifications were performed on silica gel by flash chromatography (70-230 mesh) using the eluants specified.

Where specified, reactions were carried out using a CEM Discover microwave reactor.

Example of synthesis of 5,7-bis(benzyloxy)-2-(3,4-bis(benzyloxy)phenyl)-3-hydroxy-4H-chromen-4-one: 7

Anhydrous $K_2CO_3$ (1.81 g; 13.1 mmol) and benzyl bromide (2.24 g; 13.1 mmol) were added sequentially to a solution of 2-(3,4-dihydroxyphenyl)-4,5-dihydroxy-3-[3,4,5-trihydroxy-6-[(3,4,5-trihydroxy-6-methyl-oxan-2-yl)oxymethyl]oxan-2-yl]oxy-chromen-7-one 6 (1 g; 1.6 mmol)

in DMF (12 ml). The reaction mixture is allowed to stir under argon atmosphere at room temperature. Upon completion (about 24 hours), the reaction mixture was diluted with EtOAc (40 ml) and washed with H₂O (2×30 ml). The organic phase was dried with anhydrous Na₂SO₄, filtered, and the solvent was removed under reduced pressure. The residue is added with a mixture of HCl (37%)/MeOH=2/98 v/v, and heated to reflux (T° '² 65° C.) for 2 hours.

Upon completion, the mixture is allowed to cool to room temperature, then filtered through a Buchner funnel, and finally the orange solid is washed with cold methanol.

The final product 7 thus obtained does not require a further final purification (450 mg; 42.45%).

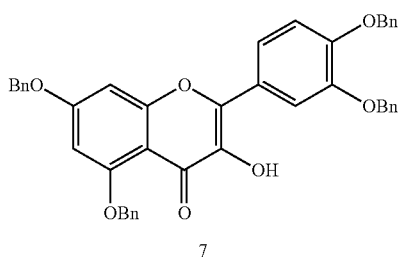 [SMILES: O=c1c(O)c(-c2ccc(OCc3ccccc3)c(OCc3ccccc3)c2)oc2cc(OCc3ccccc3)cc(OCc3ccccc3)c12]

7

¹H NMR (400 MHz, CDCl₃): 7.88 (s, 1H), 7.75 (d, 1H, J=6.5 Hz), 7.65-7.25 (m, 21H, Ph), 7.01 (d, 2H), 6.56 (s, 1H, J=8.7 Hz), 6.45 (s, 1H), 5.26 (s, 2H, CH₂Ph), 5.23 (s, 2H, CH₂Ph), 5.21 (s, 2H, CH₂Ph), 5.11 (s, 2H, CH₂Ph);

¹³C NMR (100 MHz, CDCl₃): 171.70, 163.19, 159.33, 158.63, 150.14, 148.58, 141.83, 137.68, 137.13, 136.82, 136.15, 135.59, 128.74, 128.62, 128.53, 128.45, 127.89, 127.85, 127.77, 127.62, 127.53, 127.18, 126.63, 124.26, 121.20, 114.17, 106.68, 97.52, 93.66, 71.52, 70.93, 70.67, 70.53.

Example of synthesis of 5,7-bis(benzyloxy)-2-(3,4-bis(benzyloxy)phenyl)-3-ethoxy-4H-chromon-4-one: 8a Ethyl iodide (0.072 ml; 0.0009 mol) and anhydrous K2CO3 (0.104 g; 0.0007 mol) were added sequentially to a solution of 5,7-bis(benzyloxy)-2-(3,4-bis(benzyloxy)phenyl)-3-hydroxy-4H-chromen-4-one 7 (0.2 g; 0.0003 mol) in anhydrous DMF (2.14 ml). The reaction mixture is stirred at a temperature of 65° C. for 12 hours. Upon completion, the reaction was partitioned between water (10 ml) and EtOAc/DCM (1/1; 30 ml). The organic phase was washed with a saturated aqueous solution of NaCl and the aqueous phase extracted with 10 ml of EtOAc/DCM (1/1). The combined organic phases were dried over anhydrous sodium sulphate, the solvent was removed under reduced pressure, and the residue as a yellow solid (290 mg) was purified by flash column chromatography (SiO2; EtOAc/n-hexane 25%). The product 8a was isolated as a white solid (120 mg, 60%).

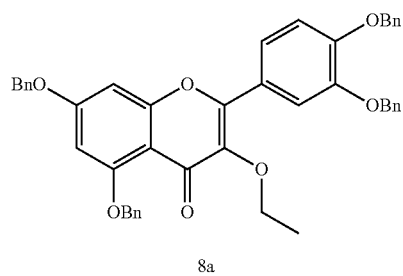 [SMILES: CCOc1c(-c2ccc(OCc3ccccc3)c(OCc3ccccc3)c2)oc2cc(OCc3ccccc3)cc(OCc3ccccc3)c2c1=O]

8a

¹H NMR (400 MHz, CDCl₃): 7.83 (d, 2H), 7.68 (dd, 1H), 7.61 (d, 2H), 7.54-7.27 (m; 19H), 7.02 (d, 1H), 6.53 (d, 1H), 6.45 (d, 1H), 5.24 (d, 6H), 5.09 (s, 1H), 4.06 (q, 2H), 1.26 (t, 3H);

¹³C NMR (100 MHz, CDCl₃): 173.95, 162.66, 159.77, 158.65, 152.70, 150.65, 148.27, 140.23, 137.05, 136.77, 136.40, 135.71, 128.74, 128.57, 128.53, 128.41, 127.95, 127.87, 127.61, 127.58, 127.31, 127.19, 126.66, 124.15, 122.20, 115.26, 113.81, 98.01, 93.86, 71.43, 70.93, 70.79, 70.45, 68.15, 15.60.

Example of synthesis of 5,7-bis(benzyloxy)-2-(3,4-bis(benzyloxy)phenyl)-3-hexyloxy-4H-chromon-4-one: 8b Hexyl bromide (0.084 ml; 0.0006 mol), anhydrous K₂CO₃ (0.104 g; 0.0007 mol) and KI (0.015 g; 0.00009 mol) were added sequentially to a solution of 5,7-bis(benzyloxy)-2-(3,4-bis(benzyloxy)phenyl)-3-hydroxy-4H-chromen-4-one 7 (0.2 g; 0.0003 mol) in anhydrous DMF (2.14 ml). The reaction mixture is stirred at a temperature of 65° C. for 12 hours. Upon completion, the mixture was partitioned between water (10 ml) and EtOAc/DCM (1/1; 30 ml). The organic phase was washed with a saturated aqueous solution of NaCl and the aqueous phase extracted with 10 ml of EtOAc/DCM (1/1).

The combined organic phases were dried over anhydrous Na₂SO₄ and the solvent was removed under reduced pressure. The residue obtained as a yellow oil (173 mg) was purified by cold precipitation from a solution of EtOAc/hexane. The white solid product corresponding to 8b was separated from the liquid by centrifugation and the traces of solvent were removed under reduced pressure.

The white solid 8b (67.5 mg; 30%).

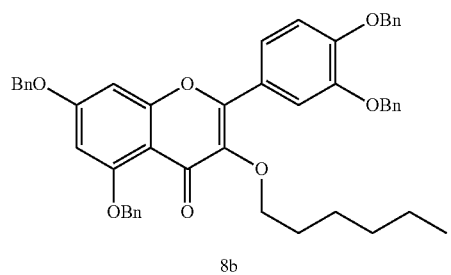 [SMILES: CCCCCCOc1c(-c2ccc(OCc3ccccc3)c(OCc3ccccc3)c2)oc2cc(OCc3ccccc3)cc(OCc3ccccc3)c2c1=O]

8b

¹H NMR (400 MHz, CDCl₃): 7.82 (d, 2H, J=1.8 Hz), 7.68 (dd, 1H, J₁=8.6 Hz; J₂=1.8, Hz), 7.62 (d, 2H, J=7.6 Hz, CH₂Ph), 7.55-7.27 (m, 18H, CH₂Ph), 7.02 (d, 1H, J=8.6 Hz), 6.53 (d, 1H, J=2.0 Hz), 6.45 (d, 1H, J=2.0 Hz), 4.02 (t, 2H, J=7.1 Hz), 1.56-1.53 (m, 2H), 1.40-1.20 (m, 6H), 0.87 (t, 3H, J=7.1 Hz).

¹³C NMR (100 MHz, CDCl₃): 173.82, 162.56, 159.68, 152.53, 150.60, 148.24, 140.43, 136.73, 136.40, 128.66, 128.45, 127.87, 127.80, 127.53, 127.28, 127.12, 126.59, 124.07, 122.28, 115.23, 113.72, 110.01, 97.96, 93.79, 72.67, 71.40, 70.85, 70.68, 70.37, 31.59, 30.08, 25.52, 22.54, 13.98.

Example of synthesis of 5,7-bis(benzyloxy)-2-(3,4-bis(benzyloxy)phenyl)-3-hexadecyloxy-4H-chromon-4-one: 8c Hexyl decyl bromide (0.2 g; 0.0007 mol), anhydrous K₂CO₃ (0.121 g; 0.0009 mol) and KI (0.017 g; 0.0001 mol) were added sequentially to a solution of 5,7-bis(benzyloxy)-2-(3,4-bis(benzyloxy)phenyl)-3-hydroxy-4H-chromen-4-one 7 (0.2 g; 0.0003 mol) in anhydrous DMF (3 ml). The reaction mixture is stirred at a temperature of 65° C. for 2 hours. Upon completion, the reaction mixture was partitioned between H₂O (10 ml) and EtOAc/DCM (1/1; 30 ml). The organic phase was washed with a saturated aqueous solution of NaCl and the aqueous phase extracted with 10 ml EtOAc/DCM (1/1). The combined organic phases were dried over anhydrous Na₂SO₄, filtered, and the solvent was removed under reduced pressure. The obtained residue (490 mg) was purified by flash column chromatography (SiO₂; EtOAc/n-hexane 15%) and the desired product 8c was isolated as a white solid (250 mg, 73.5%).

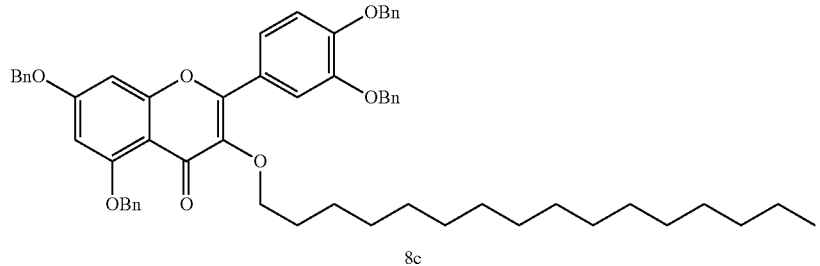 [SMILES: CCCCCCCCCCCCCCCCOc1c(-c2ccc(OCc3ccccc3)c(OCc3ccccc3)c2)oc2cc(OCc3ccccc3)cc(OCc3ccccc3)c2c1=O]

8c

¹H NMR (400 MHz, CDCl₃): 7.79 (d, 1H, J=1.8 Hz), 7.66 (dd, 1H, J₁=8.6 Hz, J₂=1.8 Hz), 7.59 (d, 2H, J=7.4 Hz, CH₂Ph), 7.53-7.28 (m, 18H, CH₂Ph), 7.01 (d, 1H, J=8.6 Hz), 6.52 (d, 1H, J=1.8 Hz), 6.44 (d, 1H, J=1.8 Hz), 5.254 (s, 3H, CH₂Ph), 5.248 (s, 3H, CH₂Ph), 5.23 (s, 3H, CH₂Ph), 5.09 (s, 3H, CH₂Ph), 3.98 (t, 2H, J=7.1 Hz), 1.67 (t, 2H), 1.30-1.19 (m, 29H), 0.38 (q, 3H);

¹³C NMR (100 MHz, CDCl₃): 173.76, 162.54, 159.65, 158.52, 152.44, 150.60, 148.25, 137.00, 136.71, 136.40, 135.70, 128.61, 128.45, 128.40, 128.26, 127.83, 127.48, 127.26, 127.10, 126.57, 122.23, 115.22, 113.71, 109.99, 97.91, 93.79, 72.65, 71.37, 70.84, 70.65, 70.32, 31.82, 30.13, 29.61, 29.55, 29.42, 29.26, 25.87, 22.59, 14.02.

Example of Synthesis of Compound 11a

Ethyl 4-bromobutyrate (218 μl; 1.508 mmol), anhydrous K2CO3 (250 mg; 1.810 mmol) and KI (36 mg; 0.226 mmol) were added sequentially to a solution of 5,7-bis(benzyloxy)-2-(3,4-bis(benzyloxy)phenyl)-3-hydroxy-4H-chromen-4-one 7 (0.5 g; 0.754 mmol) in anhydrous DMF (4 ml). The reaction mixture is stirred at a temperature of 65° C. for 12 hours. Upon completion, the reaction was partitioned between H₂O (20 ml) and EtOAc (20 ml). The organic phase was washed with a saturated aqueous solution of NaCl and the aqueous phase extracted with 10 ml EtOAc. The combined organic phases were dried over anhydrous sodium sulphate, the solvent was removed under reduced pressure, and the residue as a light yellow solid was purified by flash column chromatography (SiO2; EtOAc/n-hexane 25%). The product 11a was isolated as a white oil (440 mg, 75%).

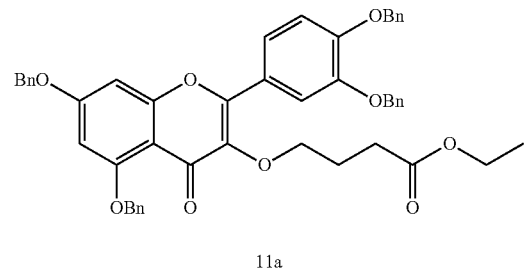 [SMILES: CCOC(=O)CCCOc1c(-c2ccc(OCc3ccccc3)c(OCc3ccccc3)c2)oc2cc(OCc3ccccc3)cc(OCc3ccccc3)c2c1=O]

11a

¹H NMR (400 MHz, DMSO-d6): 7.76 (s, 1H), 7.66 (d, 1H, J=8.0 Hz), 7.61 (d, 2H, J=7.9 Hz), 7.49 (m, 6H), 7.38 (m, 12H), 7.36 (d, 1H, J=4.8 Hz), 6.91 (d, 1H, J=2.0 Hz), 6.69 (d, 1H, J=2.0 Hz), 5.23 (m, 8H), 4.01 (q, 2H, J=6.8 Hz), 3.91 (t, 2H, J=6.4 Hz), 2.38 (t, 2H, J=7.2 Hz), 1.85 (t, 2H, J=6.8 Hz), 1.12 (t, 3H, J=7.2 Hz).

¹³C NMR (100 MHz, DMSO-d6): 173.4, 173.1, 163.5, 160.0, 159.0, 152.8, 151.2, 148.7, 140.4, 138.0, 137.8, 137.7, 137.0, 129.5, 129.4, 129.1, 129.0, 128.9, 128.5, 128.4, 127.9, 124.0, 122.9, 115.1, 114.7, 109.9, 98.7, 95.1, 71.6, 71.4, 71.0, 70.9, 30.9, 25.9, 15.0.

Example of Synthesis of Compound 11b

2-[2-(Boc-amino)ethoxy]ethyl bromide (404 mg; 1.508 mmol), anhydrous K2CO3 (250 mg; 1.810 mmol) and KI (36 mg; 0.226 mmol) were added sequentially to a solution of 5,7-bis(benzyloxy)-2-(3,4-bis(benzyloxy)phenyl)-3-hydroxy-4H-chromen-4-one 7 (500 mg; 0.754 mmol) in anhydrous DMF (4 ml). The reaction mixture is stirred at a temperature of 65° C. for 12 hours. Upon completion, the mixture was partitioned between H2O (10 ml) and EtOAc (20 ml). The organic phase was washed with a saturated aqueous solution of NaCl and the aqueous phase extracted with EtOAc (20 ml). The combined organic phases were dried over anhydrous Na₂SO₄ and the solvent was removed under reduced pressure. The residue obtained as a yellow oil was purified by flash column chromatography (SiO₂; EtOAc/n-hexane 25%). The product 11 b was isolated as a white oil (460 mg, 72%).

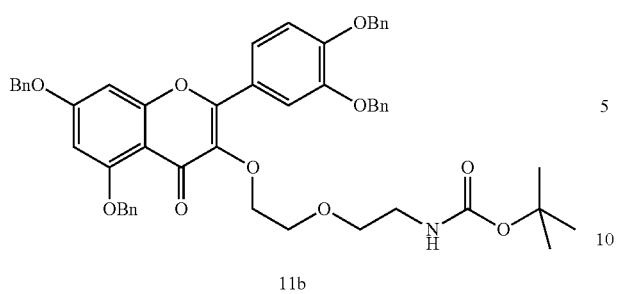

11b

1H NMR (400 MHz, DMSO-d6): 7.83 (bs, 1H), 7.63 (d, 1H, J=4.0 Hz), 7.46-7.18 (m, 21H), 6.95 (d, 1H, J=2.0 Hz), 6.76 (bt, 1H, J=8.0 Hz), 6.70 (d, 1H, J=2.0 Hz), 5.25 (m, 8H), 4.12 (m, 2H), 3.60 (m, 2H), 3.32 (m, 2H), 3.03 (m, 2H), 1.35 (s, 9H).

13C NMR (100 MHz, DMSO-d6): 173.2, 163.6, 159.0, 156.5, 152.5, 151.2, 148.6, 140.3, 138.1, 137.8, 137.7, 137.0, 129.5, 129.4, 129.3, 129.2, 129.0, 128.9, 128.8, 128.6, 128.5, 127.8, 123.9, 123.3, 115.1, 114.6, 109.8, 98.7, 95.1, 78.6, 71.6, 71.4, 71.0, 70.9, 70.3, 70.0, 29.1.

Example of Synthesis of Compound 11c

2-[2-(Benzyloxy)ethoxy]ethyl bromide (390 mg; 1.508 mmol), anhydrous K2CO3 (250 mg; 1.810 mmol) and KI (36 mg; 0.226 mmol) were added sequentially to a solution of 5,7-bis(benzyloxy)-2-(3,4-bis(benzyloxy)phenyl)-3-hydroxy-4H-chromen-4-one 7 (0.5 g; 0.754 mmol) in anhydrous DCM (4 ml). The reaction mixture is stirred at a temperature of 65° C. for 12 hours. Upon completion, the reaction was partitioned between H₂O (20 ml) and EtOAc (20 ml). The organic phase was washed with a saturated aqueous solution of NaCl and the aqueous phase extracted with EtOAc (10 ml). The combined organic phases were dried over anhydrous Na₂SO₄, the solvent was removed under reduced pressure, and the residue as a light yellow solid was purified by flash column chromatography (SiO₂; EtOAc/n-hexane 25%). The product 11a was isolated as a white oil (539 mg, 85%).

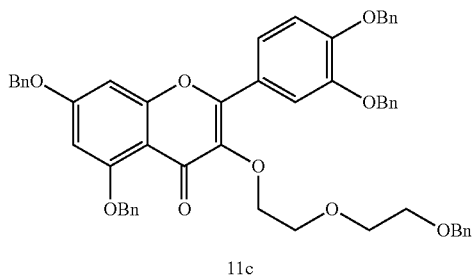 [SMILES: O=c1c(OCCOCCOCc2ccccc2)c(-c2ccc(OCc3ccccc3)c(OCc3ccccc3)c2)oc2cc(OCc3ccccc3)cc(OCc3ccccc3)c12]

11c

¹H NMR (400 MHz, DMSO-d6): 7.63 (d, 1H, J=7.6 Hz), 7.50 (d, 4H, J=7.6 Hz), 7.47-7.28 (m, 22H), 7.20 (d, 1H, J=8.4 Hz), 6.93 (d, 1H, J=1.2 Hz), 6.72 (d, 1H, J=1.2 Hz), 5.25 (m, 6H), 5.04 (m, 2H), 4.95 (m, 2H).

¹³C NMR (100 MHz, DMSO-d6): 172.9, 163.2, 159.6, 158.6, 158.4, 152.6, 150.5, 148.0, 139.6, 137.5, 136.7, 128.8, 128.5, 128.4, 128.3, 128.2, 128.1, 128.0, 127.9, 127.3, 123.3, 122.2, 114.6, 114.1, 109.3, 98.3, 94.6, 73.3, 70.6, 70.4, 70.3, 70.2.

Example of Synthesis of Compound 12

An aqueous solution of 2N NaOH (2 ml) was added to a solution of 11a (440 mg; 0.567 mmol) in ethanol (6 ml). The reaction mixture is stirred at room temperature for 12 hours. Upon completion, the reaction mixture was added with an aqueous solution of 2N HCl (~2.5 ml) to pH ~3 and then extracted with DCM (3×10 ml). The combined organic phases were dried over anhydrous Na2SO4, the solvent was removed under reduced pressure, and the residue as a white solid was used in the subsequent reaction without further chromatographic purification, 12 (quantitative).

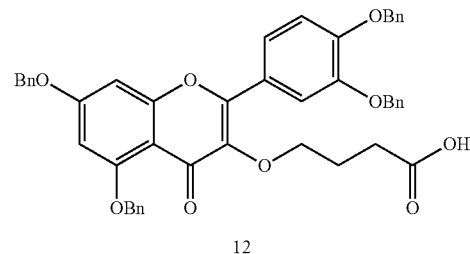 [SMILES: O=C(O)CCCOc1c(-c2ccc(OCc3ccccc3)c(OCc3ccccc3)c2)oc2cc(OCc3ccccc3)cc(OCc3ccccc3)c2c1=O]

12

Example of Synthesis of Compound 16

An aqueous solution of 4N HCl (4 ml) was added to a solution of 11a (460 mg; 0.541 mmol) in THF (6 ml). The reaction mixture is stirred at 50° C. for 6 hours. Upon completion, the reaction mixture was brought to dryness under reduced pressure, and the residue as a white solid was used in the subsequent reaction without further chromatographic purification, 16 (quantitative).

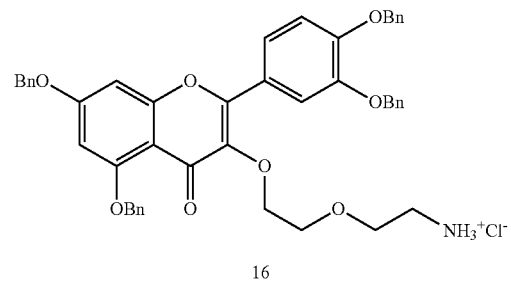

16

¹H NMR (400 MHz, CD₃OD): 7.66-7.30 (m, 22H), 7.05 (d, 1H, J=8.4 Hz), 6.57 (d, 1H, J=2.0 Hz), 6.51 (d, 1H, J=2.0 Hz), 5.27 (s, 2H), 5.25 (s, 2H), 5.17 (s, 2H), 5.12 (2H), 3.83-3.74 (m, 2H, 3.72-3.64 (m, 2H), 3.60-3.53 (m, 2H), 3.22-3.12 (m, 2H).

Example of a General Procedure for the Synthesis of the Products 14

HOBt (32 mg, 0.24 mmol), EDC*HCl (46 mg; 0.24 mmol) and DIPEA (140 µl; 0.8 mmol) were added sequentially to a solution of 12 (158 mg; 0.2 mmol) in anhydrous DCM (6 ml). The reaction mixture is stirred at room temperature for 15-30 min. and then added to a solution of the selected diamine 13 (0.08 mmol) in anhydrous DCM (6 ml) and a catalytic amount of DMAP (~1 mg, 0.008 mmol). The reaction mixture is stirred at room temperature for 12 hours. Upon completion, the reaction mixture was diluted with DCM (10 ml) and washed sequentially with a saturated aqueous solution of NH₄Cl (3×10 ml), a saturated aqueous solution of NaHCO₃(3×10 ml), and finally a saturated aqueous solution of NaCl (1×10 ml). The combined organic phases were dried over anhydrous Na2SO4, and the solvent was removed under reduced pressure. The residue was purified by flash column chromatography.

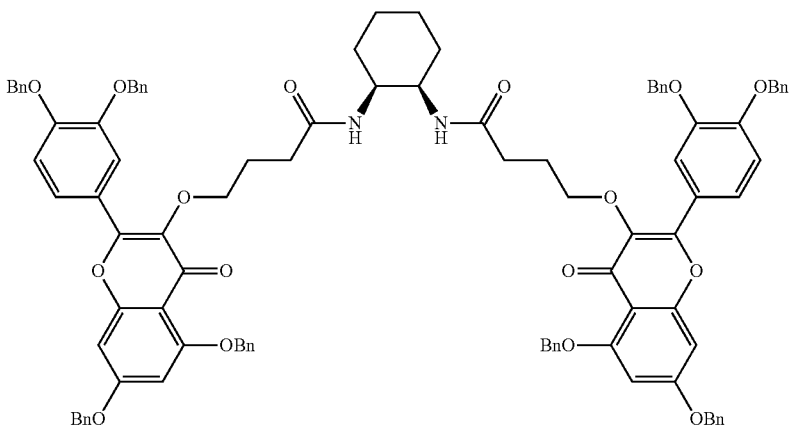

14a

Compound 14a was isolated as a white oil (274 mg, 87.5%).

$^1$H NMR (400 MHz, CDCl$_3$): 7.79 (bd, 2H, J=7.6 Hz), 7.65 (d, 2H, J=2.0 Hz), 7.58-7.50 (m, 6H), 7.47-7.25 (m, 36H), 6.83 (d, 2H, J=8.8 Hz), 6.31 (dd, 4H, J$_1$=7.1 Hz, J$_2$=2.1 Hz), 5.29 (s, 4H), 5.14 (s, 4H), 5.05 (s, 4H), 4.87 (d, 2H, J=11.3 Hz), 4.77 (d, 2H, J=11.3 Hz), 4.23 (m, 2H), 3.95 (m, 2H), 3.85 (m, 2H), 2.53 (m, 4H), 2.02 (m, 4H), 1.94 (m, 2H), 1.58 (m, 2H), 1.36 (m, 4H).

$^{13}$C NMR (100 MHz, CDCl$_3$): 173.7, 172.7, 162.6, 159.5, 158.4, 152.5, 150.9, 148.3, 139.9, 137.0, 136.6, 136.4, 135.5, 128.6, 128.5, 128.2, 127.9, 127.8, 127.7, 127.3, 127.2, 127.1, 126.5, 123.5, 122.2, 114.8, 113.4, 109.6, 97.9, 93.5, 71.5, 70.6, 70.5, 70.1, 49.0, 33.1, 28.4, 27.0.

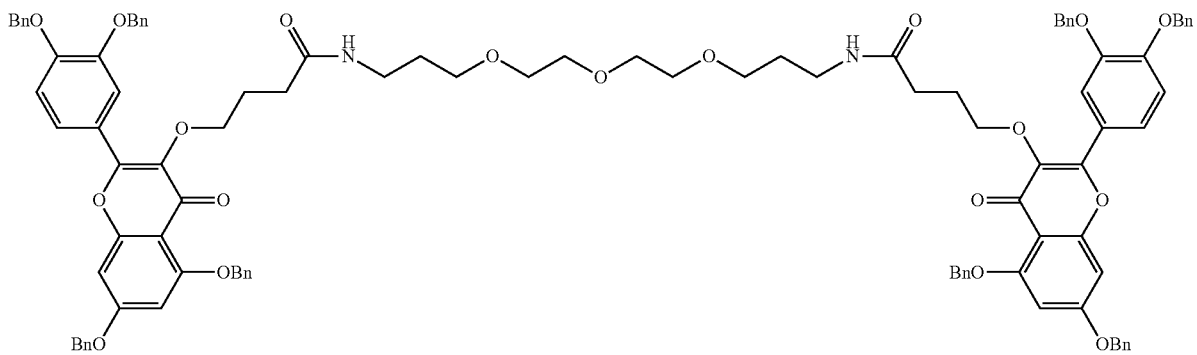

14b

Compound 14b was isolated as a white oil (312 mg, 93%).

$^1$H NMR (400 MHz, CDCl$_3$): 7.75 (d, 2H, J=2.0 Hz), 7.68 (dd, 2H, J$_1$=10.4 Hz, J$_2$=2.0 Hz), 7.59 (d, 4H, J=8.0 Hz), 7.48 (t, 8H, J=6.4 Hz), 7.45-7.30 (m, 28H), 7.16 (bt, 2H, J=5.6 Hz), 7.03 (d, 2H, J=8.0 Hz), 6.52 (d, 2H, J=2.0 Hz), 6.54 (d, 2H, J=2.0 Hz), 5.19 (s, 8H), 5.15 (s, 4H), 5.03 (s, 4H), 3.88 (t, 4H, J=5.6 Hz), 3.53 (m, 4H), 3.47 (m, 4H), 3.41 (t, 4H, J=6.4 Hz), 3.27 (q, 4H, J=12.4, 6.4 Hz), 2.46 (t, 4H, J=6.8 Hz), 1.97 (m, 4H), 1.73 (m, 4H).

$^{13}$C NMR (100 MHz, CDCl$_3$): 173.9, 173.0, 162.8, 159.7, 158.6, 153.6, 150.9, 148.4, 140.0, 137.0, 136.6, 136.3, 135.6, 128.7, 128.5, 128.4, 128.0, 127.9, 127.7, 127.5, 127.3, 127.2, 126.7, 123.6, 122.4, 115.1, 113.8, 109.8, 97.9, 93.8, 71.6, 70.8, 70.7, 70.4, 70.0, 69.3, 37.1, 33.1, 29.3, 26.7.

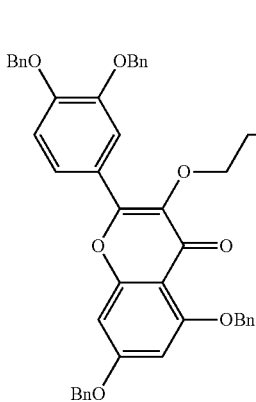 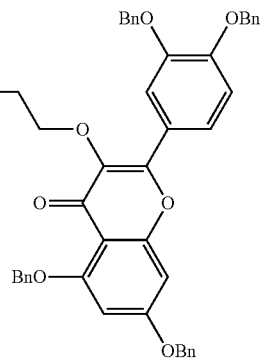

14c

Compound 14c was isolated as a white oil (298 mg, 93.2%).

$^1$H NMR (400 MHz, CDCl$_3$): 7.72 (d, 2H, J=2.0 Hz), 7.63 (dd, 2H, J$_1$=$_2$ 8.4 Hz, J$_2$=2.0 Hz), 7.55-7-20 (m, 44H), 7.01 (d, 2H, J=8.8 Hz), 6.56 (d, 2H, J=2.4 Hz), 6.45 (d, 2H, J=2.0 Hz), 5.23 (s, 4H) 5.22 (s, 4H), 5.14 (s, 4H), 5.12 (s, 4H), 4.22 (d, 4H, J=5.6 Hz), 3.82 (t, 4H, J=5.2 Hz), 2.52 (t, 4H, J=6.4 Hz), 1.96 (m, 4H).

$^{13}$C NMR (100 MHz, CDCl$_3$): 173.9, 173.1, 162.9, 159.7, 158.6, 153.1, 150.9, 148.3, 139.9, 137.5, 137.0, 136.6, 136.2, 135.6, 128.7, 128.6, 128.5, 128.4, 128.0, 127.9, 127.7, 127.6, 127.3, 127.2, 126.6, 123.6, 122.3, 115.1, 113.8, 109.8, 98.0, 93.8, 71.5, 70.8, 70.6, 70.5, 43.0, 33.4, 26.7.

127.6, 127.3, 127.2, 126.6, 123.6, 122.3, 115.2, 113.8, 109.8, 98.0, 93.9, 71.6, 70.9, 70.7, 70.5, 45.6, 37.6, 33.3, 30.0, 26.8.

Example of a General Procedure for the Synthesis of the Products 18, 21, and 24

HOBt (38 mg, 0.28 mmol), EDC*HCl (54 mg; 0.28 mmol) and DIPEA (175 μl, 1.0 mmol) were added sequentially to a solution of the appropriate dicarboxylic linker 17 (0.10 mmol) or tricarboxylic linker 20 (0.062 mmol) or tetracarboxylic linker 23 (0.050 mmol) in anhydrous DCM (6 ml). The reaction mixture is stirred at room temperature for 15-30 min. and then added to a solution of 16 (196 mg;

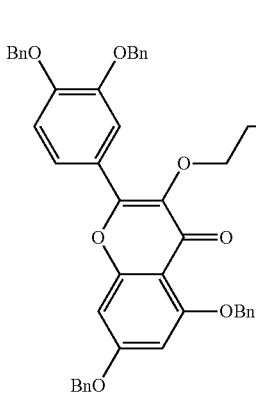 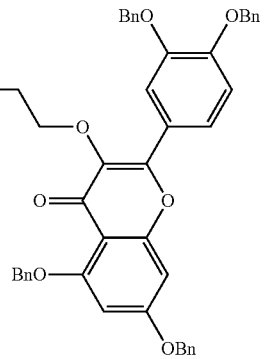

14d

Compound 14d was isolated as a white oil (294 mg, 91.6%).

$^1$H NMR (400 MHz, CDCl$_3$): 7.75 (bs, 2H), 7.67 (dd, 2H, J$_1$=8.8 Hz, J$_2$=1.6 Hz), 7.58 (d, 4H, J=7.6 Hz), 7.55-7.25 (m, 38H), 7.04 (d, 2H, J=8.4 Hz), 6.91 (bs, 2H), 6.54 (d, 2H, J=1.8 Hz), 6.47 (d, 2H, J=1.6 Hz), 5.26 (s, 4H), 5.25 (s, 4H), 5.21 (s, 4H), 5.11 (s, 4H), 3.82 (t, 4H, J=5.2 Hz), 2.93 (t, 4H, J=6.0 Hz), 1.96 (m, 4H), 1.51 (m, 4H), 1.23 (bs, 2H), 0.65 (m, 4H).

$^{13}$C NMR (100 MHz, CDCl$_3$): 174.2, 173.9, 162.9, 159.7, 158.7, 153.2, 151.0, 140.0, 136.9, 136.6, 136.3, 135.6, 128.7, 128.6, 128.5, 128.4, 128.0, 127.7, 127.9, 127.7, 0.25 mmol) in anhydrous DCM (6 ml) and a catalytic amount of DMAP (~1 mg, 0.008 mmol). The reaction mixture is stirred at room temperature for 12 hours. Upon completion, the reaction mixture was diluted with DCM (10 ml) and washed sequentially with a saturated aqueous solution of NH$_4$Cl (3×10 ml), a saturated aqueous solution of NaHCO$_3$ (3×10 ml), and finally a saturated aqueous solution of NaCl (1×10 ml). The combined organic phases were dried over anhydrous Na2SO4, and the solvent was removed under reduced pressure.

The residue was purified by flash column chromatography.

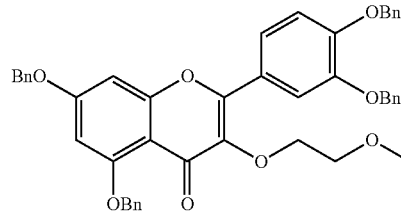
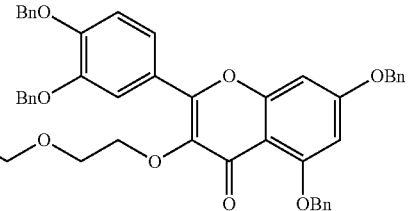
18a
Compound 18a was isolated as a white oil (298 mg, 93.4%).
¹H NMR (400 MHz, DMSO-d6): 7.83 (bs, 4H), 7.62 (d, 2H, J=7.6 Hz), 7.55-7.20 (m, 40H), 6.94 (s, 2H), 6.71 (s, 2H), 5.25 (bs, 16H), 4.13 (bs, 4H), 3.60 (bs, 4H), 3.44 (m, 4H), 3.14 (d, 4H, J=5.2 Hz), 2.17 (t, 4H, J=7.6 Hz), 2.07 (m, 4H), 1.68 (t, 2H, J=7.6 Hz).
¹³C NMR (100 MHz, DMSO-d6): 175.2, 173.2, 172.7, 163.6, 160.0, 159.0, 152.5, 151.2, 148.6, 140.3, 138.1, 137.8, 137.7, 137.0, 129.5, 129.4, 129.3, 129.2, 129.0, 128.9, 128.6, 128.5, 127.9, 123.9, 123.3, 115.1, 114.6, 109.8, 98.0, 95.1, 71.6, 71.4, 71.0, 70.9, 70.4, 70.0, 35.3, 19.5.
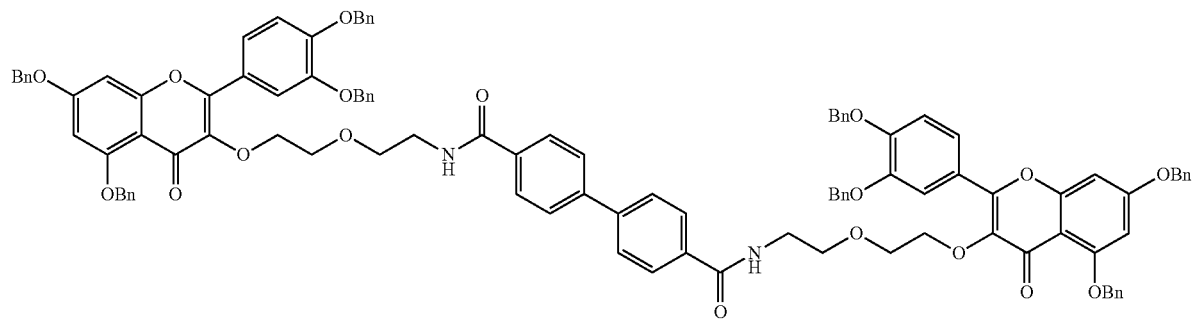
18b
Compound 18b was isolated as a white oil (264 mg, 77.4%).
¹H NMR (400 MHz, DMSO-d6): 8.54 (bt, 2H, J=5.4 Hz), 7.92 (d, 4H, J=8.4 Hz), 7.84 (m, 4H), 7.43 (d, 4H, J=8.4 Hz), 7.61 (d, 4H, J=7.2 Hz) 7.55-7.15 (m, 38H), 7.93 (d, 2H, J=1.6 Hz), 7.70 (d, 2H, J=2.0 Hz), 5.24 (s, 16H), 4.15 (bm, 4H), 3.67 (bm, 4H), 3.52 (bm, 4H), 3.42 (bm, 4H).
¹³C NMR (100 MHz, DMSO-d6): 173.4, 166.4, 163.8, 160.1, 157.9, 152.3, 151.2, 148.4, 142.2, 140.2, 138.3, 137.8, 137.7, 137.0, 134.5, 129.5, 129.4, 129.3, 129.0, 128.8, 128.6, 127.8, 127.4, 124.3, 123.5, 115.2, 114.8, 110.4, 98.9, 95.7, 71.5, 71.4, 71.2, 71.0, 70.9, 70.6, 70.0.
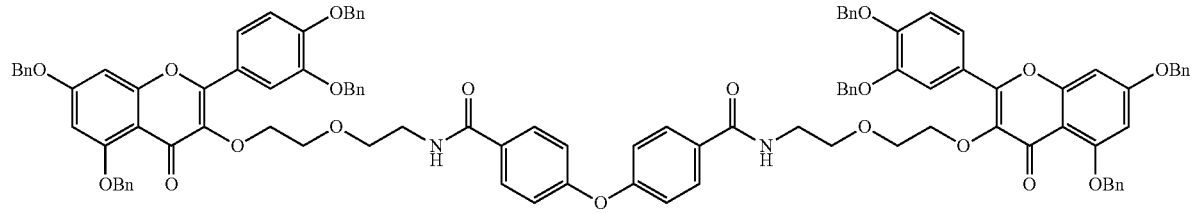
18c Compound 18c was isolated as a white oil (236 mg, 68.5%).
$^1$H NMR (400 MHz, CDCl$_3$): 7.84 (d, 2H, J=2.0 Hz), 7.76 (d, 4H, J=8.8 Hz), 7.69 (dd, 2H, J$_1$=8.4 Hz, J$_2$=1.6 Hz), 7.53 (d, 4H, J=7.6 Hz), 7.50-7.20 (m, 44H), 6.97 (d, 2H, J=8.8 Hz), 6.78 (d, 4H, J=8.8 Hz), 6.51 (d, 2H, J=2.0 Hz), 6.41 (d, 2H, J=2 Hz), 5.25 (s, 4H), 5.21 (s, 4H), 5.11 (s, 4H), 5.07 (s, 4H), 4.15 (bm, 4H), 3.72 (bm, 4H), 3.61 (bm, 8H).
$^{13}$C NMR (100 MHz, CDCl$_3$): 173.8, 166.7, 162.9, 159.6, 158.7, 158.6, 152.7, 151.0, 148.2, 140.0, 136.9, 136.5, 136.2, 135.6, 129.8, 129.3, 128.7, 128.6, 128.5, 128.4, 128.0, 127.9, 127.7, 127.6, 127.4, 127.2, 126.6, 123.6, 122.5, 118.3, 115.7, 113.6, 109.7, 98.0, 93.8, 71.7, 71.2, 70.8, 70.6, 70.5, 70.2, 69.5.
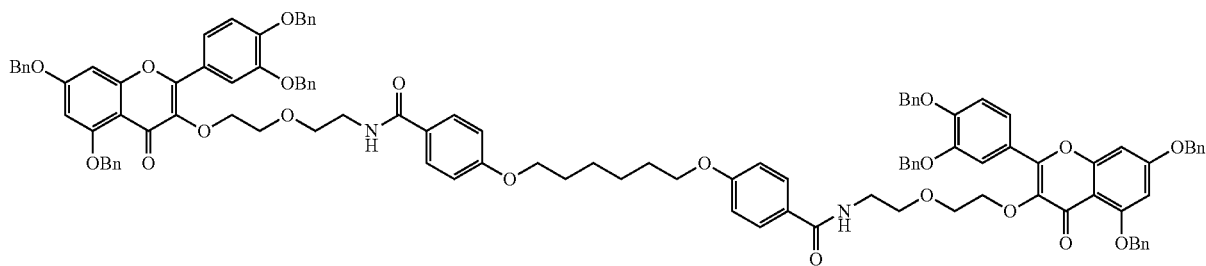
18d
Compound 18d was isolated as a white oil (242 mg, 66.4%).
$^1$H NMR (400 MHz, CDCl$_3$): 7.82 (d, 2H, J=1.6 Hz), 7.74 (d, 4H, J=3.2 Hz), 7.56 (d, 4H, J=7.2 Hz), 7.50-7.25 (m, 38H), 7.01 (bs, 2H), 6.98 (d, 2H, J=8.8 Hz), 6.75 (d, J=8.8 Hz), 6.53 (d, 2H, J=2.0 Hz), 6.44 (d, 2H, J=2.0 Hz), 5.23 (s, 4H), 5.18 (s, 8H), 5.08 (s, 4H), 0.4.18 (m, 2H), 3.85 (t, 4H, J=6.4 Hz), 3.71 (m, 4H), 3.58 (bm, 8H), 1.74 (bt, 4H), 1.46 (bt, 4H).
$^{13}$C NMR (100 MHz, CDCl$_3$): 173.7, 167.0, 162.8, 161.4, 159.7, 158.6, 152.7, 151.0, 148.2, 148.2, 140.0, 137.0, 136.6, 136.2, 135.6, 128.9, 128.7, 128.5, 128.4, 128.0, 127.9, 127.7, 127.6, 127.4, 1272, 126.6, 123.7, 122.6, 115.7, 113.9, 113.6, 109.9, 98.0, 93.8, 71.7, 71.2, 70.8, 70.7, 70.5, 70.3, 69.7, 67.8, 39.8, 37.0, 29.0, 25.8.
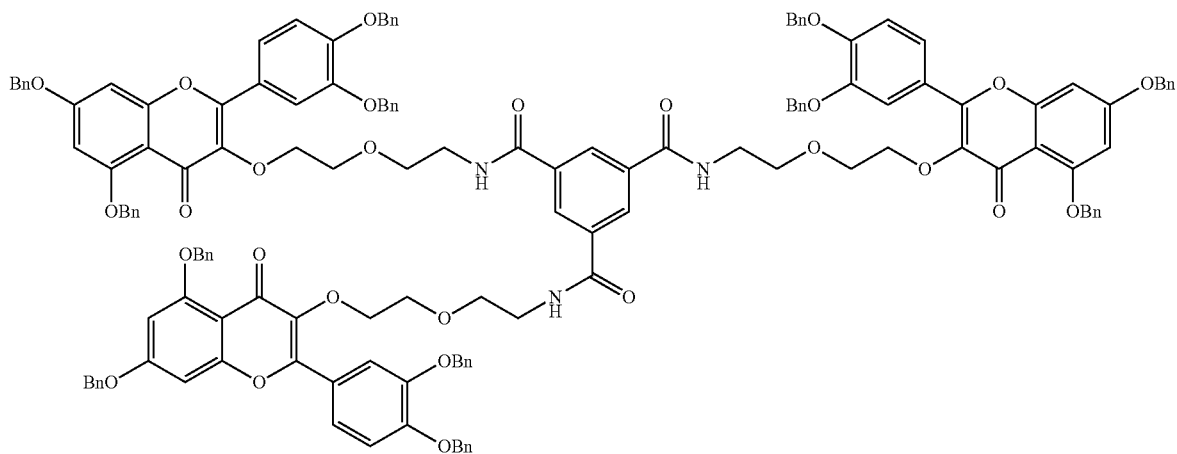
21a Compound 21a was isolated as a white oil (283 mg, 58.8%).
$^1$H NMR (400 MHz, CDCl$_3$-CD$_3$OD 80:20): 8.32 (s, 3H) 7.96 (bt, 3H, J=5.2 Hz), 7.65 (d, 6H, J=8.8 Hz), 7.45-7.15 (m, 60H); 6.91 (d, 3H, J=8.8 Hz), 6.46 (d, 3H, J=1.6 Hz), 6.38 (d, 3H, J=1.6 Hz), 5.10 (sm 6H), 5.07 (s, 6H), 5.06 (s, 6H), 4.99 (s, 6H), 4.38 (bs, 3H), 3.96 (bm, 6H), 3.54 (bm, 6H), 3.44 (m, 6H), 3.39 (m, 6H).
$^{13}$C NMR (100 MHz, CDCl$_3$-CD$_3$OD 80:20): 174.3, 166.6, 163.0, 159.5, 158.5, 153.1, 150.9, 148.0, 139.8, 136.8, 136.4, 136.0, 135.6, 134.5, 128.8, 128.5, 128.4, 128.3, 128.2, 127.9, 127.8, 127.6, 127.4, 127.3, 127.2, 126.7, 123.2, 122.7, 115.1, 113.5, 109.4, 97.9, 93.9, 71.4, 71.3, 70.7, 70.6, 70.4, 70.0, 69.3, 39.9.
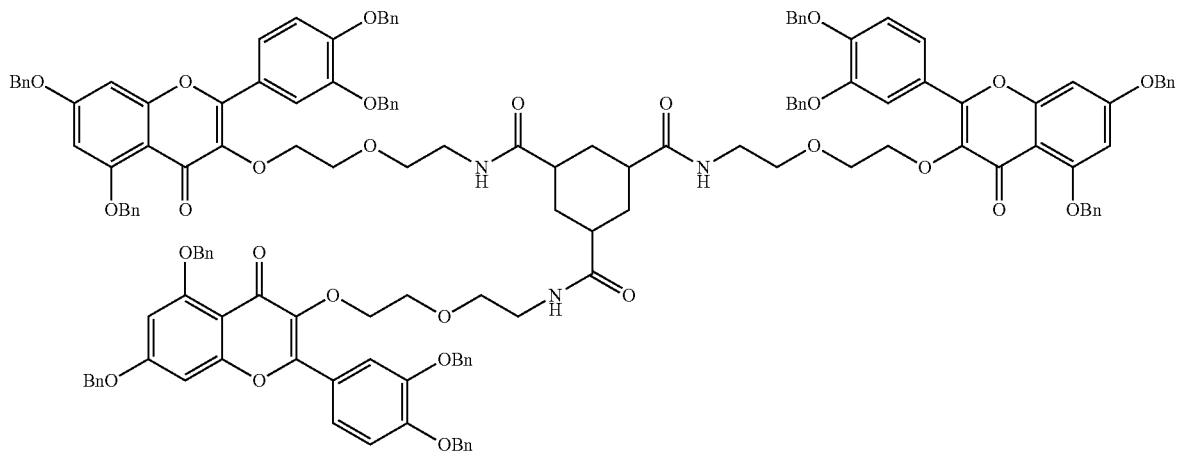
21b
Compound 21b was isolated as a white oil (293 mg, 60.7%).
$^1$H NMR (400 MHz, CDCl$_2$-CD$_3$OD 80:20): 7.79 (bs, 3H), 7.71 (d, 3H, J=8.4 Hz), 7.57 (d, 6H, J=7.6 Hz), 7.50-7.25 (m, 54H), 6.98 (d, 3H, J=8.8 Hz), 6.53 (d, 3H, J=1.8 Hz), 6.44 (d, 3H, J=1.8 Hz), 6.22 (bt, 3H), 5.21 (s, 8H), 5.20 (s, 16H), 5.06 (s, 8H), 4.13 (bs, 6H), 3.60 (bs, 6H), 3.34 (t, 6H, J=4.8 Hz), 3.23 (t, 6H, J=4.8 Hz), 1.98 (bs, 3H), 1.88 (t, 3H, J=12 Hz), 1.78 (d, 3H, J=12 Hz), 1.42 (q, 3H, J=12.8 Hz).
$^{13}$C NMR (100 MHz, CDCl$_3$-CD$_3$OD 80:20): 174.3, 173.6, 162.8, 159.7, 158.6, 152.7, 150.9, 148.2, 140.0, 137.0, 136.6, 136.3, 135.6, 128.7, 128.5, 128.4, 128.0, 127.9, 127.7, 127.6, 127.4, 127.2, 126.6, 123.6, 122.7, 115.6, 113.7, 109.8, 98.0, 93.9, 71.6, 71.2, 70.8, 70.7, 70.4, 70.1, 69.7, 43.5, 39.1, 31.5.
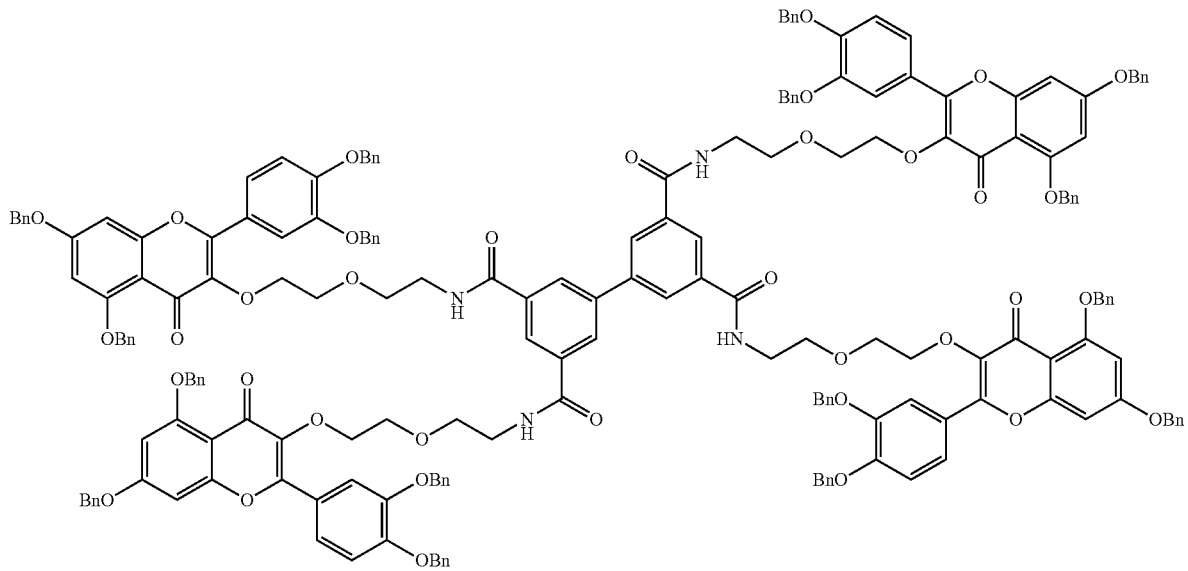
24a Compound 24a was isolated as a white oil (385 mg, 59.1%).

$^1$H NMR (400 MHz, CDCl$_3$-CD$_3$OD 80:20): 8.17 (s, 2H), 8.09 (s, 4H), 7.69 (d, 4H, J=1.6 Hz), 7.65 (dd, 4H, J$_1$=10.4 Hz, J$_2$=2.0 Hz), 7.45-7.22 (m, 80H), 7.18 (m, 4H), 6.92 (d, 4H, J=8.8 Hz), 6.46 (d, 4H, J=1.6 Hz), 6.36 (d, 4H, J=1.6 Hz).

$^{13}$C NMR (100 MHz, CDCl$_3$-CD$_3$OD 80:20): 171.5, 164.1, 158.8, 154.0, 151.7, 148.7, 143.8, 139.1, 136.8, 136.4, 135.8, 135.0, 134.3, 128.6, 128.5, 128.4, 128.3, 128.0, 127.9, 127.8, 127.7, 127.6, 127.4, 127.2, 126.9, 126.6, 124.0, 122.8, 114.7, 111.9, 105.2, 95.4, 93.3, 72.8, 71.4, 71.3, 71.0, 70.7, 70.6, 70.5, 70.4, 70.2, 69.7, 37.6.

Example of a general procedure of debenzylation of 3-O-alkylated quercetins: 2-(3,4-Dihydroxyphenyl)-3-ethoxy-5,7-dihydroxy-4H-chromen-4-one 1; 2-(3,4-Dihydroxyphenyl)-3-hexyloxy-5,7-dihydroxy-4H-chromen-4-one 2; 2-(3,4-Dihydroxyphenyl)-3-hexadecyloxy-5,7-dihydroxy-4H-chromen-4-one 3.

A solution of the product of interest dissolved in a mixture of EtOH/THF (1:2% v/v) was transferred into a hydrogenation flask. The catalyst Pd/C (10%) was added to the mixture. The reaction mixture was subjected three times to a vacuum-nitrogen cycle in order to remove the air from the system; after being vacuumed one last time, the flask was filled with hydrogen up to a pressure of 1.2 bar. Lastly, the reaction mixture was stirred at room temperature until complete debenzylation of the desired product (approximately 18 hours). Upon completion, the catalyst was removed from the reaction mixture by filtration, and the solvent was removed under reduced pressure.

The final residue corresponding to the desired product does not require a further final purification.

| SUBSTRATE (g; mol) | SOLVENT THF/EtOH = 1/2 | CATALYST Pd/C (10%) | PRODUCT (mg; mol) |
|---|---|---|---|
| 8a (0.105 g; 0.00013 mol) | 4.5 ml | 0.105 g | 1 (10 mg, 30%) |
| 8b (0.07 g; 0.00008 mol) | 5 ml | 0.07 g | 2 (51 mg, 95%) |
| 8c (0.07 g; 0.00008 mol) | 9 ml | 0.07 g | 3 (54 mg, 78%) |

2-(3,4-Dihydroxyphenyl)-3-ethoxy-5,7-dihydroxy-4H-chromen-4-one 1

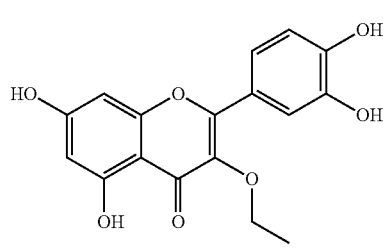

$^1$H NMR (400 MHz, CDCl$_3$): 7.62 (d, 1H, J=2.1 Hz), 7.54 (dd, 1H, J$_1$=8.5 Hz, J$_2$=2.1 Hz), 6.89 (d, 1H, J=8.5 Hz), 6.37 (d, 1H, J=2.1 Hz), 6.18 (d, 1H, J=2.1 Hz), 3.89 (q, 2H, J=7.1 Hz), 1.32 (t, 1H, J=7.1 Hz);

$^{13}$C NMR (100 MHz, CDCl$_3$): 180.29, 166.85, 163.22, 158.66, 158.39, 150.07, 146.56, 138.53, 123.34, 122.55, 122.26, 116.71, 116.46, 116.42, 116.16, 105.78, 100.15, 99.86, 95.02, 94.73, 69.77, 69.49, 15.82, 15.55.

2-(3,4-Dihydroxyphenyl)-3-hexyloxy-5,7-dihydroxy-4H-chromen-4-one 2

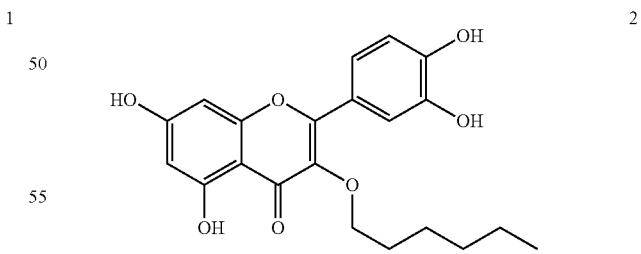

$^1$H NMR (400 MHz, CDCl$_3$): 7.55 (s, 1H); 7.47 (d, 1H, J=8.2 Hz), 6.86 (d, 1H, J=8.2 Hz), 6.35 (s, 1H), 6.17 (s, 1H), 3.88 (t, 1H, J=6.0 Hz), 1.75-1.60 (m, 2H), 1.50-1.10 (m, 6H), 0.87 (t, 3H, J=6.0 Hz);

$^{13}$C NMR (100 MHz, CDCl$_3$): 180.27, 165.90, 163.22, 158.54, 149.87, 146.44, 138.79, 123.31, 122.68, 116.87, 116.31, 106.06, 99.84, 94.80, 74.18, 32.86, 31.11, 26.89, 23.78, 14.52.

2-(3,4-Dihydroxyphenyl)-3-hexadecyloxy-5,7-dihydroxy-4H-chromen-4-one 3

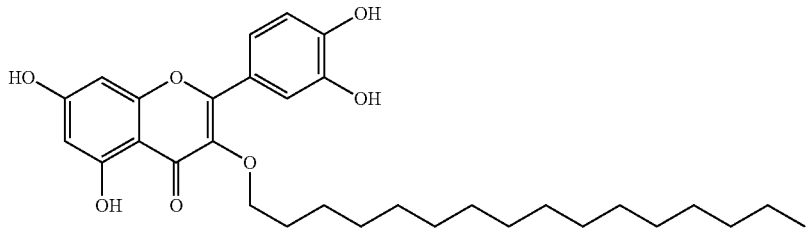

$^1$H NMR (400 MHz, CDCl$_3$): 7.49 (d, 1H, J=2.1 Hz), 7.45 (dd, 1H, J$_1$=8.5 Hz, J$_2$=2.1 Hz), 6.81 (d, 1H, J=8.5 Hz), 6.27 (d, 1H, J=2.1 Hz), 6.15 (d, 1H, J=2.1 Hz), 3.78 (t, 3H, J=7.1 Hz), 1.68-1.55 (m, 2H), 1.26-1.09 (m, 30H), 0.76 (t, 3H, J=7.1 Hz);

$^{13}$C NMR (100 MHz, CDCl$_3$): 178.72, 163.64, 161.26, 156.80, 156.58, 147.52, 144.25, 137.42, 122.11, 121.52, 115.18, 114.82, 104.91, 98.60, 93.75, 49.16, 48.95, 48.74, 48.52, 48.30, 31.67, 29.68, 29.44, 29.40, 29.36, 29.32, 29.17, 29.10, 25.60, 22.41, 13.75.

Example of synthesis of 2-(3,4-bis(palmitoyloxy)phenyl)-4-oxo-4H-chromene-3,5,7-triyl acetate: 10a Acetyl chloride (0.850 ml; 0.012 mol), DIPEA (3.09 ml; 0.018 mol) and DMAP (0.36 g; 0.003 mol) were added sequentially to a solution of 3,3',4',5,7-pentahydroxy flavone 9 (0.56 g; 0.0016 mol) in anhydrous DCM (50 ml). The reaction mixture was stirred at room temperature. Upon completion (after 24 hours), a white precipitate forms. The reaction mixture was partitioned between H$_2$O and DCM and the combined organic phases were dried over anhydrous Na$_2$SO$_4$, filtered, and the solvent was removed under reduced pressure. The solid residue was recrystallized from MTBE (tert-butyl methyl ether) from which a yellow solid product corresponding to 10a (74.7%) is obtained.

Example of synthesis of 2-(3,4-dihydroxyphenyl)-5,7-dihydroxy-4-oxo-4H-chromen-3-yl acetate: 4

Lypozime® (2 g) and butanol (1 ml; 0.01 mol) were added sequentially to a suspension of 2-(3,4-bis(palmitoyloxy)phenyl)-4-oxo-4H-chromene-3,5,7-triyl acetate 10a (0.512 g; 0.001 mol) in MTBE. The reaction was placed inside an orbital shaker (300 rpm/min) at a temperature of 45° C. until complete conversion to the desired product. The course of the reaction is monitored by TLC (DCM and DCM/MeOH=9/1). Upon completion (approximately 9 days), the solution was filtered, the solvent was removed under reduced pressure, and the residue was purified by flash column chromatography (silica Diol: DCM/MeOH=9/1). The product 4 was thus isolated as a yellow solid (260 mg, 76.3%).

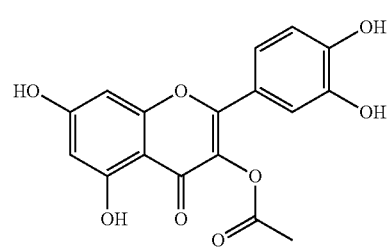

$^1$H NMR (400 MHz, CDCl$_3$): 7.45 (d, 1H, J=2.1 Hz), 7.37 (dd, 1H, J$_1$=8.5 Hz, J$_2$=2.1 Hz), 6.99 (d, 1H, J=8.5 Hz), 6.53 (d, 1H, J=2.1 Hz), 6.30 (d, 1H, J=2.1 Hz), 2.63 (t, 2H, J=7.4 Hz), 1.79-1.62 (m, 2H), 0.87 (t, 3H, J=7.4 Hz); $^{13}$C NMR (100 MHz, CDCl$_3$): 176.58, 171.22, 165.31, 162.79, 158.12, 157.32, 149.55, 146.05, 131.46, 122.00, 121.95, 116.36, 115.95, 105.12, 99.86, 23.31, 14.34.

Example of synthesis of 2-(3,4-bis(palmitoyloxy)phenyl)-4-oxo-4H-chromene-3,5,7-triyl tripalmitate: 10b Palmitoyl chloride (3.51 ml; 0.012 mol), DIPEA (3.09 ml; 0.018 mol) and DMAP (0.36 g; 0.003 mol) were added sequentially to a solution of 3,3',4',5,7-pentahydroxy flavone 9 (0.56 g; 0.0016 mol) in anhydrous DCM (50 ml). The reaction mixture is stirred at room temperature. Upon completion (after 24 hours), a white precipitate forms. The reaction mixture was partitioned between H$_2$O and DCM and the combined organic phases were dried over anhydrous Na2SO4, filtered, and the solvent was removed under reduced pressure. The solid residue was recrystallized from MTBE from which a yellow solid product corresponding to 10b (64.7%) is obtained.

Example of synthesis of 2-(3,4-dihydroxyphenyl)-5,7-dihydroxy-4-oxo-4H-chromen-3-yl palmitate: 5

Lypozime® (2 g) and butanol (1 ml; 0.01 mol) were added sequentially to a suspension of 2-(3,4-bis(palmitoyloxy)phenyl)-4-oxo-4H-chromene-3,5,7-triyl tripalmitate 10b (1.3 g; 0.001 mol) in MTBE. The reaction was placed inside an orbital shaker (300 rpm/min) at a temperature of 45° C. until complete conversion to the desired product. The course of the reaction is monitored by TLC (DCM and DCM/MeOH=9/1). Upon completion (approximately 9 days), the solution was filtered, the solvent was removed under reduced pressure, and the residue was purified by flash column chromatography (silica Diol: DCM/MeOH=9/1). The product 5 was thus isolated as a yellow solid (250 mg, 46.3%).

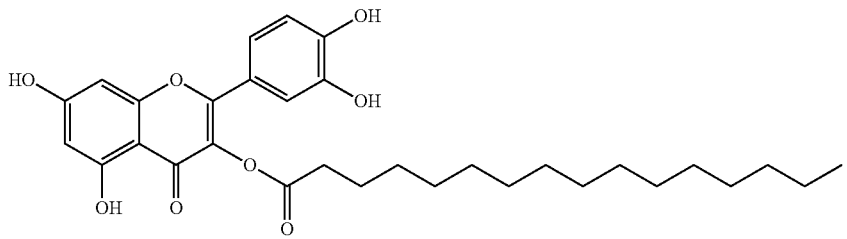

¹H NMR (400 MHz, CDCl₃): 7.45 (d, 1H, J=2.1 Hz), 7.37 (dd, 1H, J₁=8.5 Hz, J₂=2.1 Hz), 6.99 (d, 1H, J=8.5 Hz), 6.53 (d, 1H, J=2.1 Hz), 6.30 (d, 1H, J=2.1 Hz), 2.63 (t, 2H, J=7.4 Hz), 1.79-1.62 (m, 2H), 1.47-1.36 (m, 2H), 1.28 (s, 22H), 0.87 (t, 3H, J=7.4 Hz); ¹³C NMR (100 MHz, CDCl₃): 176.58, 171.22, 165.31, 162.79, 158.12, 157.32, 149.55, 146.05, 131.46, 122.00, 121.95, 116.36, 115.95, 105.12, 99.81, 99.76, 94.89, 34.28, 32.63, 30.42, 30.29, 30.22, 30.10, 30.03, 29.90, 29.84, 29.65, 29.46, 29.26, 25.55, 23.31, 14.34.

Example of a General Debenzylation Procedure

A solution of the product of interest (0.01 mmol) in a mixture of EtOH/THF (1:2% v/v) is transferred into a hydrogenation flask. The catalyst Pd/C (10%) was added to the mixture. The reaction mixture was subjected three times to a vacuum-nitrogen cycle in order to remove the air from the system; after being vacuumed one last time, the flask was filled with hydrogen up to a pressure of 1.2 bar. Lastly, the reaction mixture was stirred at room temperature until complete debenzylation of the desired product (approximately 12 hours). Upon completion, the catalyst was removed from the reaction mixture by filtration, and the solvent was removed under reduced pressure.

The residue was washed with a mixture of n-hexane/Et₂O 70:30 (3×10 ml). Unless otherwise indicated, the final residue corresponding to the desired product did not require a final chromatographic purification.

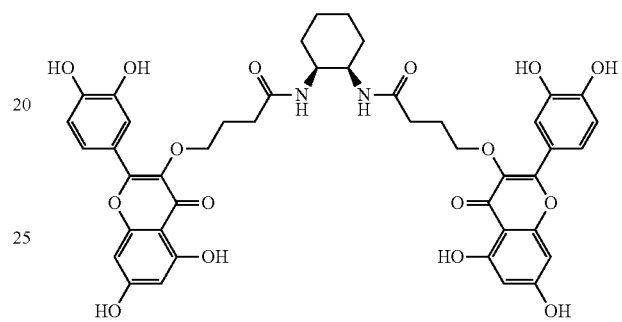

15a

The product 15a was isolated as a yellow amorphous solid (65 mg, 76%).

¹H NMR (400 MHz, DMSO-d6): 12.70 (s, 2H), 10.85 (s, 2H), 9.73 (bs, 2H), 9.39 (bs, 2H), 7.55 (bs, 2H), 7.45 (d, 2H, J=8.4 Hz), 7.39 (d, 2H, J=8.0 Hz), 6.89 (d, 2H, J=8.4 Hz), 6.40 (s, 2H), 6.18 (s, 2H), 3.89 (m, 6H), 2.22 (q, 4H, J=6.8 Hz), 1.87 (t, 4H, J=6.8 Hz), 1.55 (m, 4H), 1.43 (m, 4H), 1.35 (m, 2H), 1.23 (m, 2H).

¹³C NMR (100 MHz, CD₃OD): 178.5, 176.3, 174.6, 171.6, 164.0, 163.6, 161.2, 158.5, 156.8, 148.1, 145.4, 144.5, 137.0, 136.8, 125.7, 124.6, 121.6, 121.4, 121.1, 116.5, 115.4, 115.2, 108.9, 107.0, 104.8, 98.8, 96.2, 93.9, 67.4, 33.9, 30.0, 27.8, 25.7, 19.6, 17.6.

15b

The product 15b was isolated as a yellow amorphous solid (70 mg, 72.8%).
¹H NMR (400 MHz, CD₃OD): 7.57 (s, 2H, J=2.4 Hz), 7.45 (dd, 2H, J=8.4, 2.0 Hz), 6.88 (d, 2H, J=8.4 Hz), 6.31 (dd, 2H, J=2.0 Hz), 6.14 (d, 2H, J=2.0 Hz), 3.89 (t, 4H, J=6.0 Hz), 3.58 (m, 4H), 3.52 (m, 4H), 3.48 (t, 4H, J=6.4 Hz), 3.27 (t, 4H, J=6.8 Hz), 2.40 (t, 4H, J=7.2 Hz), 2.01 (t, 4H, J=6.4 Hz), 1.74 (t, 4H, J=6.4 Hz).
¹³C NMR (100 MHz, CD₃OD): 178.5, 176.3, 164.0, 163.6, 161.2, 158.5, 156.8, 148.1, 145.4, 137.0, 124.7, 121.6, 115.0, 104.8, 98.4, 93.3, 71.3, 68.5, 57.0, 36.6, 33.9, 32.2, 28.8, 27.4, 26.0, 16.9.
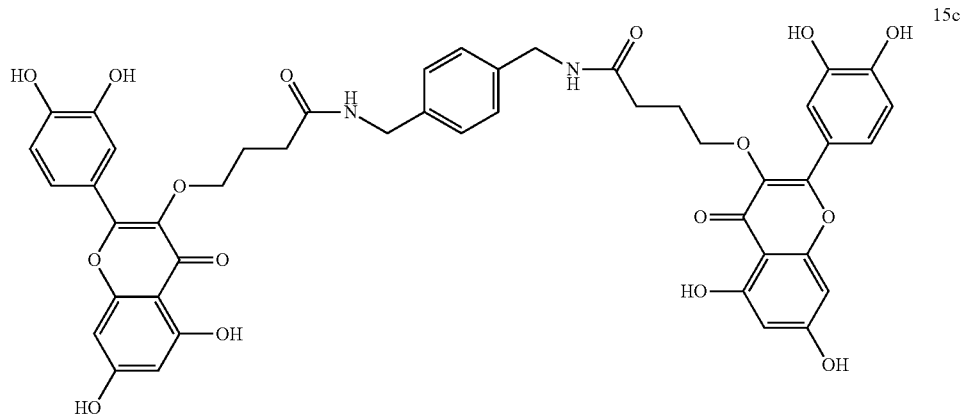 [SMILES: O=C(CCCOc1c(-c2ccc(O)c(O)c2)oc2cc(O)cc(O)c2c1=O)NCc1ccc(CNC(=O)CCCOc2c(-c3ccc(O)c(O)c3)oc3cc(O)cc(O)c3c2=O)cc1]
The product 15c was isolated as a yellow amorphous solid (82 mg, 93.5%).
¹H NMR (400 MHz, CD₃OD): 7.52 (d, 2H, J=2.0 Hz), 7.41 (dd, 4H, J=8.4, 2.0 Hz), 7.09 (s, 4H); 6.83 (d, 2H, J=8.8 Hz), 6.26 (d, 2H, J=1.6 Hz), 6.09 (d, 2H, J=2.0 Hz), 4.25 (s, 4H), 3.83 (t, 4H, J=6.0 Hz), 2.42 (t, 4H, J=6.8 Hz), 1.99 (t, 4H, J=6.4 Hz).
¹³C NMR (100 MHz, CD₃OD): 178.3, 176.4, 164.17, 161.4, 156.7, 156.6, 148.3, 144.8, 137.2, 136.8, 127.4, 121.5, 121.0, 115.16, 114.9, 104.4, 98.3, 93.3, 71.2, 65.4, 42.6, 32.4, 26.0.
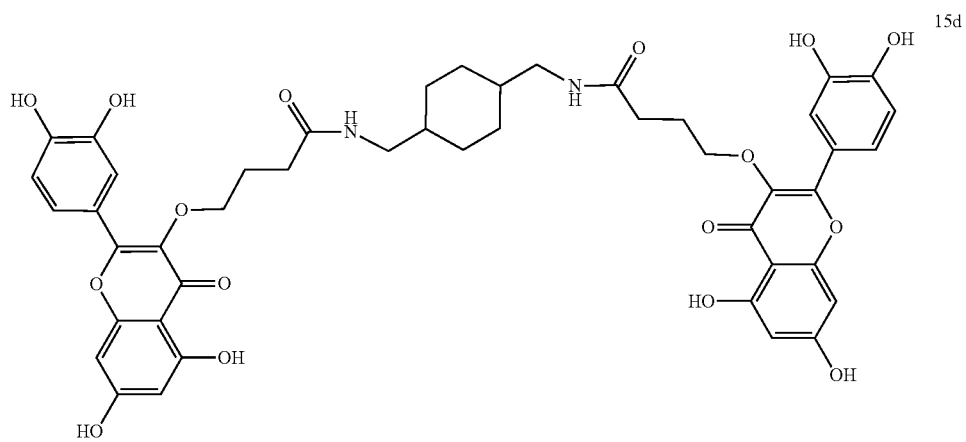 [SMILES: O=C(CCCOc1c(-c2ccc(O)c(O)c2)oc2cc(O)cc(O)c2c1=O)NCC1CCC(CNC(=O)CCCOc2c(-c3ccc(O)c(O)c3)oc3cc(O)cc(O)c3c2=O)CC1]

The product 15d was isolated as a yellow amorphous solid (74 mg, 83.8%).

¹H NMR (400 MHz, CD₃OD): 7.57 (bs, 1H), 7.47 (d, 2H, J=8.0 Hz), 6.87 (d, 2H, J=8.0 Hz), 6.31 (bs, 2H), 6.13 (m, 2H), 3.89 (m, 4H), 2.99 (m, 4H), 2.39 (m, 4H), 2.00 (m, 4H), 1.70 (m, 4H), 1.36 (m, 2H), 0.86 (m, 4H).

¹³C NMR (100 MHz, CD₃OD): 178.5, 174.3, 164.3, 161.5, 156.9, 156.7, 148.4, 144.8, 136.9, 121.6, 121.0, 115.2, 114.9, 104.4, 98.3, 93.3, 71.3, 37.7, 32.3, 29.9, 26.0.

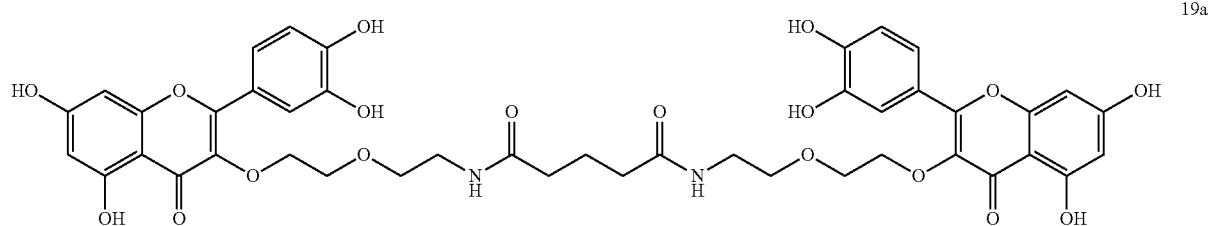 [SMILES: O=C(CCCC(=O)NCCOCCOc1c(-c2ccc(O)c(O)c2)oc2cc(O)cc(O)c2c1=O)NCCOCCOc1c(-c2ccc(O)c(O)c2)oc2cc(O)cc(O)c2c1=O]

19a

The product 19a was isolated as a yellow amorphous solid (85 mg, 97.2%).

¹H NMR (400 MHz, DMSO-d6): 7.82 (s, 2H), 7.56 (m, 2H), 6.88 (d, 2H, J=8.4 Hz), 6.40 (s, 2H), 6.18 (s, 2H), 4.26 (m, 4H), 3.64 (m, 4H), 3.63 (t, 4H, J=5.6 Hz), 3.18 (m, 4H), 2.17 (t, 4H, J=6.8 Hz), 2.09 (t, 4H, J=7.2 Hz), 1.69 (m, 4H).

¹³C NMR (100 MHz, DMSO-d6): 178.8, 175.4, 172.8, 165.5, 162.2, 157.3, 156.6, 149.9, 146.2, 137.5, 122.0, 121.7, 116.6, 104.9, 99.6, 94.5, 72.0, 70.3, 70.0, 35.4, 34.3, 31.4, 21.8.

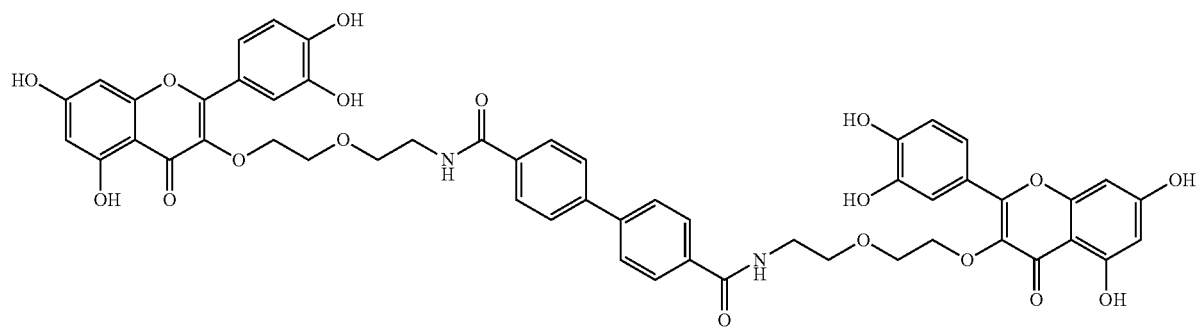

19b

The product 19b was isolated as a yellow amorphous solid (95 mg, 96.4%).

¹H NMR (400 MHz, DMSO-d6): 12.70 (s, 2H), 10.92 (s, 2H), 9.81 (s, 2H), 9.38 (s, 2H), 8.57 (bt, 2H), 7.95 (d, 4H, J=8.0 Hz), 7.79 (d, 4H, J=8.0 Hz), 7.57 (m, 2H), 6.92 (d, 2H, J=8.4 Hz), 6.43 (d, 2H, J=1.6 Hz), 6.20 (d, 2H, J=1.6 Hz), 4.15 (m, 4H), 3.71 (m, 4H), 3.53 (m, 4H), 3.43 (m, 4H).

¹³C NMR (100 MHz, DMSO-d6): 178.8, 166.9, 165.1, 162.2, 157.2, 156.7, 149.6, 146.6, 146.1, 142.6, 140.1, 137.6, 134.6, 129.2, 128.9, 127.60, 125.9, 122.1, 121.9, 116.6, 105.1, 99.5, 72.0, 70.3, 69.8, 69.2.

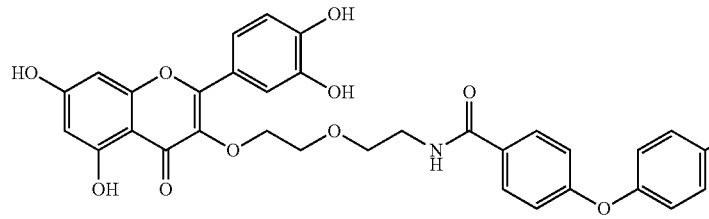
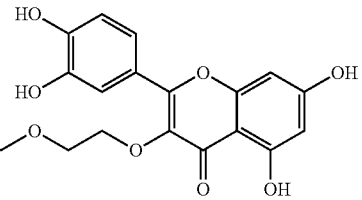
The product 19c was isolated as a yellow amorphous solid (87 mg, 86.9%).
$^1$H NMR (400 MHz, CD$_3$OD): 7.74 (d, 4H, J=8.0 Hz), 7.63 (bs, 2H), 7.48 (d, 2H, J=8.4 Hz), 6.91 (d, 4H, J=8.0 Hz), 6.82 (d, 2H, J=8.4 Hz), 6.26 (s, 2H), 6.08 (s, 2H), 4.05 (m, 4H), 3.72 (m, 4H), 3.60 (m, 4H), 3.56 (m, 4H).
$^{13}$C NMR (100 MHz, CD$_3$OD): 178.3, 168.2, 164.2, 161.5, 159.1, 156.8, 156.5, 148.4, 144.7, 136.8, 129.5, 129.1, 121.5, 121.2, 118.2, 115.5, 114.8, 104.4, 98.3, 93.3, 71.3, 69.7, 69.1, 39.7.
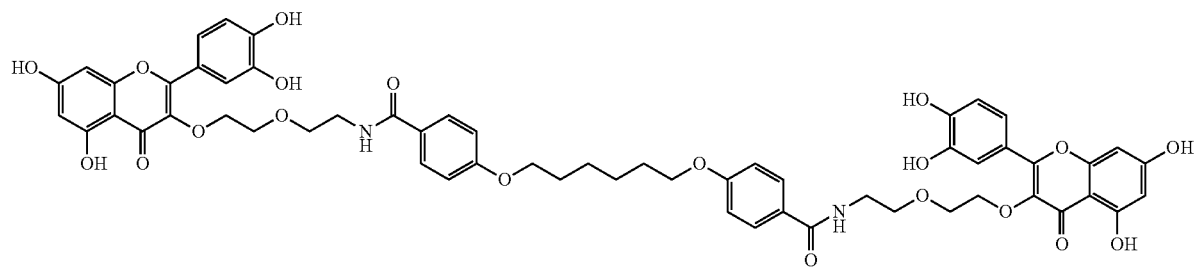
The product 19d was isolated as a yellow amorphous solid (93 mg, 84.5%).
$^1$H NMR (400 MHz, CD$_3$OD): 7.68 (m, 6H), 7.53 (dd, 2H, J=8.4, 2.0 Hz), 6.87 (d, 2H, J=8.4 Hz), 6.81 (d, 4H, J=8.8 Hz), 6.33 (d, 2H, J=1.6 Hz), 6.17 (d, 2H, J=1.6 Hz), 4.08 (m, 4H), 3.92 (t, 4H, J=6.0 Hz), 3.74 (m, 4H), 3.63 (m, 4H), 3.57 (t, 4H, J=4.4 Hz), 1.75 (m, 4H), 1.48 (m, 4H).
$^{13}$C NMR (100 MHz, CD$_3$OD): 178.4, 168.7, 164.2, 161.8, 161.5, 156.9, 156.7, 148.4, 144.7, 136.9, 128.7, 126.0, 121.6, 121.3, 115.7, 114.9, 113.8, 104.6, 98.5, 93.5, 71.4, 69.8, 69.3, 67.6, 39.6, 28.7, 25.4
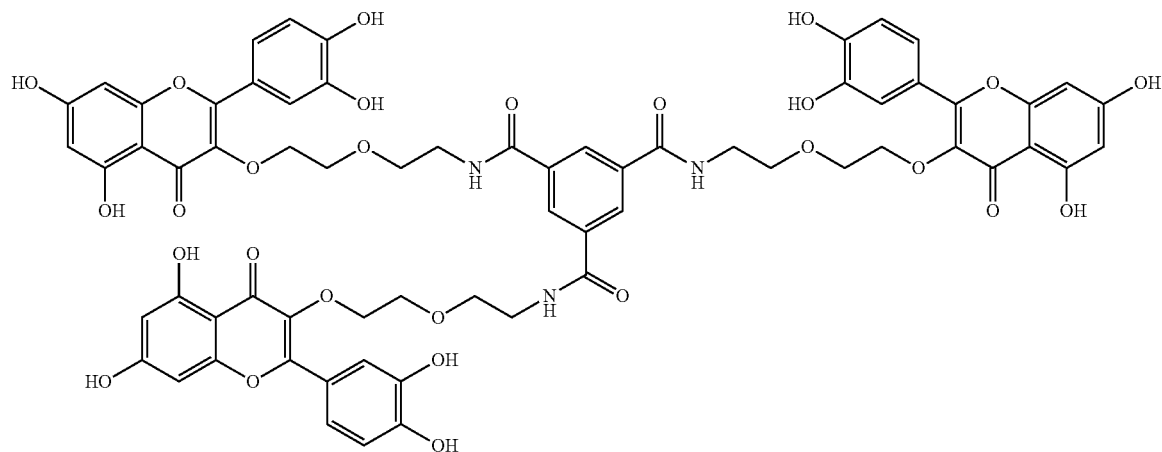

The product 22a was isolated as a yellow amorphous solid (132 mg, 99.7%).
$^1$H NMR (400 MHz, CD$_3$OD): 8.32 (s, 3H), 7.60 (d, 3H, J=2.0 Hz), 7.47 (dd, 3H, J=8.4, 2.0 Hz), 6.82 (d, 3H, J=8.4 Hz), 6.27 (d, 3H, J=2.4 Hz), 6.09 (d, 3H, J=2.0 Hz), 4.02 (m, 6H), 3.70 (m, 6H), 3.65 (m, 6H), 3.58 (m, 6H), 3.53 (m, 6H).
$^{13}$C NMR (100 MHz, CD$_3$OD): 181.8, 178.1, 172.6, 167.3, 166.0, 161.4, 159.4, 156.9, 156.4, 148.6, 144.8, 136.6, 134.9, 128.5, 121.4, 121.2, 115.4, 114.9, 103.9, 98.9, 93.7, 71.3, 69.7, 69.0, 39.8.
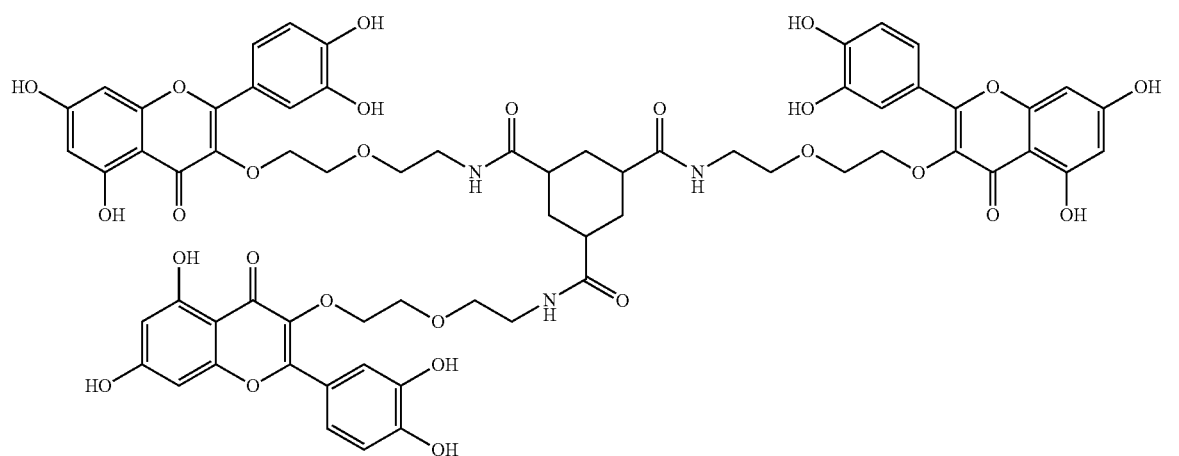
22b
The product 22b was isolated as a yellow amorphous solid (126 mg, 94.7%).
$^1$H NMR (400 MHz, CD$_3$OD): 7.61 (bs, 3H), 7.49 (d, 3H, J=6.8 Hz), 6.84 (bs, 3H), 6.25 (m, 3H), 6.12 (m, 3H), 3.98 (bs, 6H), 3.65 (bs, 6H), 3.46 (m, 6H), 3.35 (m, 3H), 2.32 (bs, 3H), 1.88 (m, 3H), 1.59 (m, 3H).
$^{13}$C NMR (100 MHz, CD$_3$OD): 178.3, 176.0, 164.2, 161.4, 156.7, 156.5, 148.3, 144.7, 136.8, 121.5, 121.2, 115.5, 114.8, 104.3, 98.3, 93.3, 71.3, 69.6, 68.9, 43.2, 39.0, 31.3.
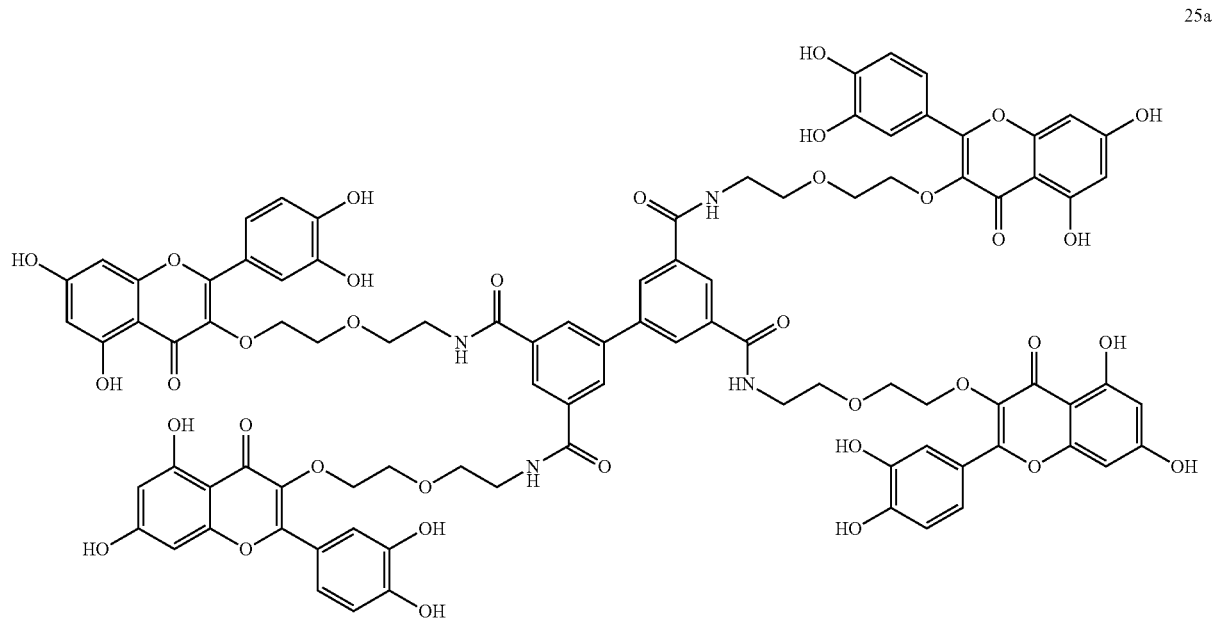 [SMILES: O=C(NCCOCCOc1c(-c2ccc(O)c(O)c2)oc2cc(O)cc(O)c2c1=O)c1cc(C(=O)NCCOCCOc2c(-c3ccc(O)c(O)c3)oc3cc(O)cc(O)c3c2=O)cc(-c2cc(C(=O)NCCOCCOc3c(-c4ccc(O)c(O)c4)oc4cc(O)cc(O)c4c3=O)cc(C(=O)NCCOCCOc3c(-c4ccc(O)c(O)c4)oc4cc(O)cc(O)c4c3=O)c2)c1]
25a The product 25a was isolated as a yellow amorphous solid (142 mg, 78.2%).

1H NMR (400 MHz, CD$_3$OD): 8.09 (s, 2H), 7.94 (d, 4H, J=1.2 Hz), 7.53 (d, 4H, J=1.2 Hz), 7.42 (dd, 4H, J=8.4, 2.4 Hz), 6.75 (dd, 4H, J=8.4, 1.6 Hz), 6.22 (s, 4H), 6.04 (s, 4H), 4.06 (bs, 8H), 3.74 (m, 8H), 3.61 (bt, 8H, J=4.8 Hz), 5.52 (bt, 8H, J=4.8 Hz).

13C NMR (100 MHz, CD$_3$OD): 178.2, 167.6, 164.2, 161.4, 156.9, 156.2, 148.2, 144.6, 139.5, 136.8, 134.9, 128.2, 125.5, 121.5, 121.2, 115.4, 114.8, 104.3, 98.2, 93.3, 71.1, 69.7, 68.8, 39.8.

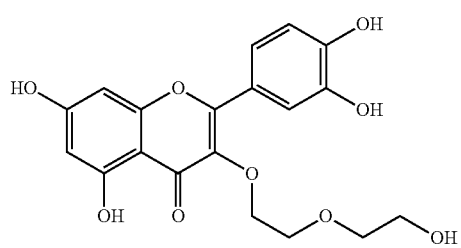

26

The product 26 was isolated as a yellow amorphous solid (74 mg, 95.0%).

$^1$H NMR (400 MHz, DMSO-d6): 12.47 (bs, 1H), 9.36 (bs, 1H), 7.67 (bs, 1H), 7.53 (d, 1H, J=8.4 Hz), 6.87 (m, 1H), 6.41 (bs, 1H), 3.45-3.20 (m, 8H).

$^{13}$C NMR (100 MHz, DMSO-d6): 175.9, 164.0, 160.8, 156.2, 147.8, 146.9, 145.1, 135.8, 125.0, 122.0, 120.1, 115.7, 115.1, 103.1, 98.2, 93.4.

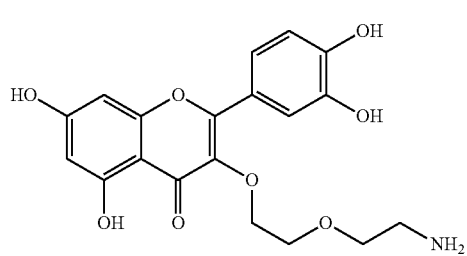

27

The product 27 was isolated as a yellow amorphous solid (74 mg, 95.0%).

$^1$H NMR (400 MHz, CD$_3$OD): 7.67 (d, 1H, J=2.0 Hz), 7.52 (dd, 1H, J$_2$=8.4 Hz, J$_2$=2.0 Hz), 6.39 (d, 1H, J=1.6 Hz), 6.19 (d, 1H, J=2.0 Hz), 4.10-4.01 (m, 2H), 3.83-3.75 (2H, m), 3.74-3.67 (2H, m), 3.19-3.10 (2H, m); $^{13}$C NMR (100 MHz, CD$_3$OD): 179.9, 166.0, 163.0, 158.5, 158.4, 150.0, 146.3, 138.3, 122.8, 122.5, 117.0, 116.4, 105.8, 99.9, 94.8, 72.9, 71.2, 67.8, 40.6.

Example of synthesis of compounds 29 (a-g) Procedure performed in the dark. EDC·HCl (1.5 eq.), followed 30 minutes later by HOBt (1.2 eq.) were added to a solution of the acid 28 (a-g) (approximately 0.025 M) in anhydrous DMF, under argon atmosphere and magnetic stirring. After a further 30 minutes, the solution obtained as above was added dropwise over 5 minutes via a syringe to a solution of compound 27 (1.1 eq. 0.029 M approx.) and DIPEA (6-8 eq.) in anhydrous DMF, under stirring, kept at 0° C. and under argon atmosphere.

The reaction thus obtained was brought to room temperature and maintained under stirring and argon atmosphere for 24 hours. After the 24 hours, the reaction mixture was diluted with EtOAc (5 times the reaction volume) and extracted with water (twice) and a saturated NaCl solution (once). The organic phase was dried over anhydrous Na$_2$SO$_4$, filtered, and concentrated under vacuum to dryness to yield a crude product, which was purified by flash column chromatography (SiO$_2$; DCM/MeOH=2→4%) to afford the final compound, that is 29(a-g).

Examples of Synthesis Conditions for Individual Compounds

29a: 27 (15 mg; 0.028 mmol), DIPEA (40 μl; 0.23 mmol); anhydrous DMF (1 ml); 28a (6.5 mg; 0.025 mmol); EDC·HCl (7.5 mg; 0.038 mmol); HOBt (3.8 mg;

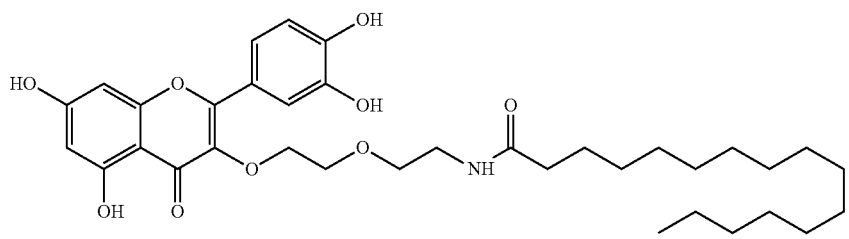

29a 0.028 mmol); anhydrous DMF (1.5 ml). Compound 29a was obtained as a yellow solid (5 mg, 30%).

$^1$H NMR (400 MHz, CD$_3$OD): 7.68 (d, 1H, J=2.0 Hz), 7.52 (dd, 1H, J$_1$=8.4 Hz, J$_2$=2.0 Hz), 6.86 (d, 1H, J=8.4 Hz), 6.35 (d, 1H, J=2.0 Hz), 6.21 (d, 1H, J=2.0 Hz), 4.06-4.00 (m, 2H), 3.72-3.66 (m, 2H), 3.49 (t, 2H, J=4.8 Hz), 3.36 (t, 2H, J=4.8 Hz), 2.12 (t, 2H, J=8 Hz), 1.58-1.46 (m, 2H), 1.30-1.10 (m, 24H), 0.81 (t, 3H, J=7.2 Hz);

$^{13}$C NMR (100 MHz, CD$_3$OD): 178.8, 175.2, 164.3, 161.6, 157.2, 157.0, 148.3, 144.8, 137.3, 122.0, 121.7, 115.9, 115.3, 105.1, 99.1, 94.2, 71.7, 70.1, 69.8, 39.4, 32.0, 29.8, 29.76, 29.6, 29.5, 29.47, 29.41, 26.0, 22.8, 14.1.

29b: 27 (15 mg; 0.028 mmol), DIPEA (40 μl; 0.23 mmol); anhydrous DMF (1 ml); 28b (8.7 mg; 0.025 mmol); EDC·HCl (7.5 mg; 0.038 mmol); HOBt (3.8 mg; 0.028 mmol); anhydrous DMF (1.5 ml). Compound 29b was obtained as a

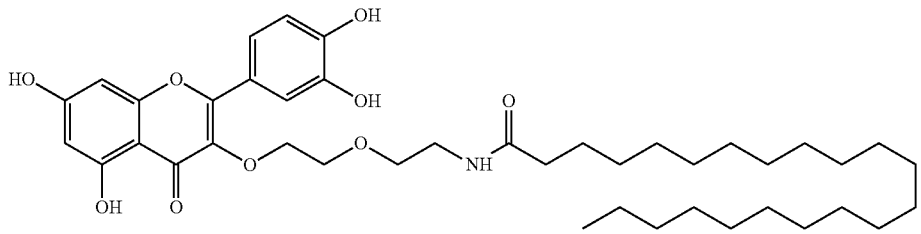

29b yellow solid (4.5 mg, 25%).

$^1$H NMR (400 MHz, CD$_3$OD): 7.70 (d, 1H, J=2.0 Hz), 7.54 (dd, 1H, J$_1$=8.4 Hz, J$_2$=1.6 Hz), 6.88 (d, 1H, J=8.4 Hz), 6.37 (d, 1H, J=2.4 Hz), 6.23 (d, 1H, J=2.4 Hz), 4.08-4.02 (m, 2H), 3.75-3.68 (m, 2H), 3.52 (t, 2H, J=5.2 Hz), 3.38 (t, 2H, J=5.2 Hz), 2.15 (t, 2H, J=7.6 Hz), 1.62-1.48 (m, 2H), 1.31-1.11 (m, 36H), 0.84 (t, 3H, J=6.8 Hz);

$^{13}$C NMR (100 MHz, CD$_3$OD): 179.0, 175.5, 164.6, 161.9, 157.4, 157.3, 148.6, 145.1, 137.5, 122.2, 121.9, 116.2, 115.5, 105.3, 99.3, 94.3, 71.9, 70.3, 70.0, 39.6, 36.7, 32.2, 30.9, 30.0, 29.8, 29.69, 29.65, 29.60, 26.2, 23.0, 14.2.

29c: 27 (21 mg; 0.042 mmol), DIPEA (44 µl; 0.25 mmol); anhydrous DMF (1 ml); 28c (10.6 mg; 0.038 mmol); EDC·HCl (11 mg; 0.057 mmol); HOBt (5.6 mg;

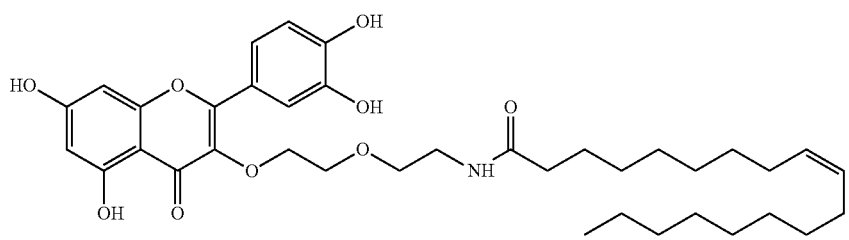

29c 0.042 mmol); anhydrous DMF (1.5 ml). Compound 29c was obtained as a yellow solid (2 mg, 8%).

$^1$H NMR (400 MHz, CD$_3$OD): 7.68 (d, 1H, J=1.6 Hz), 7.53 (dd, 1H, J$_1$=8.4 Hz, J$_2$=1.6 Hz), 6.86 (d, 1H, J=8.4 Hz), 6.35 (d, 1H, J=2.0 Hz), 6.21 (d, 1H, J=2.0 Hz), 5.29-5.22 (m, 2H), 3.72-3.65 (m, 2H), 3.49 (t, 2H, J=5.2 Hz), 3.36 (t, 2H, J=5.2 Hz), 2.12 (t, 2H, J=7.6 Hz), 1.98-1.85 (m, 4H), 1.70-1.40 (m, 2H), 11.35-1.10 (m, 20H), 0.81 (t, 3H, J=7.6 Hz);

$^{13}$C NMR (100 MHz, CD$_3$OD): 178.8, 175.1, 164.3, 161.6, 157.2, 157.0, 148.3, 144.8, 137.3, 130.0, 129.9, 122.0, 121.7, 115.9, 115.2, 105.1, 99.1, 94.2, 71.7, 70.1, 69.8, 39.4, 36.6, 32.0, 29.9, 29.8, 29.6, 29.4, 29.3, 27.3, 26.0, 22.8, 14.1.

29d: 27 (15 mg; 0.028 mmol), DIPEA (40 µl; 0.23 mmol); anhydrous DMF (1 ml); 28d (7.1 mg; 0.025 mmol); EDC·HCl (7.5 mg; 0.038 mol); HOBt (3.8 mg; 0.028 mmol); anhydrous DMF (1.5 ml). Compound 29d was obtained as a yellow solid

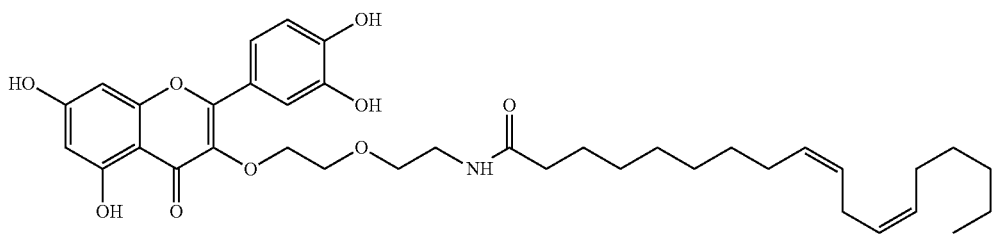

29d (5 mg, 30%).

$^1$H NMR (400 MHz, CD$_3$OD): 7.69 (d, 1H, 2.4 Hz), 7.54 (dd, 1H, J$_1$=8.4 Hz J$_2$=2.0 Hz), 6.88 (d, 1H, J=8.4 Hz), 6.37 (d, 1H, J=2.0 Hz), 6.22 (d, 1H, J=2.0 Hz), 5.37-5.20 (m, 4H), 4.08-4.01 (m, 2H), 3.73-3.67 (m, 4H), 3.51 (t, 2H, J=5.2 Hz), 3.38 (t, 2H, J=5.2 Hz), 2.70 (t, 2H, J=6.4 Hz), 21.47 (t, 2H, J=7.6 Hz), 2.04-1.92 (m, 4H), 1.61-1.50 (m, 2H), 1.35-1.13 (m, 14H), 0.84 (t, 3H, J=7.2 Hz);

$^{13}$C NMR (100 MHz, CD$_3$OD): 178.9, 175.3, 164.5, 161.8, 157.3, 157.1, 148.5, 145.0, 137.4, 130.4, 130.3, 128.21, 128.15, 122.1, 121.8, 116.0, 115.4, 105.2, 99.2, 94.3, 71.9, 70.2, 69.9, 39.5, 36.6, 31.7, 29.9, 29.8, 29.6, 29.5, 29.4, 27.4, 26.1, 25.8, 22.8, 14.1

29e: 27 (14 mg; 0.026 mmol), DIPEA (27 μl; 0.16 mmol); anhydrous DMF (1 ml); 28e (7.2 mg; 0.024 mmol); EDC·HCl (6.8 mg; 0.036 mmol); HOBt (3.5 mg; 0.026 mmol); anhydrous DMF (1.5 ml). Compound 29e was obtained as a yellow solid (5 mg, 31%).

$^1$H NMR (400 MHz, CD$_3$OD): 7.69 (d, 1H, J=2.0 Hz), 7.54 (dd, 1H, J$_1$=8.4 Hz, J$_2$=2.4 Hz), 6.88 (d, 1H, J=8.4 Hz), 6.37 (d, 1H, J=1.6 Hz), 6.22 (d, 1H J=1.6 Hz), 5.38-5.21 (m, 8H), 4.08-4.00 (m, 2H), 3.74-3.66 (m, 2H), 3.51 (t, 2H, J=5.2 Hz), 3.38 (t, 2H, J=5.2 Hz), 2.82-2.68 (m, 6H), 2.17 (t, 2H, J=8.0 Hz) 2.1-1.94 (m, 4H), 1.70-1.58 (m, 2H), 1.35-1.15 (m, 6H), 0.831 (t, 3H, J=6.8 Hz);

$^{13}$C NMR (100 MHz, CDCl$_3$): 178.7, 175.5, 163.1, 161.93, 156.9, 156.7, 148.2, 144.2, 137.4, 130.7, 129.1, 128.9, 128.8, 128.4, 128.2, 128.0, 127.6, 122.3, 121.6, 116.1, 115.1, 105.6, 99.4, 94.3, 71.6, 70.1, 69.7, 39.6, 36.2, 31.6, 29.8, 29.4, 27.3, 26.7, 25.8, 25.7, 22.7, 14.2.

29f: 27 (25 mg; 0.05 mmol), DIPEA (63 μl; 0.36 mmol); anhydrous DMF (1.5 ml), 28f (15 mg; 0.046 mmol), EDC·HCl (13 mg; 0.069 mmol), HOBt (8 mg; 0.06

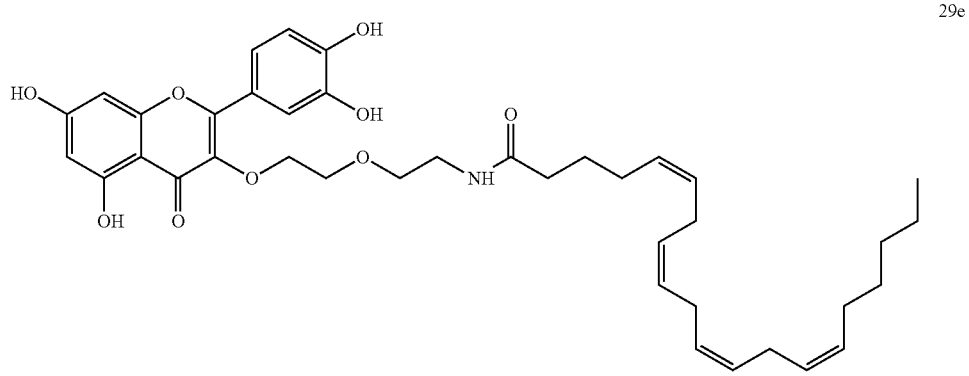 [SMILES: CCCCC/C=C\C/C=C\C/C=C\C/C=C\CCCC(=O)NCCOCCOc1c(-c2ccc(O)c(O)c2)oc2cc(O)cc(O)c2c1=O]

29e

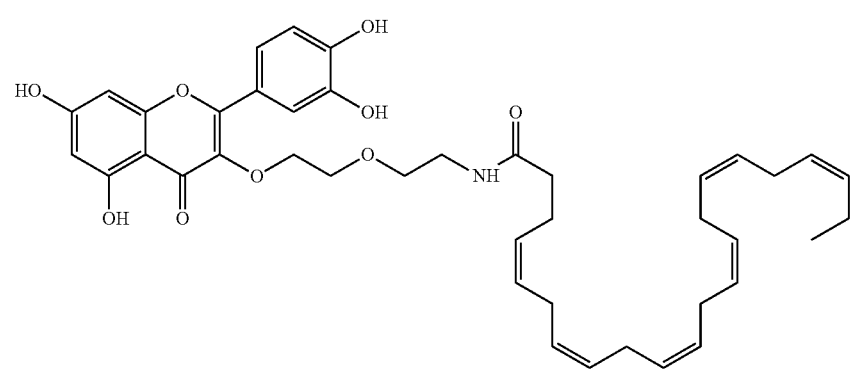

29f mmol), anhydrous DMF (2.5 ml). Compound 29f was obtained as a yellow solid (14 mg, 44%).

$^1$H NMR (400 MHz, CD$_3$OD): 7.69 (d, 1H, J=2.0), 7.54 (dd, 1H, J$_1$=8.8 Hz, J$_2$=2.4 Hz), 6.88 (d, 1H, J=8.8 Hz), 6.37 (d, 1H, J=2.0 Hz), 6.22 (d, 1H, J=2.0), 5.38-5.23 (m, 12H), 4.08-4.01 (m, 2H), 3.74-3.66 (m, 2H), 3.51 (t, 2H, J=5.2 Hz), 3.38 (t, 2H, J=5.2 Hz), 2.85-2.70 (m, 10H), 2.39-2.30 (m, 2H), 2.22 (t, 2H, J=6.8 Hz), 2.08-1.97 (m, 2H), 0.92 (t, 3H, J=7.2 Hz);

$^{13}$C NMR (100 MHz, CD$_3$OD): 178.9, 174.4, 164.5, 161.8, 157.3, 157.2, 148.5, 145.0, 137.4, 132.2, 129.4, 128.8, 128.5, 128.43, 128.37, 128.33, 128.13, 127.3, 122.2, 121.8, 116.1, 115.4, 105.3, 99.2, 94.3, 71.9, 70.2, 69.9, 39.6, 36.3, 25.83, 25.81, 25.74, 23.8, 20.8, 14.3.

29g: 27 (32 mg; 0.063 mmol), DIPEA (100 µl; 0.57 mmol), anhydrous DMF (2 ml), 28g (15.8 mg; 0.069 mmol), EDC·HCl (19.8 mg; 0.10 mmol); HOBt (11.2

29g

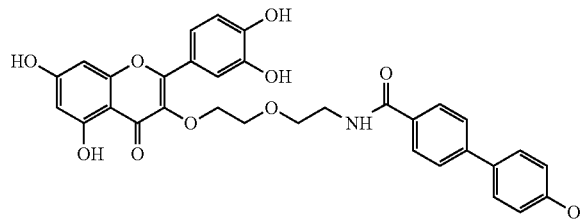

mg; 0.083 mmol), anhydrous DMF (3 ml). Compound 29g was obtained as a yellow solid (9 mg, 22%).

$^1$H NMR (400 MHz, CD$_3$OD): 7.82-7.77 (m, 2H), 7.68 (d, 1H, J=2.4 Hz), 7.59-7.47 (m, 5H), 6.99-6.93 (m, 2H), 6.89 (d, 1H, J=8.4 Hz), 6.34 (d, 1H, J=1.6 Hz), 6.16 (d, 1H, J=1.6 Hz), 4.15-4.09 (m, 2H), 3.81 (s, 3H), 3.79-3.73 (m, 2H), 3.66-3.61 (m, 2H), 3.61-3.55 (m, 2H);

$^{13}$C NMR (100 MHz, CD$_3$OD): 179.9, 170.3, 165.8, 163.0, 161.2, 158.3, 158.0, 149.9, 146.3, 145.2, 138.3, 133.52, 133.48, 129.1, 128.8, 127.3, 123.0, 122.6, 117.0, 116.3, 115.3, 105.8, 99.8, 94.7, 72.8, 71.3, 70.6, 55.7, 41.1.

Examples of significant reactions and syntheses, also associated with obtaining the heterotrimer Q$_2$E 36

Example of Synthesis of Intermediate 31

EDC·HCl (379 mg; 1.98 mmol), followed approximately 30 minutes later by HOBt (214 mg; 1.58 mmol) were added to a solution of palmitic acid (372 mg; 1.45 mmol) in anhydrous DMF (2 ml) under magnetic stirring and argon atmosphere. The reaction mixture thus obtained was stirred for about thirty minutes and then added dropwise over 5 minutes via a syringe to a solution of dopamine-HCl (30; 250 mg; 1.32 mmol) and DIPEA (1.38 ml; 7.9 mmol) in anhydrous DMF (10 ml) kept at 0° C. (in an ice bath).

When the addition was complete, the reaction mixture was slowly allowed to reach room temperature and then kept stirring under argon atmosphere for further 24 hours before being diluted with AcOEt (30 ml) and washed sequentially with H$_2$O (2×30 ml) and a saturated NaCl solution (20 ml).

The organic phase was dried over anhydrous Na2SO4, filtered, and concentrated under vacuum to dryness to yield a crude product, which was purified by flash column chromatography (SiO$_2$, EtOAc/n-hexane=30→45%) to afford intermediate 31 as a white solid (190 mg, 37%).

31

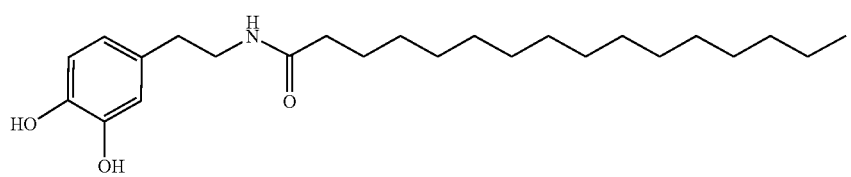

1H NMR (400 MHz, CD$_3$OD): 6.67 (d, 1H, J=7.6 Hz), 6.64 (d, 1H, J=2.0 Hz), 6.51 (dd, 1H, J$_1$=7.6 Hz, J$_2$=2.0 Hz), 3.33 (t, 2H, J=7.2 Hz), 2.62 (t, 2H, J=7.2 Hz), 2.14 (t, 2H, J=7.6 Hz), 1.62-1.51 (m, 2H), 1.37-1.22 (m, 24H), 0.90 (t, 3H, J=6.8 Hz);

13C NMR (100 MHz, CD$_3$OD): 178.3, 146.3, 144.8, 132.0, 121.0, 116.8, 116.3, 42.2, 37.2, 36.0, 33.1, 30.79, 30.76, 30.6, 30.5, 30.4, 30.3, 27.1, 23.7, 14.4.

Example of Synthesis of Intermediate 33

K2CO3 (230 mg) and KI (43 mg) were added sequentially to a solution of amide 31 (170 mg; 0.43 mmol) and ethyl 4-bromobutanoate (32) (319 mg; 1.91 mmol) in anhydrous DMF (10 ml), under argon atmosphere. The reaction thus obtained was magnetically stirred for 24 hours before being diluted with EtOAc (40 ml) and washed with H$_2$O (2×30 ml) and a saturated aqueous solution of NaCl (20 ml).

The final organic phase was dried over anhydrous Na2SO4, filtered, and concentrated under vacuum to dryness to yield a crude product from which intermediate 33 was obtained as a white solid (192 mg, 72%) after purification by flash column chromatography.

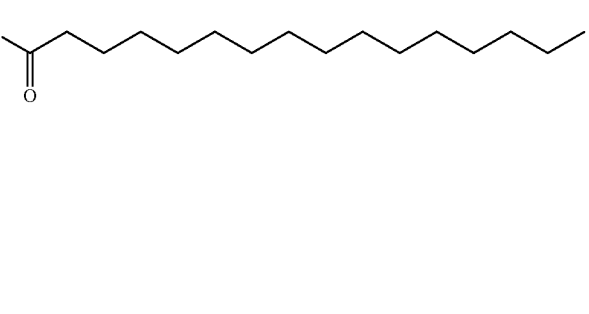

33

1H NMR (400 MHz, CDCl$_3$):6.81 (d, 1H, J=5.6 Hz), 6.75-6.65 (m, 2H), 5.47 (bt, 1H), 4.13 (q, 4H, J=7.2 Hz), 4.013 (t, 2H, J=6.0 Hz), 4.007 (t, 2H, J=6.0 Hz), 4.04-3.98 (m, 4H), 3.51-3.42 (m, 2H), 2.72 (t, 2H, J=6.8 Hz), 2.53 (t, 4H, J=7.6 Hz), 2.16-2.06 (m, 6H), 1.64-1.53 (m, 2H), 1.34-1.19 (m, 30H), 0.87 (t, 3H, J=7.2 Hz); 13C NMR (100 MHz CDCl$_3$): 173.22, 173.19, 173.10, 149.0, 147.5, 132.1, 121.3, 114.9, 114.5, 68.3, 68.1, 60.4, 40.5, 36.8, 35.2, 30.70, 30.68, 29.7, 29.62, 29.59, 29.5, 29.34, 29.32, 29.29, 25.7, 24.73, 24.70, 22.7, 14.2, 14.1.

Example of Synthesis of Intermediate 34

NaOH (66 mg) was added to a solution of ester 33 (58 mg; 0.095 mmol) in THF/MeOH/H2O=2/2/1 (5 ml): the reaction thus obtained was stirred for 18 hours before being cautiously adjusted to approximately pH 5 with successive additions of small amounts of 2N HCl (780 µl total). The reaction was then diluted with AcOEt (10 ml) and washed with H$_2$O (2×6 ml) and a saturated aqueous solution of NaCl (6 ml).

Lastly, the organic phase was dried over anhydrous Na2SO4, filtered, and concentrated under vacuum to dryness to yield diacid 34 as a white solid (49 mg, 91%). This appeared to be pure by NMR analysis, requiring no further purification in order to be used in the subsequent step.

1H NMR (400 MHz, CD$_3$OD): 6.82 (d, 1H, J=8.4 Hz), 6.78 (d, 1H, J=1.6 Hz), 6.71 (dd, 1H, J$_1$=8.4 Hz, J$_2$=2.0 Hz), 4.07-3.97 (m, 4H), 3.36 (t, 2H, J=7.2 Hz), 2.70 (t, 2H, J=7.6 Hz), 2.52 (t, 2H, J=7.6 Hz), 2.51 (t, 2H, 7.2 Hz), 2.16-2.01 (m, 6H), 1.60-1.50 (m, 2H), 1.32-1.17 (m, 24H), 0.86 (t, 3H, J=6.8 Hz); 13C NMR (100 MHz, CD$_3$OD): 176.6, 175.7, 149.7, 148.2, 133.3, 122.2, 115.84, 115.48, 69.22, 68.98, 41.5, 36.9, 35.6, 32.5, 31.1, 30.28, 30.26, 30.1, 29.995, 29,968, 29.863, 26.6, 25.4, 23.2, 14.3.

Example of Synthesis of Intermediate 35

EDC·HCl (51 mg; 0.27 mmol) first and 30 minutes later HOBt (26 mg; 0.31 mmol) were added to a solution of 34 (50 mg; 0.089 mmol) in anhydrous DMF (3 ml) under stirring and argon atmosphere. The reaction mixture was stirred for thirty minutes and then added dropwise via a syringe (over 5 minutes) to a solution of 16 (0.23 mol) and DIPEA (247 µl; 1.42 mmol) in anhydrous DMF (2 ml), kept under stirring at 0° C. (using an ice bath) under argon atmosphere.

The reaction mixture thus obtained was slowly allowed to warm to room temperature and then kept stirring for 24 hours before being diluted with EtOAc (20 ml) and washed sequentially with H$_2$O (2×10 ml) and a saturated aqueous solution of NaCl (10 ml). The organic phase is finally dried over anhydrous Na2SO4, filtered, and concentrated under vacuum to dryness to yield a crude product, which was purified by flash column chromatography (DCM/MeOH=1→3%) to afford intermediate 35 as a white solid (40 mg, 22%).

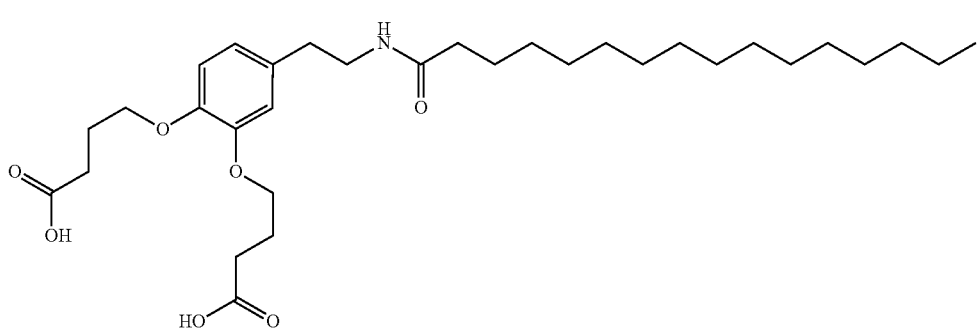

34

35

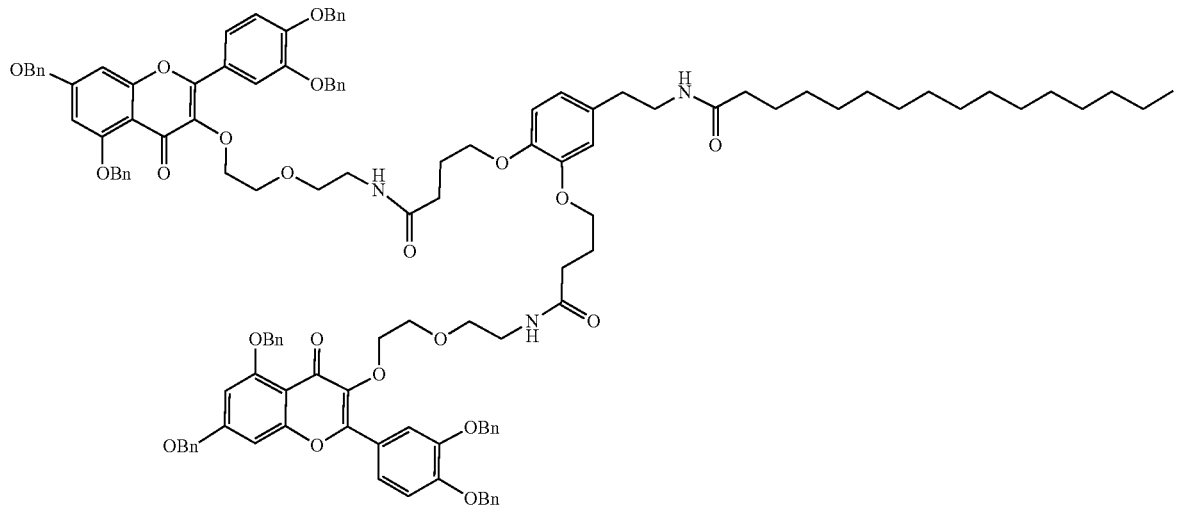

1H NMR (400 MHz, CD$_3$OD, TMS): 7.78, (m, 2H), 7.73 (dd, 2H, J$_1$=8.8 Hz, J$_2$=2.4 Hz), 7.56-7.51 (m, 4H), 7.49-7.24 (m, 36H), 7.03 (d, 2H, J=8.8), 6.74-6.60 (m, 3H), 6.56 (d, 2H, J=1.6 Hz), 6.45 (d, 2H, J=2.0 Hz), 5.24-5.17 (m, 12H), 5.09 (s, 4H), 4.07-4.0 (m, 4H), 3.89 (t, 2H, J=6.4 Hz), 3.86 (t, 2H, J=6.4 Hz), 3.63-3.57 (m, 4H), 3.44 (t, 4H, J=3.2 Hz), 3.39-3.34 (m, 2H), 3.34-3.28 (m, 4H), 2.65 (t, 2H, J=7.2 Hz), 2.36-2.27 (m, 4H), 2.09 (t, 2H, J=7.6 Hz), 2.03-1.93 (m, 4H), 1.61-1.50 (m, 2H), 1.33-1.18 (m, 24H), 0.87 (t, 3H, J=6.8); $^{13}$C NMR (100 MHz, CD$_3$OD): 174.7, 174.5, 174.0, 163.4, 159.9, 160.0, 159.0, 153.6, 151.4, 149.0, 148.5, 147.6, 140.2, 137.2, 136.9, 136.5, 135.9, 132.5, 129.0, 128.81, 128.79, 128.67, 128.29, 128.23, 128.05, 127.8, 127.7, 127.6, 127.0, 123.7, 123.2, 121.6, 116.0, 115.2, 114.8, 114.1, 109.9, 98.4, 94.3, 72.0, 71.5, 71.2, 71.0, 70.8, 70.2, 69.7, 68.8, 68.6, 40.9, 39.5, 36.7, 35.2, 32.70, 32.65, 32.1, 29.9, 29.7, 29.60, 29.56, 29.53, 26.1, 25.63, 25.58, 22.9, 14.2.

Example of Synthesis of Compound 36

Pd/C (18 mg) and a solution of compound 35 (33 mg; 0.016 mmol) in EtOH/THF=2/1 (4 ml) were added in this order to a 100 ml hydrogenation flask under argon atmosphere. The reaction mixture was subjected to four nitrogen/vacuum cycles before introducing an atmosphere of hydrogen (1 bar) into the flask. The reaction was kept under stirring at room temperature for 24 hours before being degassed under vacuum and filtered through 0.45 μm PTFE. The solution thus obtained was dried under vacuum to dryness: the crude product obtained as above was washed with an Et$_2$O/n-hexane=2.5/7.5 (2×5 ml) mixture and finally dried again in vacuo to yield 36 as a yellow solid (13 mg, 60%).

36

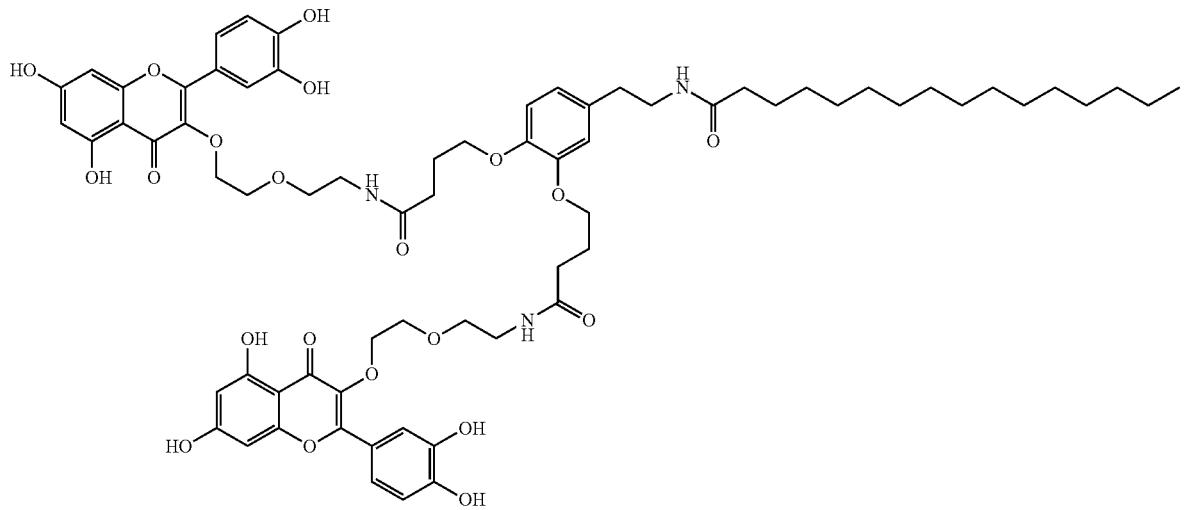

$^1$H NMR (400 MHz, CD$_3$OD/MeOH=4/1, TMS): 7.74 (d, 2H, J=1.6 Hz), 7.54 (dd, 2H, J$_1$=8.4 Hz, J$_2$=2.0 Hz), 6.96-6.88 (m, 2H) 6.75-6.67 (m, 2H), 6.62 (dd, 1H, J$_1$=8.0 Hz, J$_2$=1.2 Hz), 6.39 (d, 2H, J=1.2 Hz), 6.25 (dd, 2H, J$_1$=4.4 Hz, J$_2$=1.6 Hz), 4.08-4.01 (m, 4H), 3.98-3.88 (m, 4H), 3.73-3.67 (m, 4H), 3.57-3.49 (m, 4H), 3.46-3.39 (m, 4H), 3.39-3.35 (m, 2H), 2.65 (t, 2H, J=7.2 Hz), 2.41 (t, 4H, J=7.2 Hz), 2.15 (t, 2H, J=8.0 Hz), 2.11-2.01 (m, 4H), 1.64-1.52 (m, 2H), 1.37-1.20 (m, 24H), 0.89, (t, 3H, J=7.2 Hz);

$^{13}$C NMR (100 MHz, CD$_3$OD/MeOH=4/1, TMS): 178.9, 175.2, 174.6, 164.5, 161.8, 157.3, 157.1, 149.0, 148.6, 147.6, 145.0, 137.4, 132.6, 125.7, 122.2, 121.8, 121.7, 116.3, 115.5, 115.2, 114.8, 105.3, 99.3, 94.3, 71.8, 70.2, 69.9, 68.8, 68.7, 57.9, 41.1, 39.7, 36.8, 35.3, 33.0, 30.5, 30.0, 29.9, 29.8, 29.7, 29.62, 29.57, 26.2, 25.8, 22.9, 18.0, 14.2.

The compound comprises molecules (1) which may be connected to each other resulting, in particular, in homo- or hetero-dimers, trimers and tetramers according to formula (I), as described above with the exception of R1 or R1' which consists of a Linker L.

The formula (I) thus modified is designated as formula (II), and is preferably as follows:

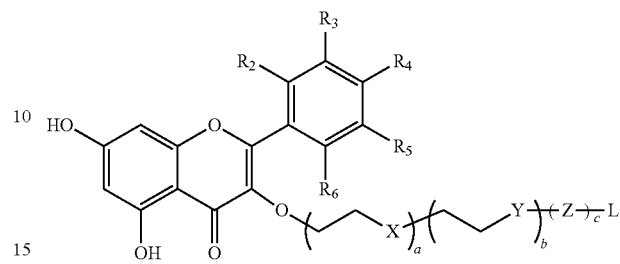

(II)

X, Y, Z and a, b, c are as previously defined.

The Linker L is more preferably selected from the compounds listed below.

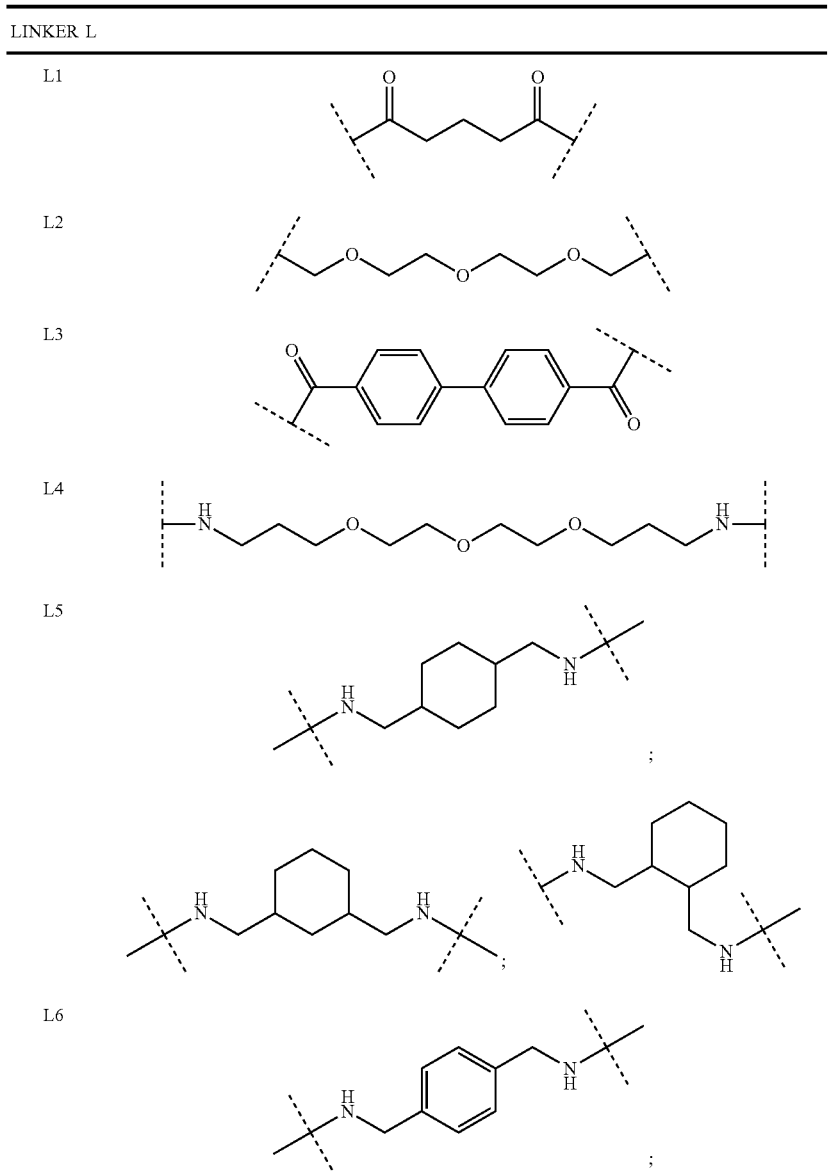

| LINKER L | |
|---|---|
| L1 | |
| L2 | |
| L3 | |
| L4 | |
| L5 | |
| L6 | |

| LINKER L | |
|---|---|
| | 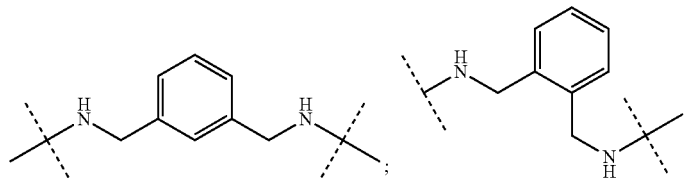 |
| L7 | 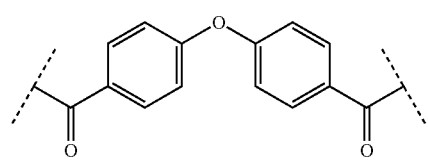 |
| L8 | 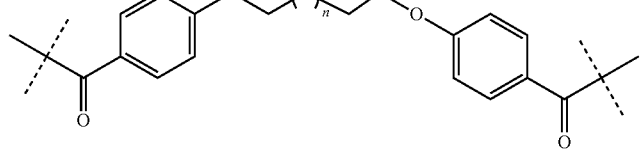
n = 0-8 |
| L9 | 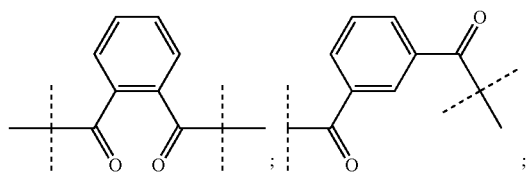 |
| L11 | 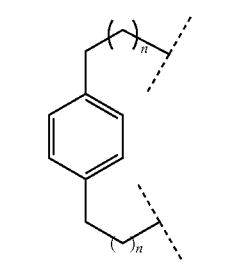
n = 1-6, each independently |

| LINKER L | |
|---|---|
| L12 | 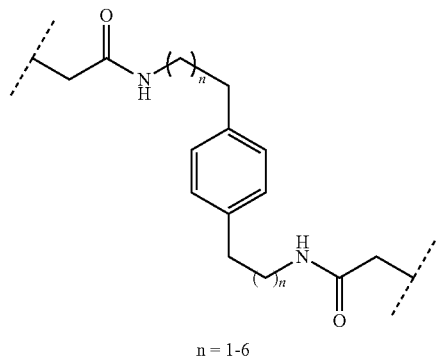<br>n = 1-6 |
| L13 | 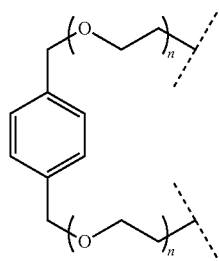<br>n = 1-3, each independently |
| L14 | 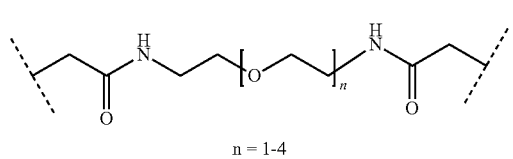<br>n = 1-4 |
| L15 | 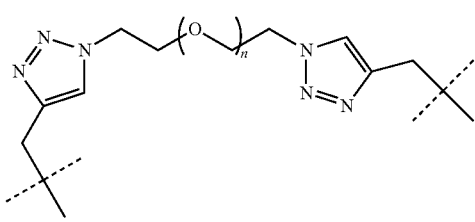<br>n = 1-4, each independently |
| L16 | 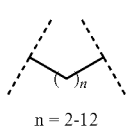<br>n = 2-12 |
| L17 | 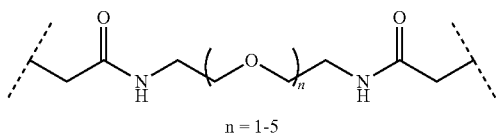<br>n = 1-5 |
| L18 | 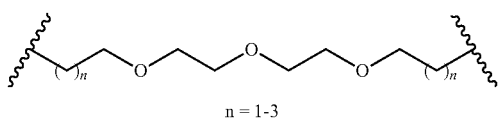<br>n = 1-3 |

| LINKER L | |
|---|---|
| L19 | 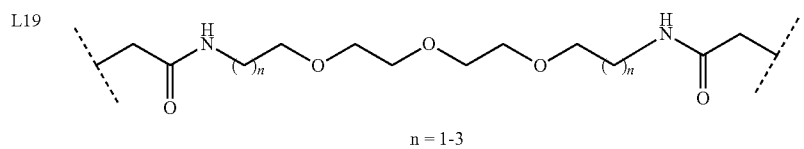<br>n = 1-3 |
| L20 | 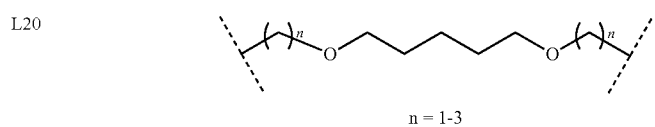<br>n = 1-3 |
| L21 | 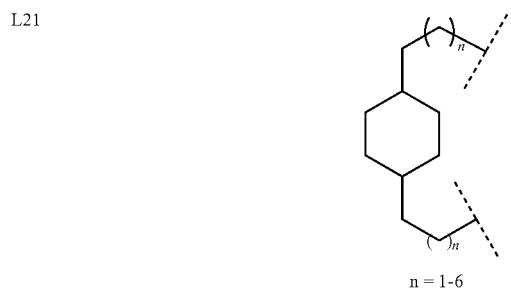<br>n = 1-6 |
| L22 | 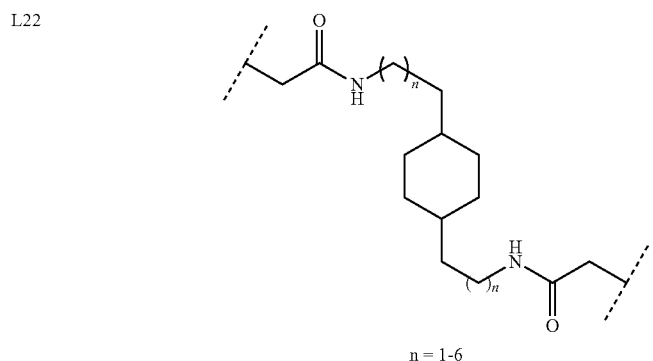<br>n = 1-6 |
| L23 | 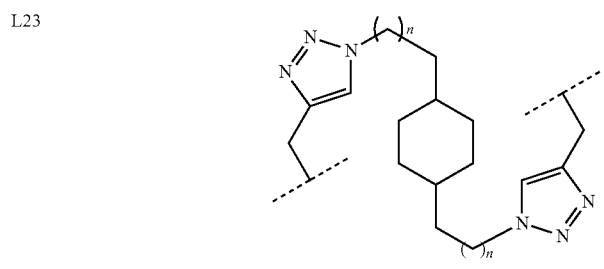<br>n = 1-6, each independently |
| L24 | 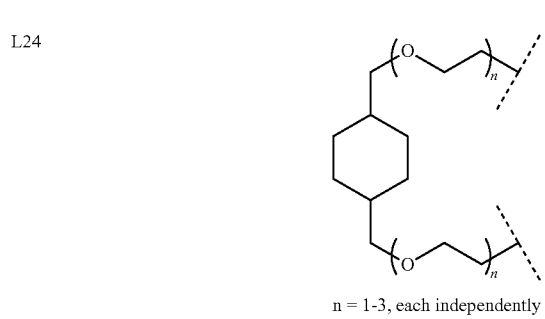<br>n = 1-3, each independently |

| LINKER L | |
|---|---|
| L25 | 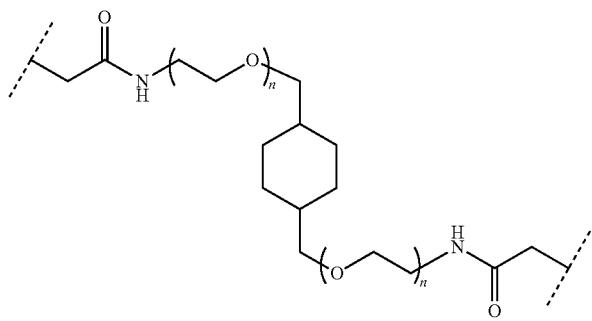<br>n = 1-3, each independently |
| L26 | 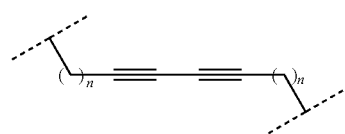<br>n = 1-6, each independently |
| L27 | 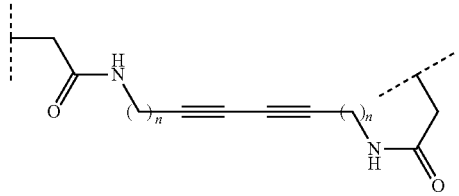<br>n = 1-6, each independently |
| L28 | 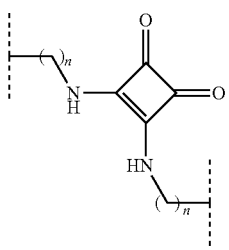<br>n = 1-6, each independently |
| L29 | 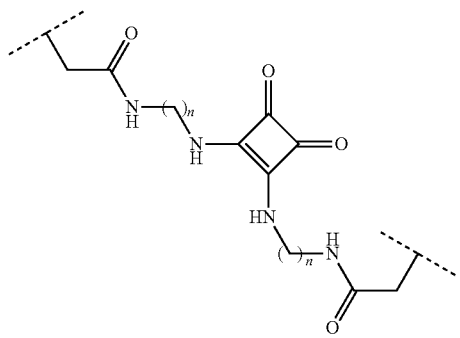<br>n = 1-6, each independently |
| L30 | 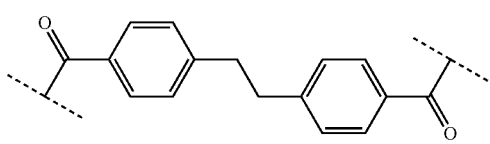 |

| LINKER L | |
|---|---|
| L31 | 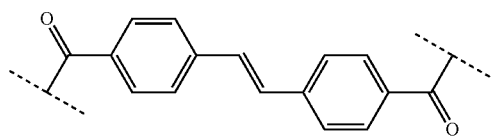 |
| L32 | 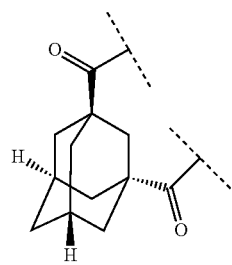 |
| L33 | 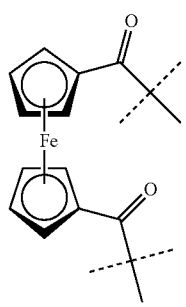 |
| L34 | 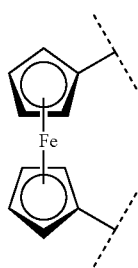 |
| L35 | 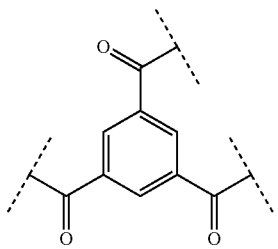 |
| L36 | 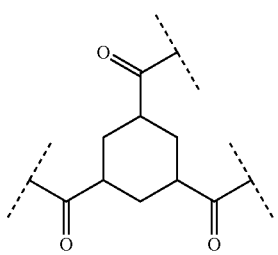 |

| LINKER L | |
|---|---|
| L37 | 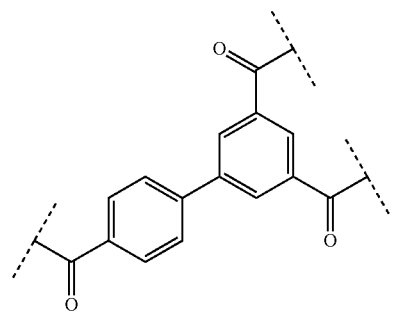 |
| L38 | 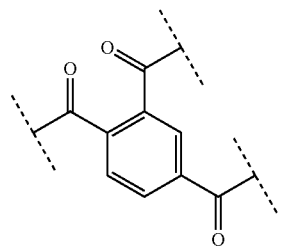 |
| L39 | 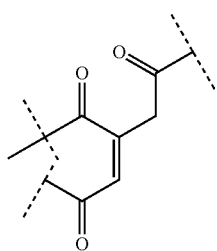 |
| L40 | 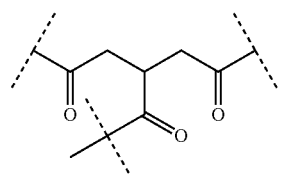 |
| L41 | 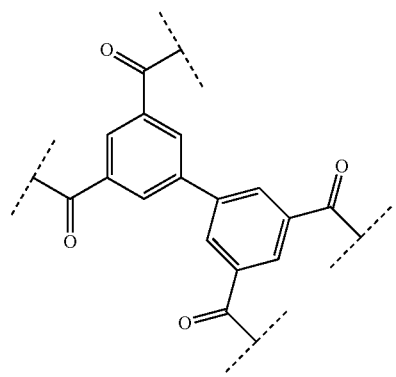 |

| LINKER L |
|---|
| L42 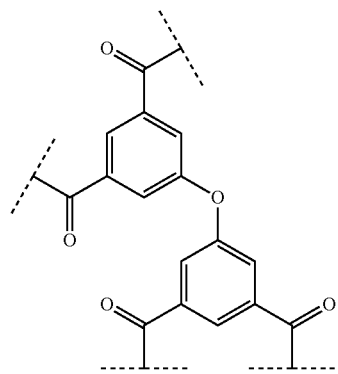 |
| L43 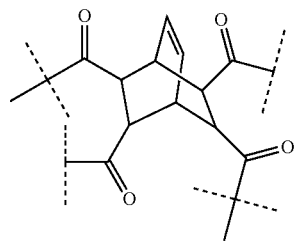 |
| L44 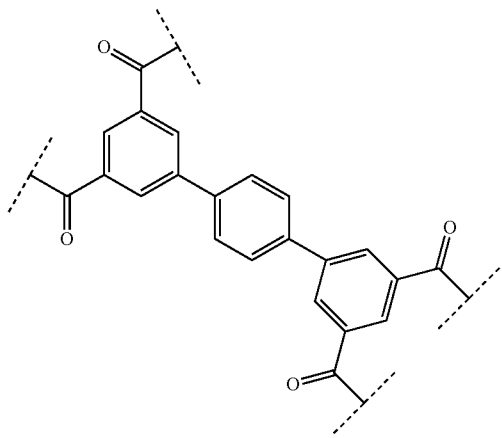 |
| L45 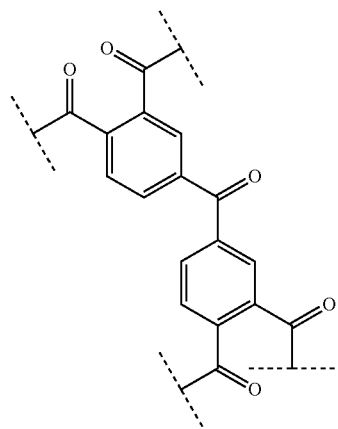 |

| LINKER L |
|---|
| L46 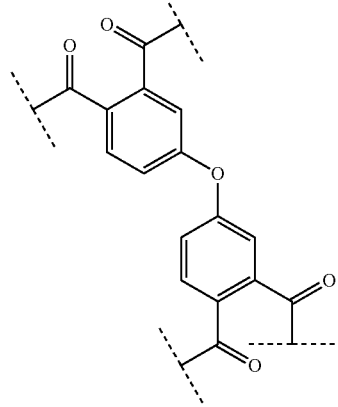 |
| L47 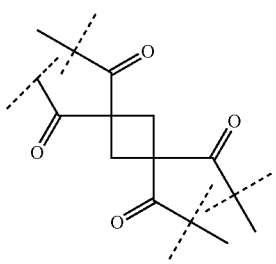 |
| L48 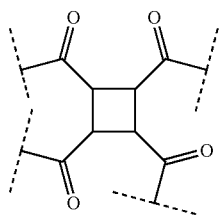 |
| L49 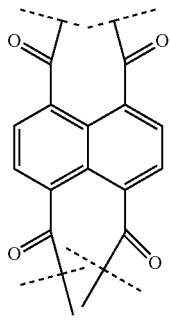 |
| L50 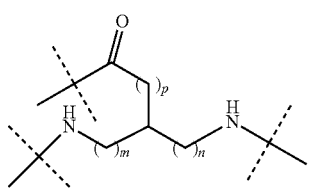<br>n, m, p = 0-6; each independently |

| LINKER L | |
|---|---|
| L51 | 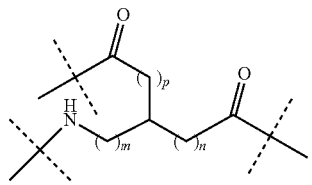
n, m, p = 0-6; each independently |
| L52 | 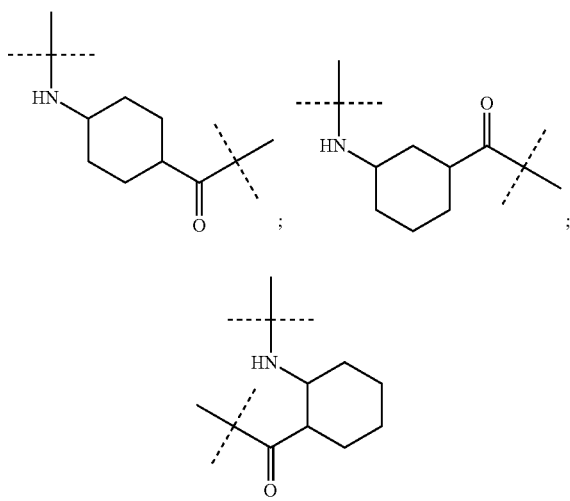 |
| L53 | 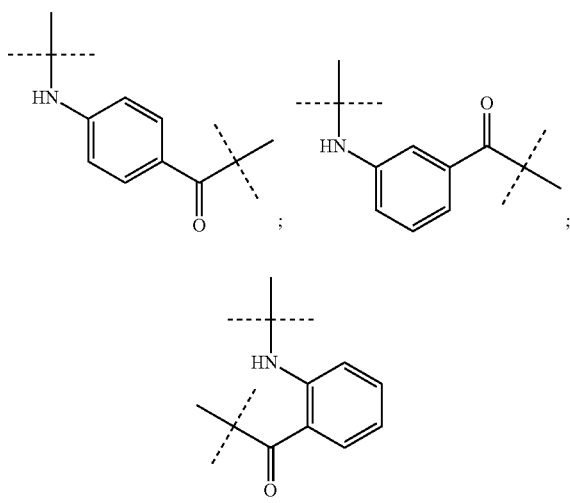 |
| L54 | 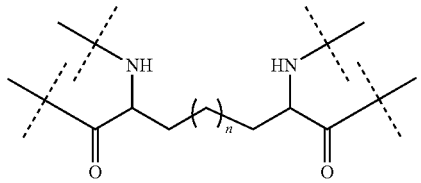
n = 0, 5 |

| LINKER L |
|---|
| L55 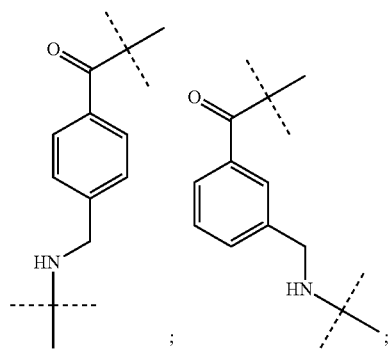 |
| 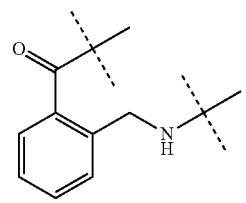 |
| L56 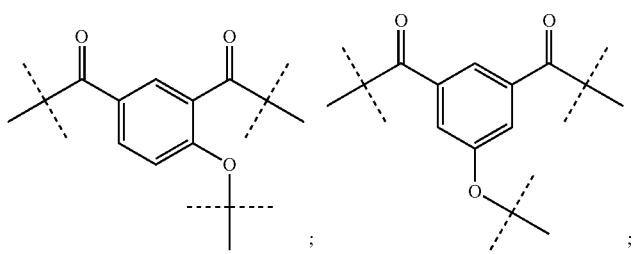 |
| 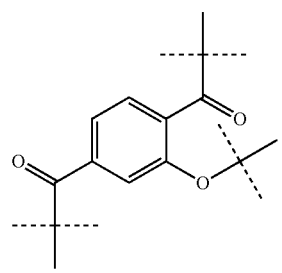 |
| L57 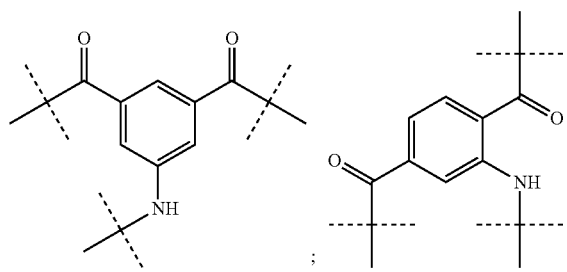 |

| LINKER L |
|---|
| L58 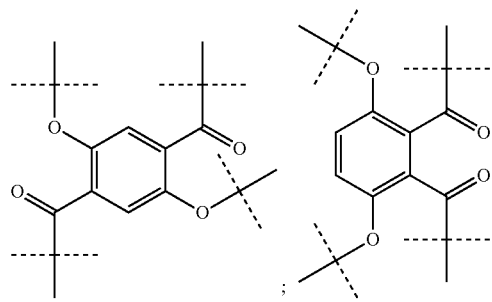 |
| L59 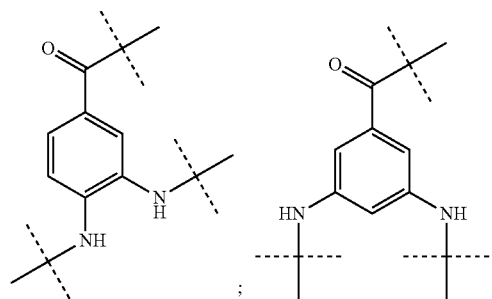 |
| L60 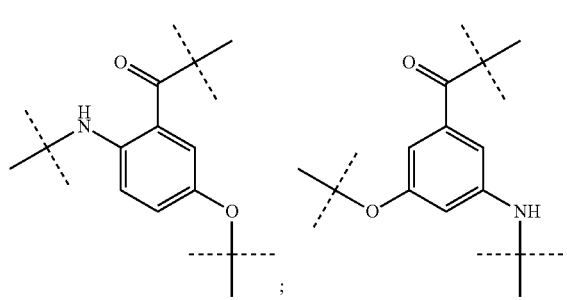 |
| L61 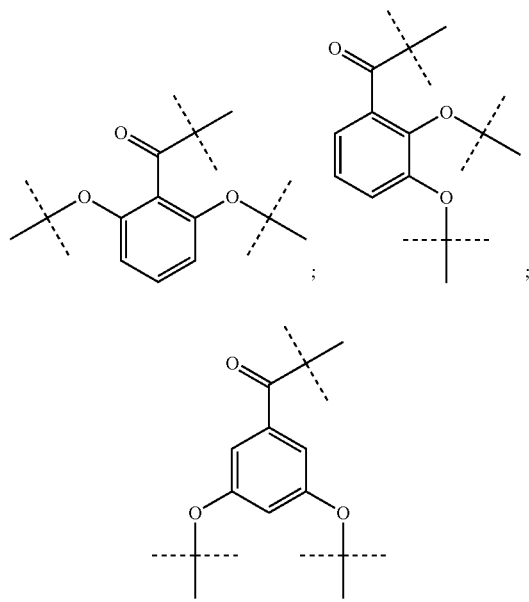 |

| LINKER L |
|---|
| L62 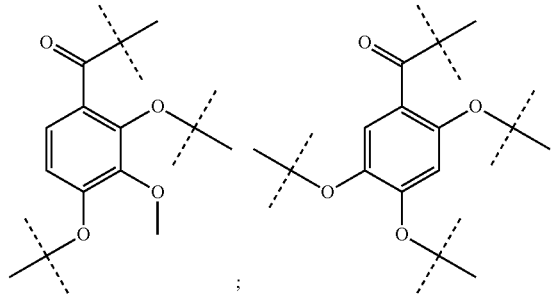 |
| L63 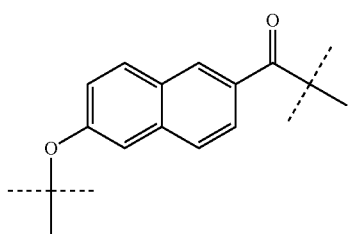 |
| L64 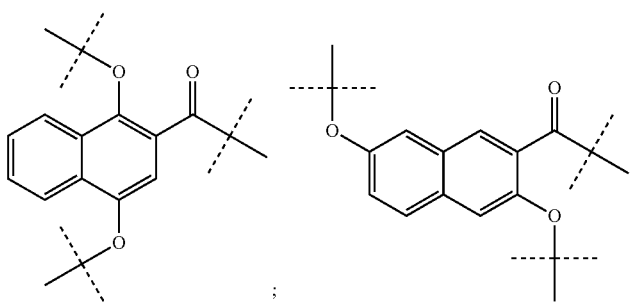 |
| L65 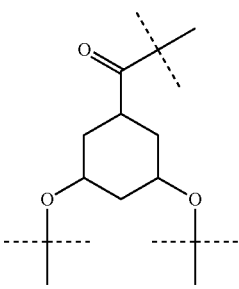 |
| L66 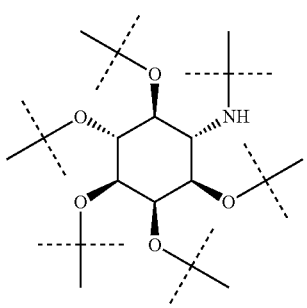 |

| LINKER L | |
|---|---|
| L67 | 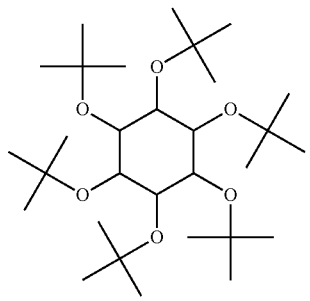 |
| L68 | 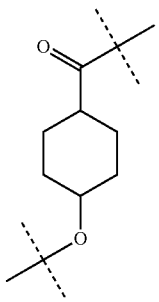 |
| L69 | 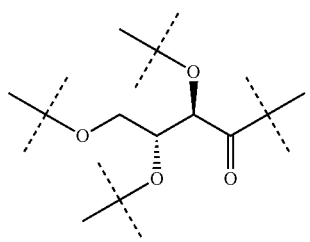 |
| L70 | 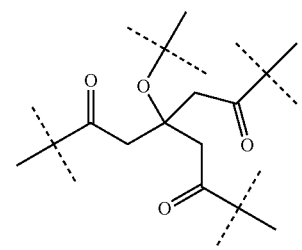 |
| L71 | 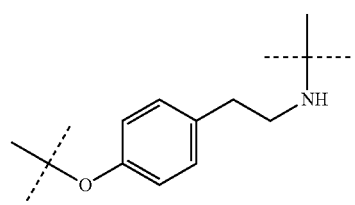 |
| L72 | 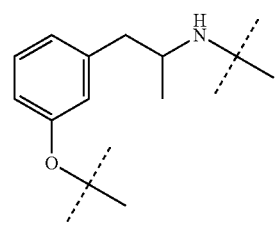 |

-continued
| LINKER L | |
|---|---|
| L73 | 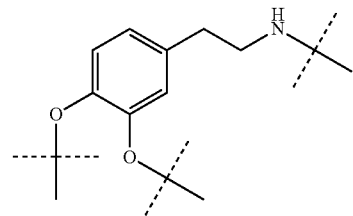 |
| L74 | 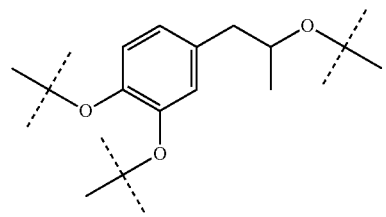 |
| L75 | 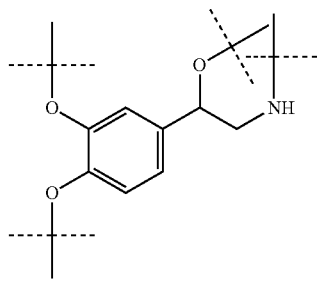 |
| L76 | 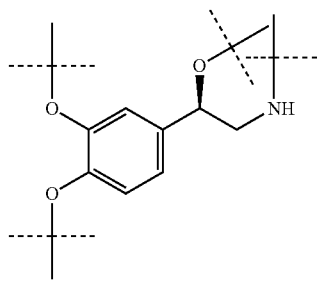 |
| L77 | 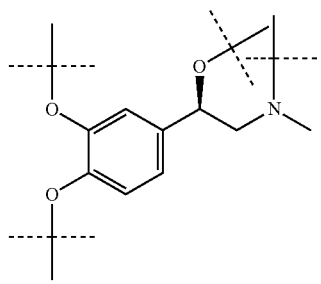 |
| L78 | 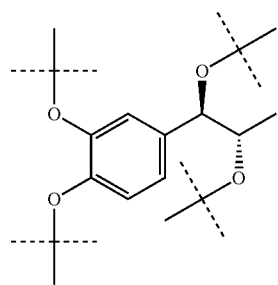 |

| LINKER L | |
|---|---|
| L79 | 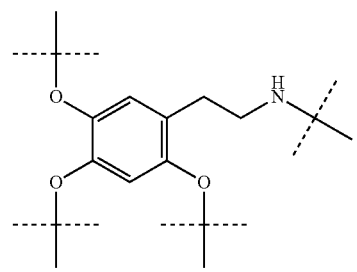 |
| L80 | 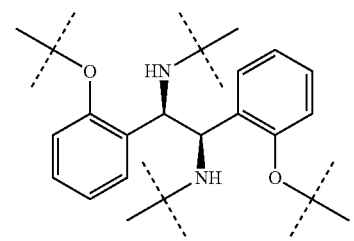 |
| L81 | 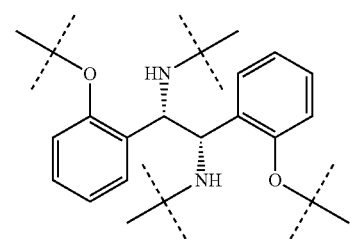 |
| L82 | 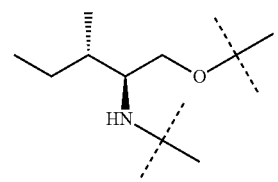 |
| L83 | 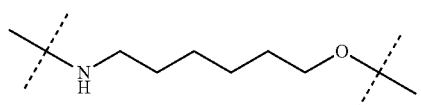 |
| L84 | 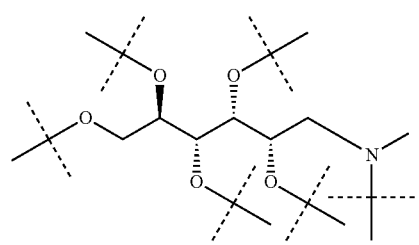 |
| L85 | 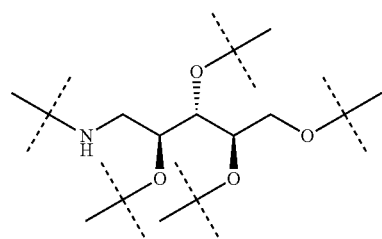 |

| LINKER L | |
|---|---|
| L86 | 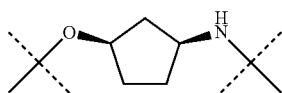 |
| L87 | 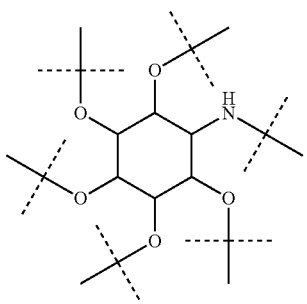 |
| L88 | 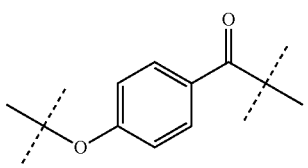 |
| L89 | 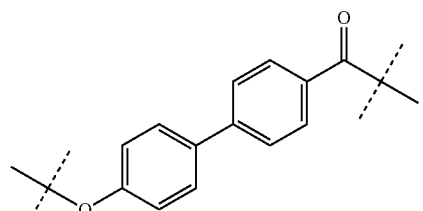 |
| L90 | 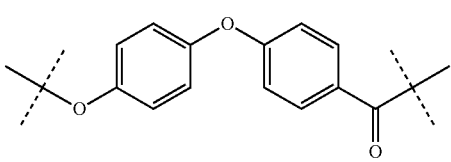 |
Most of the linkers shown in the table are known and commercially available. Any other linker can be easily prepared according to known methods.
1. According to the general formula (I) or (II), the compound may have the following general structures (III), (IV), (V), (VI), (VII), (VIII), (IX), (X) and (XI):
(III)
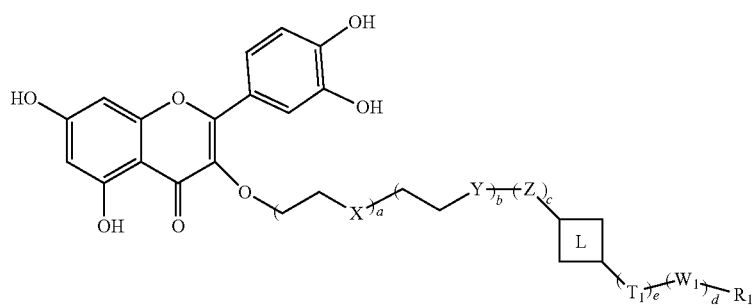

-continued
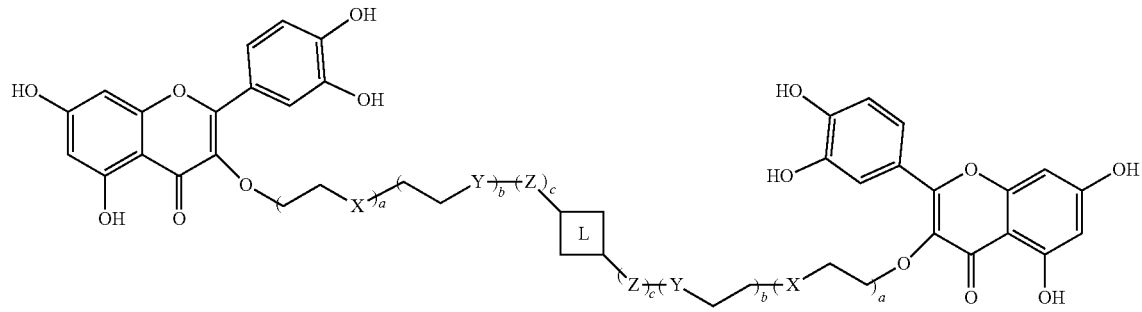
(IV)
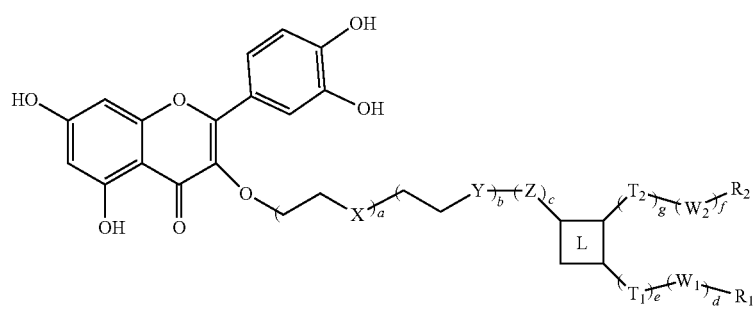
(V)
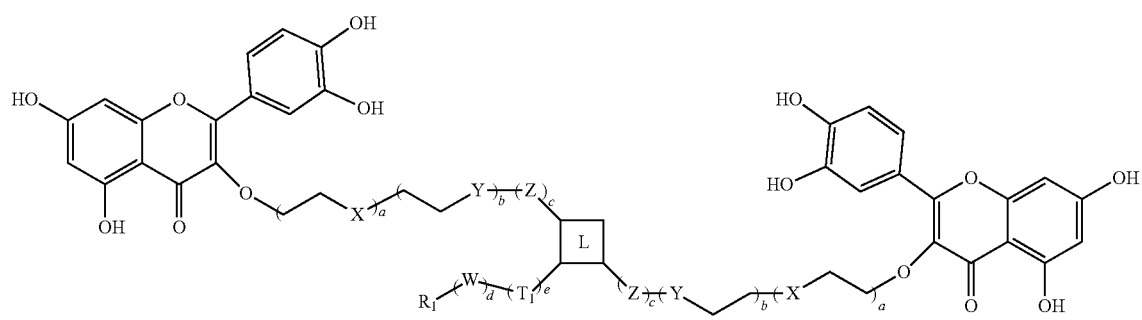
(VI)
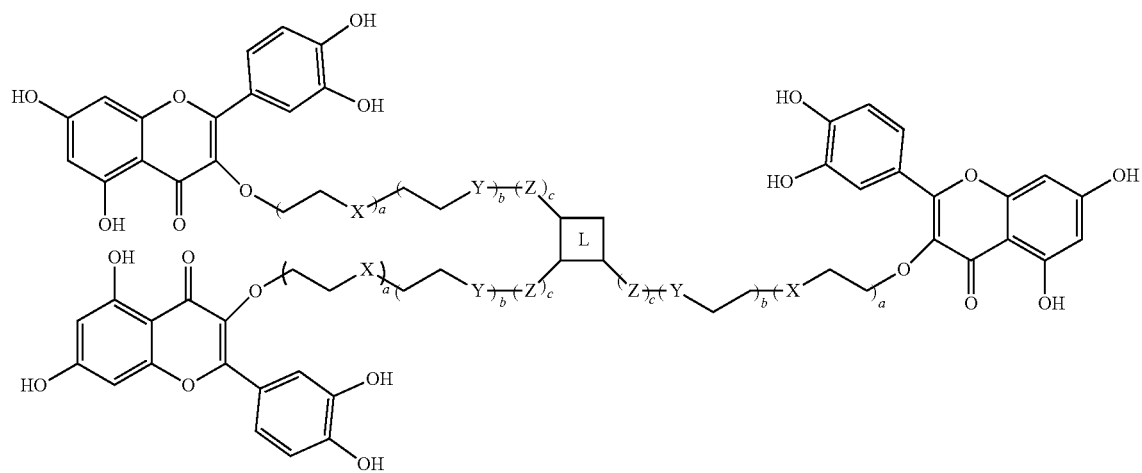
(VII)

(VIII)
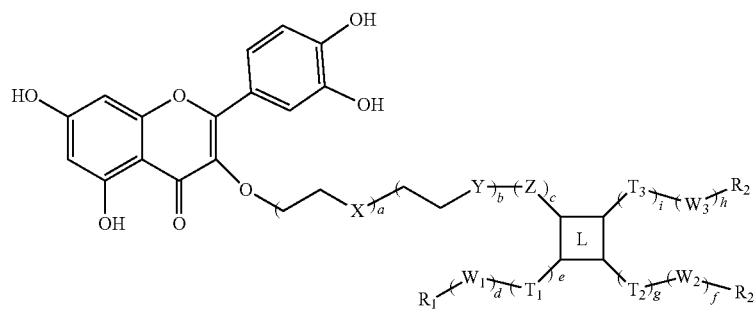
(IX)
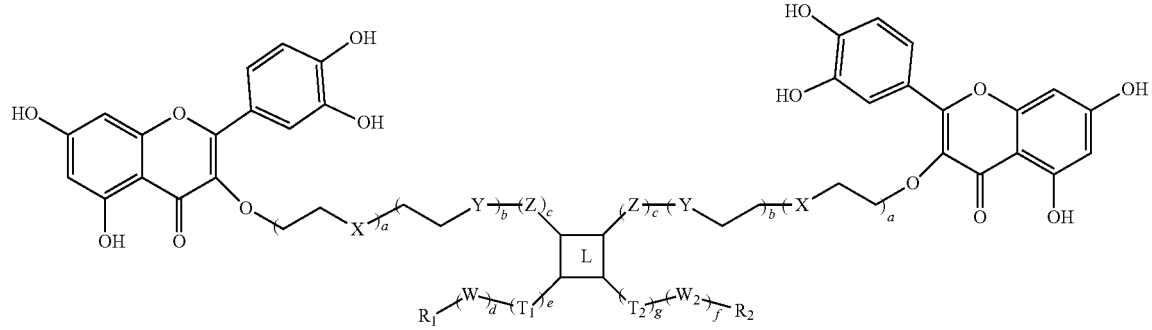
(X)
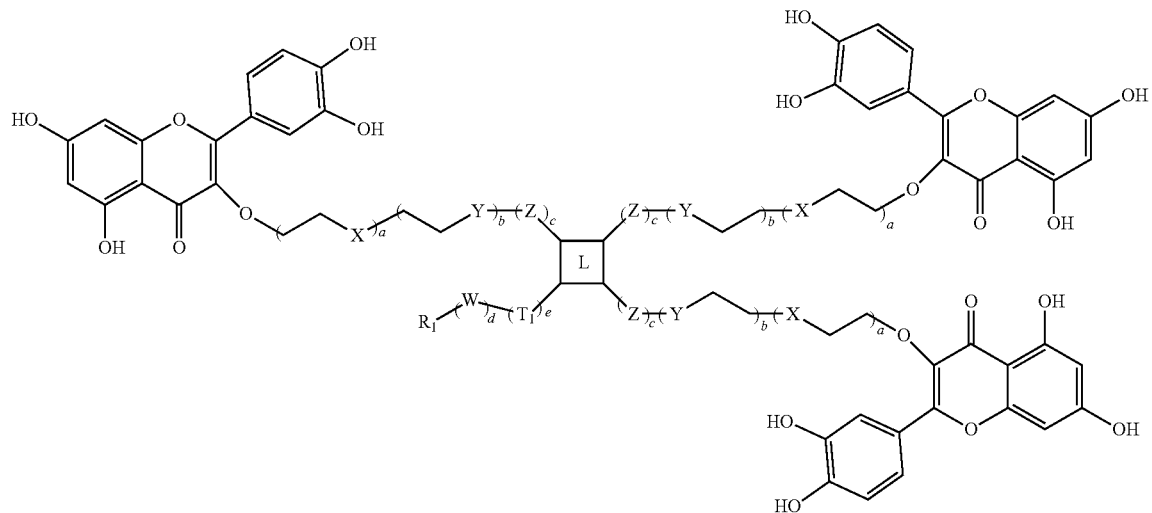

-continued

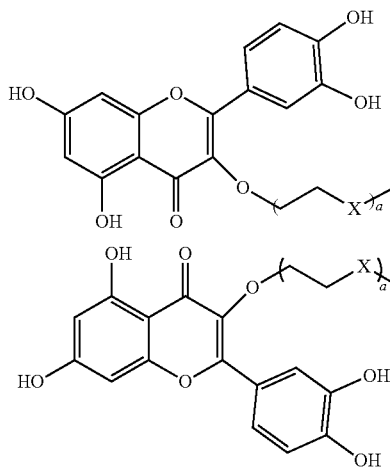
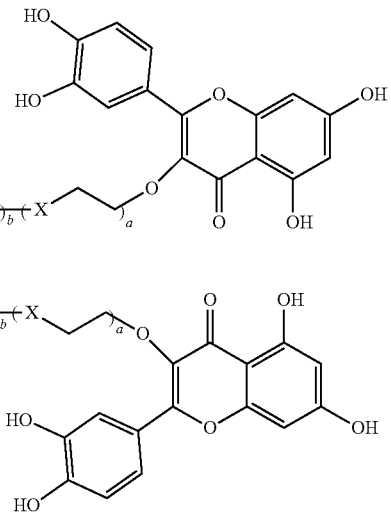

(XI)

where d, e, f, g, h, i each range from 0 to 12, where $T_1$-$T_3$, $W_1$-$W_3$ are each independently selected from: $CH_2$, O, N(R1), S, NH, SO, $SO_2$, OC(O), CO, NHC(O), C(O)NH, NH—C(O)—NH, NH—C(S)—NH.

2. According to the general formula (I), the compound may have the following general structures (XII), (XIII), (XIV) and (XV):

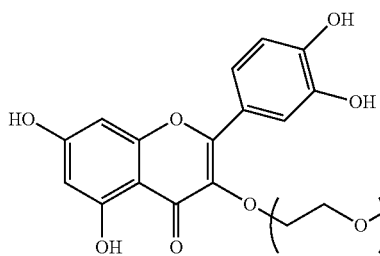

(XII)

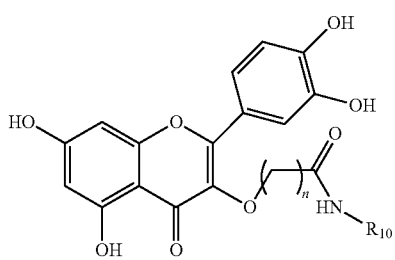

(XIII)

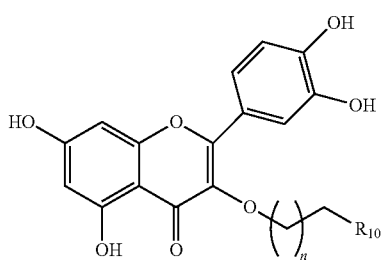

(XIV)

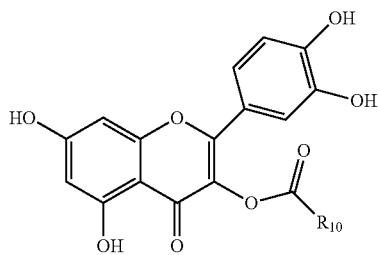

(XV)

where n can independently take a value between 0 and 12.

$R_{10}$, could be independently, but not exclusively and in possible combinations of the following:

Hydrogen;

$C_{1-24}$ alkyl or heteroalkyl, $C_{1-24}$ alkenyl or heteroalkenyl; $C_{1-24}$ alkynyl or heteroalkynyl An acyl residue of a saturated/unsaturated/polyunsaturated fatty acid, of either synthetic or natural origin A residue that may be preferably, but not exclusively selected from those shown in the table below:

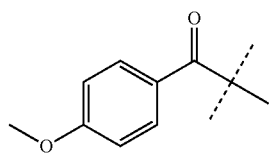

L91

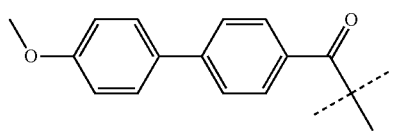

L92

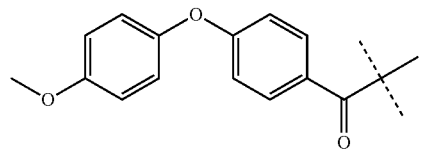
L93
Below are some examples of the compounds according to the invention, whose technical effect has been proved.

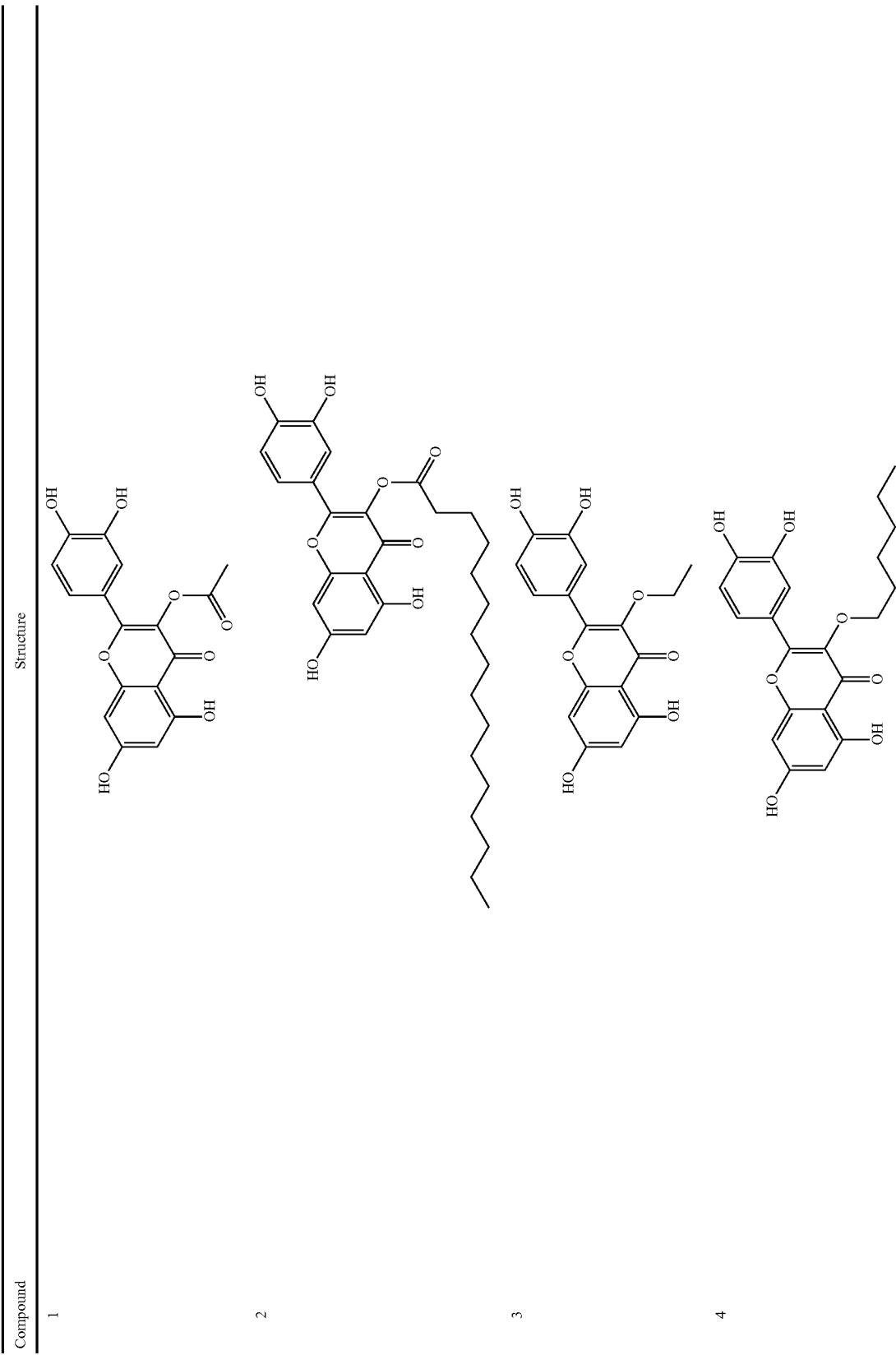

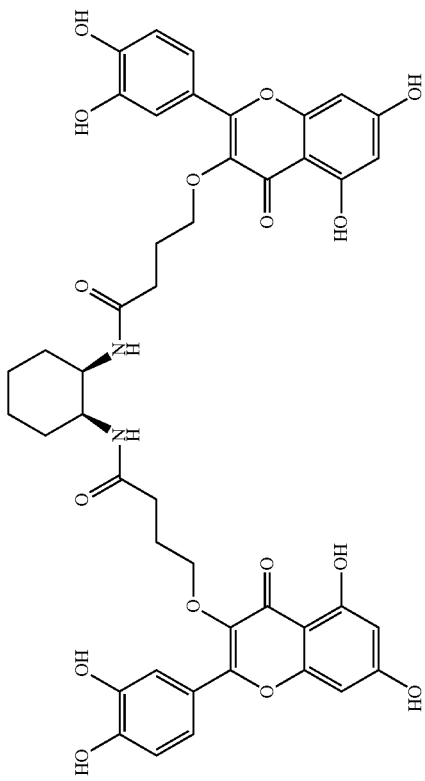

| Compound | Structure |
|---|---|
| 15b | *-continued* (structure) |
| 15c | (structure) |

| Compound | Structure |
|---|---|
| 15d | (chemical structure) |
| 19a | (chemical structure) |
| 19b | (chemical structure) |

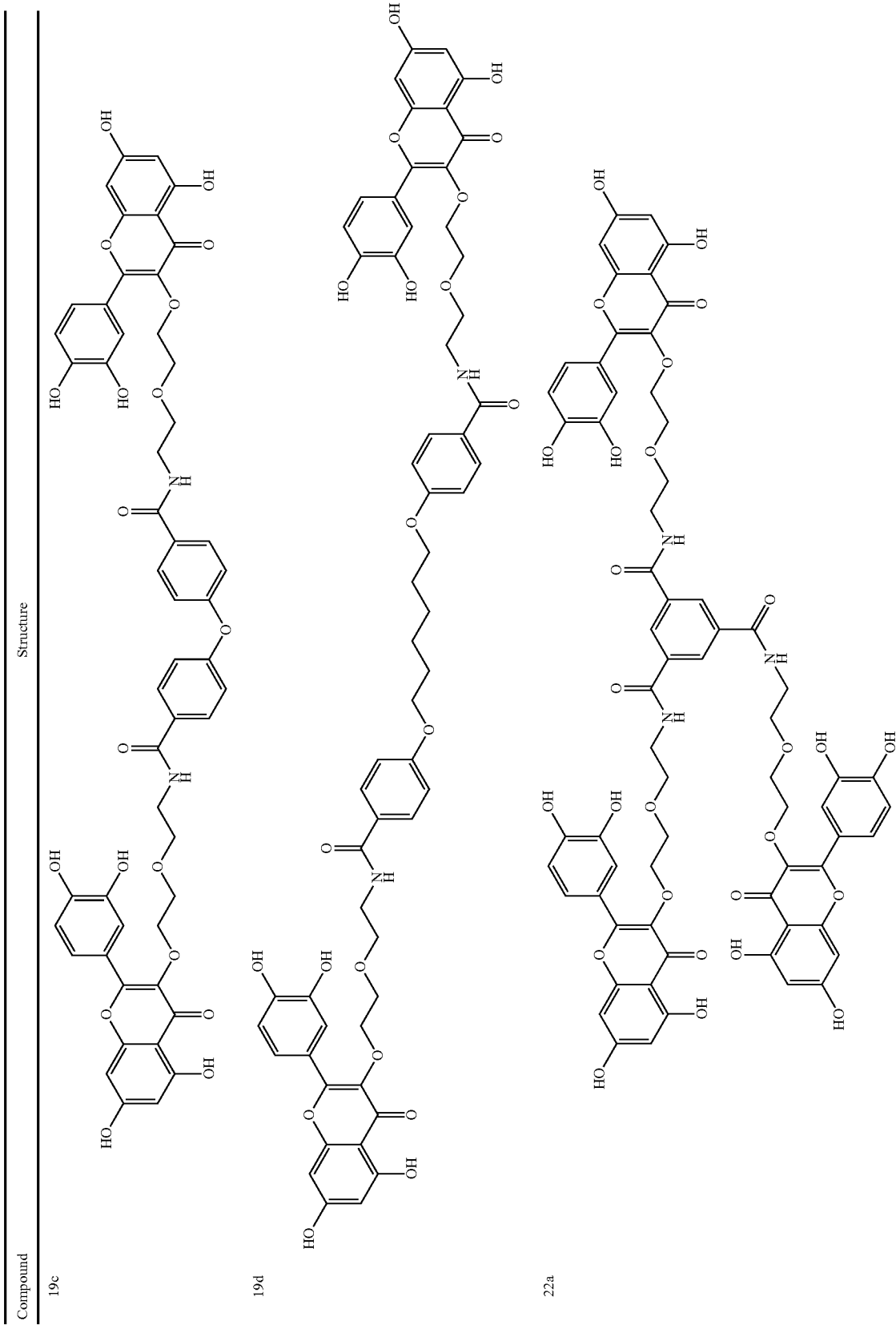

| Compound | Structure |
|---|---|
| 22b | 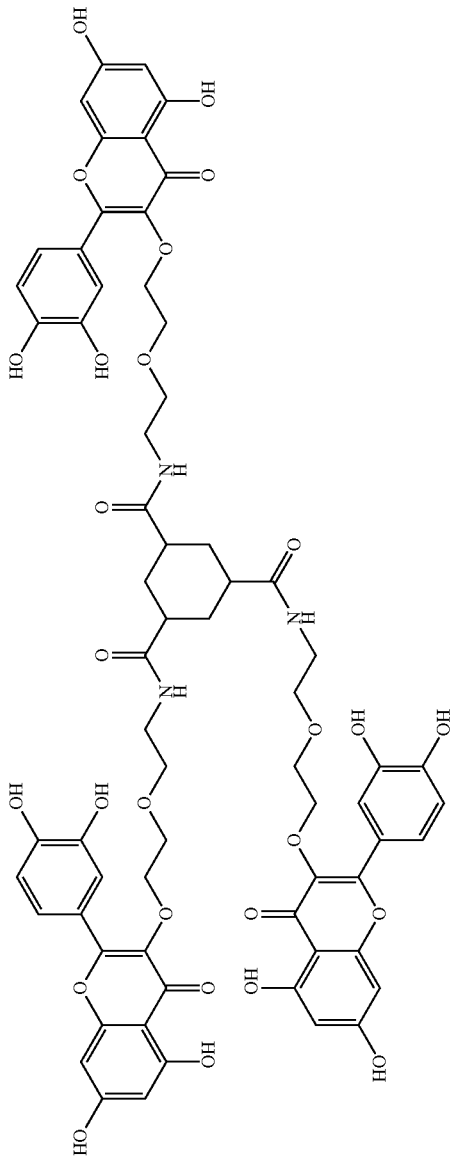 |
| 25a | 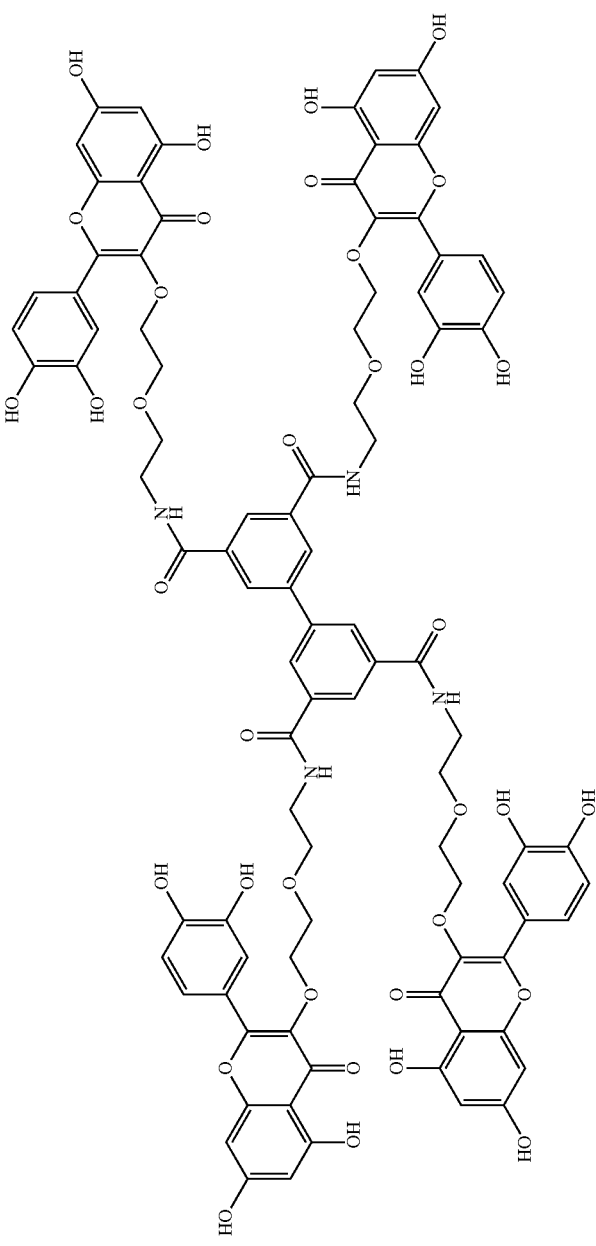 |

-continued

| Compound | Structure |
|---|---|
| 26 | (quercetin 3-O-(2-hydroxyethoxy)ethyl ether structure) |
| 27 | (quercetin 3-O-(2-aminoethoxy)ethyl ether structure) |
| 29a | (quercetin 3-O-ethoxyethyl-NH-C(O)-long alkyl chain structure) |
| 29b | (quercetin 3-O-ethoxyethyl-NH-C(O)-longer alkyl chain structure) |

-continued
| Compound | Structure |
|---|---|
| 29c | 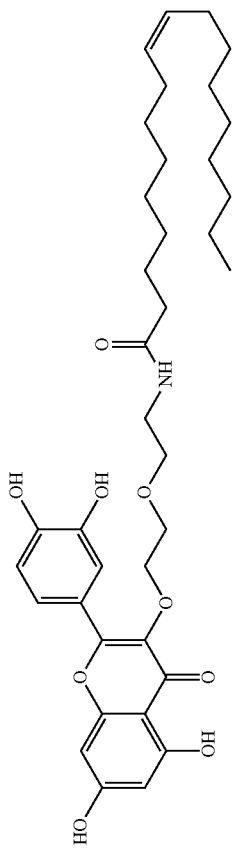 |
| 29d | 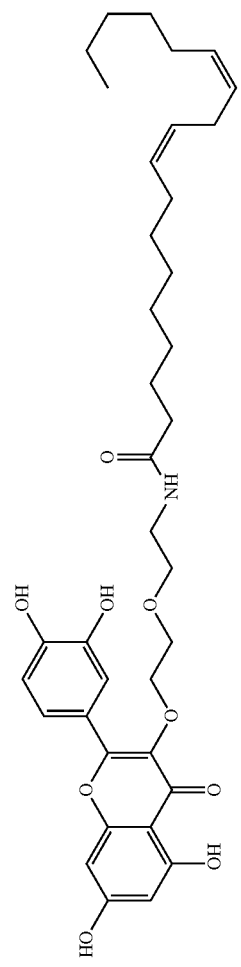 |
| 29e | 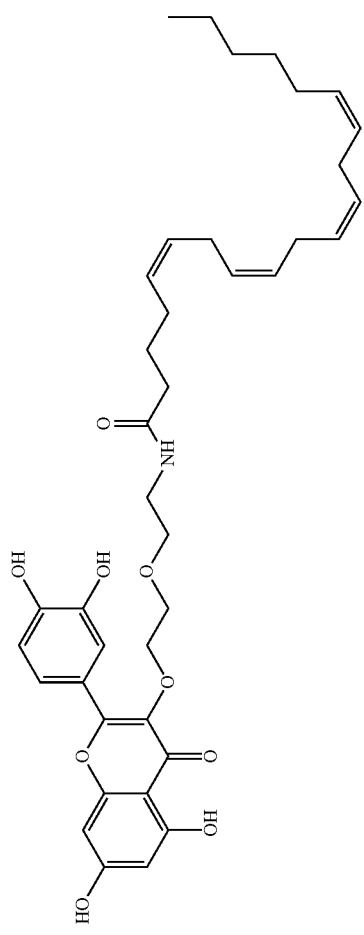 |

-continued

| Compound | Structure |
|---|---|
| 29f | (quercetin-like flavonoid with 3-O-CH₂CH₂-NH-C(O)- linked to polyunsaturated fatty acid chain) |
| 29g | (quercetin-like flavonoid with 3-O-CH₂CH₂-NH-C(O)- linked to 4'-methoxybiphenyl-4-carbonyl) |

-continued
| Compound | Structure |
|---|---|
| 36 | 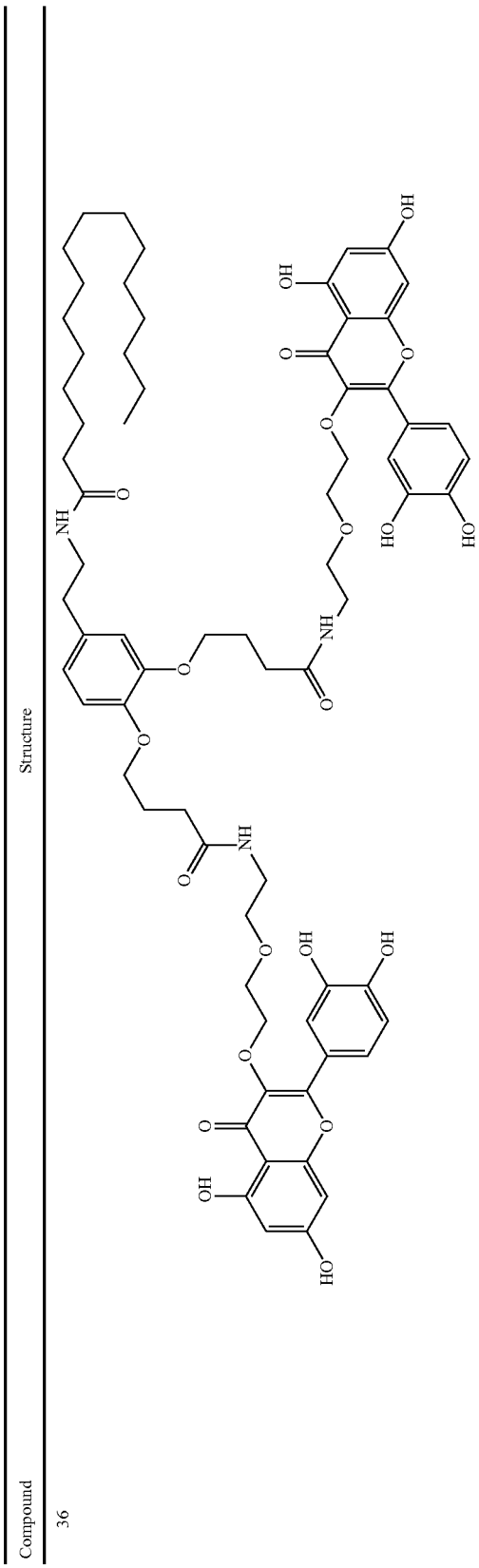 |

Said compound can also be made by a method described in patent application WO-A-99/66062 by the National Research Council and Felice Rao's Rao-Erbe. In this patent it is described from page 3 line 8 to page 9 line 22, which are incorporated herein by reference. However, other similar methods may be used.

The invention therefore also defines a new method for treating the aforementioned tumours with the aforementioned compound and a new method for manufacturing drugs for treating the aforementioned tumours.

The compound according to the invention, and in particular the synthetic quercetin derivatives described and illustrated herein were investigated in vitro by using human tumour cells and assessing their impact on the tumour proliferative capacity, with regard to the tumours described above. In particular, the following human tumour cell lines were assessed experimentally: 1) HCT116, colon adenocarcinoma cells; 2) H1299, lung adenocarcinoma cells; 3) A375, melanoma cells, and 4) A431, squamous skin cell carcinoma; 5) 786-0, renal carcinoma cells; 6) PC3, prostate carcinoma cells; 7) BT549, mammary carcinoma cells; 8) CAL27, tongue carcinoma cells (belonging to the head-and-neck carcinomas); 9) HepG2, hepatocellular carcinoma cells; 10) PANC-1, pancreas carcinoma cells; 11) T24, bladder carcinoma cells; 12) OVCAR-3, ovarian carcinoma cells. In addition, a normal human cell line, WS1 (skin fibroblasts) was also treated with the novel synthetic compounds.

Cell proliferation was quantified by the crystal violet method with a spectrophotometer. In short, after acquiring serial images (0, 24 and 48 hrs) with the EVOS XL Cell Imaging System microscope (Thermo Fisher Scientific), the cells imaged at 48 hrs were fixed with paraformaldehyde (4%) and stained with Crystal Violet (1%). Then, the specific absorbance ($\lambda=590$ nm) at 48 hrs was measured with a spectrophotometer (Infinite®200 PRO, Tecan). Data analysis was carried out by using ad-hoc Excel files for graphical representation and statistical processing (t-test). Moreover, the results obtained with Crystal Violet were confirmed by using another cell proliferation assessment method based on the real time cellular analyzer XCELLigence RTCA DP (ACEA Biosciences, Inc.). This tool allows cell growth to be monitored from electrical impedance-derived quantitative values (the so-called Cell Index) measured by tiny electrodes located at the base of the culture wells. Proliferation is monitored for several days (5-7) by setting a Cell Index per minute measure on the instrument. The data are analysed by processing various parameters calculated by the dedicated software, such as the cell duplication time, the slope and the Max Cell Index.

The results show that, compared to the controls (treated with the solvent-vehicle alone), the compounds according to the invention, and in particular the various compounds described and illustrated herein significantly inhibit the proliferation of the colon (HCT116) and lung (H1299) adenocarcinoma cells, the melanoma cells (A375), and the skin squamous carcinoma (A431), renal carcinoma (786-0), prostate carcinoma (PC3), mammary carcinoma (BT549), tongue carcinoma (CAL27), hepatocellular carcinoma (HepG2), pancreas carcinoma (PANC-1), bladder carcinoma (T24) and ovarian carcinoma (OVCAR-3) cells.

Tumour cell apoptosis was quantified by the acridine orange/ethidium bromide (AO/EB) method and by using a fluorescence microscope and image-J. In short, after treatment with the test compounds (2 hrs), the tumour cells were placed in contact with an AO/EB solution (in sterile $H_2O$) and photographed with a fluorescence microscope (Leica) by using the $\geq 20\times$ objective (so as to distinguish the morphology of cell nuclei). In this way, the living cells are labelled with AO and emit fluorescence in the green channel, while the necrotic cells, which have undergone the rupture of the plasma membrane, are permeable to EB and emit fluorescence in the red channel. In contrast, apoptotic cells are permeable to both AO and EB, and as a consequence of the colocalization of the two fluorescences appear yellow-orange when the two individual microscope-acquired fluorescences are superimposed by using the editing program Image J. The objective quantification of the colocalization areas (apoptotic cells) and the non-colocalization areas (living or necrotic cells) was carried out on a number of cells $\geq 300$/condition through the use of Apoptosis Correlator (ImageJ plug-in) and shown as the percentage of living (green), necrotic (red) or apoptotic (yellow-orange) tumour cells. Data analysis was carried out by using GraphPad Prism 6 for graphical representation and statistical processing (2-way ANOVA test).

The compounds according to the invention were compared with the simple quercetin. In these comparisons, the dose-response curves showed that the compounds according to the invention are significantly more powerful and effective in inhibiting proliferation and inducing apoptosis of all tested tumour cells of the type described above.

In addition, compared to the controls (treated with the solvent-vehicle alone), the compounds according to the invention induce cell death and apoptosis of colon adenocarcinoma (HCT116) and melanoma (A375) cells in a very short time (<2 hrs).

Highly importantly, the compounds according to the invention, and in particular all the compounds described and illustrated herein were shown to be significantly less effective in inhibiting proliferation and incapable of inducing apoptosis in normal human cells (WS1 skin fibroblasts), compared to tumour cells, indicating the possibility of a clinical selectivity of the toxic action of the compounds object of this patent, which may only be focused on the tumour while preserving the healthy cells of the patient. Progression through the tumour cell cycle was assessed by the propidium iodide method and quantification of the cell DNA content with a cytofluorimeter. Briefly, after treatment (in duplicate) with the test compounds (24 hrs), the tumour cells were washed (with PBS), detached with trypsin-EDTA and pelleted by centrifugation (125 g for 6 min). The cells were then fixed in ethanol (70%) and stored in the freezer (−20° C.) for 1-3 days. After further washing (PBS) and treatment with RNAse (50 ug/ml), the cells were contacted (on ice in the dark; 30 min) with propidium iodide (50 µg/ml). FL2 and FL3 cytofluorimeter readings analysed approximately 50,000 cells (1 µl/second) per sample. Statistical analysis and graphical representation were performed by using t-tests and preset Excel property files.

Intracellular ROS levels were measured in tumour cells by using the probe 2,7-dichlorodihydrofluorescein diacetate (DCFH2-DA) and a fluorescence spectrophotometer. DCFH2-DA diffuses readily through the cell membrane into the cytosolic space of the cell where it is hydrolyzed by intracellular esterases into the non-permeable DCFH2 product. DCFH2 oxidation by intracellular ROS (mainly $H2O2$, $HO\cdot$, $ROO\cdot$, $NO\cdot$ and $ONOO$) results in the production of intracellular fluorescent DCF, whose concentration is directly proportional to the levels of ROS in the cell. Once the treatment with the test compounds was ended (1 hr), the tumour cells were washed (with PBS), the probe DCFH2-DA (10 µM) was added over 30 min, and after further washing in PBS, intracellular DCF fluorescence was quantified with a spectrophotometer (Synergy; emission at 498 nm and emission at 530 nm). All the experiments were repeated at least 3 times. Data analysis was carried out with GraphPad Prism 6 for graphical representation and statistical processing (1-way ANOVA test).

The results demonstrate that the compounds according to the invention halt the replicative tumour cell cycle. In fact, compared to the control treated with the solvent-vehicle, the tumour cells (in particular the colon carcinoma and melanoma cells) treated with the compounds according to the invention accumulate significantly in the S and G2 phases of the cell cycle. This effect on the cell cycle is partly mediated by ROS, as also confirmed by the fact that the compounds according to the invention promote a fast (≤1 h) increase in the intracellular ROS levels in malignant tumour cells.

Therefore, the synthetic flavone derivatives object of this invention selectively inhibit the growth and proliferation of malignant epithelial tumours at least through: promoting the cell death and apoptosis processes, halting the cell cycle and producing intracellular ROS.

Figure 1B:
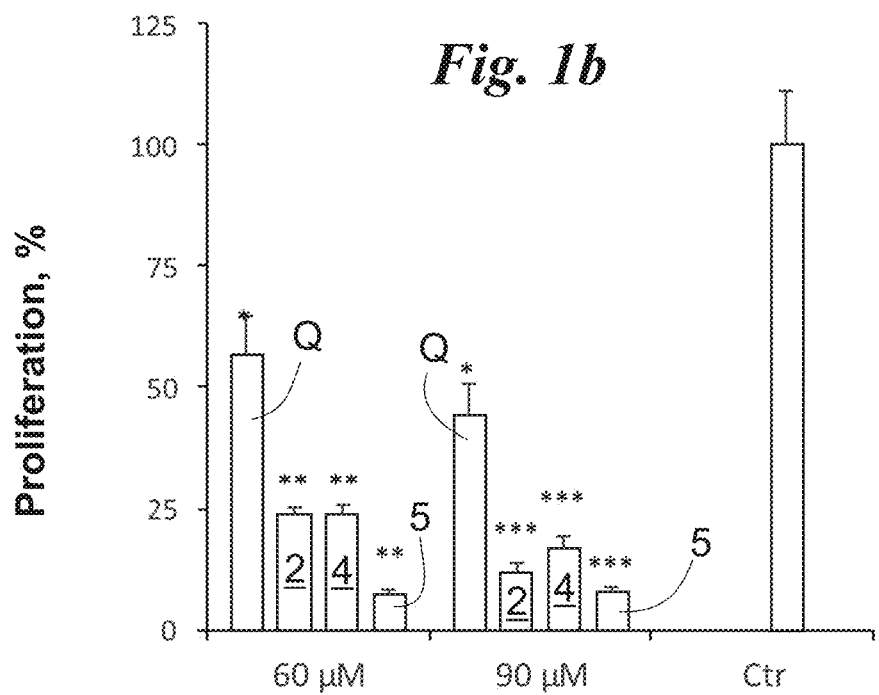

In detail, the medical compounds according to the invention were shown to exhibit greater anti-proliferative effects than the parent chemical scaffold in melanoma. The proliferation of human melanoma cells (A375) was quantitated by using the crystal violet method and a spectrophotometer, as illustrated in FIG. 1a. Quercetin (Que) and synthetic derivatives thereof (Compound 2, Compound 4, and Compound 5) were compared (FIG. 1a; 60, 60 µM). Compounds 2, 4, and 5 significantly inhibit the growth of melanoma cells, with a higher efficiency than that of quercetin (FIG. 1b). Ctr, control (treated with the vehicle). *, $p<0.05$ , $p<0.01$ and *, $p<0.001$ compared to the control, by Student's t-test.

Figure 2A:
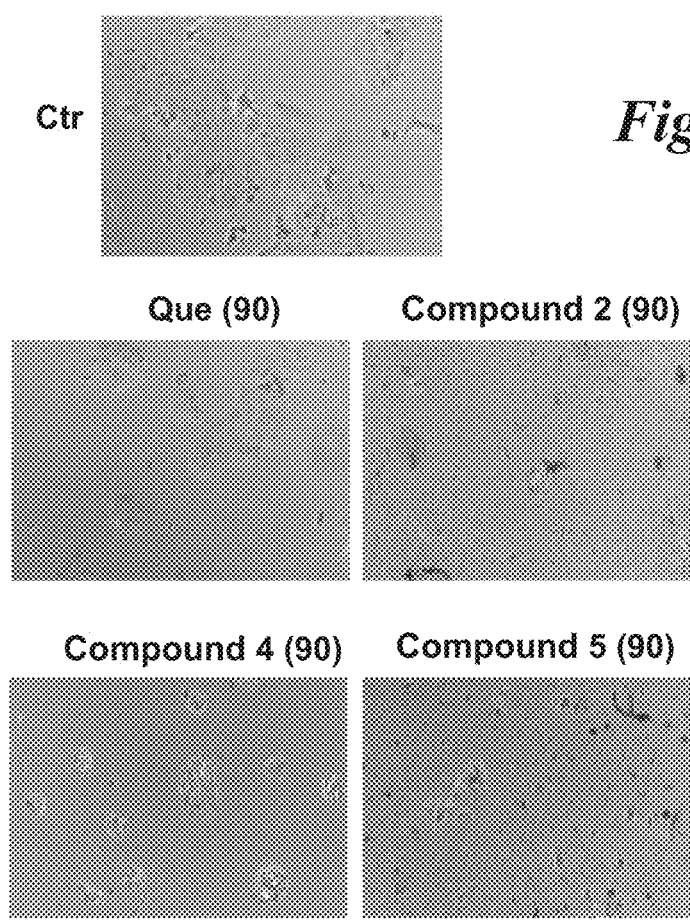
Figure 2B:
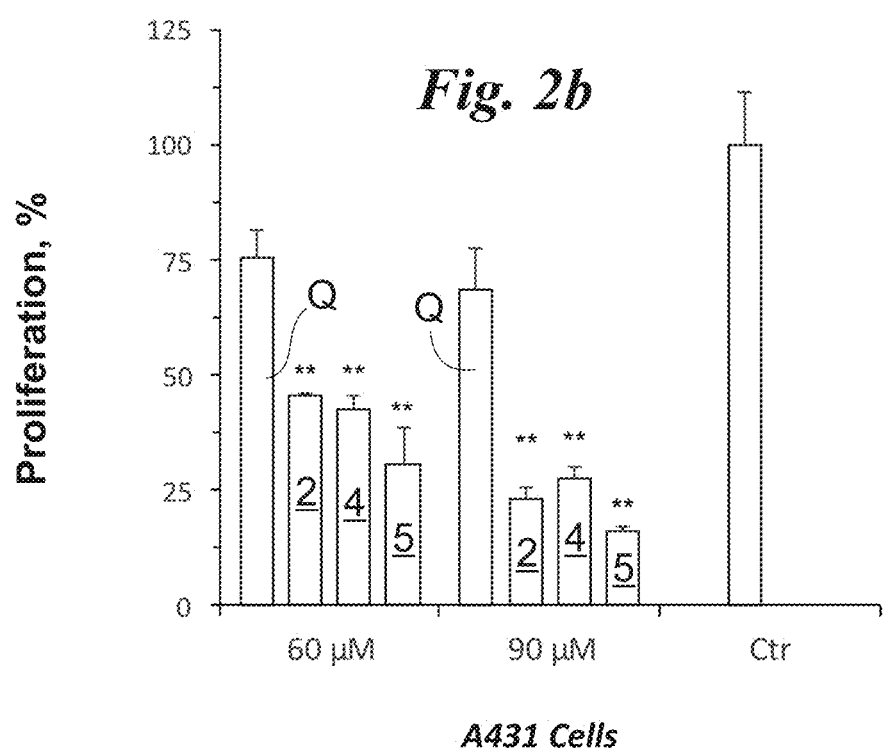

Synthetic flavone derivatives exhibit greater anti-proliferative effects than the parent chemical scaffold in skin squamous carcinoma (SCC). The proliferation of SCC cells (A431) was quantitated by using the crystal violet method and a spectrophotometer. Quercetin (Que) and synthetic derivatives thereof (Compound 2, Compound 4, and Compound 5) were compared (FIG. 2a; 90, 90 µM). While quercetin has no effect, compounds 2, 4, and 5 significantly inhibit A431 cell growth (FIG. 2b). Ctr, control (treated with the vehicle). **, $p<0.01$ compared to the control, by Student's t-test. Synthetic flavone derivatives exhibit greater anti-proliferative effects than the parent chemical scaffold in colorectal carcinoma. The proliferation of human colon carcinoma cells (HCT116) was quantitated by using the crystal violet method and a spectrophotometer. Quercetin (Que) and synthetic derivatives thereof (Compound 2, Compound 3, Compound 4, and Compound 5) were compared (FIG. 3a; 100, 100 µM). Compounds 2, 3, 4, and 5 significantly inhibit HCT116 cell growth (FIG. 3b). Ctr, control (treated with the vehicle). *, $p<0.05$ **, $p<0.01$ compared to the control, by Student's t-test.

Figure 4B:
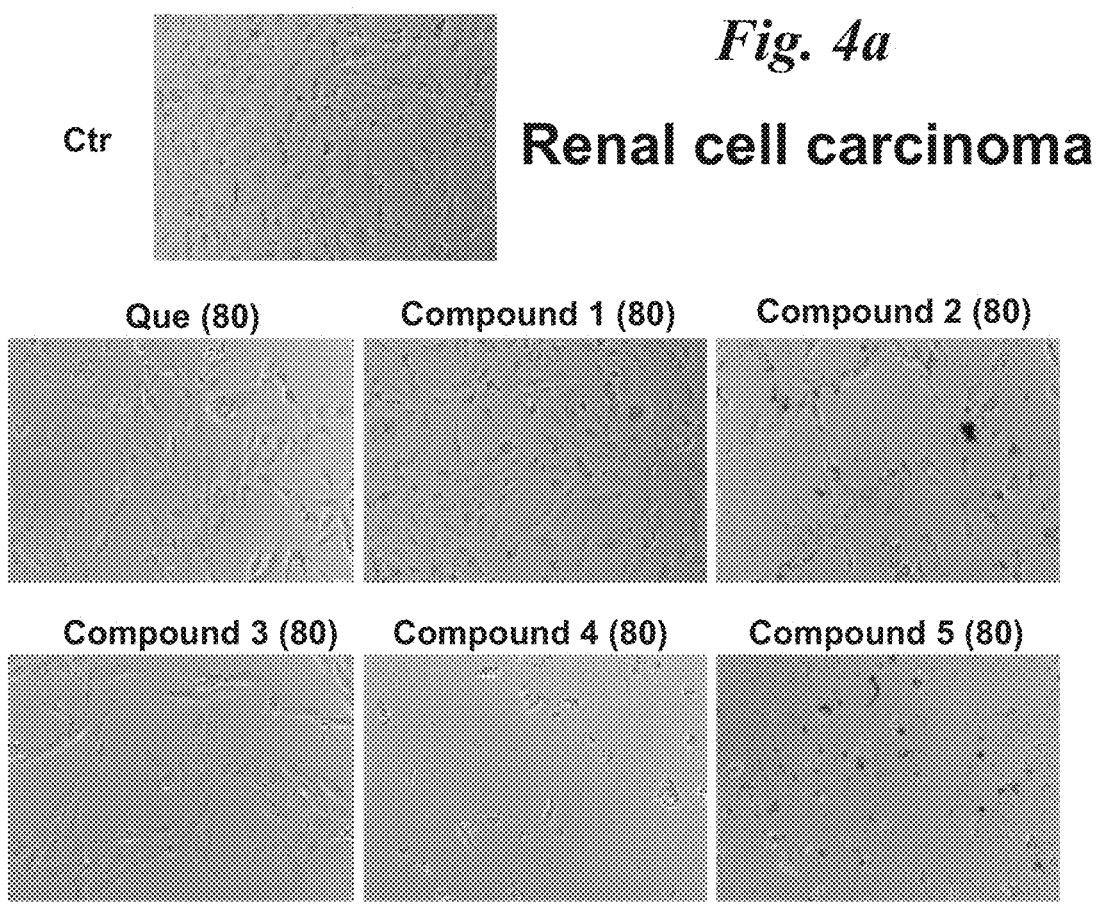
Figure 4B:
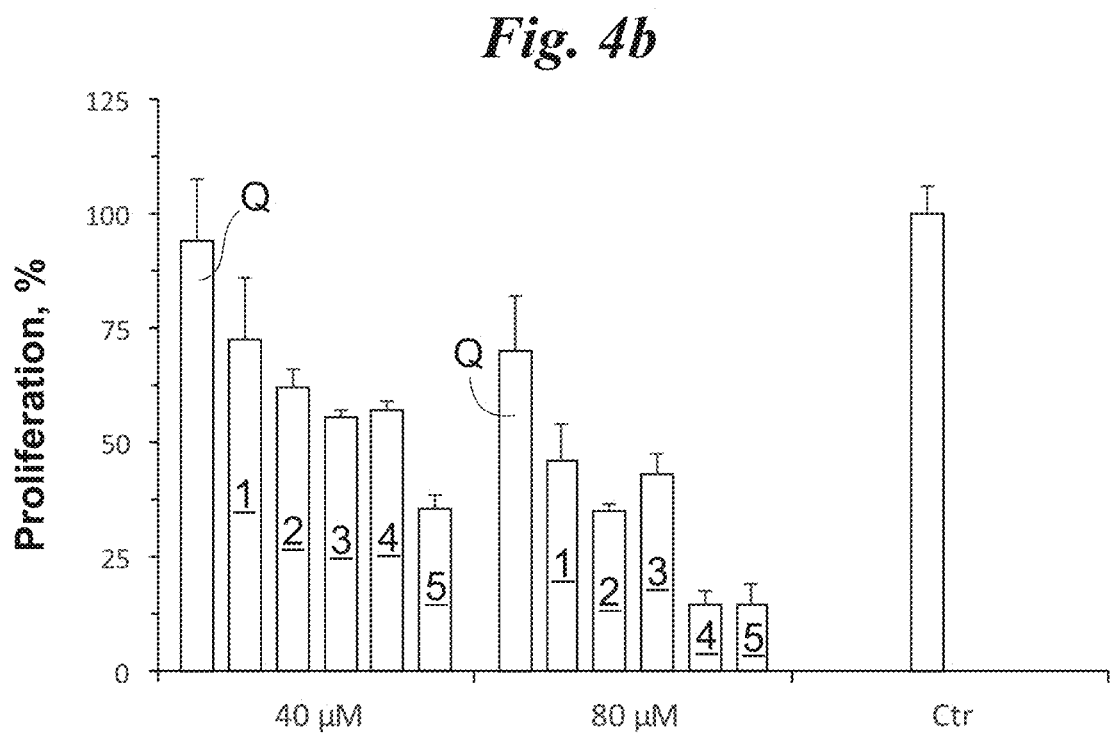

Synthetic flavone derivatives exhibit greater anti-proliferative effects than the parent chemical scaffold in renal carcinoma. The proliferation of human renal carcinoma cells (786-0) was quantitated by using the crystal violet method and a spectrophotometer. Quercetin (Que) and synthetic derivatives thereof (Compound 1, Compound 2, Compound 3, Compound 4, and Compound 5) were compared (FIG. 4a; 80, 80 µM). While quercetin has no effect, compounds 1, 2, 3, 4, and 5 significantly inhibit 786-0 cell growth (FIG. 4b). Ctr, control (treated with the vehicle). *, $p<0.05$ , $p<0.01$ and *, $p<0.001$ compared to the control, by Student's t-test.

Figure 5A:
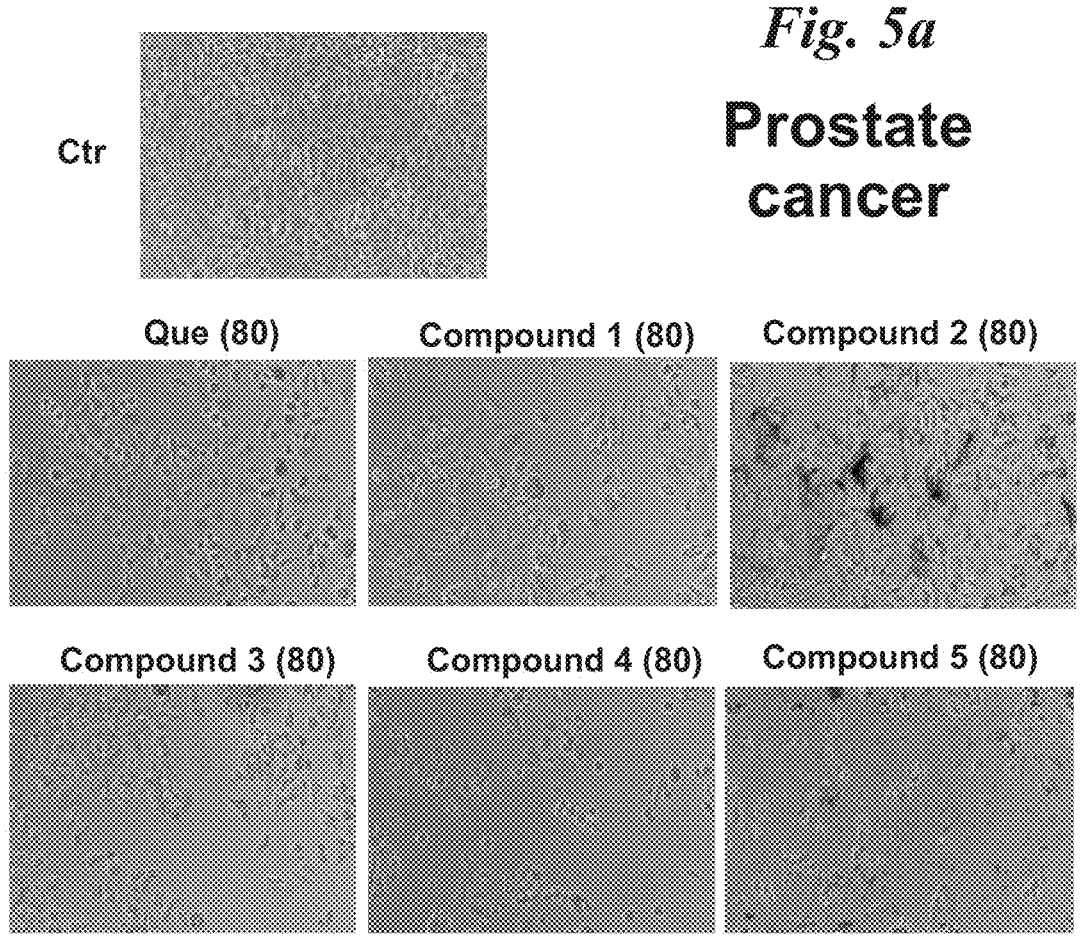
Figure 5B:
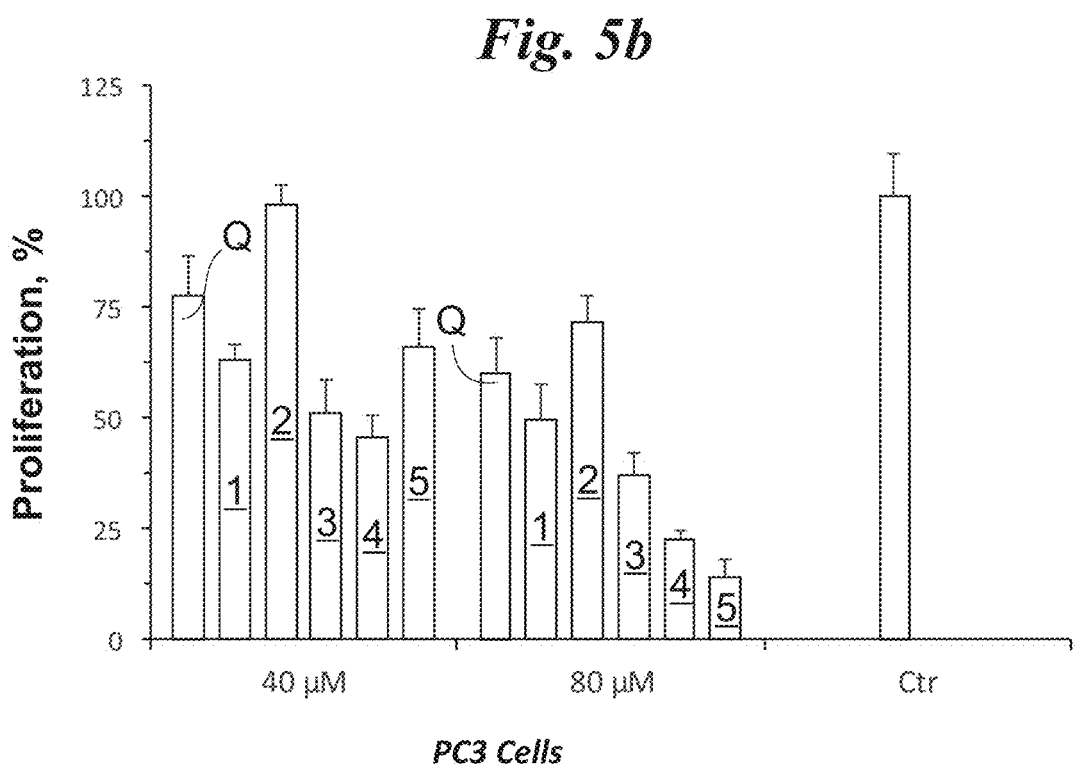

Synthetic flavone derivatives exhibit greater anti-proliferative effects than the parent chemical scaffold in prostate carcinoma. The proliferation of human prostate carcinoma cells (PC3) was quantitated spectrophotometrically by using the crystal violet method. Quercetin (Que) and synthetic derivatives thereof (Compound 1, Compound 2, Compound 3, Compound 4, and Compound 5) were compared (FIG. 5a; 80, 80 µM). While quercetin exhibits modest anti-proliferative effects, compounds 1, 3, 4, and 5 are superior and significantly inhibit PC3 cell growth (FIG. 5b). Ctr, control (treated with the vehicle). *, $p<0.05$ and **, $p<0.01$ compared to the control, by Student's t-test.

Figure 6A:
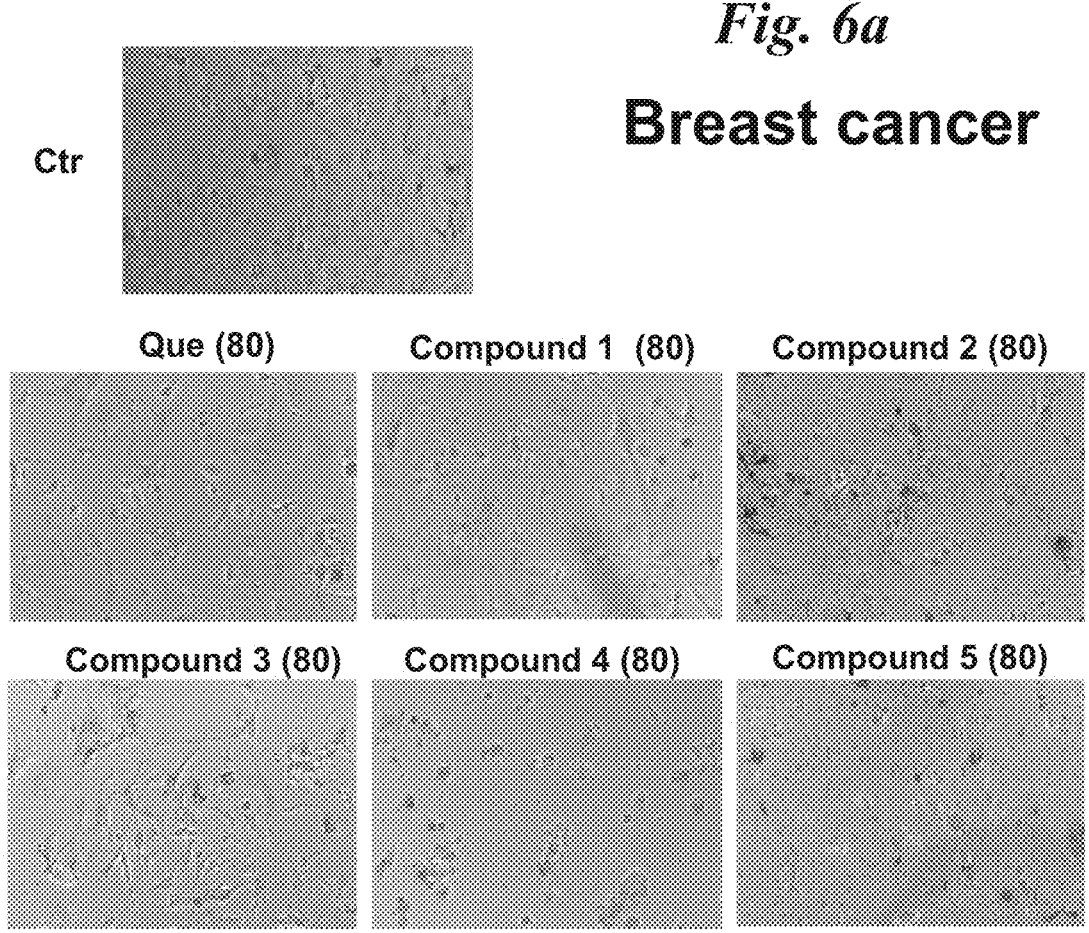
Figure 6B:
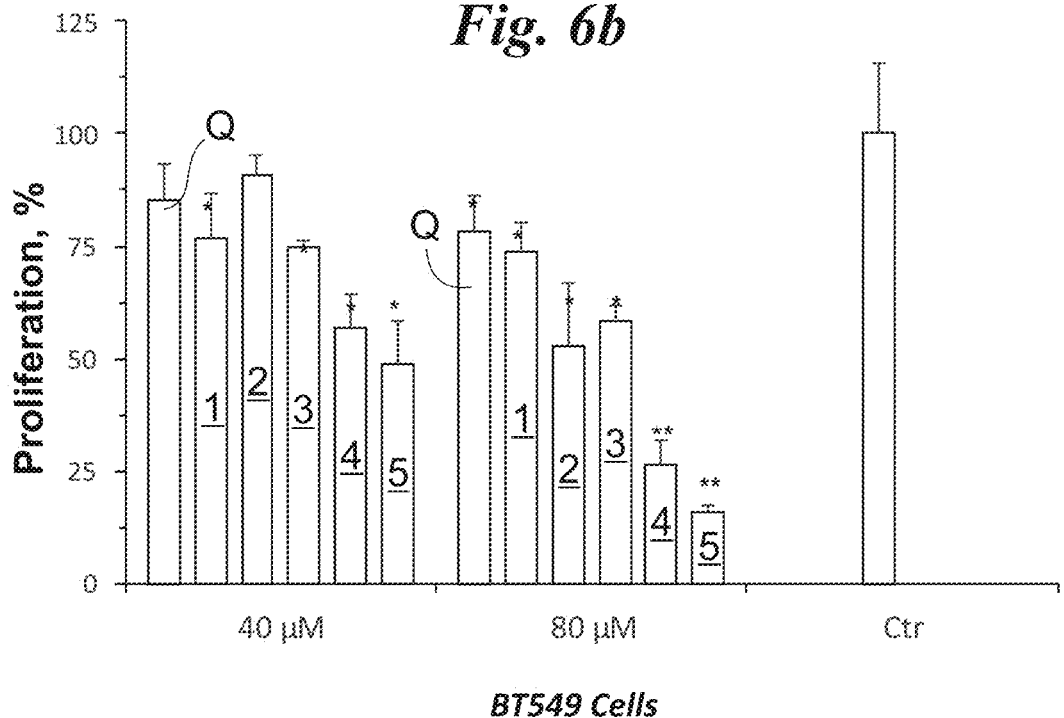

Synthetic flavone derivatives exhibit greater anti-proliferative effects than the parent chemical scaffold in mammary carcinoma. The proliferation of human mammary carcinoma cells (BT549) was quantitated spectrophotometrically by using the crystal violet method. Quercetin (Que) and synthetic derivatives thereof (Compound 1, Compound 2, Compound 3, Compound 4, and Compound 5) were compared (FIG. 6a; 80, 80 µM). Compounds 1, 2, 3, 4, and 5 significantly inhibit BT549 cell growth (FIG. 6b). Ctr, control (treated with the vehicle). *, $p<0.05$ and **, $p<0.01$ compared to the control, by Student's t-test.

Figure 7B:
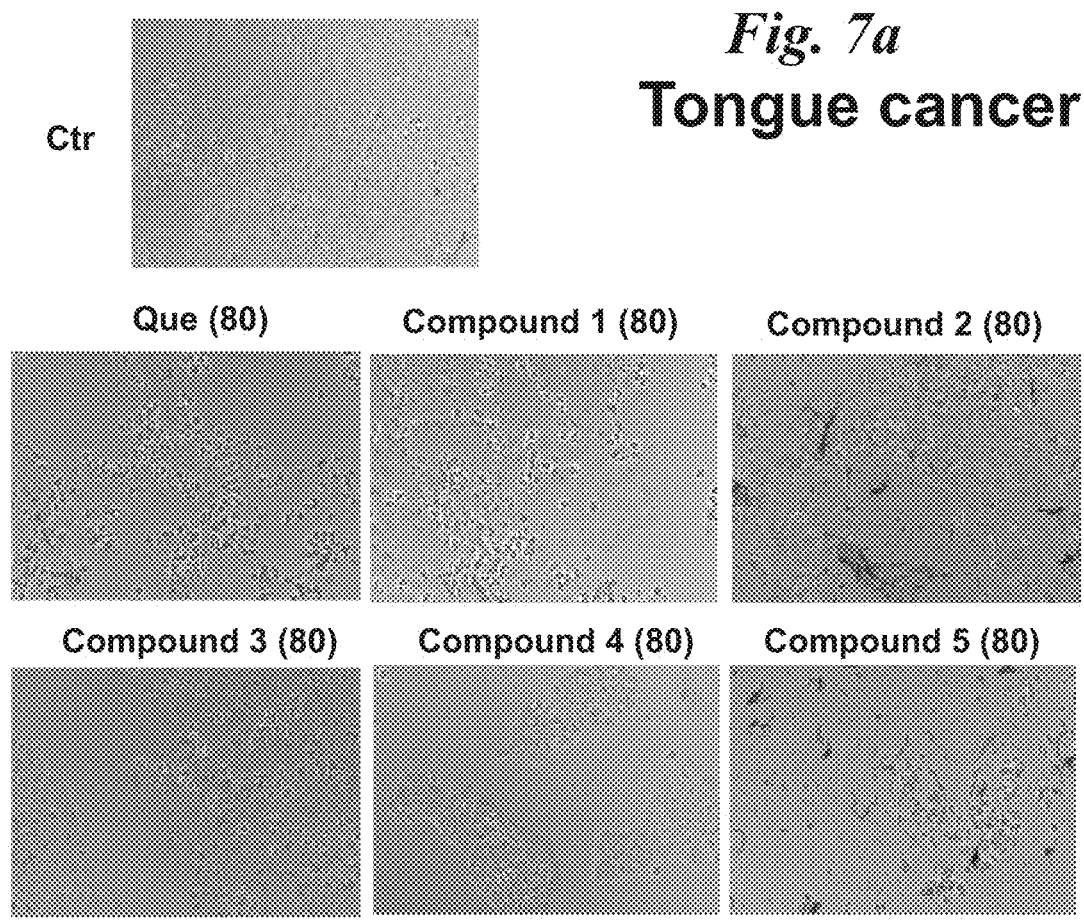
Figure 7B:
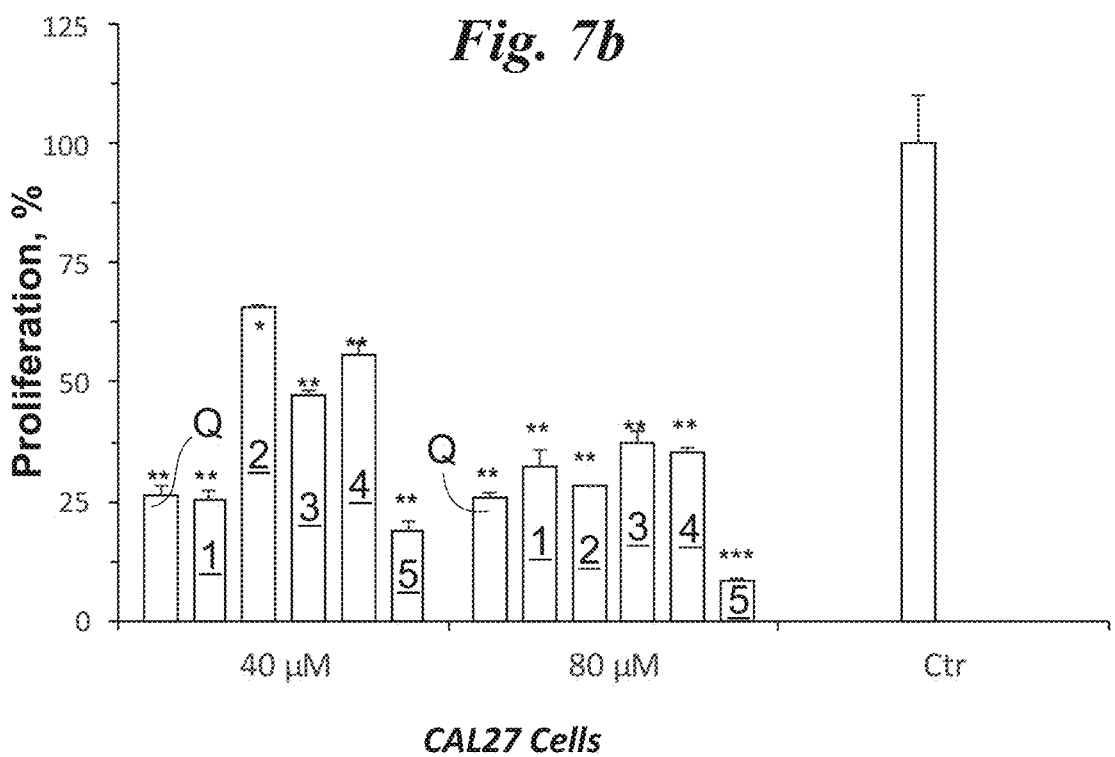

Synthetic flavone derivatives exhibit greater anti-proliferative effects than the parent chemical scaffold in tongue carcinoma (belonging to the head-and-neck carcinomas, HNC). The proliferation of human tongue carcinoma cells (Cal27) was quantitated spectrophotometrically by using the crystal violet method. Quercetin (Que) and synthetic derivatives thereof (Compound 1, Compound 2, Compound 3, Compound 4, and Compound 5) were compared (FIG. 7a; 80, 80 µM). All synthetic compounds significantly inhibit tumour growth, with Compound 5 showing an anti-proliferative effect superior to that of quercetin (FIG. 7b). Ctr, control (treated with the vehicle). *, $p<0.05$ , $p<0.01$ and *, $p<0.001$ compared to the control, by Student's t-test.

Figure 8A:
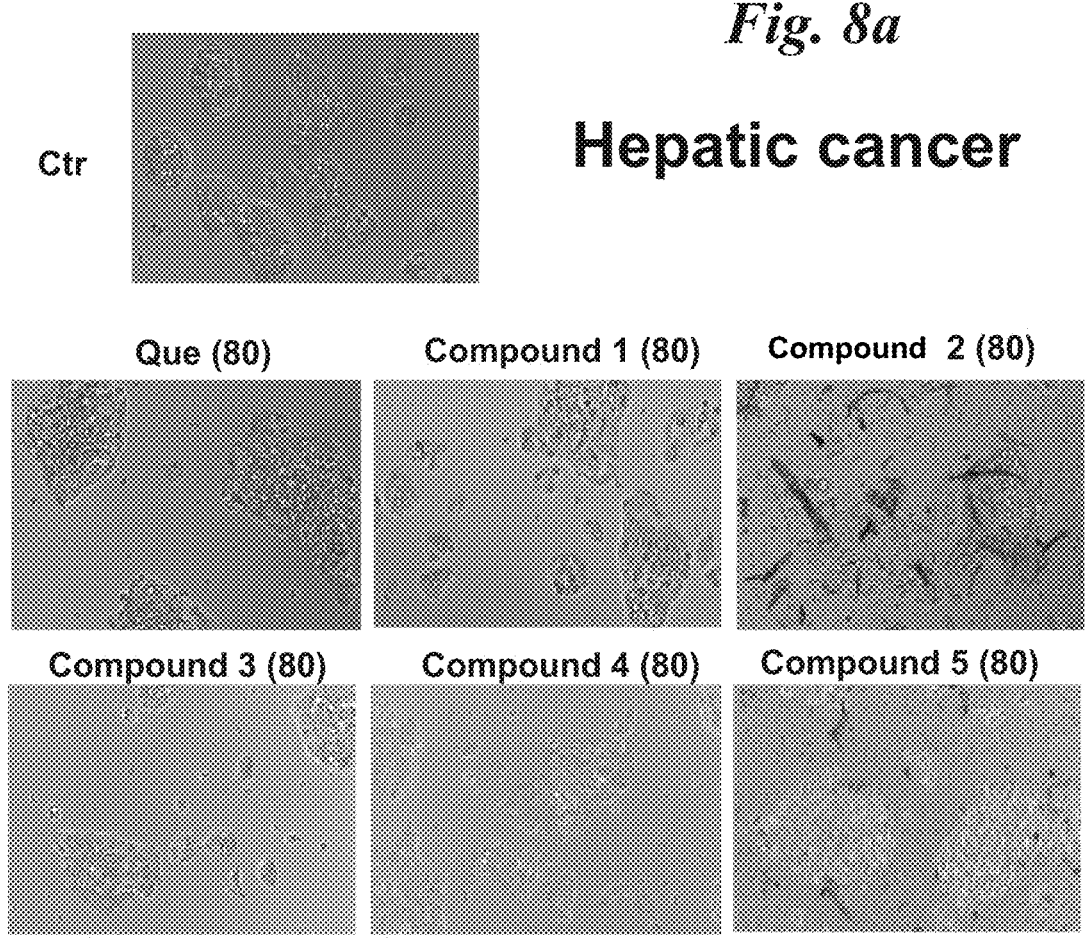
Figure 8B:
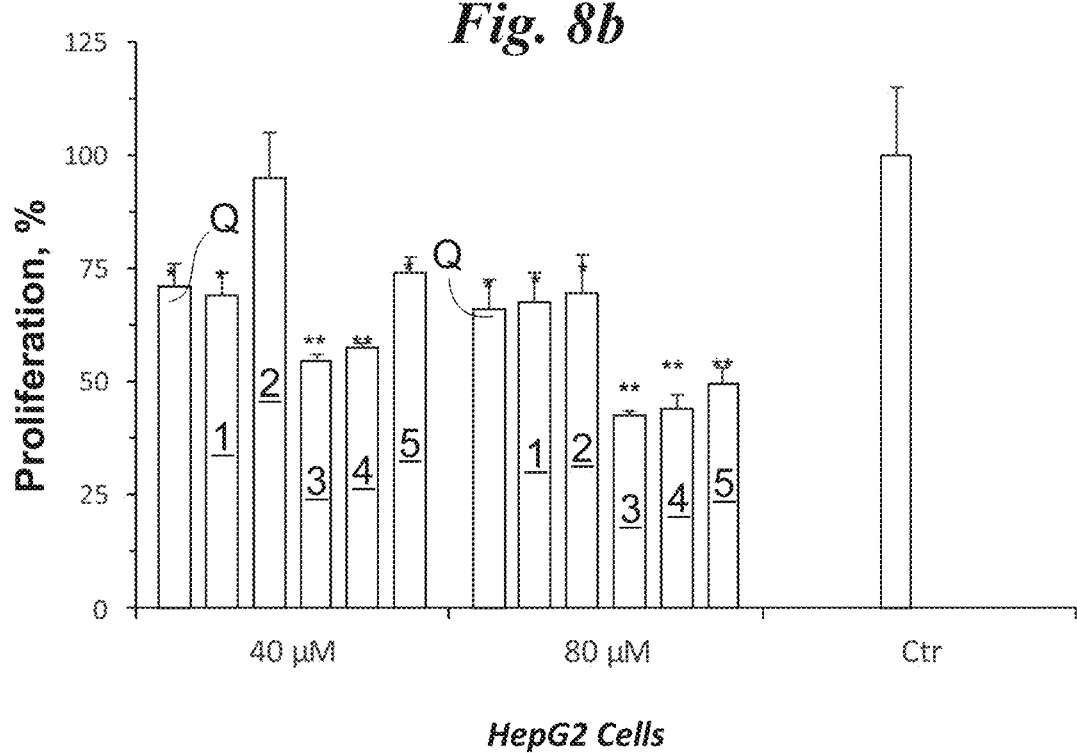

Synthetic flavone derivatives exhibit greater anti-proliferative effects than the parent chemical scaffold in liver carcinoma. The proliferation of human hepatocellular carcinoma cells (HepG2) was quantitated spectrophotometrically by using the crystal violet method. Quercetin (Que) and synthetic derivatives thereof (Compound 1, Compound 2, Compound 3, Compound 4, and Compound 5) were compared (FIG. 8a; 80, 80 µM). All synthetic compounds significantly inhibit tumour growth, with compounds 3, 4, and 5 showing an anti-proliferative effect superior to that of quercetin (FIG. 8b). HepG2. Ctr, control (treated with the vehicle). *, $p<0.05$ **, $p<0.01$, compared to the control, by Student's t-test.

Figure 9A:
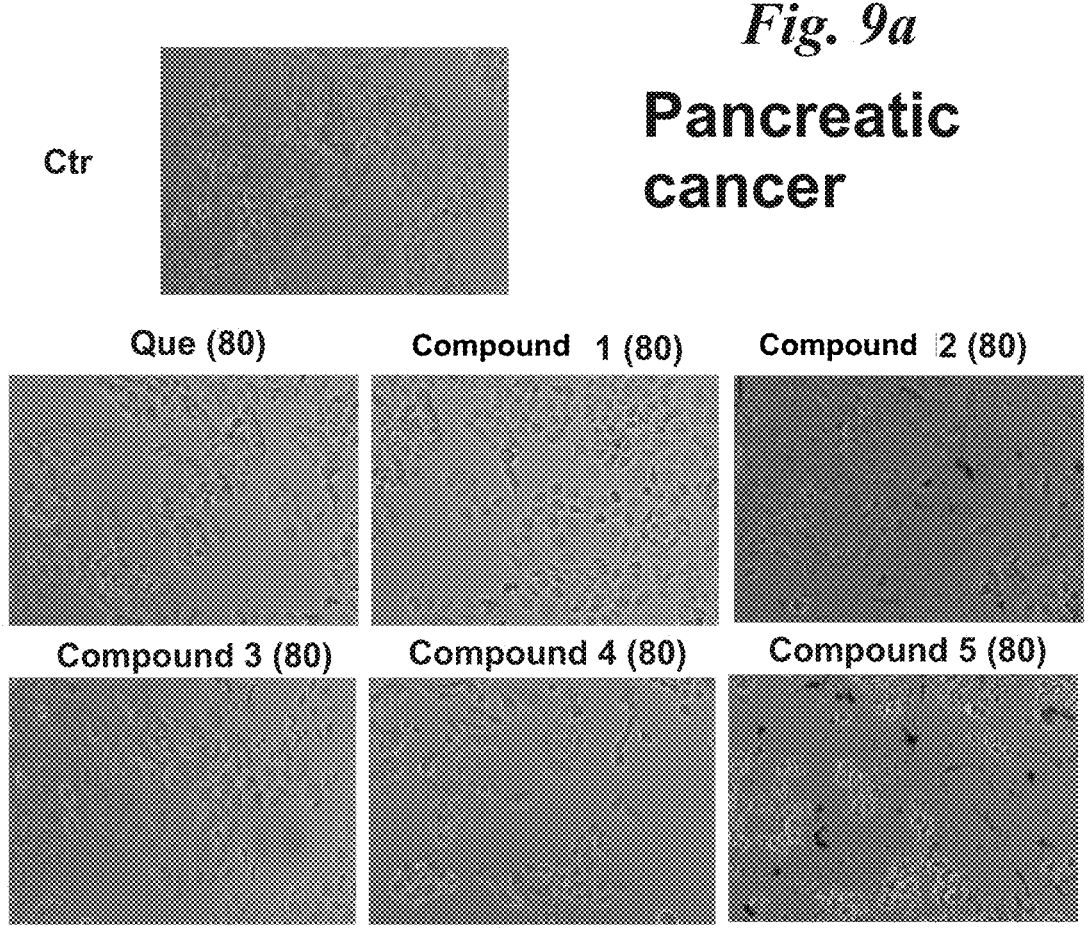
Figure 9B:
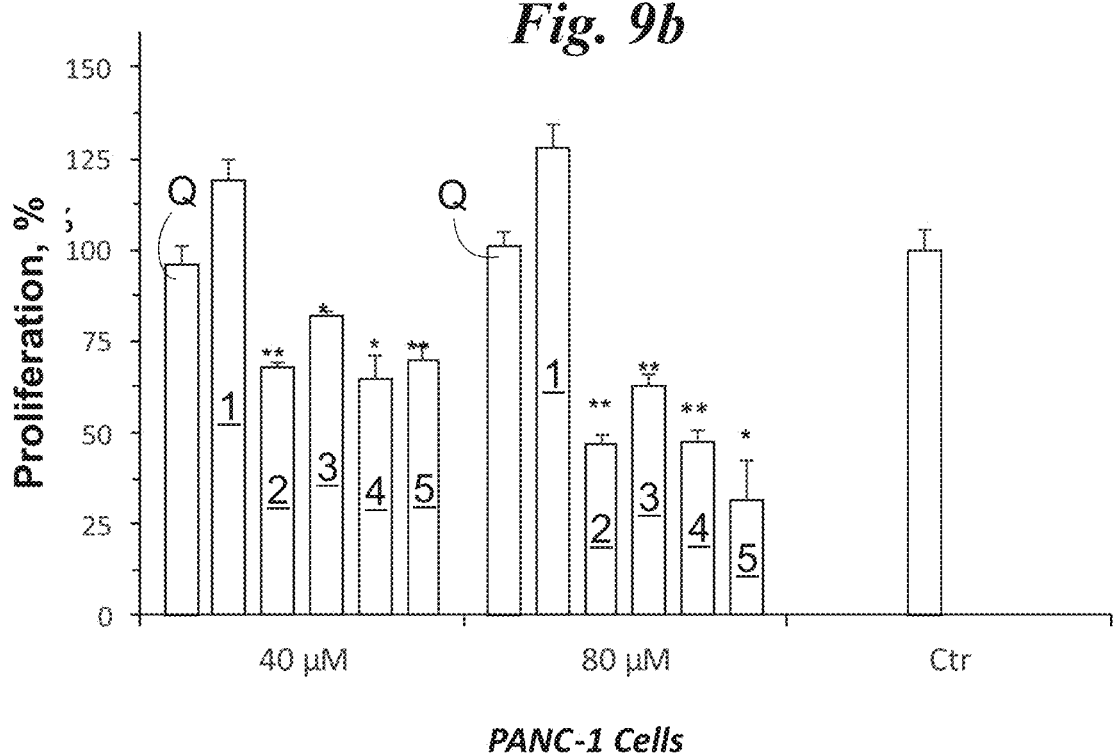

Synthetic flavone derivatives exhibit greater anti-proliferative effects than the parent chemical scaffold in pancreatic carcinoma. The proliferation of human pancreatic carcinoma cells (PANC-1) was quantitated spectrophotometrically by using the crystal violet method. Quercetin (Que) and synthetic derivatives thereof (Compound 1, Compound 2, Compound 3, Compound 4, and Compound 5) were compared (FIG. 9a; 80, 80 µM). While quercetin has no effect, compounds 2, 3, 4, and 5 significantly inhibit PANC-1 cell growth (FIG. 9b). Ctr, control (treated with the vehicle). *, $p<0.05$ **, $p<0.01$, compared to the control, by Student's t-test.

Figure 10A:
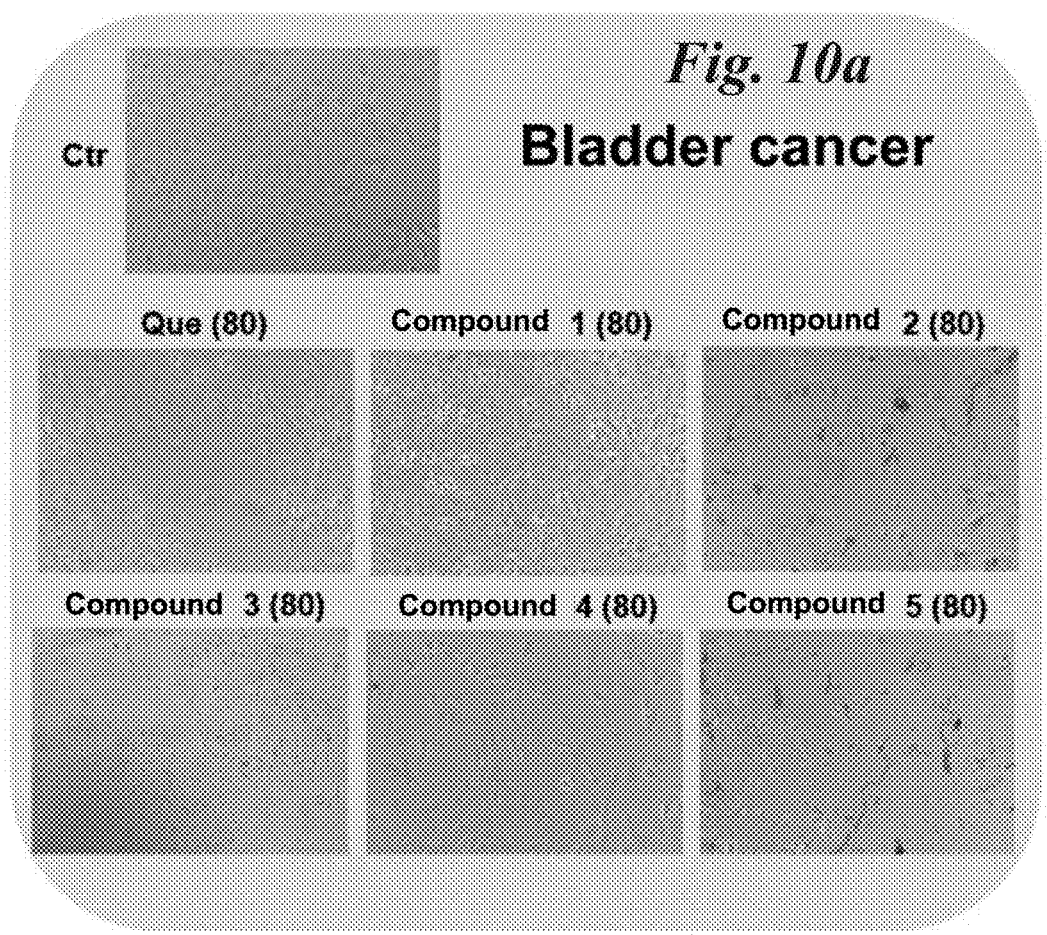
Figure 10B:
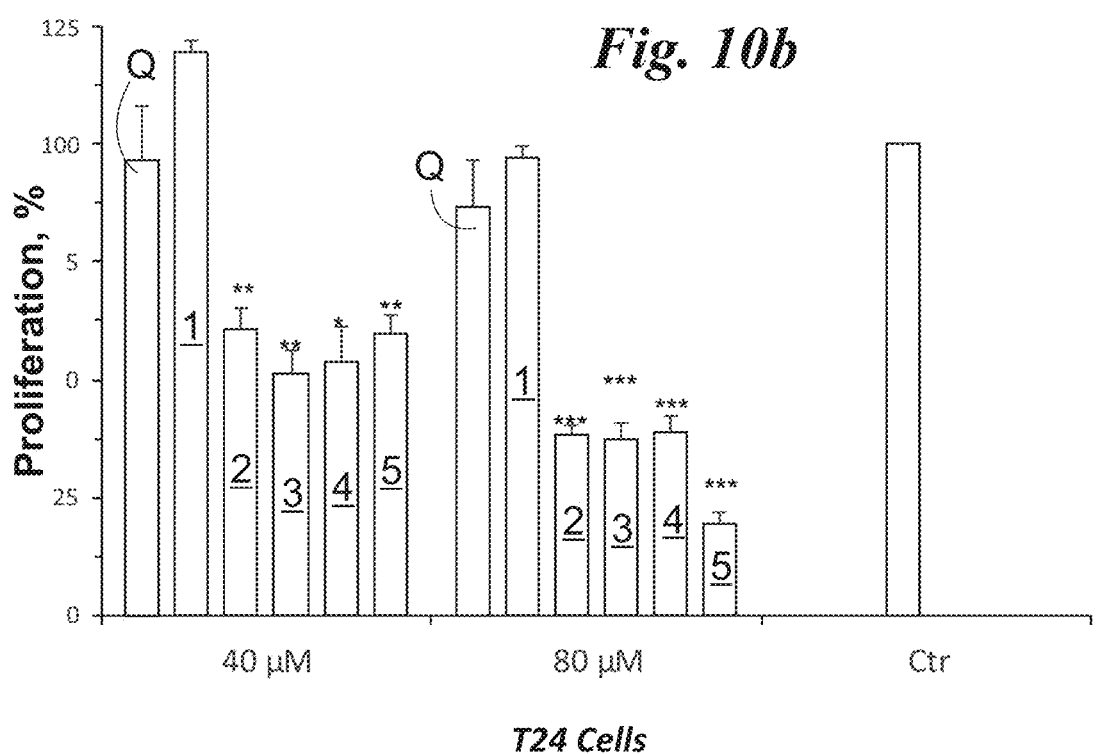

Synthetic flavone derivatives exhibit greater anti-proliferative effects than the parent chemical scaffold in bladder carcinoma. The proliferation of human bladder carcinoma cells (T24) was quantitated spectrophotometrically by using the crystal violet method. Quercetin (Que) and synthetic derivatives thereof (Compound 1, Compound 2, Compound 3, Compound 4, and Compound 5) were compared (FIG. 10a; 80, 80 µM). While quercetin has no effect, compounds 2, 3, 4, and 5 significantly inhibit T24 cell growth (FIG. 10b). Ctr, control (treated with the vehicle). *, p<0.05 , p<0.01 and *, p<0.001 compared to the control, by Student's t-test.

Figure 11A:
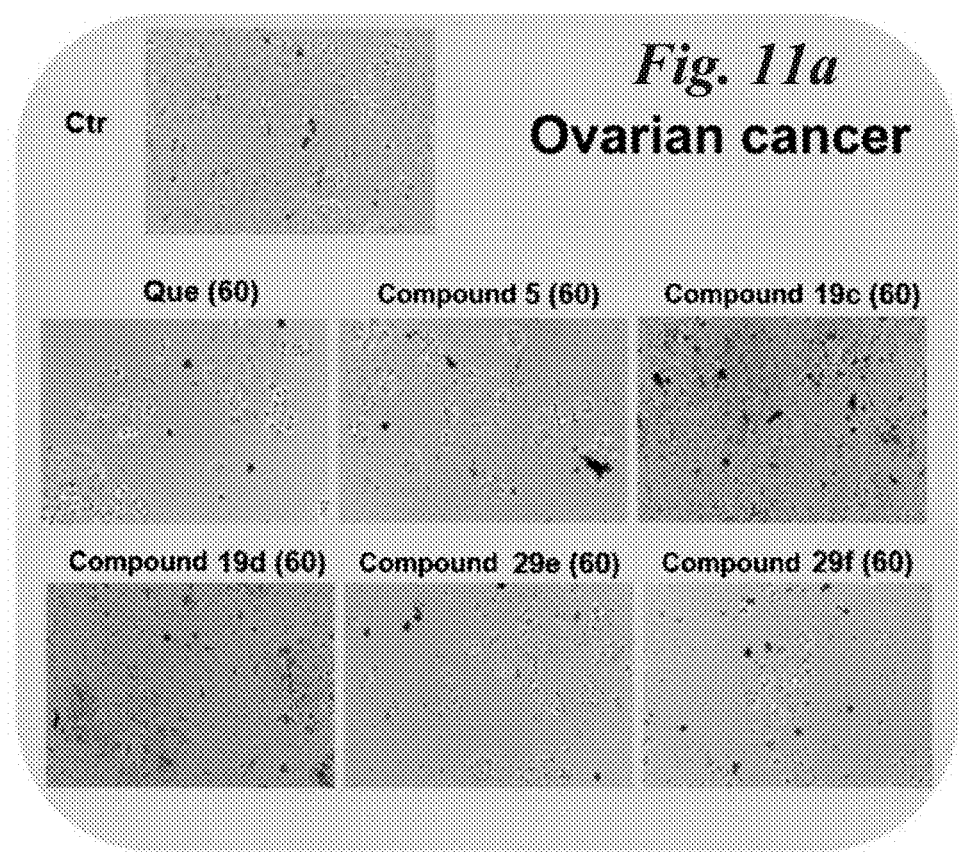
Figure 11B:
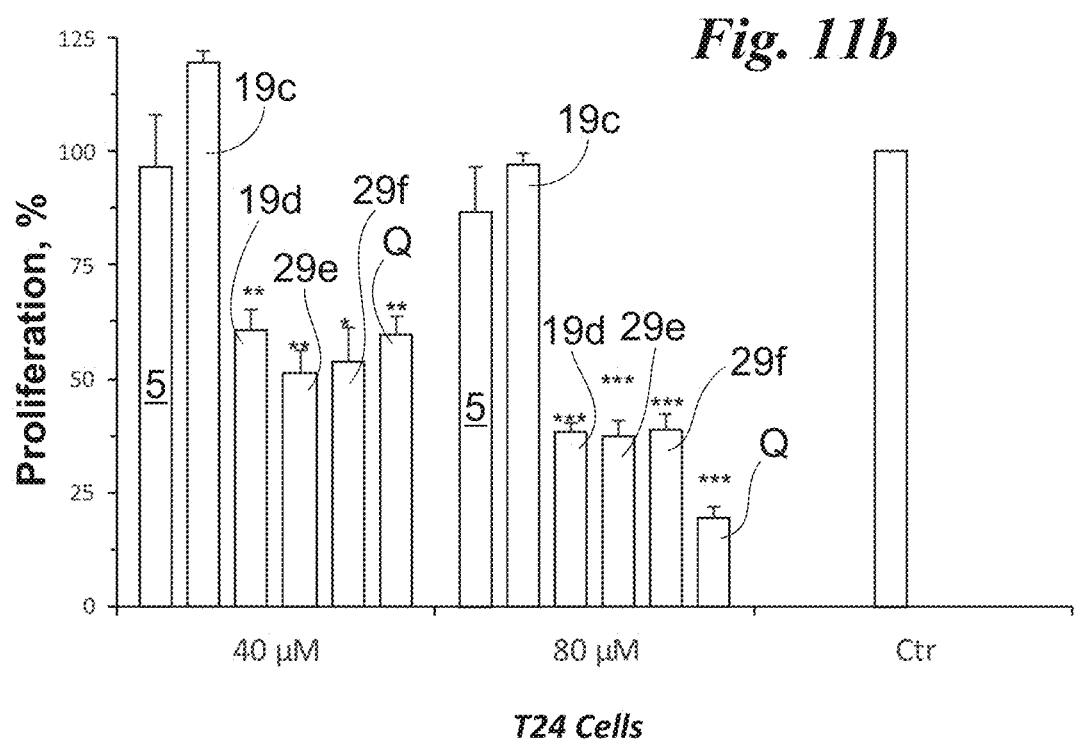

Synthetic flavone derivatives exhibit greater anti-proliferative effects than the parent chemical scaffold in ovarian carcinoma. The proliferation of human ovarian carcinoma cells (OVCAR-3) was quantitated spectrophotometrically by using the crystal violet method. Quercetin (Que) and synthetic derivatives thereof (Compound 5, Compound 19c, Compound 19d, Compound 29e, and Compound 29f) were compared (FIG. 11a; 60, 60 µM). While quercetin has no effect, compounds 5, 19c, 19d, 29e, and 29f significantly inhibit OVCAR-3 cell growth (FIG. 11b). Ctr, control (treated with the vehicle). *, p<0.05 ; p<0.01, and *, p<0.001 compared to the control, by Student's t-test.

Synthetic flavone derivative Compound 26 exhibits greater anti-proliferative effects than the parent chemical scaffold in melanoma. The proliferation of human melanoma cells (A375) was quantitated spectrophotometrically by using the crystal violet method.

Figure 12:
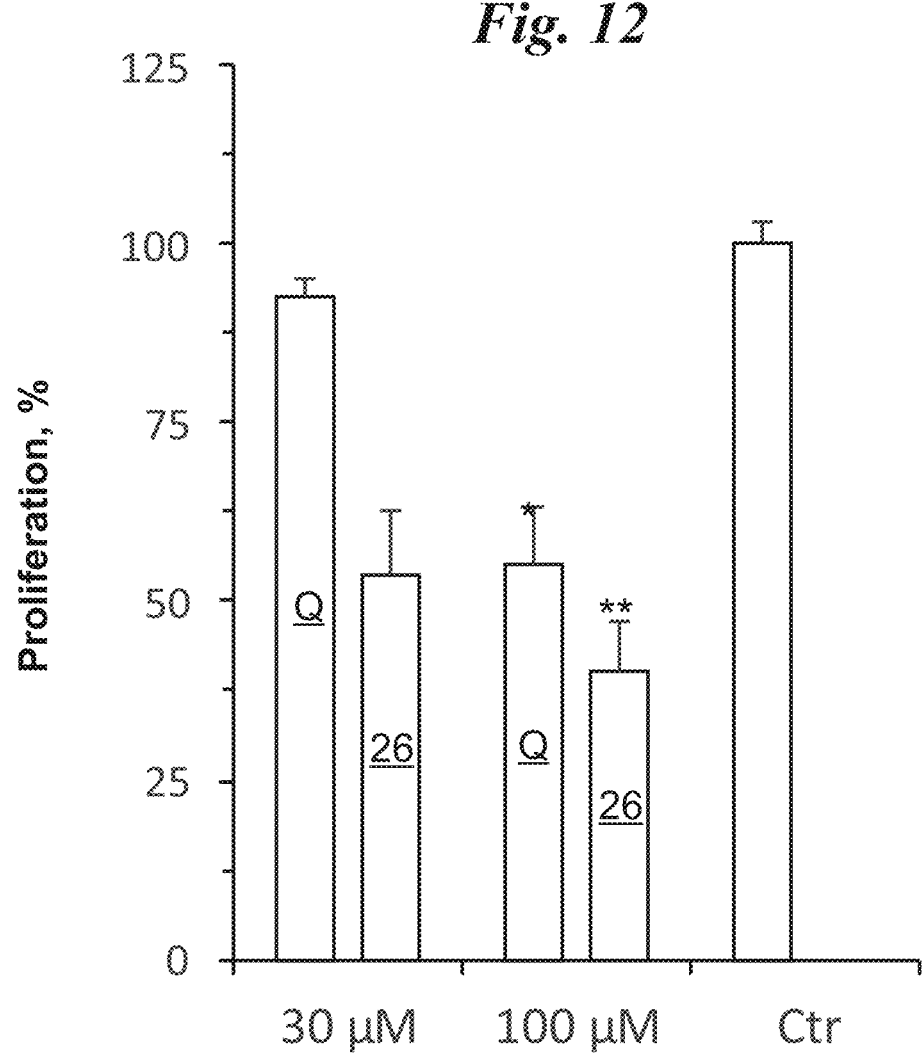

Compound 26 significantly inhibits A375 cell proliferation with greater effectiveness compared to quercetin. Ctr, control (treated with the vehicle). *, p<0.05 and **, p<0.01 compared to the control, by Student's t-test (FIG. 12).

Figure 13A:
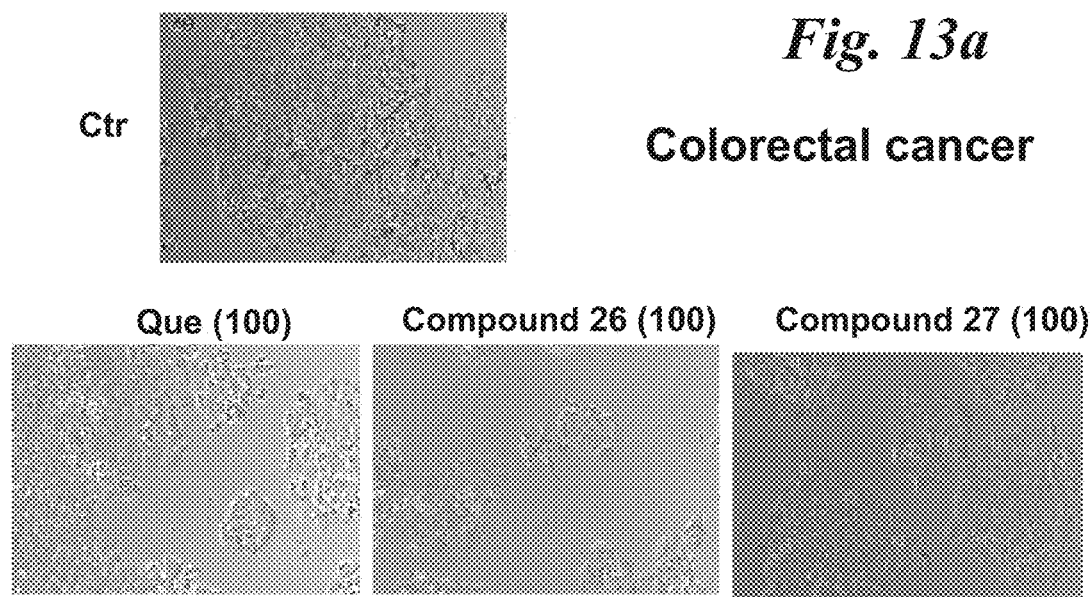
Figure 13B:
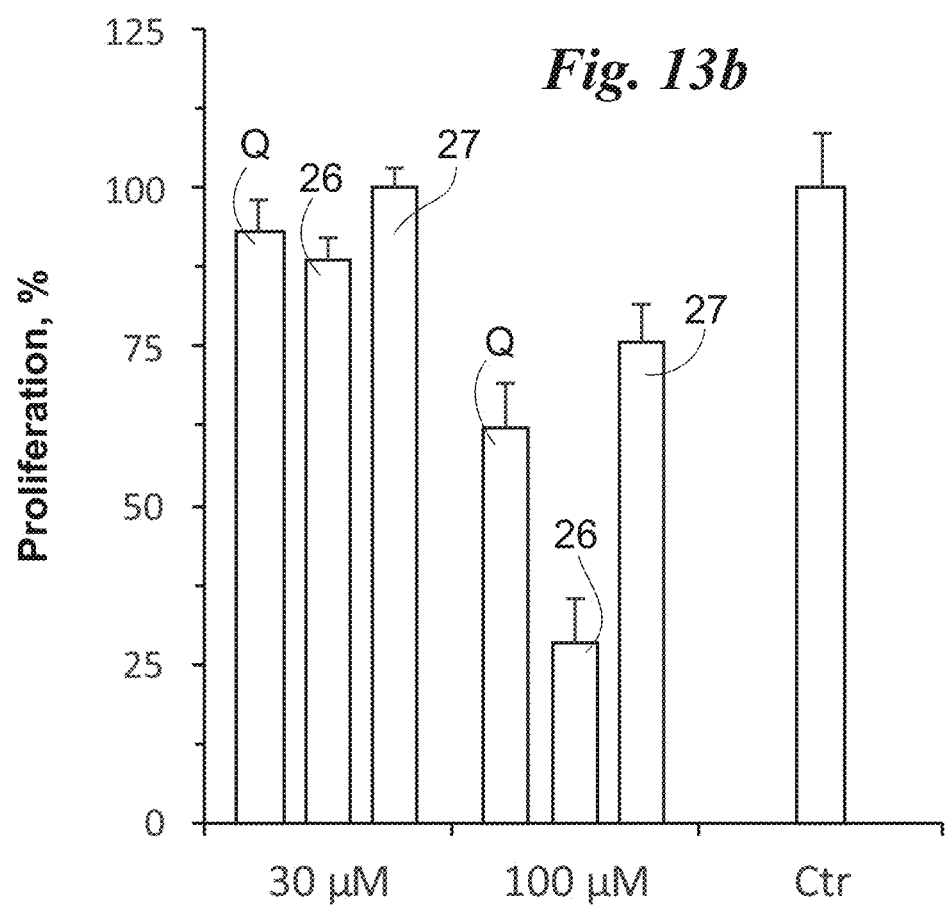

Synthetic flavone derivatives Compound 26 and Compound 27 exhibit greater anti-proliferative effects than the parent chemical scaffold in colorectal carcinoma. The proliferation of human colon carcinoma cells (HCT116) was quantitated by using the crystal violet method and a spectrophotometer. Quercetin (Que) and synthetic derivatives thereof (Compound 26 and Compound 27) were compared (FIG. 13a; 100, 100 µM). Compound 26 significantly inhibits HCT116 cell growth with greater effectiveness compared to quercetin (FIG. 13b). Ctr, control (treated with the vehicle). *, p<0.05 and **, p<0.01 compared to the control, by Student's t-test.

Figure 14:
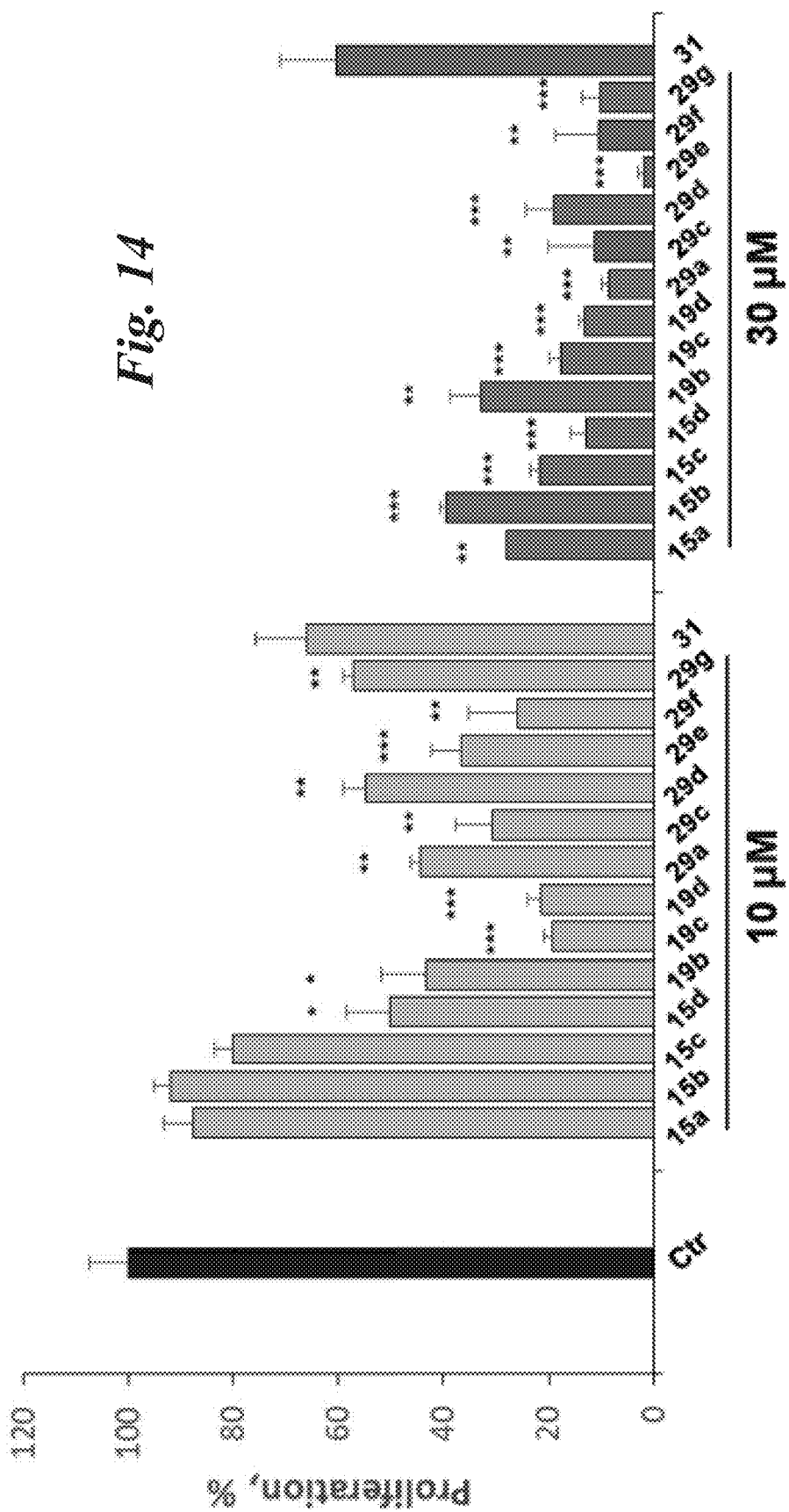

Synthetic flavone derivatives exhibit significant anti-proliferative effects in melanoma. The proliferation of human melanoma cells (A375) was quantitated spectrophotometrically by using the crystal violet method. The synthetic compounds used at 10 µM and 30 µM concentrations significantly inhibited A375 cell growth with high potency. Ctr, control (treated with the vehicle). 15a, Compound 15a; 15b, Compound 15b; 15c, Compound 15c; 15d, Compound 15d; 19b, Compound 19b; 19c, Compound 19c; 19d, Compound 19d; 29a, Compound 29a; 29c, Compound 29c; 29d, Compound 29d; 29e, Compound 29e; 29f, Compound 29f, and 29g, Compound 29g. *, p<0.05 ; p<0.01, and *, p<0.001 compared to the control, by Student's t-test (FIG. 14).

Figure 15:
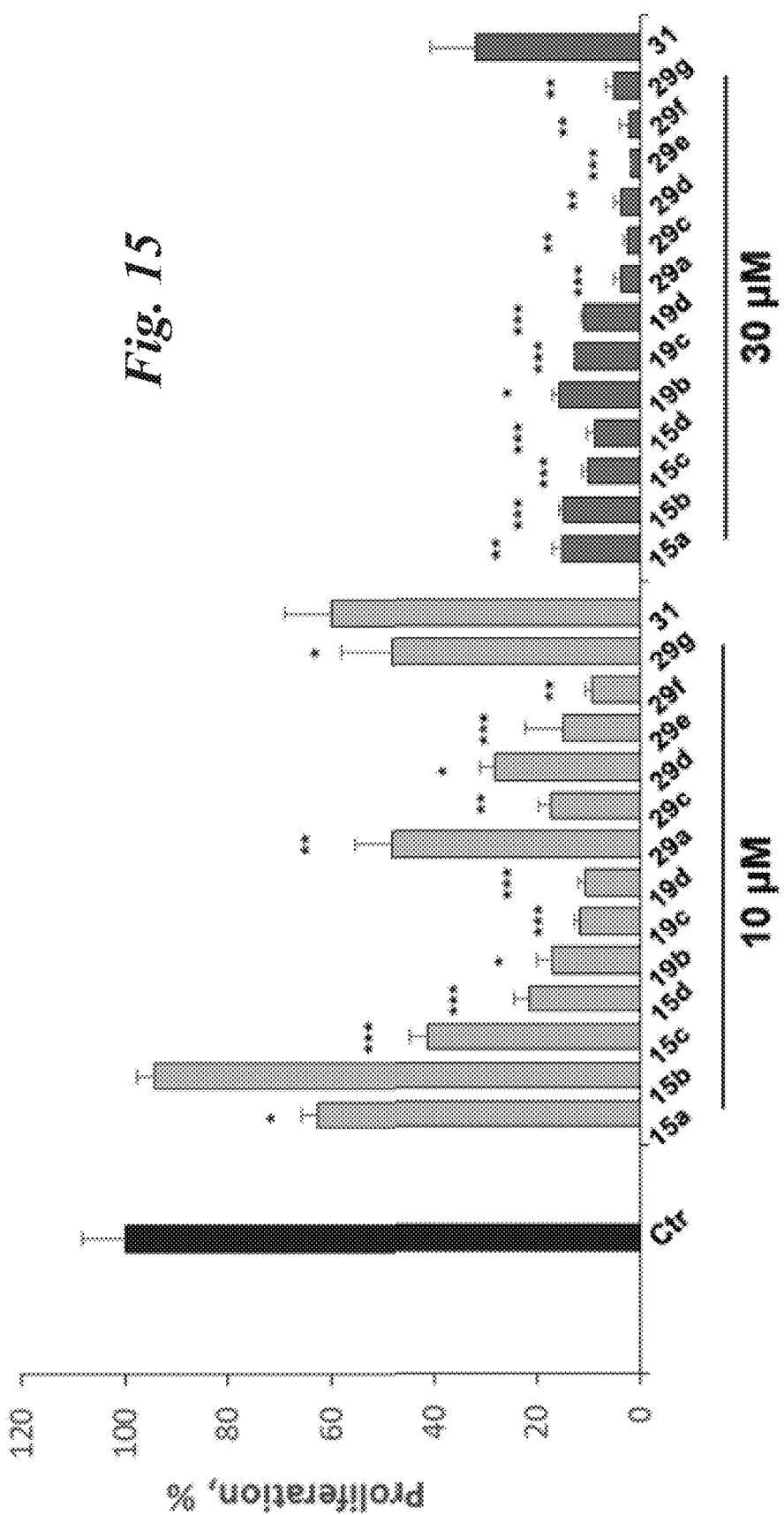

Synthetic flavone derivatives exhibit significant anti-proliferative effects in colorectal carcinoma. The proliferation of human colon carcinoma cells (HCT116) was quantitated by using the crystal violet method and a spectrophotometer. The synthetic compounds used at 10 µM and 30 µM concentrations significantly inhibited HCT116 cell growth with high potency. Ctr, control (treated with the vehicle). 15a, Compound 15a; 15b, Compound 15b; 15c, Compound 15c; 15d, Compound 15d; 19b, Compound 19b; 19c, Compound 19c; 19d, Compound 19d; 29a, Compound 29a; 29c, Compound 29c; 29d, Compound 29d; 29e, Compound 29e; 29f, Compound 29f, and 29g, Compound 29g. *, p<0.05 ; p<0.01, and *, p<0.001 compared to the control, by Student's t-test (FIG. 15).

Figure 16:
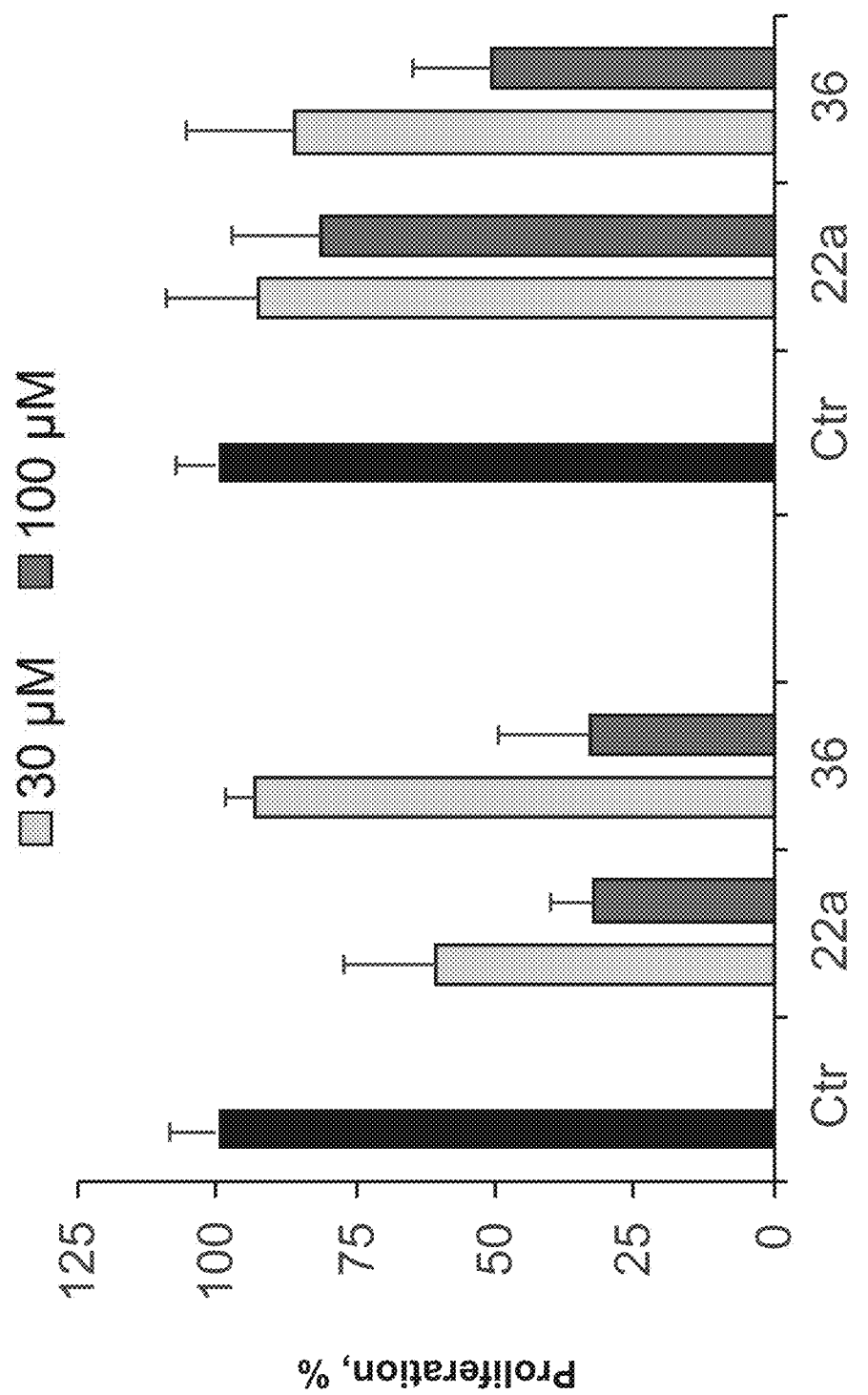

Synthetic trimeric flavone derivatives exhibit anti-proliferative effects in colorectal carcinoma and melanoma. The proliferation of human colon carcinoma (HCT116) and melanoma (A375) cells was quantitated spectrophotometrically by using the crystal violet method. Synthetic trimeric compounds (Compound 22a and Compound 36), used at 30 µM and 100 µM concentrations, inhibit HCT116 and A375 cell growth. Ctr, control (treated with the vehicle). 22a, Compound 22a; 36, Compound 36. *, p<0.05 compared to the control, by Student's t-test (FIG. 16).

Figure 17:
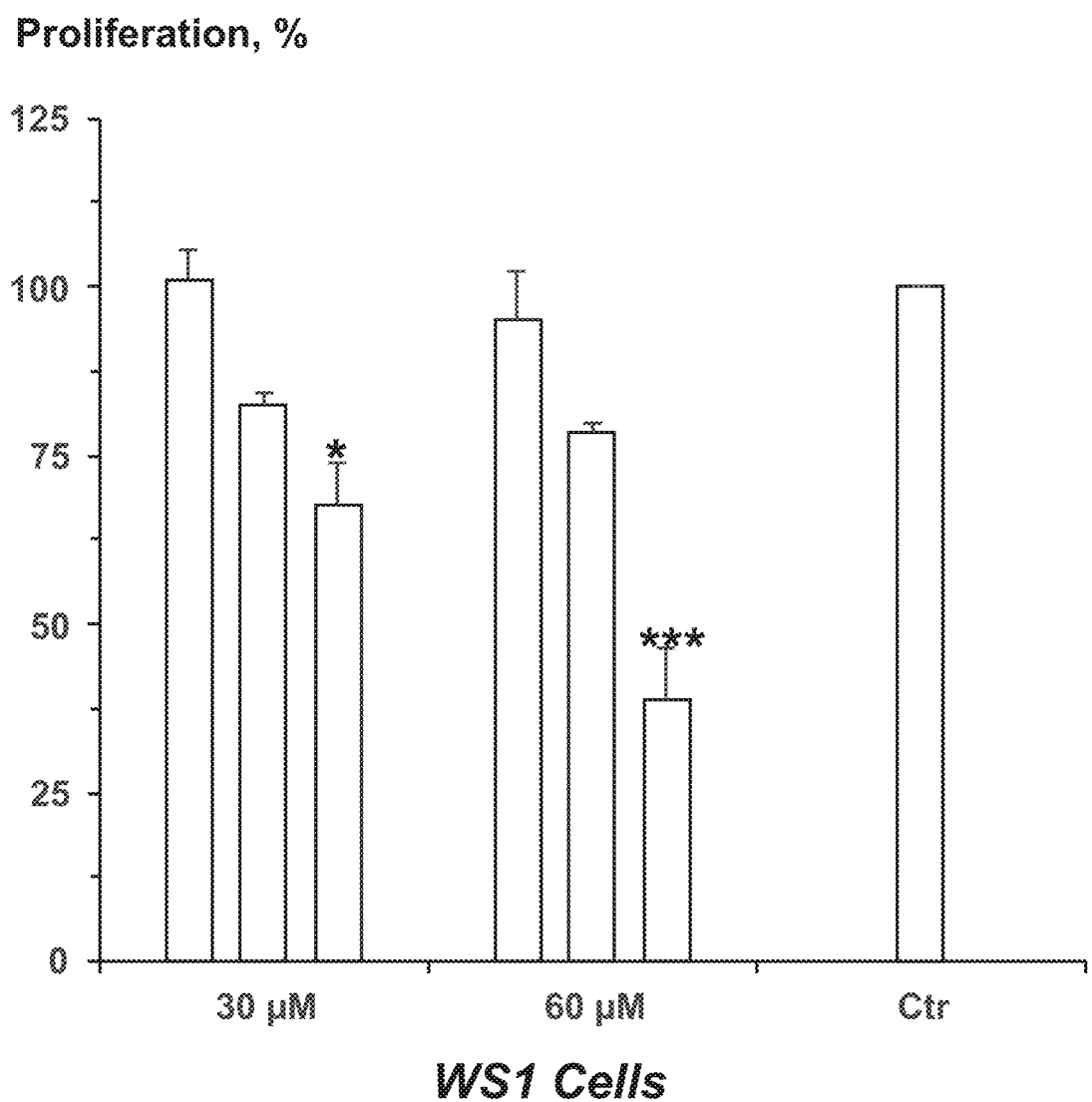

Synthetic flavone derivatives do not disrupt normal human cell proliferation. The proliferation of human skin fibroblasts (WS1) was studied with crystal violet and a spectrophotometer. Quercetin (Que), a synthetic derivative thereof (Compound 2), and apigenin (API) were examined at the indicated concentrations. While apigenin significantly inhibits the proliferation of normal human skin cells, quercetin and Compound 2 do not disrupt their growth. Ctr, control (treated with the vehicle). *, p<0.05 and ***, p<0.005 compared to the control, by Student's t-test (FIG. 17).

Figure 18:
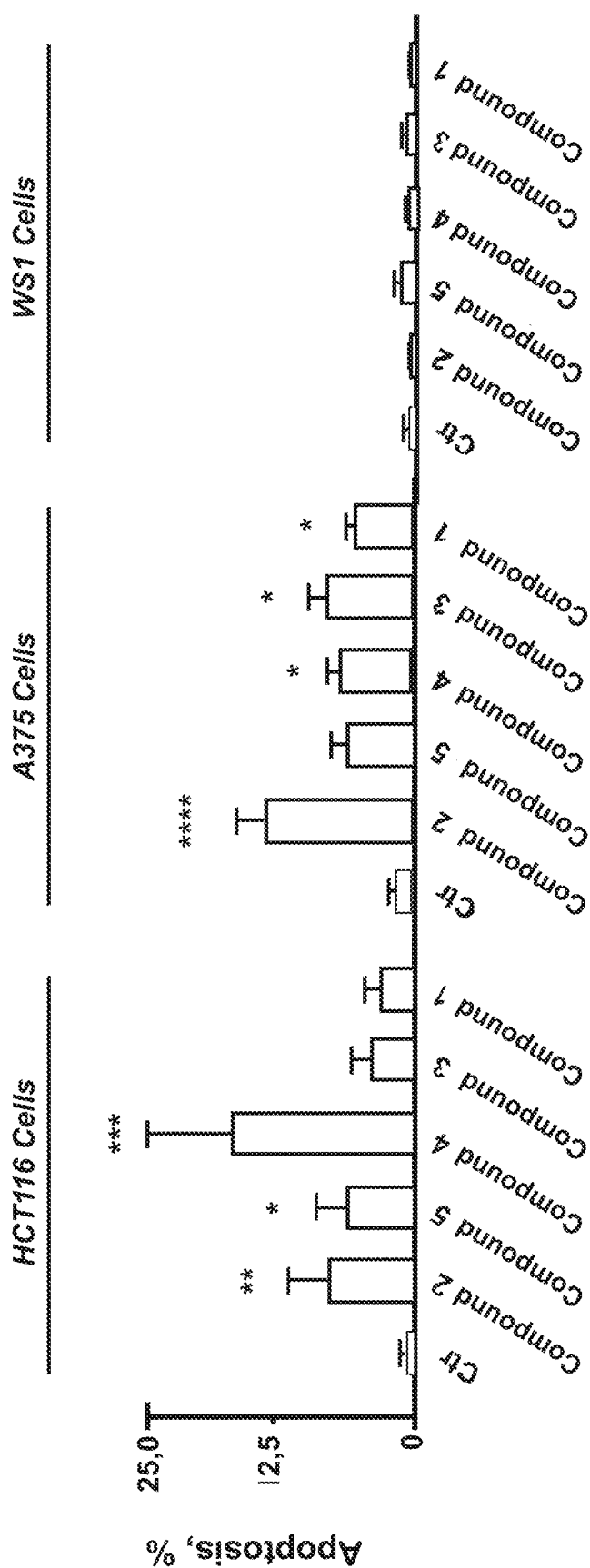

Synthetic flavone derivatives selectively induce apoptosis in tumour cells. The percentage of cells that have launched the cell death program (apoptosis) was quantified by the acridine orange/ethidium bromide method and using a fluorescence microscope and Image-J. All synthetic quercetin derivatives (Compound 2, Compound 5, Compound 4, Compound 3, and Compound 1) induced apoptosis (at 2 hrs) in human colon (HCT116) and skin (melanoma, A375) tumour lines, but not in normal cells (human skin fibroblasts, WS1). The substances were used at the following concentrations (with regard to the respective anti-proliferative IC50s): Compound 2, 50 µM (HCT116) or 40 µM (A375; WS1); Compound 5, 40 µM; Compound 4, 40 µM; Compound 3, 60 µM; Compound 1, 60 µM (HCT116) or 80 µM (A375; WS1). Ctr, control (treated with the vehicle). *, p<0.05; , p<0.01; *, p<0.005 and ****, p<0.001 compared to the control, by the 2-way ANOVA test (FIG. 18).

Figure 19:
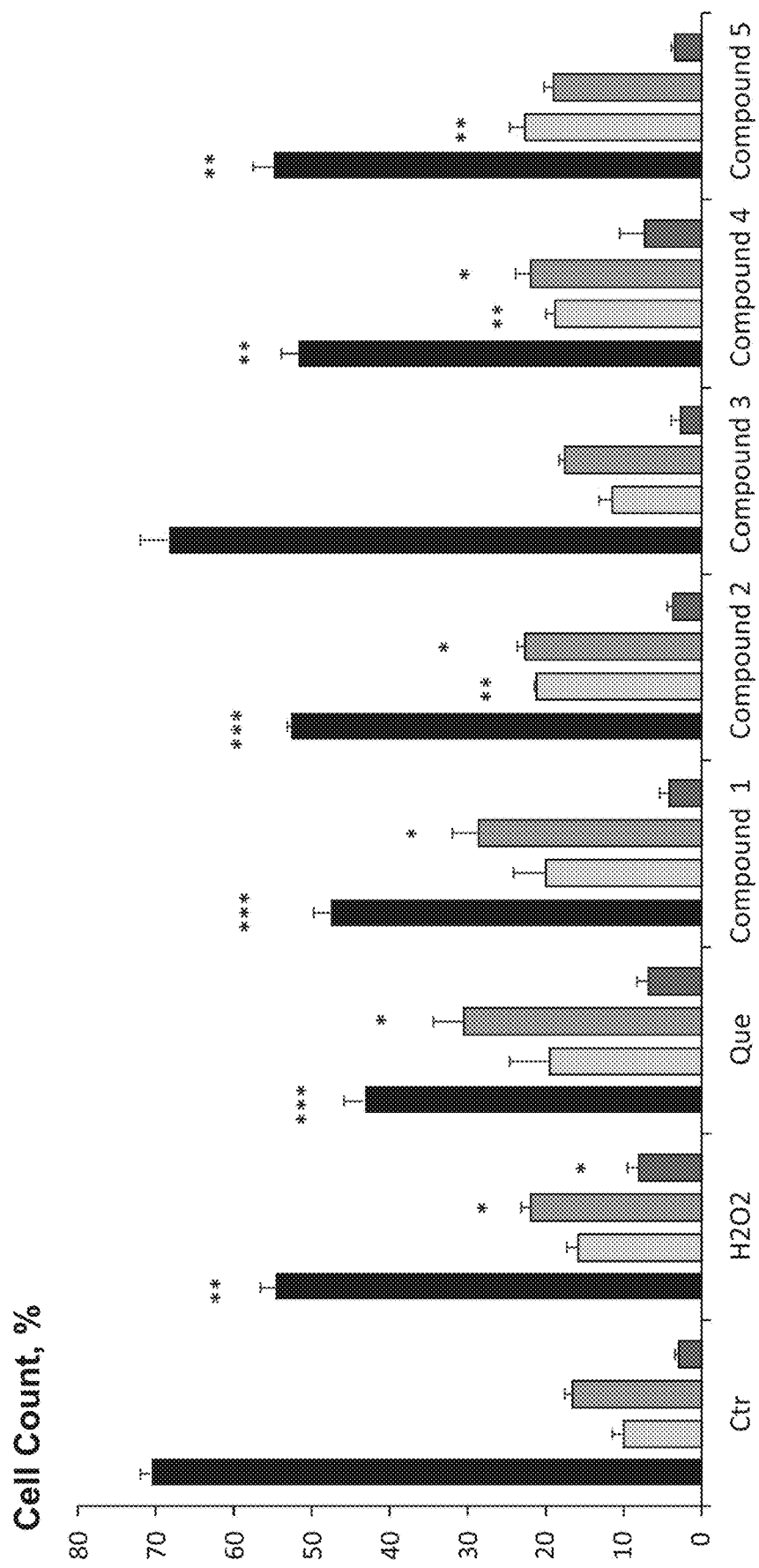

Synthetic flavone derivatives halt the cell cycle in melanoma. Progression of human melanoma cells (A375) through the cell cycle was quantified by using the propidium iodide (PI) method and a cytofluorimeter. Quercetin (Que) and synthetic derivatives thereof (Compound 1, Compound 2, Compound 3, Compound 4, and Compound 5) were used at the respective anti-proliferative IC50s. With the exception of Compound 3, all compounds investigated significantly halt the tumour cells in S and/or G2. Ctr, control (treated with the vehicle). $H_2O_2$, hydrogen peroxide (positive control; 200 µM). *, p<0.05 ; p<0.01, and *, p<0.001 compared to the control, by Student's t-test (FIG. 19).

Figure 20:
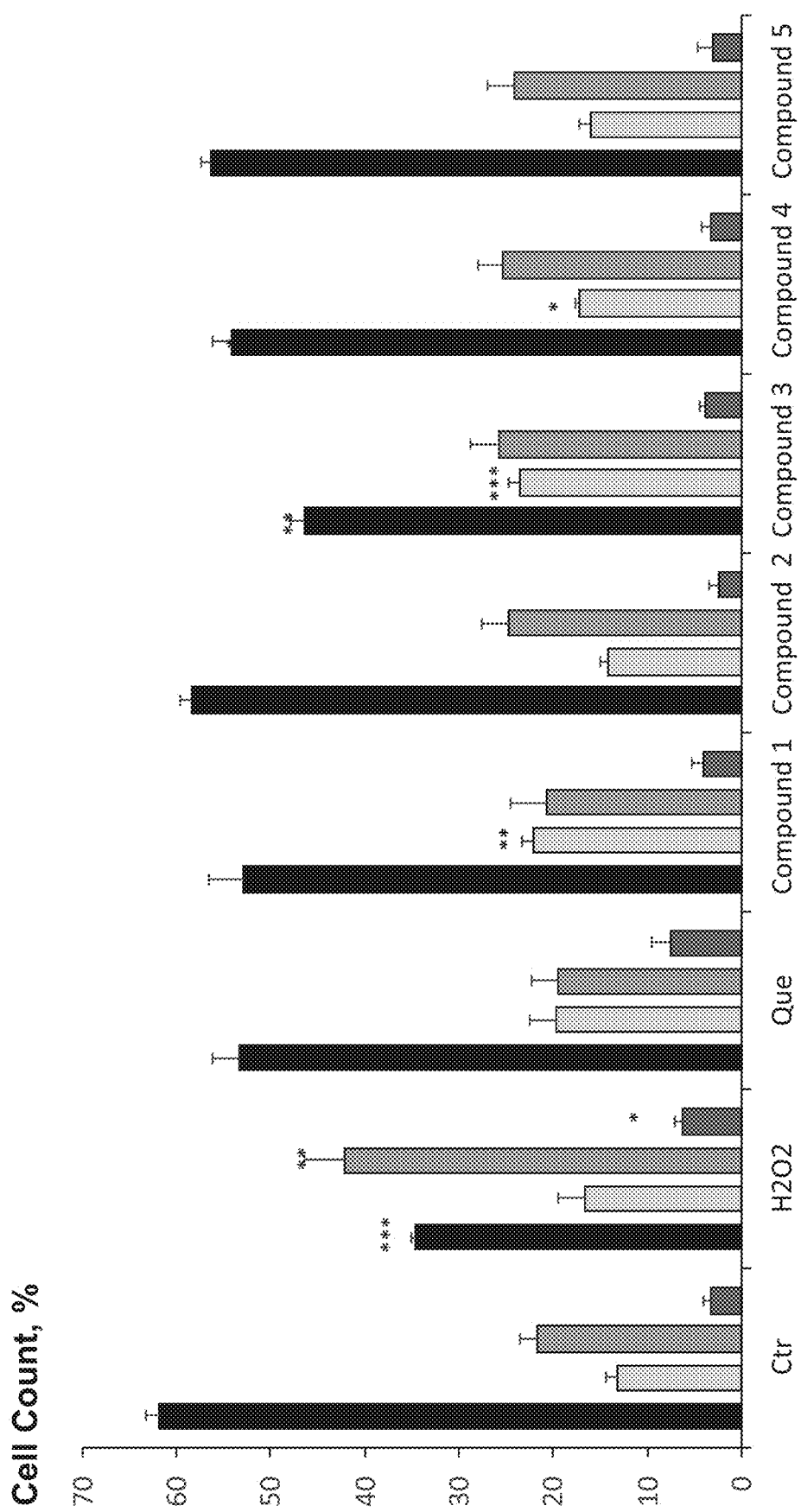

Synthetic flavone derivatives halt the cell cycle in colorectal carcinoma. Progression of human colon carcinoma cells (HCT116) through the cell cycle was quantified by using the propidium iodide (PI) method and a cytofluorimeter. Quercetin (Que) and synthetic derivatives thereof (Compound 1, Compound 2, Compound 3, Compound 4, and Compound 5) were used at the respective anti-proliferative IC50s. Compounds 1, 3, and 4 significantly halt the tumour cells in S. Ctr, control (treated with the vehicle). $H_2O_2$, hydrogen peroxide (positive control; 200 µM). *, p<0.05; , p<0.01 and , p<0.001 compared to the control, by Student's t-test (FIG. 20).

The effects of Compound 1 on the tumour cell cycle are partly mediated by ROS. The cell cycle of human colon carcinoma (HCT116) and melanoma (A375) cells was examined by using the propidium iodide method and a cytofluorimeter. A reactive oxygen species (ROS) scavenger, i.e. N-Acetyl Cysteine (NAC; 10 mM), prevents—at least in part—the effect on the cell cycle induced by Compound 1

Figure 21:
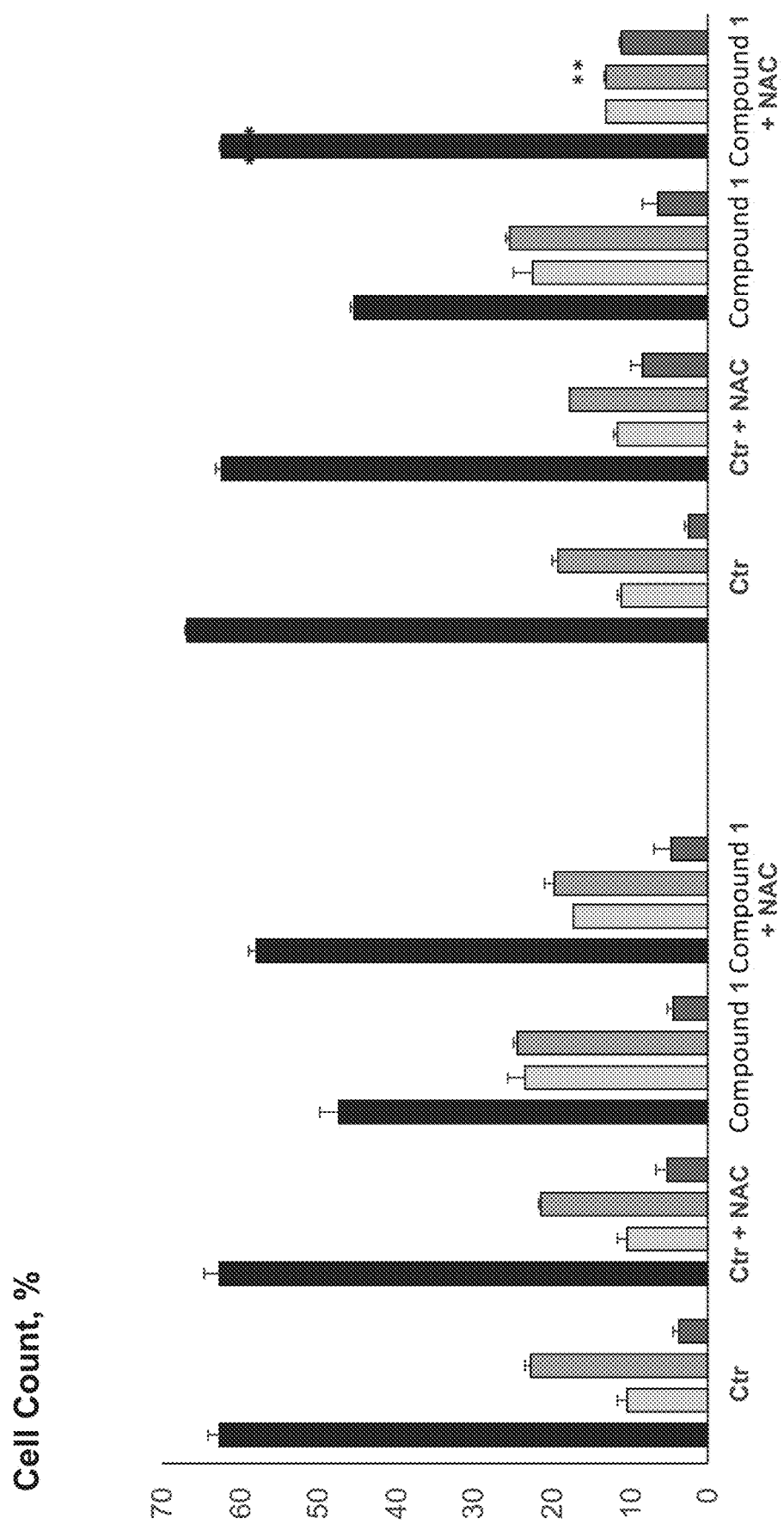
Figure 22A:
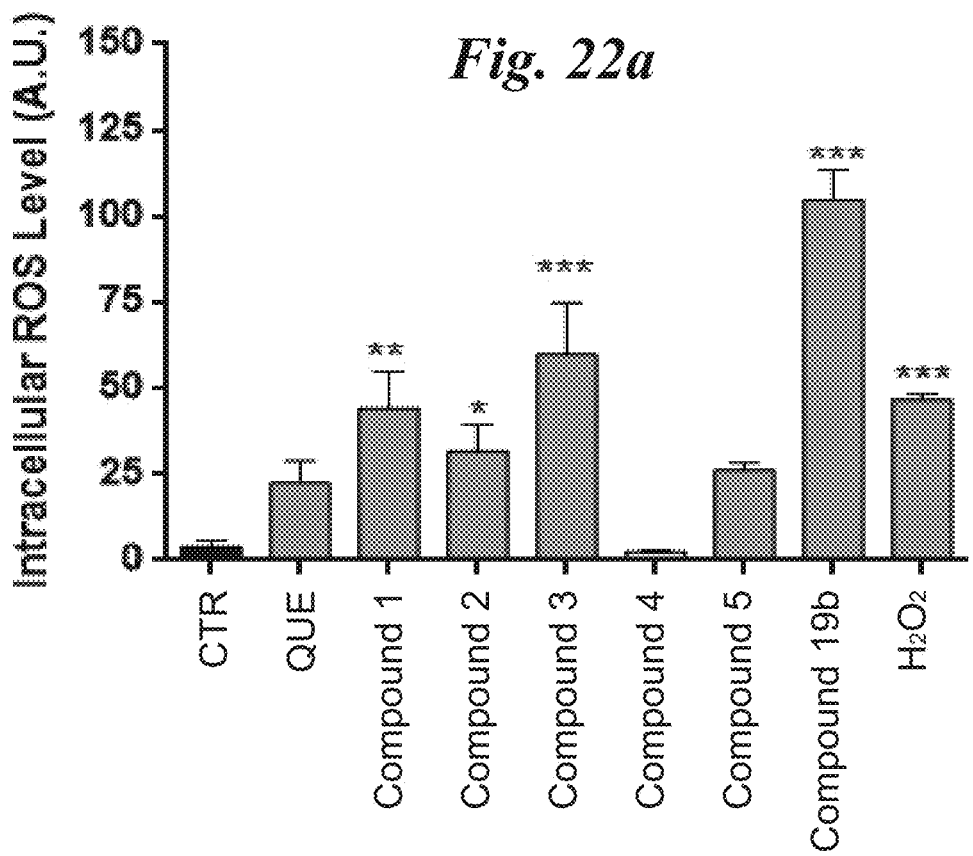
Figure 22B:
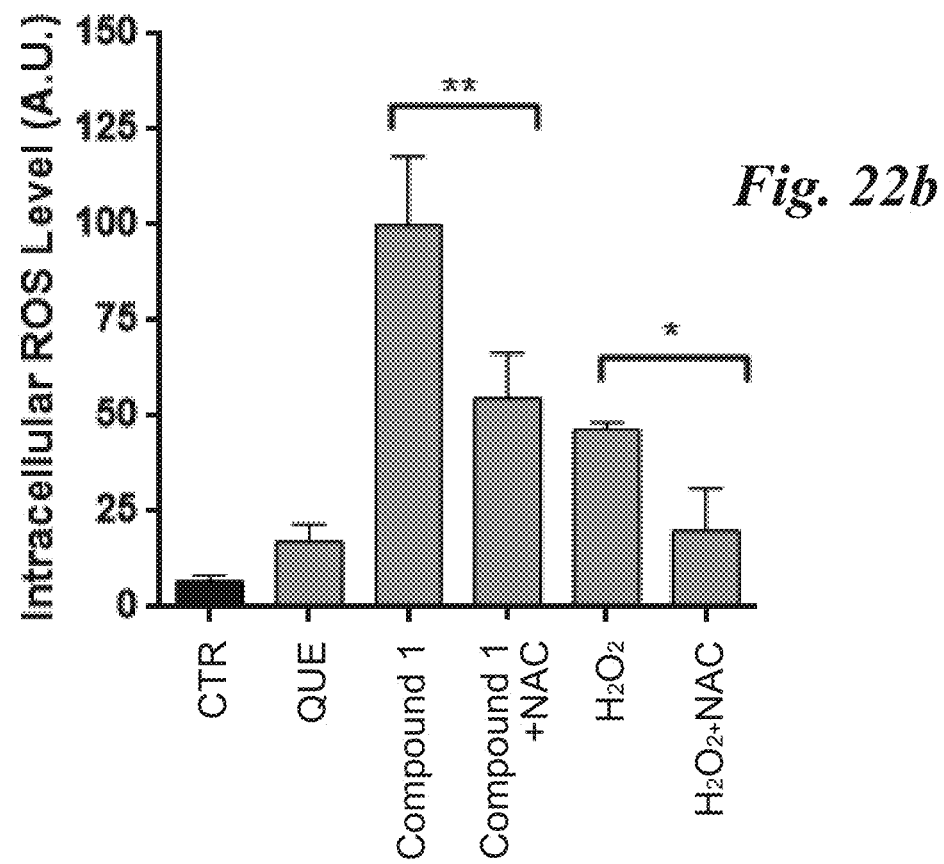

(used at its anti-proliferative IC50) in HCT116 (left) and A375 (right) cells. Ctr, control (treated with the vehicle). *, p<0.05; , p<0.01 and *, p<0.001 compared to the respective control (Compound 1 for Compound 1+NAC), by Student's t-test (FIG. 21).

Synthetic flavone derivatives cause an increase in intracellular ROS levels in colorectal carcinoma. Intracellular levels of reactive oxygen species (ROS) after 2 hrs of treatment of the human colon carcinoma cells (HCT116) were quantified by using the fluorescent DCFH2-DA probe. Fluorescence data were measured with a spectrophotometer and expressed in Arbitrary Units (A.U.). Quercetin (QUE) and synthetic derivatives thereof (Compound 1, Compound 2, Compound 3, Compound 4, Compound 5, and Compound 19b) were used at the respective anti-proliferative IC50s. While quercetin has no effect, Compound 1, Compound 2, Compound 3, and Compound 19b significantly raise ROS levels in HCT116 cells (left panel). The effect of Compound 1 is blocked by pretreatment with N-Acetyl-L-Cysteine (NAC; 10 mM), a ROS scavenger (right panel). $H_2O_2$, hydrogen peroxide (positive control; 500 µM). CTR, control (treated with the vehicle). *, p<0.05; , p<0.01 and *, p<0.001 compared to the control, by the 1-way ANOVA test (FIG. 22).

The following table, divided into two parts, shows the inhibitory concentrations representing 50% of the maximum anti-proliferative effect ($IC_{50}$), expressed in µM, corresponding to individual compounds according to the invention (no. indicated in the first column on the left) for each human malignant tumour cell line tested (top row, from column 2 onwards). Cell proliferation was quantitated spectrophotometrically by the crystal violet method.

| Compound | CRC (HCT116) | Melanoma (A375) | LC (H1299) | SCC (A431) | PCC (PANC-1) | BC (T24) |
|---|---|---|---|---|---|---|
| 1 | 165.90 | 67.07 | 100.40 | N.D. | >1000 | >1000 |
| 2 | 42.82 | 19.26 | 50.68 | 40.32 | 95.37 | 66.79 |
| 3 | 59.78 | 48.15 | 34.89 | N.D. | 155.5 | 44.91 |
| 4 | 22.89 | 20.10 | 15.89 | 30.99 | 69.58 | 45.49 |
| 5 | 28.83 | 16.38 | 50.45 | 25.50 | 69.39 | 50.45 |
| 15a | 13.27 | 23.00 | N.D. | N.D. | N.D. | N.D. |
| 15b | 18.63 | 24.55 | N.D. | N.D. | N.D. | N.D. |
| 15c | 15.78 | 15.47 | N.D. | N.D. | N.D. | N.D. |
| 15d | 12.08 | 7.16 | N.D. | N.D. | N.D. | N.D. |
| 19a | >1000 | N.D. | N.D. | N.D. | N.D. | N.D. |
| 19b | 5.51 | 9.48 | N.D. | N.D. | N.D. | N.D. |
| 19c | 1.28 | 3.95 | N.D. | N.D. | N.D. | N.D. |
| 19d | 0.74 | 1.62 | N.D. | N.D. | N.D. | N.D. |
| 22a | 49.87 | 136.10 | N.D. | N.D. | N.D. | N.D. |
| 22b | 407.31 | >1000 | N.D. | N.D. | N.D. | N.D. |
| 25a | 303.84 | >1000 | N.D. | N.D. | N.D. | N.D. |
| 26 | 81.19 | 52.28 | N.D. | N.D. | N.D. | N.D. |
| 27 | 378 | N.D. | N.D. | N.D. | N.D. | N.D. |
| 29a | 15.74 | 5.21 | N.D. | N.D. | N.D. | N.D. |
| 29b | >1000 | >1000 | N.D. | N.D. | N.D. | N.D. |
| 29c | 3.64 | 7.03 | N.D. | N.D. | N.D. | N.D. |
| 29d | 2.89 | 7.73 | N.D. | N.D. | N.D. | N.D. |
| 29e | 4.36 | 5.89 | N.D. | N.D. | N.D. | N.D. |
| 29f | 3.08 | 5.17 | N.D. | N.D. | N.D. | N.D. |
| 29g | 5.93 | 7.84 | N.D. | N.D. | N.D. | N.D. |
| 36 | 112.11 | 89.79 | N.D. | N.D. | N.D. | N.D. |

| Compound | RCC - (786-O) | PC - (PC3) | BRC - (BT549) | HNC - (Cal27) | HCC - HepG2) | OCC - (OVCAR) |
|---|---|---|---|---|---|---|
| 1 | 148.90 | 79.34 | 190.80 | 15.57 | 144.00 | N.D. |
| 2 | 72.50 | 309.10 | 156.30 | 63.21 | 264.9 | N.D. |
| 3 | 65.37 | 46.16 | 119.4 | 36.72 | 50.21 | N.D. |
| 4 | 41.22 | 34.91 | 48.55 | 22.86 | 54.44 | N.D. |
| 5 | 32.6 | 56.86 | 46.45 | 19.7 | 105.7 | 79.20 |
| 15a | N.D. | N.D. | N.D. | N.D. | N.D. | N.D. |
| 15b | N.D. | N.D. | N.D. | N.D. | N.D. | N.D. |
| 15c | N.D. | N.D. | N.D. | N.D. | N.D. | N.D. |
| 15d | N.D. | N.D. | N.D. | N.D. | N.D. | N.D. |
| 19a | N.D. | N.D. | N.D. | N.D. | N.D. | N.D. |
| 19b | N.D. | N.D. | N.D. | N.D. | N.D. | N.D. |
| 19c | N.D. | N.D. | N.D. | N.D. | N.D. | 7.44 |
| 19d | N.D. | N.D. | N.D. | N.D. | N.D. | 5.01 |
| 22a | N.D. | N.D. | N.D. | N.D. | N.D. | N.D. |
| 22b | N.D. | N.D. | N.D. | N.D. | N.D. | N.D. |
| 25a | N.D. | N.D. | N.D. | N.D. | N.D. | N.D. |
| 26 | N.D. | N.D. | N.D. | N.D. | N.D. | N.D. |
| 27 | N.D. | N.D. | N.D. | N.D. | N.D. | N.D. |
| 29a | N.D. | N.D. | N.D. | N.D. | N.D. | N.D. |
| 29b | N.D. | N.D. | N.D. | N.D. | N.D. | N.D. |
| 29c | N.D. | N.D. | N.D. | N.D. | N.D. | N.D. |
| 29d | N.D. | N.D. | N.D. | N.D. | N.D. | N.D. |
| 29e | N.D. | N.D. | N.D. | N.D. | N.D. | 16.09 |
| 29f | N.D. | N.D. | N.D. | N.D. | N.D. | 11.84 |
| 29g | N.D. | N.D. | N.D. | N.D. | N.D. | N.D. |
| 36 | N.D. | N.D. | N.D. | N.D. | N.D. | N.D. |

Legend:
CRC, Colon-Rectal Cancer;
LC, Lung Cancer;
SCC, Squamous Cell Carcinoma;
PCC, Pancreatic Cancer Cell;
RCC, Renal Cell Carcinoma;
PC, Prostate Cancer;
BC, Bladder Carcinoma;
BRC, Breast Cancer;
HNC, Head and Neck Cancer;
HCC, Hepatocellular Carcinoma;
OCC, Ovarian Cell Carcinoma;
N.D., not determined.

The invention claimed is:

1. A medical compound comprising a synthetic flavone derivative, according to the formula (III) with allotment in position C-3 of a group as shown below:

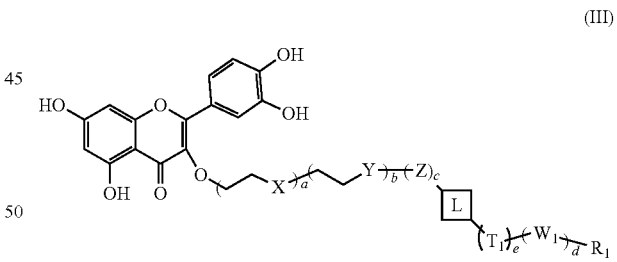

(III)

where X is O,
where L is a linker,
where a is 1,
where b, c, d, e each are 0 or 1,
where Y, Z, $T_1$, and $W_1$ are each independently selected from: CH2, O, NH, C(O), NHC(O), and C(O)NH, NH GO) NH;
where $R_1$ is a member selected from the group consisting of:
H,
$C_{1-24}$ alkyl or heteroalkyl,
$C_{1-24}$ alkenyl or heteroalkenyl,
$C_{1-24}$ alkynyl or heteroalkynyl, and
an acyl residue of a fatty acid;

wherein L is selected from the following compounds:
| LINKER L | |
|---|---|
| L1 | 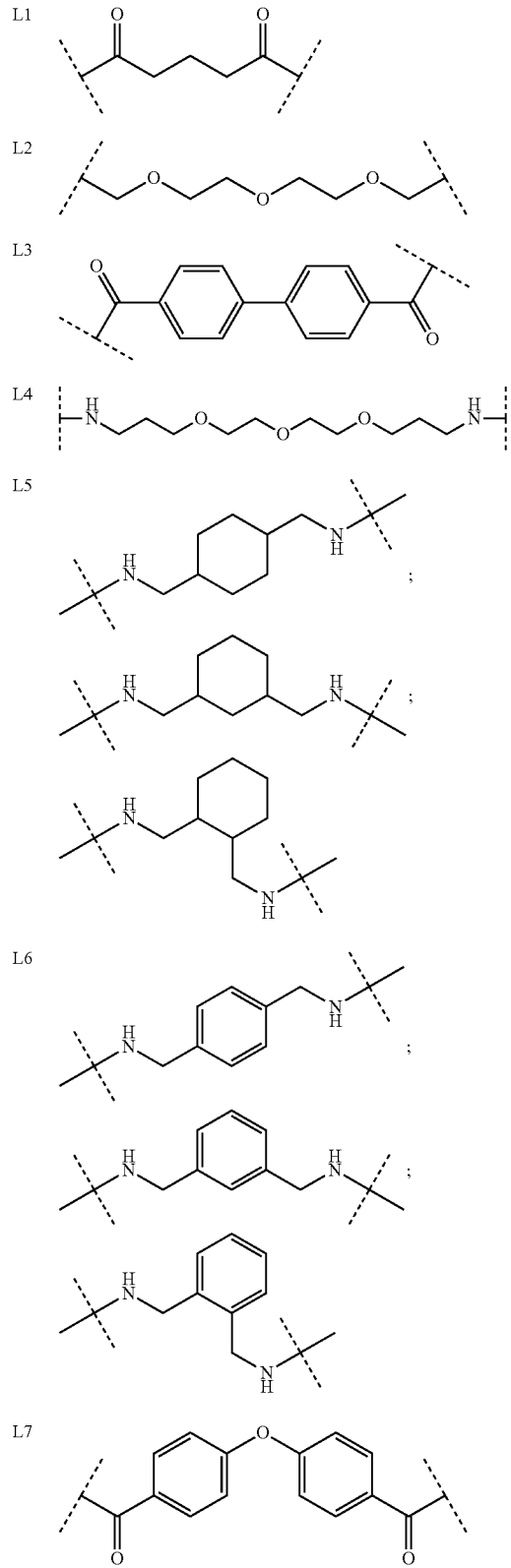 |
| L2 | |
| L3 | |
| L4 | |
| L5 | |
| L6 | |
| L7 | |
-continued
| LINKER L | |
|---|---|
| L8 | 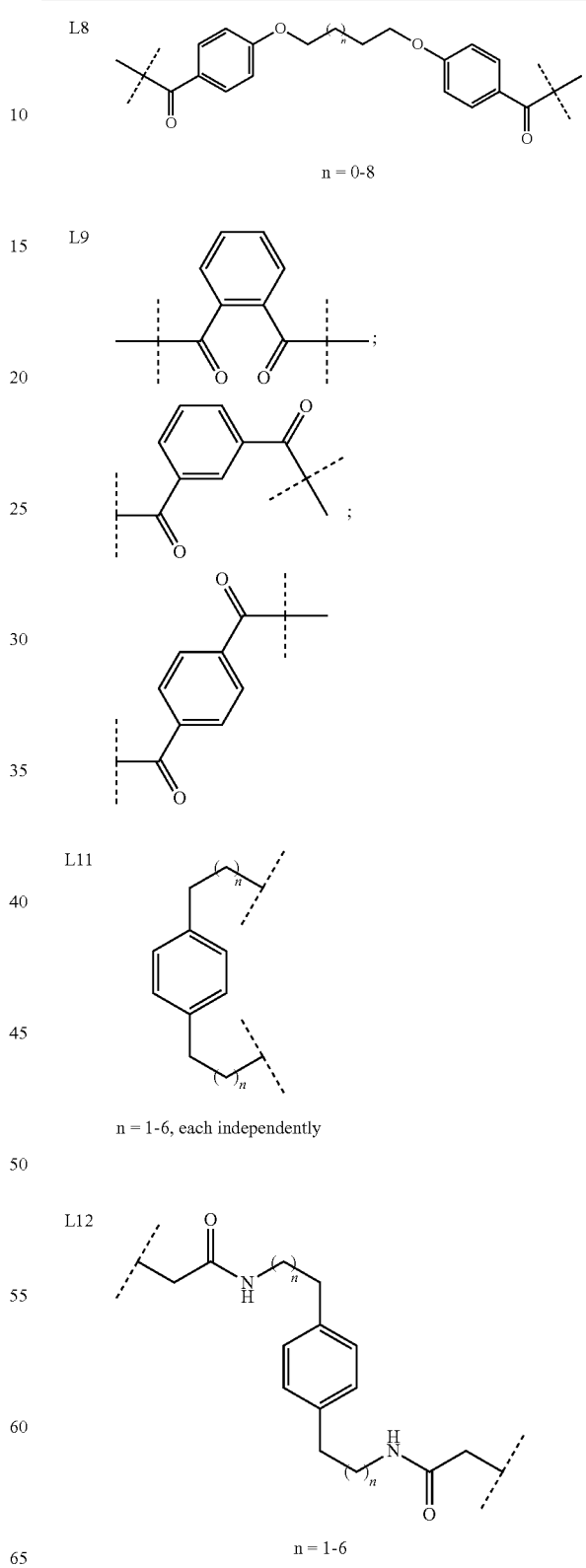 |
| | n = 0–8 |
| L9 | |
| | |
| L11 | |
| | n = 1–6, each independently |
| L12 | |
| | n = 1–6 |

| LINKER L | | LINKER L | |
|---|---|---|---|
| L13 | 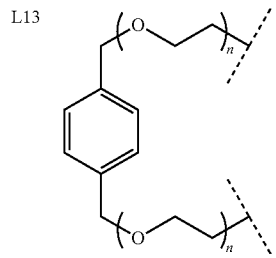 n = 1-3, each independently | L22 | 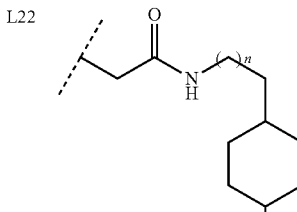 n = 1-6 |
| L14 | 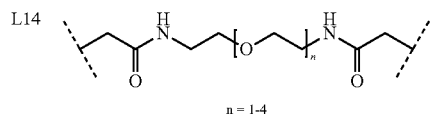 n = 1-4 | L23 | 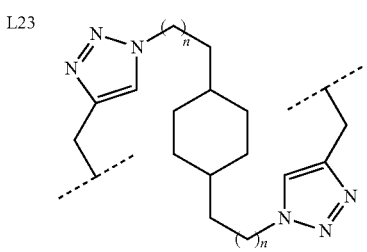 n = 1-6, each independently |
| L15 | 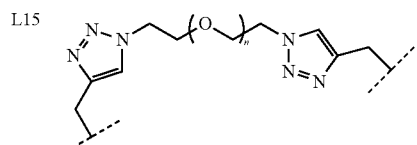 n = 1-4, each independently | | |
| L16 | 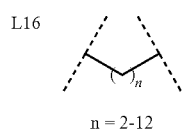 n = 2-12 | L24 | 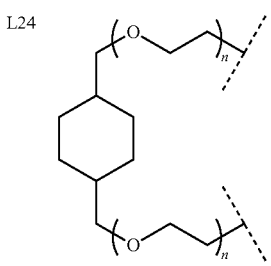 n = 1-3, each independently |
| L17 | 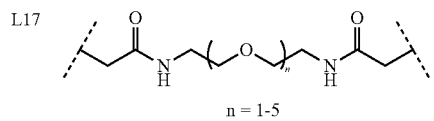 n = 1-5 | | |
| L18 | 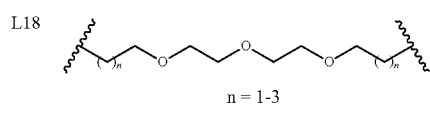 n = 1-3 | L25 | 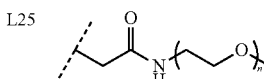 n = 1-3, each independently |
| L19 | 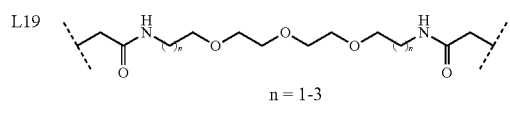 n = 1-3 | | |
| L20 | 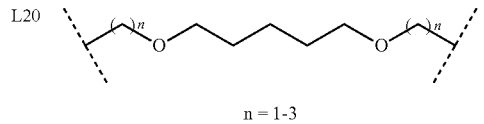 n = 1-3 | | |
| L21 | 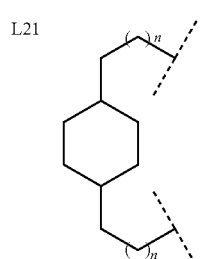 n = 1-6 | L26 | 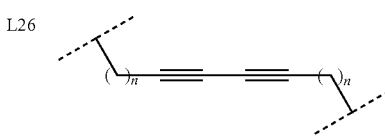 n = 1-6, each independently |

| LINKER L | |
|---|---|
| L27 | 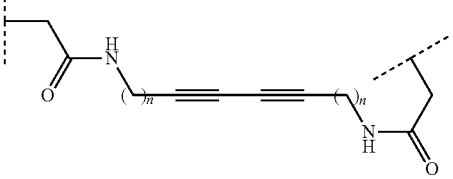<br>n = 1-6, each independently |
| L28 | 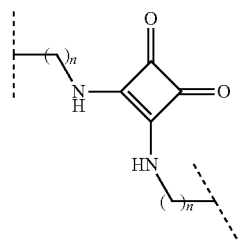<br>n = 1-6, each independently |
| L29 | 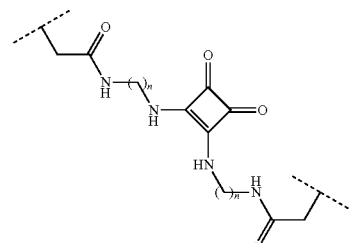<br>n = 1-6, each independently |
| L30 | 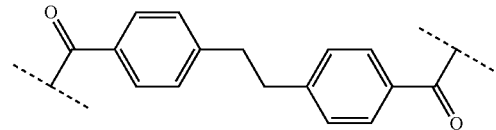 |
| L31 | 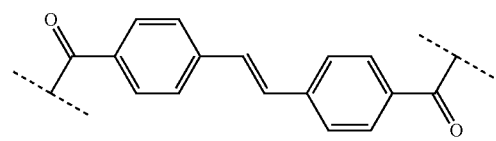 |
| L32 | 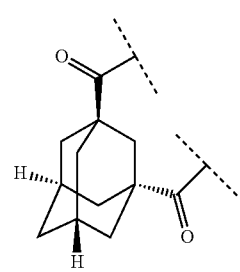 |
| LINKER L | |
|---|---|
| L33 | 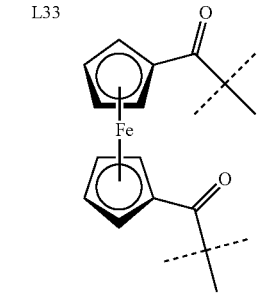 |
| L34 | 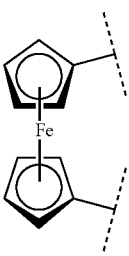 |
| L35 | 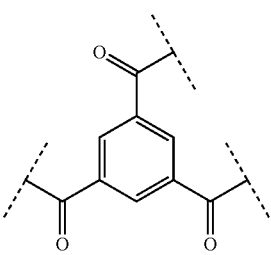 |
| L36 | 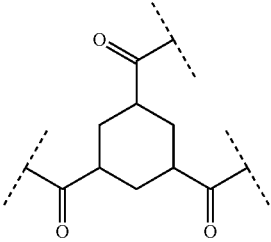 |
| L37 | 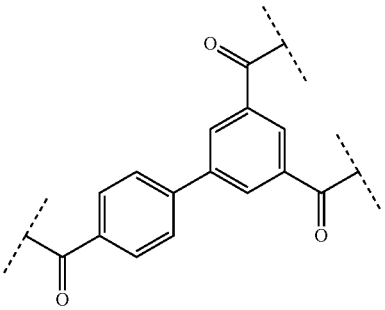 |

| LINKER L |
|---|
| L38 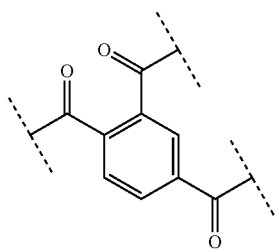 |
| L39 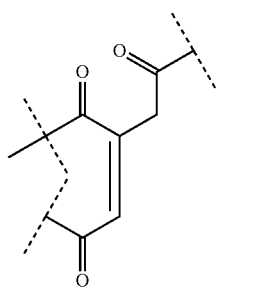 |
| L40 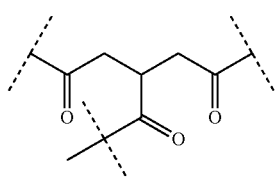 |
| L41 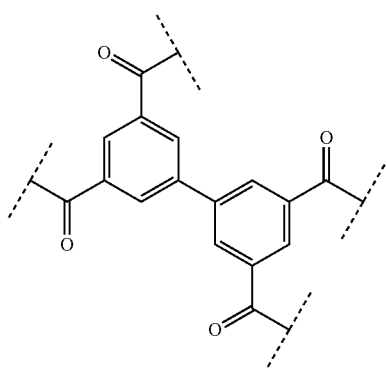 |
| L42 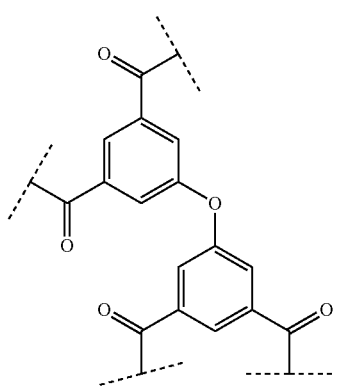 |
| LINKER L |
|---|
| L43 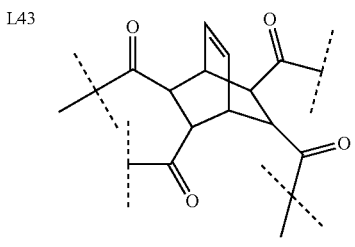 |
| L44 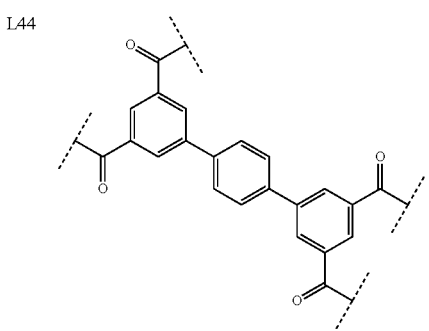 |
| L45 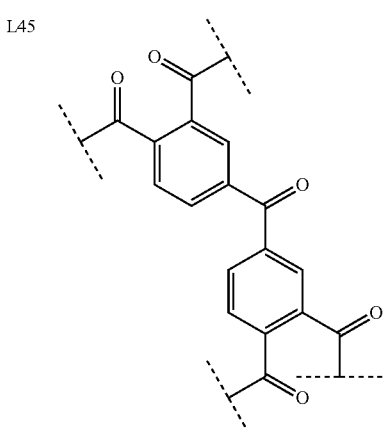 |
| L46 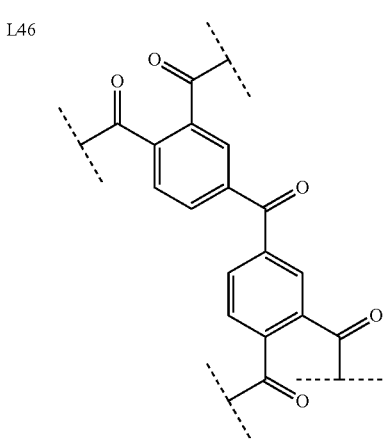 |

| LINKER L |
|---|
| L47 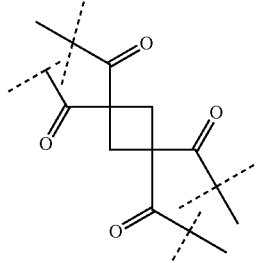 |
| L48 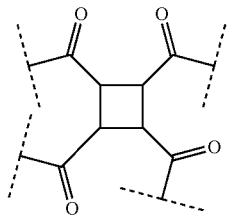 |
| L49 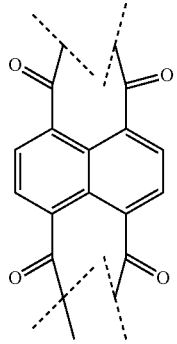 |
| L50 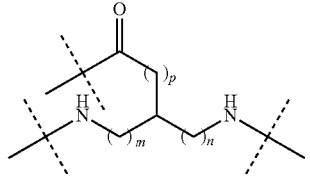
n, m, p = 0-6; each independently |
| L51 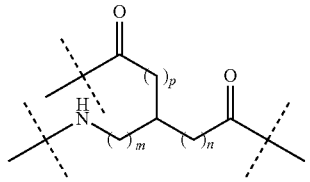
n, m, p = 0-6; each independently |
| L52 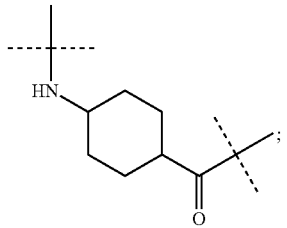 |
| LINKER L |
|---|
| 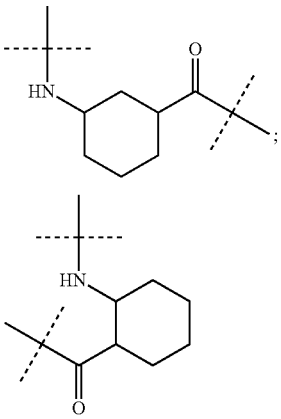 |
| L53 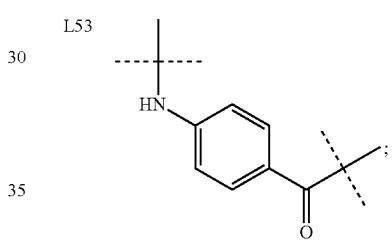 |
| 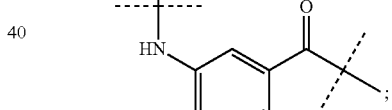 |
| 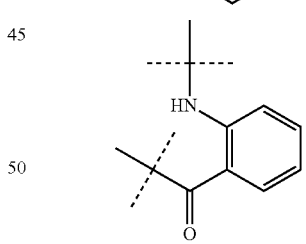 |
| L54 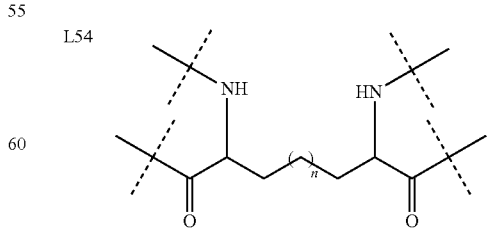
n = 0, 5 |

| LINKER L |
|---|
| L55 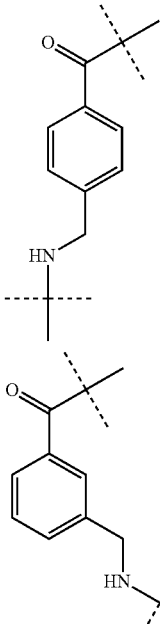 |
| L56 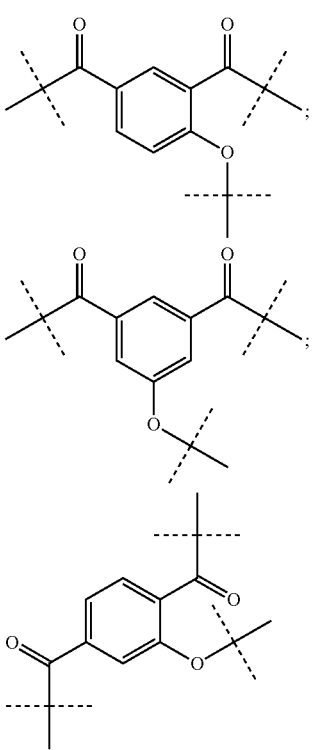 |
| LINKER L |
|---|
| L57 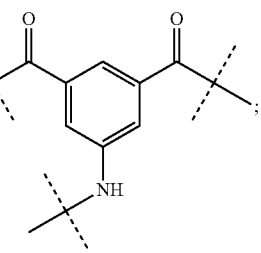 |
| L58 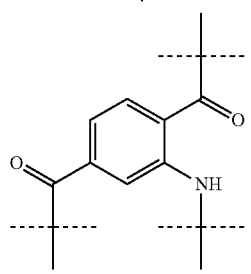 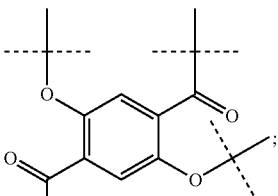 |
| L59 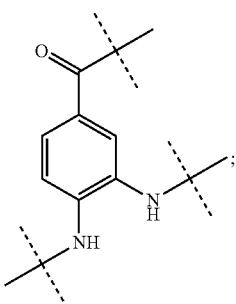 |
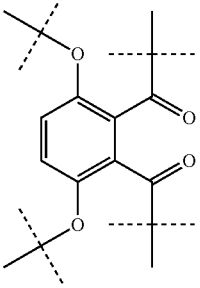

LINK-
ER L
L60
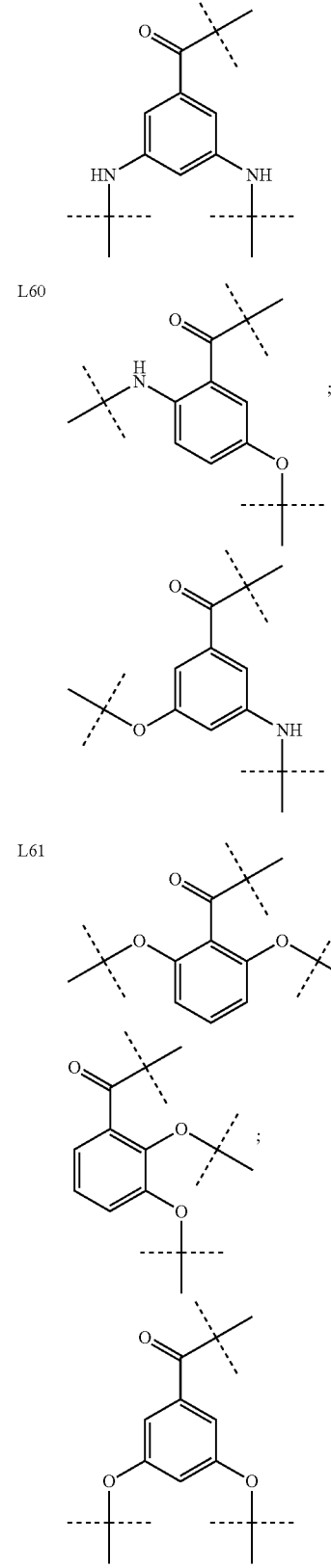
L61
LINK-
ER L
L62
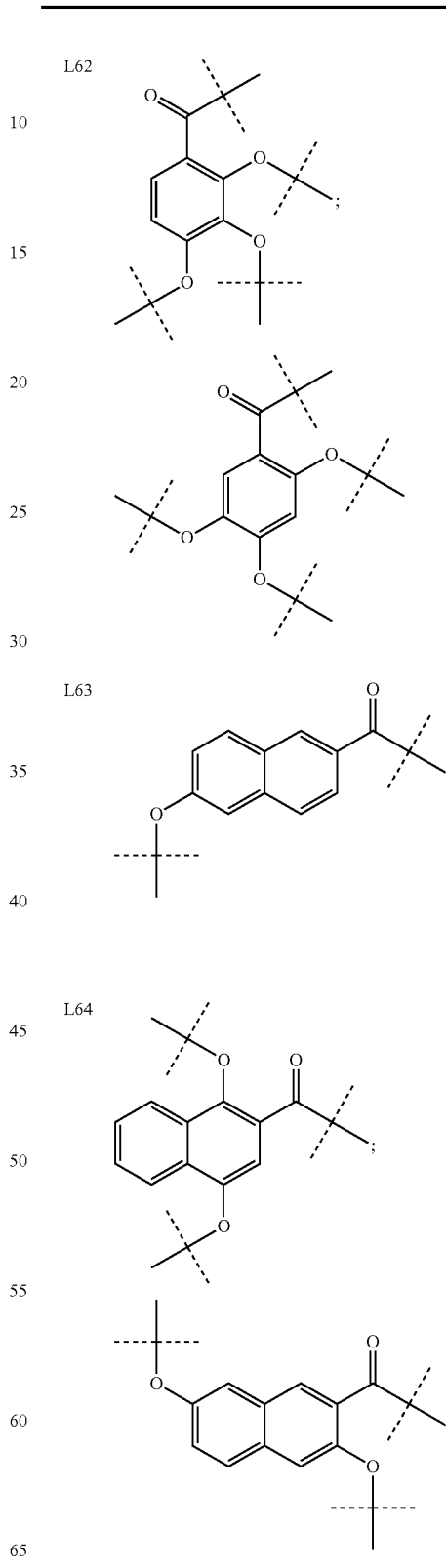
L63
L64

| LINKER L | | LINKER L | |
|---|---|---|---|
| L65 | 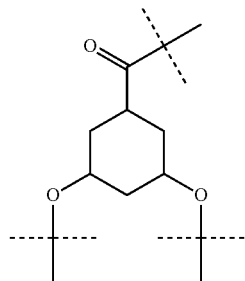 | L70 | 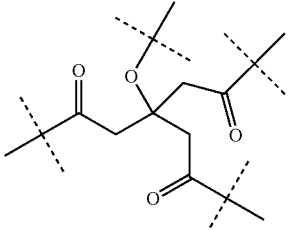 |
| L66 | 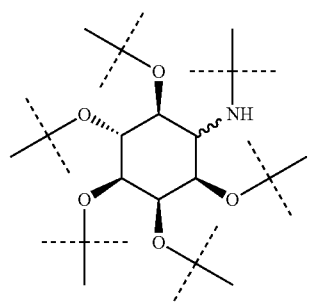 | L71 | 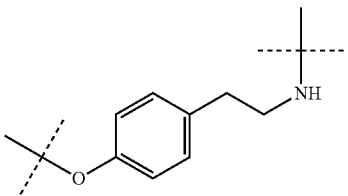 |
| L67 | 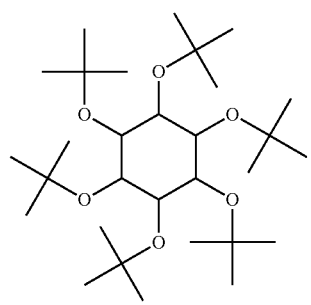 [SMILES: CC(C)(C)OC1C(OC(C)(C)C)C(OC(C)(C)C)C(OC(C)(C)C)C(OC(C)(C)C)C1OC(C)(C)C] | L72 | 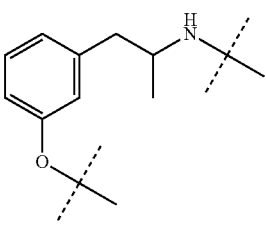 |
| L68 | 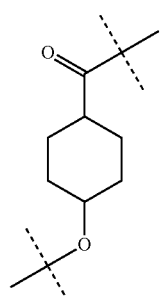 | L73 | 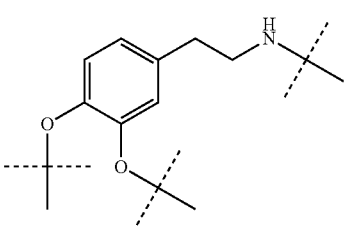 |
| L69 | 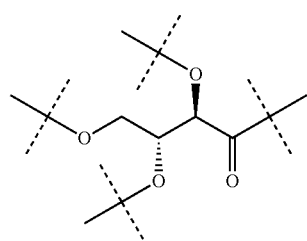 | L74 | 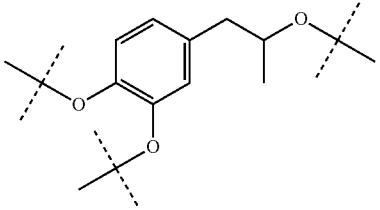 |
| | | L75 | 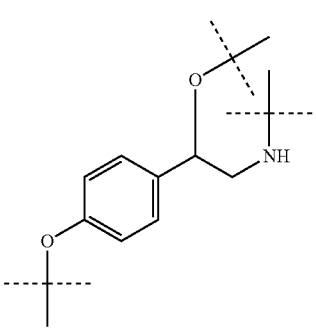 |

| LINKER L | LINKER L |
|---|---|
| L76 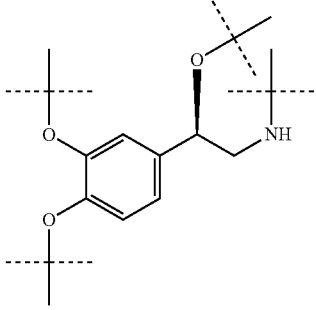 | L81 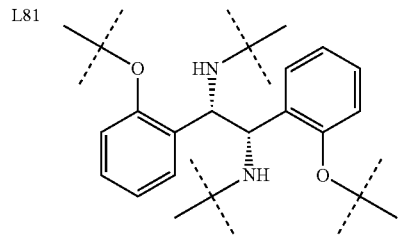 |
| L77 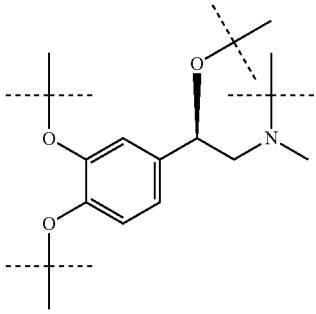 | L82 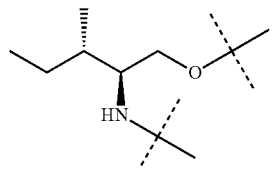 |
| L78 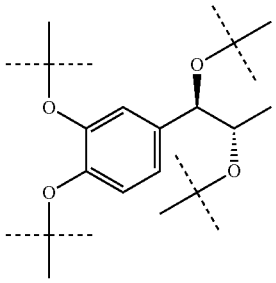 | L83 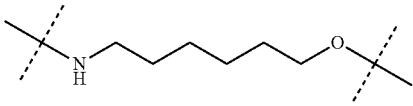 |
| L79 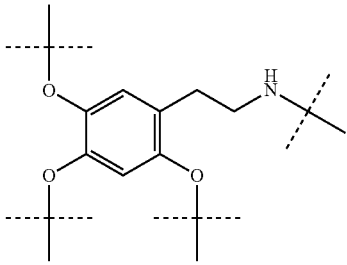 | L84 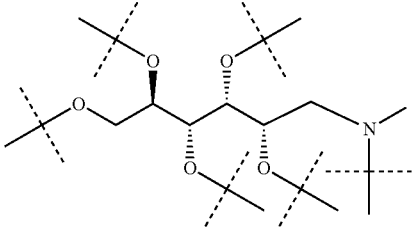 |
| L80 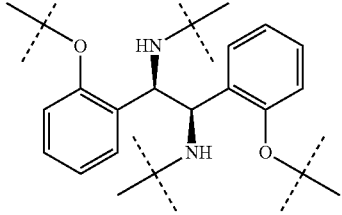 | L85 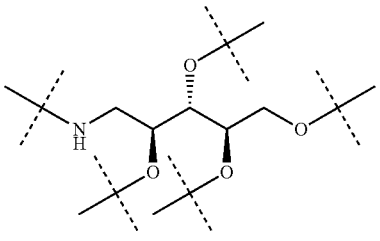 |
| | L86  |
| | L87 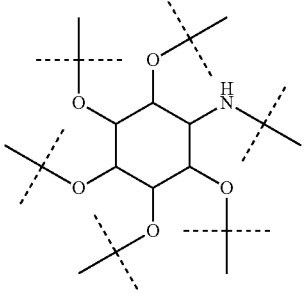 |

| LINKER L | |
|---|---|
| L88 | 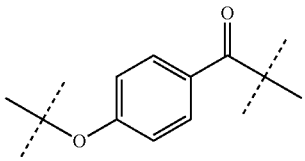 |
| L89 | 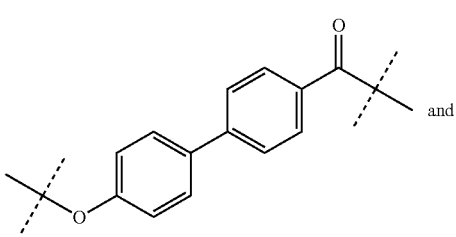 and |
| L90 | 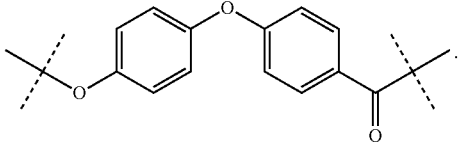 |

2. The medical compound according to claim 1, wherein L16 is:

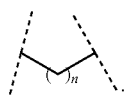

n = 3-12

3. The compound according to claim 1, for the treatment of lung carcinoma.

4. The compound according to claim 1, for the treatment of colon carcinoma.

5. The compound according to claim 1, for the treatment of melanoma.

6. The compound according to claim 1, for the treatment of skin squamous carcinoma.

7. The compound according to claim 1, for the treatment of basal cell carcinoma (basalioma).

8. A dimer comprising at least one medical compound according to claim 1.

9. A trimer comprising at least one medical compound according to claim 1.

10. A tetramer comprising at least one medical compound according to claim 1.

11. A medical compound comprising a synthetic flavone derivative, wherein the overall structure is selected from the following structure (XII):

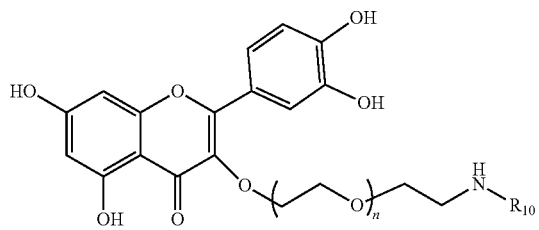

(XII)

where n is 1, $R_{10}$, is a member independently, and in possible combinations, selected from the group consisting of:

H;

$C_{1-24}$ alkyl or heteroalkyl, $C_{1-24}$ alkenyl or heteroalkenyl, $C_{1-24}$ alkynyl or heteroalkynyl, an acyl residue of a saturated/unsaturated/polyunsaturated fatty acid, of either synthetic or natural origin, a residue that may be selected from those residues L91, L92, and L93 shown in the table below:

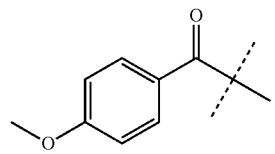

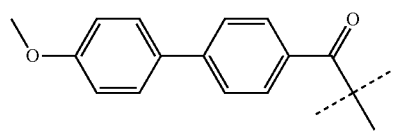

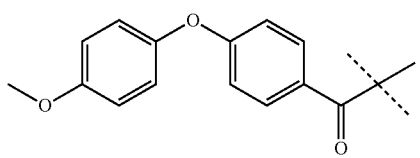

12. A medical compound comprising a synthetic flavone derivative, wherein the compound has a structure selected from compound 2 or 5
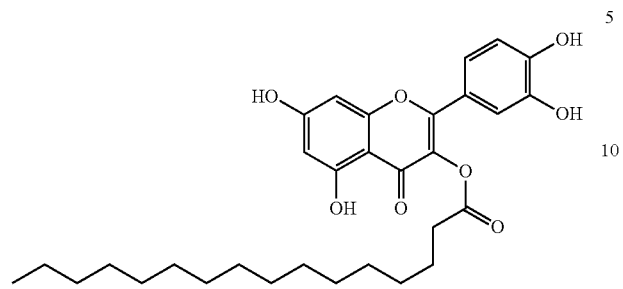
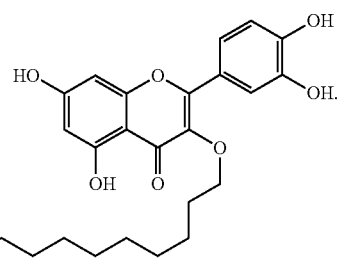
13. A medical compound comprising a synthetic flavone derivative, wherein the compound has a structure selected from compound 19c, 19d, 26, 29e, or 29f:
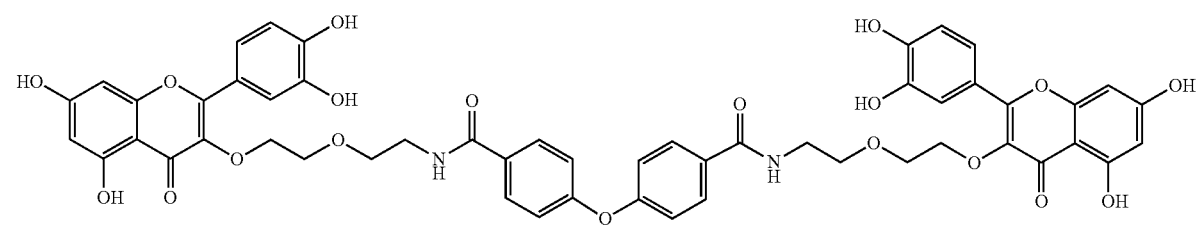
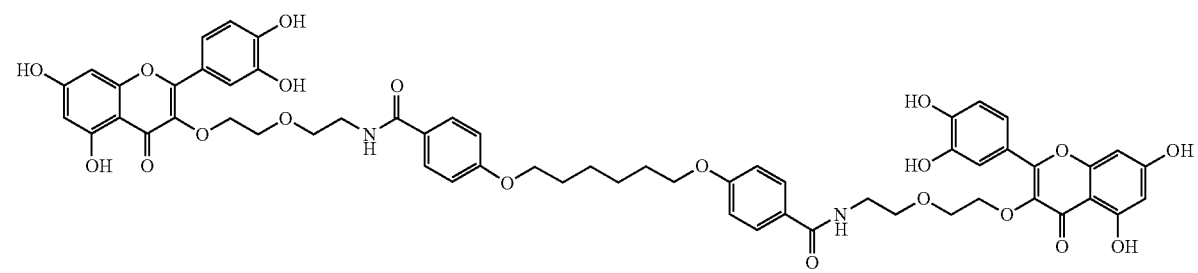
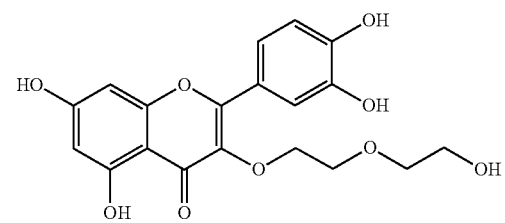
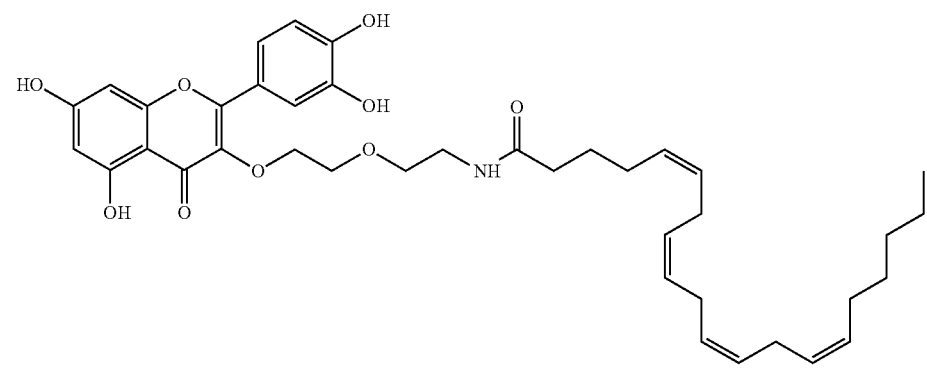

-continued
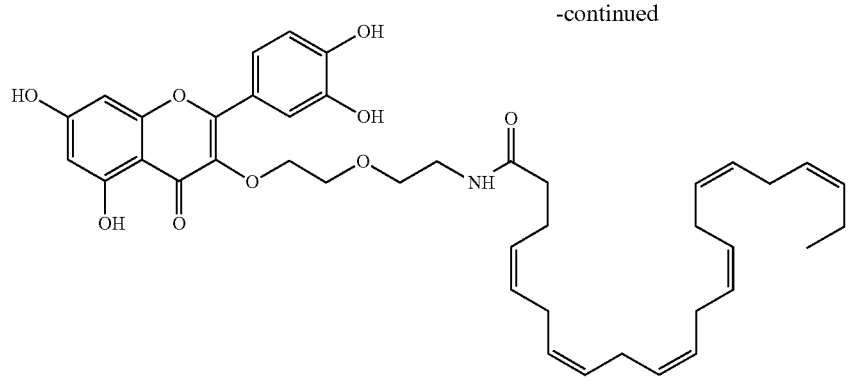
14. The medical compound according to claim 1, wherein L is selected from the following compounds:
| LINKER L |
| --- |
| L1 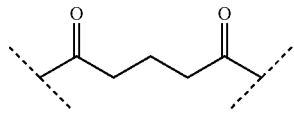 |
| L2 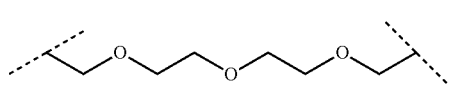 |
| L3 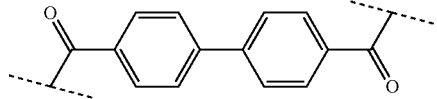 |
| L4 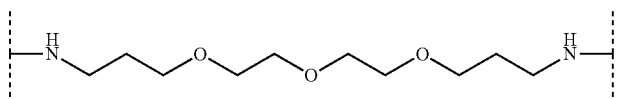 |
| L5 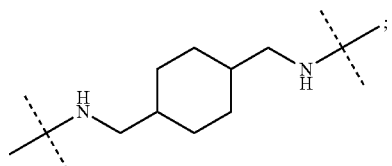 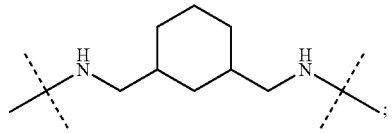 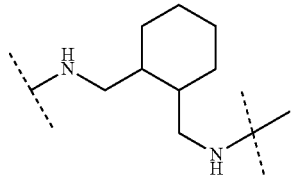 |
| L6 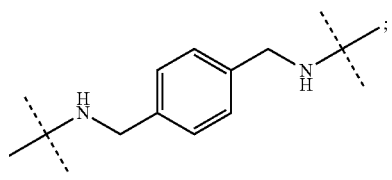 |

-continued
| LINKER L | |
|---|---|
| | 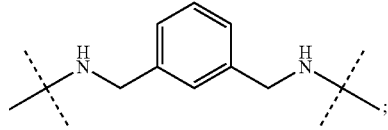 |
| | 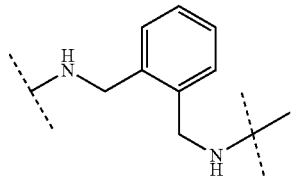 |
| L7 | 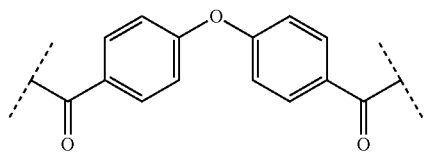 |
| L8 | 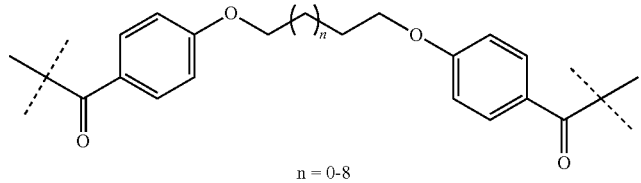
n = 0-8 |
| L9 | 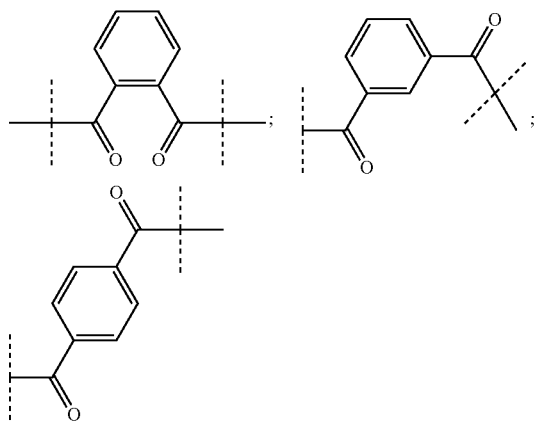 |
| L11 | 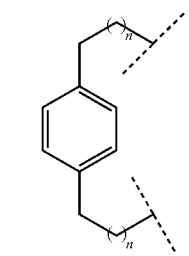
n = 1-6, each independently |

| LINKER L | |
|---|---|
| L12 | 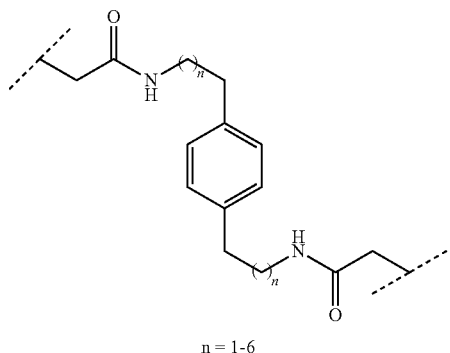<br>n = 1-6 |
| L13 | 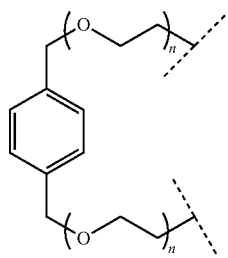<br>n = 1-3, each independently |
| L14 | 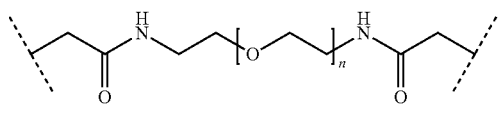<br>n = 1-4 |
| L15 | 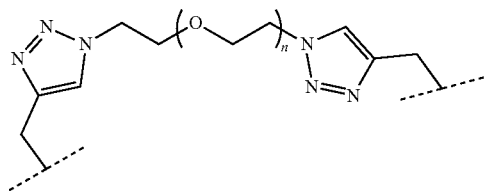<br>n = 1-4, each independently |
| L16 | 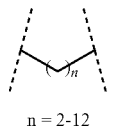<br>n = 2-12 |
| L17 | 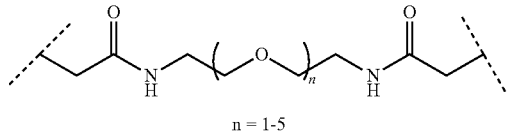<br>n = 1-5 |
| L18 | 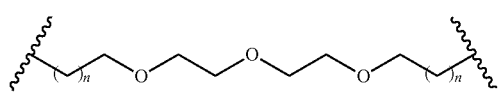<br>n = 1-3 |

-continued
| LINKER L | |
|---|---|
| L19 | 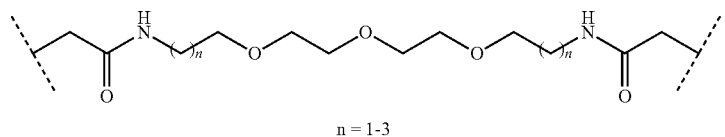
n = 1-3 |
| L20 | 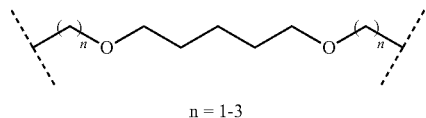
n = 1-3 |
| L21 | 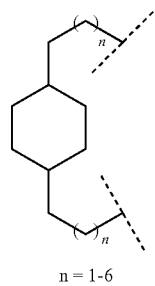
n = 1-6 |
| L22 | 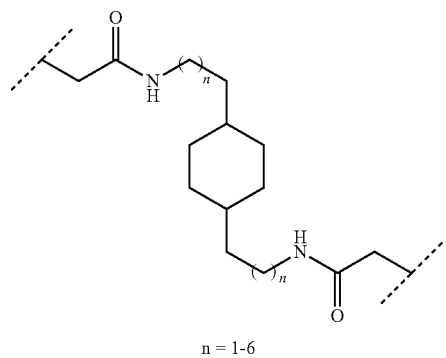
n = 1-6 |
| L23 | 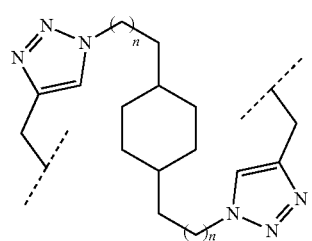
n = 1-6, each independently |
| L24 | 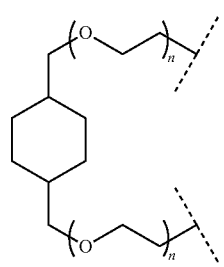
n = 1-3, each independently |

| LINKER L |
|---|
| L25 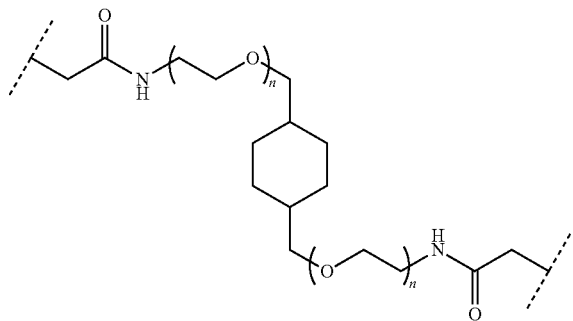
n = 1-3, each independently |
| L26 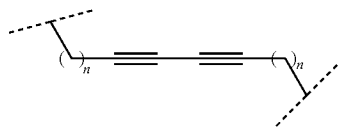
n = 1,6 each independently |
| L27 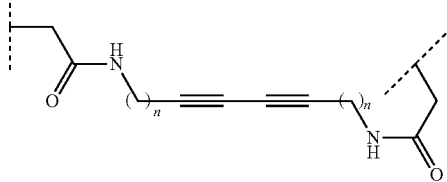
n = 1-6, each independently |
| L28 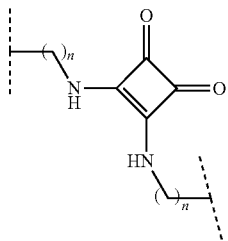
n = 1-6, each independently |
| L29 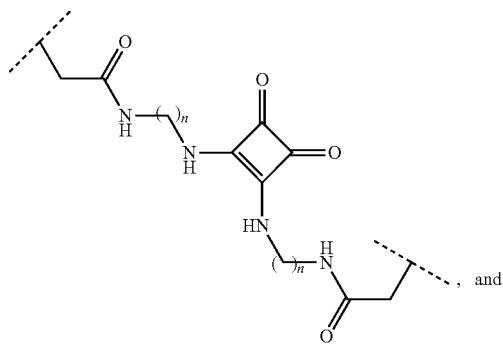, and
n = 1-6, each independently |
and

| LINKER L |
| --- |
| L30 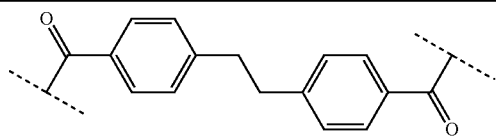 |
15. The medical compound according to claim 14, wherein for L16 n=3-12.
16. The medical compound according to claim 15, wherein at least one of b, c, d, and e is 1.
17. The medical compound according to claim 1, wherein L is selected from:
| LINKER L |
| --- |
| L31 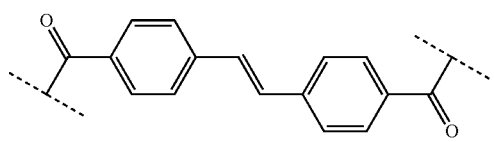 |
| L32 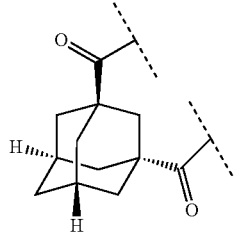 |
| L33 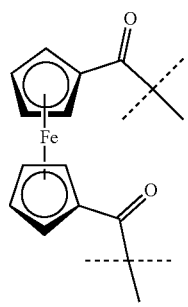 |
| L34 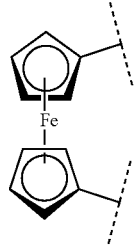 |

| LINKER L | |
|---|---|
| L35 | 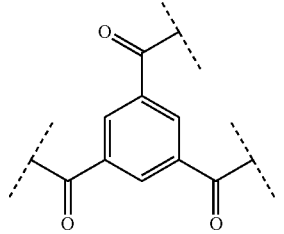 |
| L36 | 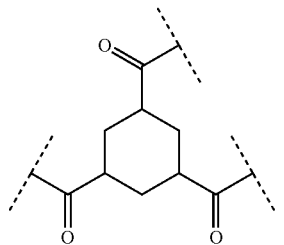 |
| L37 | 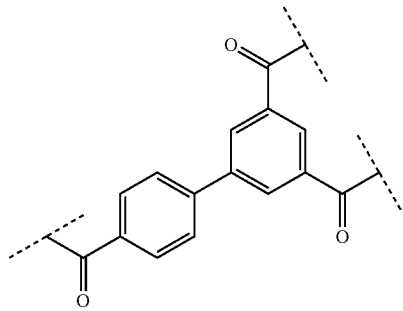 |
| L38 | 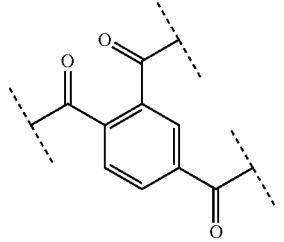 |
| L39 | 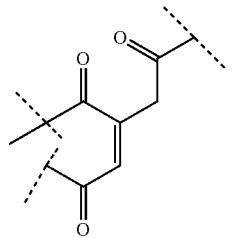 |
| L40 | 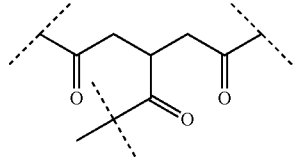 |

| LINKER L |
|---|
| L41 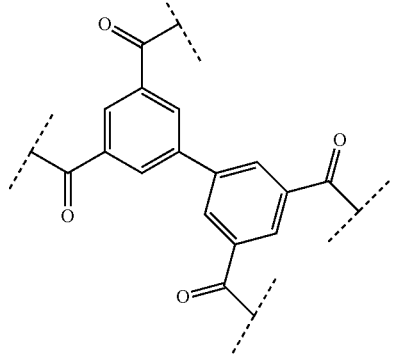 |
| L42 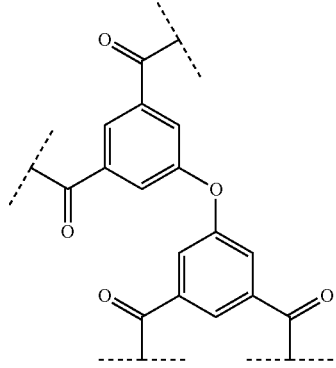 |
| L43 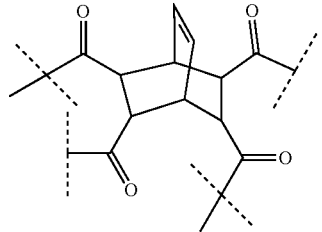 |
| L44 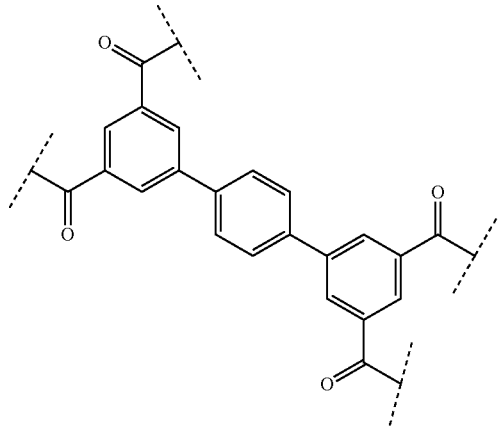 |

| LINKER L |
|---|
| L45 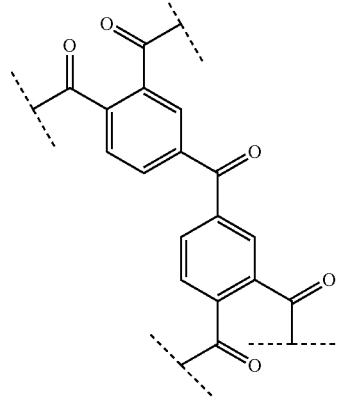 |
| L46 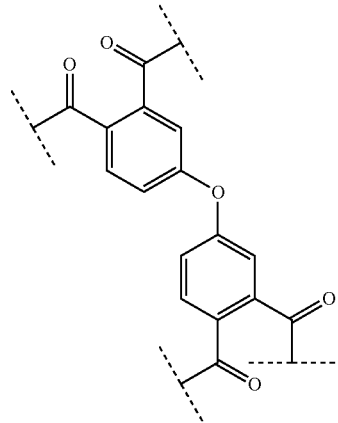 |
| L47 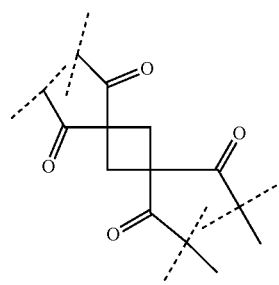 |
| L48 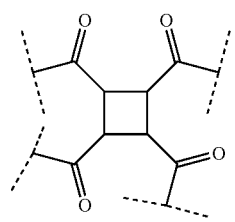 |

| LINKER L | |
|---|---|
| L49 | 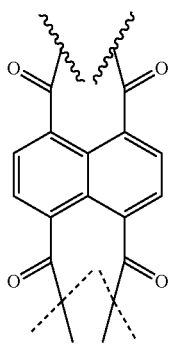 |
| L50 | 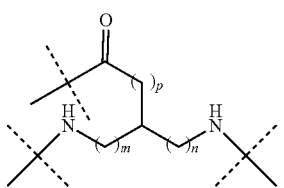<br>n,m,p = 0-6; each independently |
| L51 | 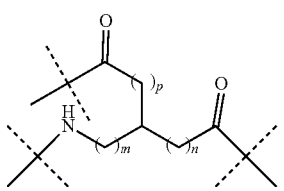<br>n,m,p = 0-6; each independently |
| L52 | 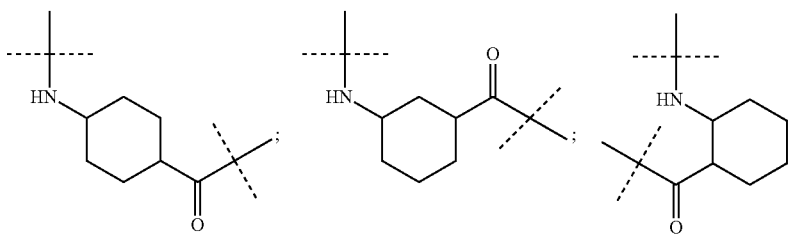 |
| L53 | 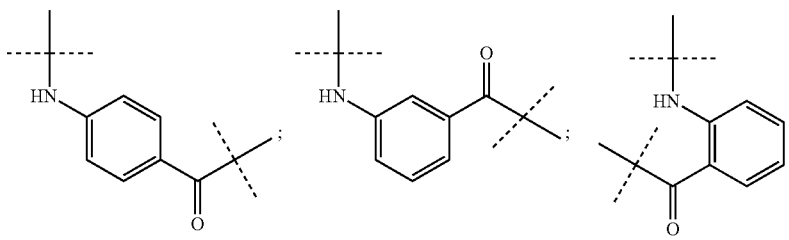 |
| L54 | 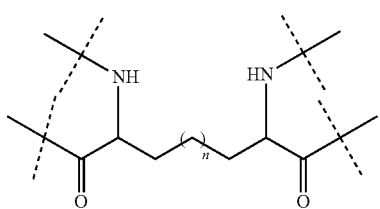<br>n = 0, 5 |

| LINKER L |
|---|
| L55 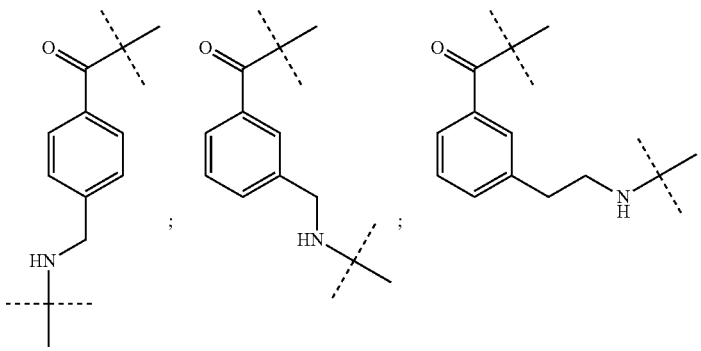 |
| L56 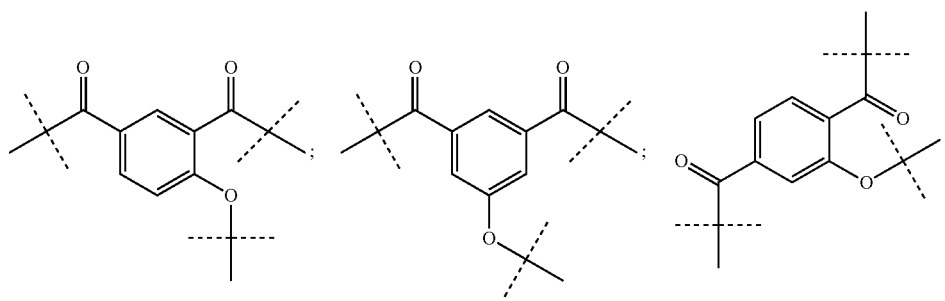 |
| L57 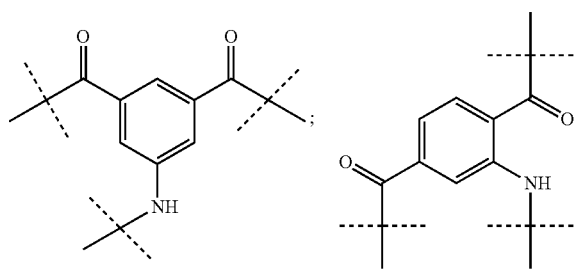 |
| L58 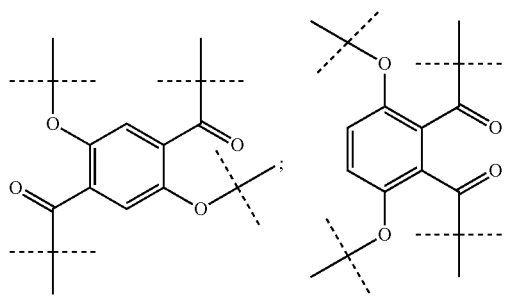 |
| L59 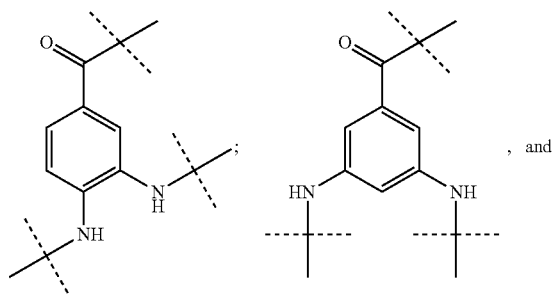, and |
and -continued
| LINKER L |
|---|
| L60 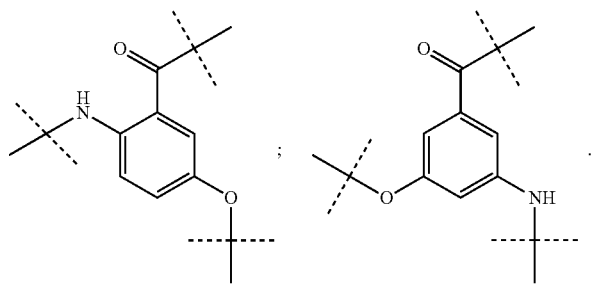 |
18. The medical compound according to claim 17, wherein at least one of b, c, d, and e is 1.
19. The medical compound according to claim 1, wherein L is selected from:
| LINKER L |
|---|
| L61 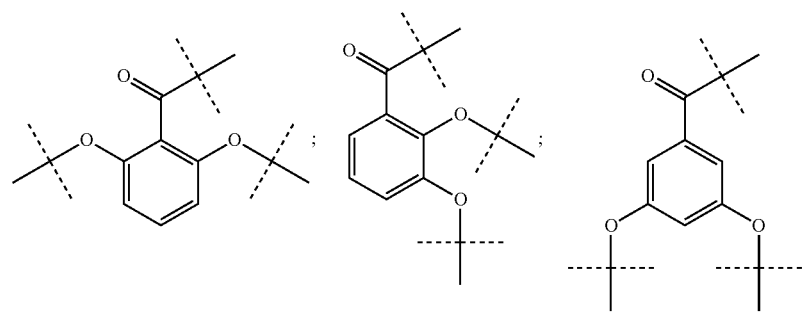 |
| L62 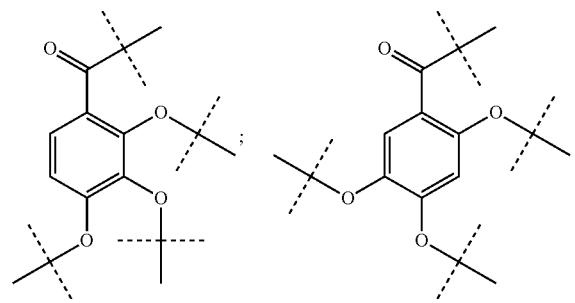 |
| L63 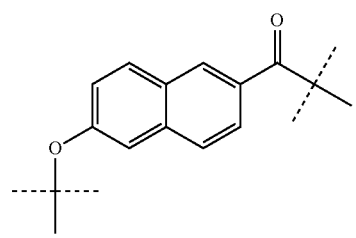 |

| LINKER L | |
|---|---|
| L64 | 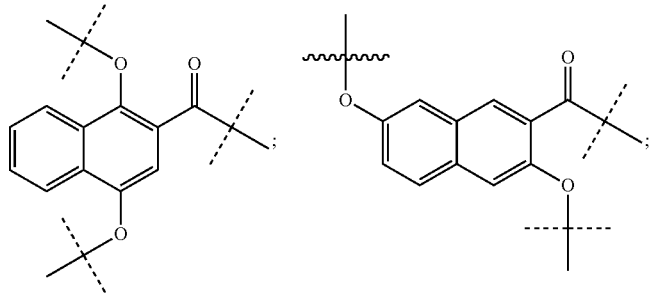 |
| L65 | 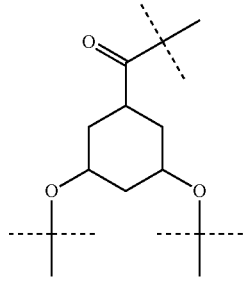 |
| L66 | 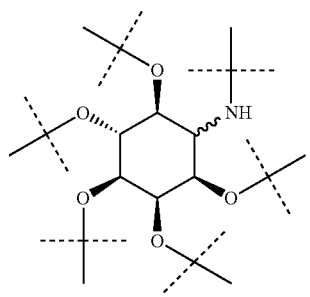 |
| L67 | 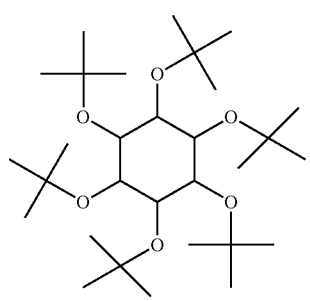 [SMILES: CC(C)(C)OC1C(OC(C)(C)C)C(OC(C)(C)C)C(OC(C)(C)C)C(OC(C)(C)C)C1OC(C)(C)C] |
| L68 | 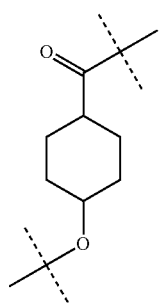 |

| LINKER L |
|---|
| L69 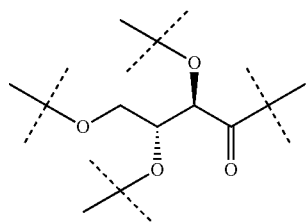 |
| L70 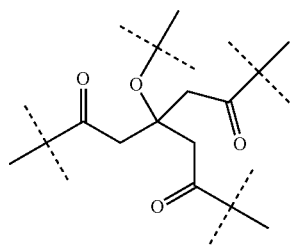 |
| L71 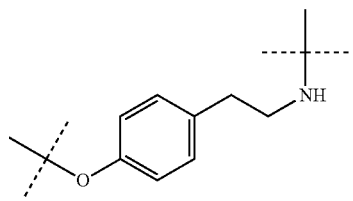 |
| L72 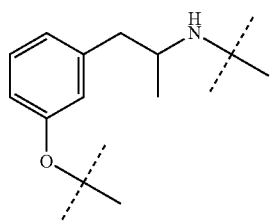 |
| L73 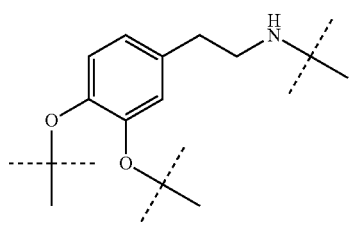 |
| L74 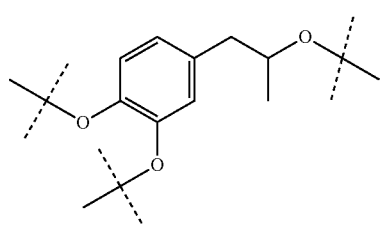 |

-continued
| LINKER L |
|---|
| L75 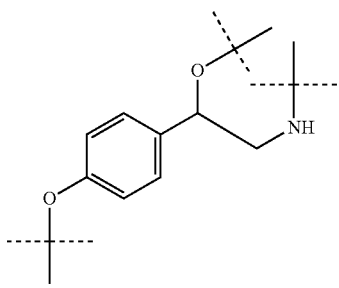 |
| L76 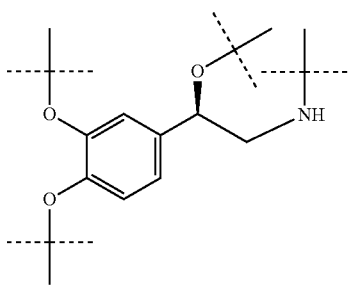 |
| L77 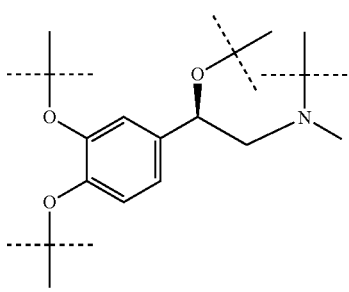 |
| L78 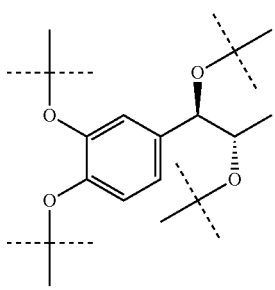 |
| L79 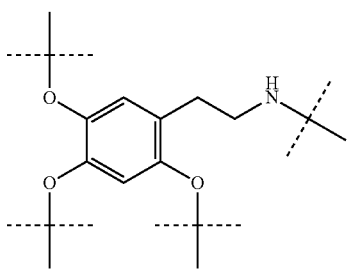 |

| LINKER L |
|---|
| L80 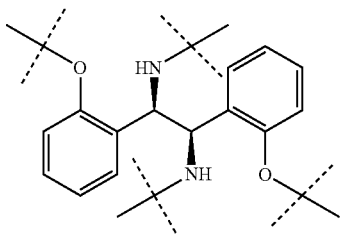 |
| L81 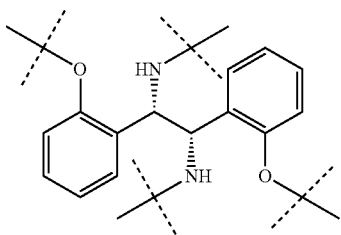 |
| L82 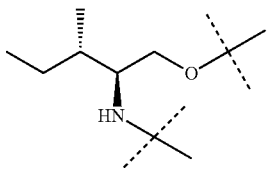 |
| L83 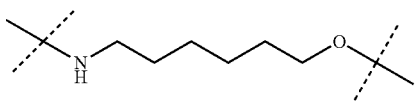 |
| L84 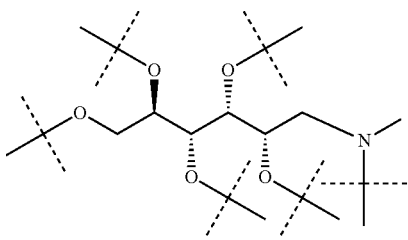 |
| L85 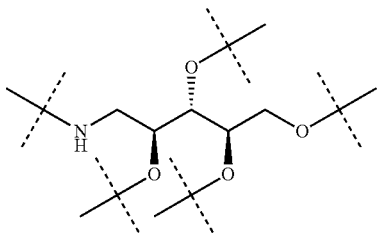 |
| L86 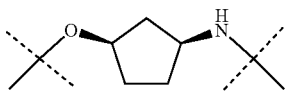 |

| LINKER L | |
|---|---|
| L87 | 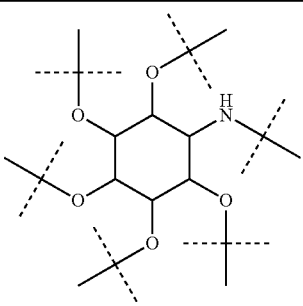 |
| L88 | 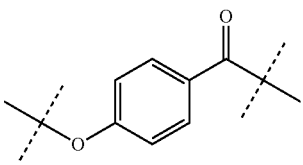 |
| L89 | 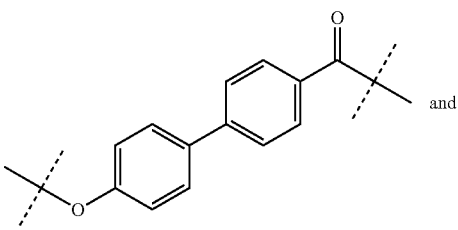 and |
| L90 | 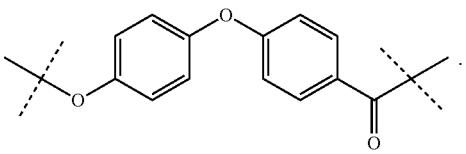 |
20. The medical compound according to claim 19, wherein at least one of b, c, d, and e is 1.
21. The medical compound according to claim 1, wherein $R_1$ is a member selected from the group consisting of:
H,
$C_{1-24}$ alkyl or heteroalkyl,
$C_{1-24}$ alkenyl or heteroalkenyl,
and
an acyl residue of a fatty acid.
* * * * *